United States Patent
Han et al.

(10) Patent No.: US 10,367,149 B2
(45) Date of Patent: Jul. 30, 2019

(54) ORGANIC LIGHT-EMITTING DEVICE

(71) Applicant: LG Chem, Ltd., Seoul (KR)

(72) Inventors: Miyeon Han, Daejeon (KR); Dong Hoon Lee, Daejeon (KR); Jungoh Huh, Daejeon (KR); Boonjae Jang, Daejeon (KR); Dong Uk Heo, Daejeon (KR); Min Woo Jung, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/770,606

(22) PCT Filed: Oct. 27, 2016

(86) PCT No.: PCT/KR2016/012154
§ 371 (c)(1),
(2) Date: Apr. 24, 2018

(87) PCT Pub. No.: WO2017/074052
PCT Pub. Date: May 4, 2017

(65) Prior Publication Data
US 2018/0315930 A1    Nov. 1, 2018

(30) Foreign Application Priority Data
Oct. 27, 2015    (KR) .................. 10-2015-0149714

(51) Int. Cl.
*H01L 51/00* (2006.01)
*C09K 11/06* (2006.01)
(Continued)

(52) U.S. Cl.
CPC ........ *H01L 51/0067* (2013.01); *C07D 235/06* (2013.01); *C07D 251/12* (2013.01); *C07D 263/52* (2013.01); *C07D 277/60* (2013.01); *C07D 403/10* (2013.01); *C09K 11/06* (2013.01); *H01L 51/001* (2013.01); *H01L 51/0052* (2013.01); *H01L 51/0058* (2013.01); *H01L 51/0072* (2013.01); *H01L 51/0073* (2013.01); *H01L 51/5024* (2013.01);
(Continued)

(58) Field of Classification Search
None
See application file for complete search history.

(56) References Cited

U.S. PATENT DOCUMENTS

2004/0251816 A1    12/2004   Leo et al.
2013/0240796 A1    9/2013    Parham et al.
(Continued)

FOREIGN PATENT DOCUMENTS

EP    2629346 A2    8/2013
EP    2991128 A1    3/2016
(Continued)

OTHER PUBLICATIONS

Extended European Search Report including Written Opinion for Application No. EP16860235.7 dated Sep. 26, 2018.
(Continued)

*Primary Examiner* — Su C Kim
*Assistant Examiner* — David S Wilbert
(74) *Attorney, Agent, or Firm* — Lerner, David, Littenberg, Krumholz & Mentlik, LLP

(57) ABSTRACT

The present application relates to an organic light emitting device.

17 Claims, 1 Drawing Sheet

| 601 |
|---|
| 501 |
| 401 |
| 301 |
| 201 |
| 101 |

(51) Int. Cl.
    *C09K 11/02*     (2006.01)
    *C07D 235/06*     (2006.01)
    *C07D 403/10*     (2006.01)
    *C07D 251/12*     (2006.01)
    *C07D 263/52*     (2006.01)
    *C07D 277/60*     (2006.01)
    *H01L 51/50*     (2006.01)
    *H01L 51/52*     (2006.01)

(52) U.S. Cl.
    CPC ...... *H01L 51/5056* (2013.01); *H01L 51/5072* (2013.01); *H01L 51/5092* (2013.01); *H01L 51/5096* (2013.01); *H01L 51/5206* (2013.01); *H01L 51/5221* (2013.01)

(56) References Cited

U.S. PATENT DOCUMENTS

| | | |
|---|---|---|
| 2014/0299192 A1 | 10/2014 | Lee et al. |
| 2015/0102321 A1 | 4/2015 | Kwong et al. |
| 2015/0228908 A1 | 8/2015 | Lee et al. |
| 2015/0337197 A1 | 11/2015 | Jatsch et al. |
| 2015/0349270 A1 | 12/2015 | Lee et al. |
| 2016/0020404 A1* | 1/2016 | Ito ................... H01L 51/0067 257/40 |
| 2016/0126471 A1* | 5/2016 | Lui ................... H01L 51/0059 257/40 |
| 2016/0172598 A1 | 6/2016 | Lee et al. |
| 2016/0181548 A1* | 6/2016 | Parham ............. C07D 487/04 257/40 |
| 2016/0322583 A1* | 11/2016 | Kim ................... H01L 51/0067 |
| 2016/0351822 A1 | 12/2016 | Lee et al. |
| 2017/0018718 A1 | 1/2017 | Jang et al. |
| 2017/0033294 A1 | 2/2017 | Jang et al. |
| 2017/0062736 A1 | 3/2017 | Parham et al. |
| 2017/0222158 A1* | 8/2017 | Jung .................. C09K 11/06 |
| 2017/0331067 A1* | 11/2017 | Park .................. C09K 11/06 |

FOREIGN PATENT DOCUMENTS

| | | |
|---|---|---|
| EP | 3016169 A1 | 5/2016 |
| EP | 3137458 A1 | 3/2017 |
| EP | 3296293 A2 | 3/2018 |
| JP | 201583566 A | 4/2015 |
| KR | 20140145456 A | 12/2014 |
| KR | 20150074603 A | 7/2015 |
| KR | 101542714 B1 | 8/2015 |
| KR | 20150104261 A | 9/2015 |
| KR | 101560102 B1 | 10/2015 |
| KR | 20150115622 A | 10/2015 |
| KR | 20150117173 A | 10/2015 |
| WO | 2003012890 A2 | 2/2003 |
| WO | 2012069121 A1 | 5/2012 |
| WO | 2014094963 A1 | 6/2014 |
| WO | 2014209028 A1 | 12/2014 |
| WO | 2015014434 A1 | 2/2015 |
| WO | 2015073343 A1 | 5/2015 |
| WO | 2015115744 A1 | 8/2015 |
| WO | 2015152650 A1 | 10/2015 |
| WO | 2015152651 A1 | 10/2015 |

OTHER PUBLICATIONS

Extended European Search Report including Written Opinion for Application No. EP16860236.5 dated Sep. 26, 2018.
Search report from International Application No. PCT/KR2016/012157, dated Feb. 7, 2017.
Search report from International Application No. PCT/KR2016/012154, dated Jan. 31, 2017.

* cited by examiner

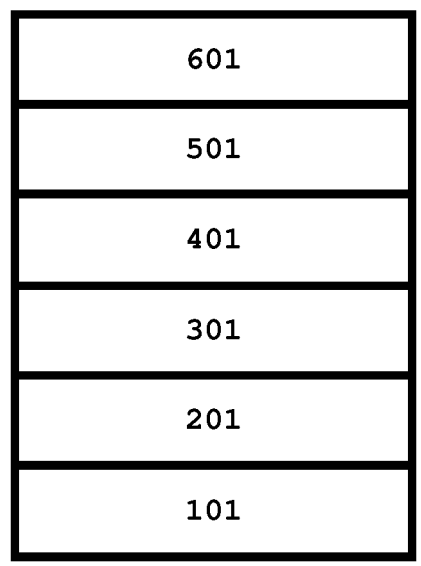

ORGANIC LIGHT-EMITTING DEVICE

CROSS-REFERENCE TO RELATED APPLICATIONS

The present application is a national phase entry under 35 U.S.C. § 371 of International Application No. PCT/KR2016/012154 filed Oct. 27, 2016, which claims priority from Korean Patent Application No. 10-2015-0149714 filed Oct. 27, 2015, all of which are incorporated herein by reference.

TECHNICAL FIELD

The present application relates to an organic light emitting device.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present application has been made in an effort to provide an organic light emitting device.

Technical Solution

The present application provides an organic light emitting device including: a positive electrode; a negative electrode provided to face the positive electrode; and an organic material layer between the positive electrode and the negative electrode, in which the organic material layer includes a light emitting layer, the organic material layer further includes an electron adjusting layer and an electron transport layer provided between the light emitting layer and the negative electrode, the electron adjusting layer includes a compound represented by the following Chemical Formula 1, and the electron transport layer includes a compound represented by the following Chemical Formula 11.

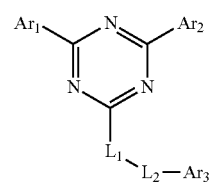

[Chemical Formula 1]

In Chemical Formula 1, $Ar_1$ and $Ar_2$ are the same as or different from each other, and are each independently a substituted or unsubstituted aryl group; or a substituted or unsubstituted heterocyclic group, and $L_1$ is represented by any one of the following Chemical Formulae 2 to 5,

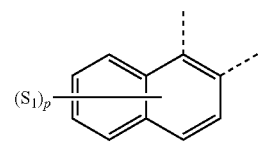

[Chemical Formula 2]

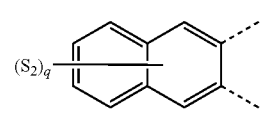

[Chemical Formula 3]

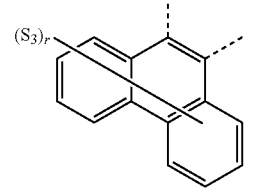

[Chemical Formula 4]

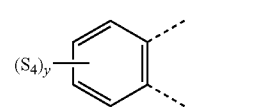

[Chemical Formula 5]

in Chemical Formulae 2 to 5, a dotted line " ------ " is each a moiety bonded to a triazine group or $L_2$ of Chemical Formula 1, $S_1$ to $S_4$ are the same as or different from each other, and are each independently hydrogen; deuterium; a halogen group; a substituted or unsubstituted alkyl group; a substituted or unsubstituted aryl group; or a substituted or unsubstituted heterocyclic group, p and q are the same as or different from each other, and are each independently an integer of 0 to 6, r is an integer of 0 to 8, y is an integer of 0 to 4, when p, q, r, and y are each an integer of 2 or more, a plurality of $S_1$ to $S_4$ are each the same as or different from each other, $L_2$ is a direct bond; or a substituted or unsubstituted arylene group, $Ar_3$ is represented by a substituted or unsubstituted aryl group; a substituted or unsubstituted heterocyclic group including S or O; a substituted or unsubstituted carbazole group; or any one of the following Chemical Formulae 6 to 10, when $L_1$ is Chemical Formulae 2 to 4, $Ar_3$ is represented by a substituted or unsubstituted aryl group; a substituted or unsubstituted heterocyclic group including S or O; or any one of the following Chemical Formulae 6 to 10, when L₁ is Chemical Formula 5,

[Chemical Formula 6]

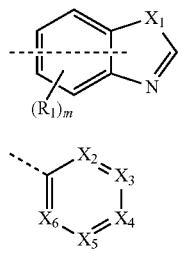

[Chemical Formula 7]

[Chemical Formula 8]

[Chemical Formula 9]

[Chemical Formula 10]

in Chemical Formulae 6 to 10, $X_1$ is O, S, or NR, at least two of $X_2$ to $X_6$ are N, and the others are each independently CR', R and R' are the same as or different from each other, and are each independently hydrogen; deuterium; a halogen group; a substituted or unsubstituted alkyl group; or a substituted or unsubstituted aryl group, $R_1$ to $R_6$, $R_9$, and $R_{10}$ are the same as or different from each other, and are each independently hydrogen; deuterium; a halogen group; a substituted or unsubstituted alkyl group; a substituted or unsubstituted aryl group; or a substituted or unsubstituted heterocyclic group, at least one of $Y_1$ to $Y_4$ is N, and the others are CR", R" is each independently hydrogen or deuterium, $R_7$ and $R_8$ are directly bonded, or combine with each other to form a substituted or unsubstituted ring, m, n, t, u, v, and x are each an integer of 0 to 4, w is an integer of 0 to 3, and when m, n, t, u, v, w, and x are each an integer of 2 or more, a plurality of $R_1$ to $R_6$, $R_9$, and $R_{10}$ are each the same as or different from each other, s is an integer of 0 to 2, and when s is 2, two $R_a$s are the same as or different from each other, " ------ " means a moiety bonded to $L_2$ of Chemical Formula 1, and the bonding moiety of Chemical Formula 10 is bonded to a ring formed by bonding $R_6$, $R_9$, $R_{10}$ or $R_7$, and $R_8$,

[Chemical Formula 11]

in Chemical Formula 11, at least two of $X_{10}$ to $X_{12}$ are N, and the other is each independently CR''', R''' is hydrogen; deuterium; a halogen group; a substituted or unsubstituted alkyl group; or a substituted or unsubstituted aryl group, Ar₄ to Ar₆ are the same as or different from each other, and are each independently a substituted or unsubstituted aryl group; or a substituted or unsubstituted heterocyclic group, L₃ is a direct bond; a substituted or unsubstituted arylene group; or a substituted or unsubstituted divalent heterocyclic group, and l is 1 or 2, and when l is 2, Ar₆s are the same as or different from each other.

Advantageous Effects

An organic light emitting device according to an exemplary embodiment of the present application has a low driving voltage, and the lifetime characteristics of the device may be improved by the thermal stability of a compound.

A triazine-type compound represented by Chemical Formula 1 may exhibit excellent characteristics as a material for an electron adjusting layer because triazine and another functional group are each disposed ortho to L1 to exhibit characteristics which easily adjust the amount of holes (hole blocking). A pyrimidine-type compound represented by Chemical Formula 11 and a triazine-type compound usually have high LUMO values, and accordingly, have characteristics which easily transfer electrons to an electron adjusting layer, and have low voltage and high efficiency characteristics.

Accordingly, electrons may be easily transferred from an electron transport layer to an electron adjusting layer by using the compound of Chemical Formula 1 in the electron adjusting layer, and simultaneously, using the compound of Chemical Formula 11 together in the electron transport layer, and when a charge balance is established by efficiently adjusting the amount of holes from a positive electrode through wide bandgap characteristics, it is possible to have low driving voltage and long lifetime characteristics, and to improve efficiency characteristics.

DESCRIPTION OF DRAWINGS

FIG. 1 illustrates an example of an organic light emitting device according to an exemplary embodiment of the present specification.

BEST MODE

Hereinafter, the present specification will be described in more detail.

When one part "includes" one constituent element in the present specification, unless otherwise specifically described, this does not mean that another constituent element is excluded, but means that another constituent element may be further included.

The present specification provides an organic light emitting device including: a positive electrode; a negative electrode provided to face the positive electrode; and an organic material layer between the positive electrode and the negative electrode, in which the organic material layer includes a light emitting layer, the organic material layer further includes an electron adjusting layer and an electron transport layer provided between the light emitting layer and the negative electrode, the electron adjusting layer includes the compound represented by Chemical Formula 1, and the electron transport layer includes the compound represented by Chemical Formula 11.

The electron adjusting layer means a layer which serves to adjust the mobility of electrons in an organic light emitting device.

In an exemplary embodiment of the present specification, the organic light emitting device includes a light emitting layer, and the electron adjusting layer is provided to be brought into contact with the light emitting layer. In this case, the electron adjusting layer may serve to adjust the electron mobility, and simultaneously, may serve as a hole barrier which prevents holes supplied from a positive electrode from migrating into a negative electrode, particularly, an electron transport layer.

In an exemplary embodiment of the present specification, the thickness of the electron transport layer is larger than that of the electron adjusting layer. When the thickness of the electron adjusting layer, which adjusts the movement of electrons, is larger than that of the electron transport layer, the amount of electrons, which may move to the light emitting layer per unit time, is decreased, and thus, holes may be relatively excessively supplied from the positive electrode to the negative electrode, so that the efficiency of the device may be decreased. Therefore, when the thickness of the electron transport layer is larger than that of the electron adjusting layer, the amount of electrons, which may move to the light emitting layer per unit time, is appropriately adjusted, and thus, may be balanced with the amount of holes supplied from the positive electrode, so that it may be expected that the formation of excitons of the light emitting layer is maximized and the device has high efficiency.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; an alkyl group; a cycloalkyl group; an alkenyl group; an alkoxy group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branch-chained, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the group may be

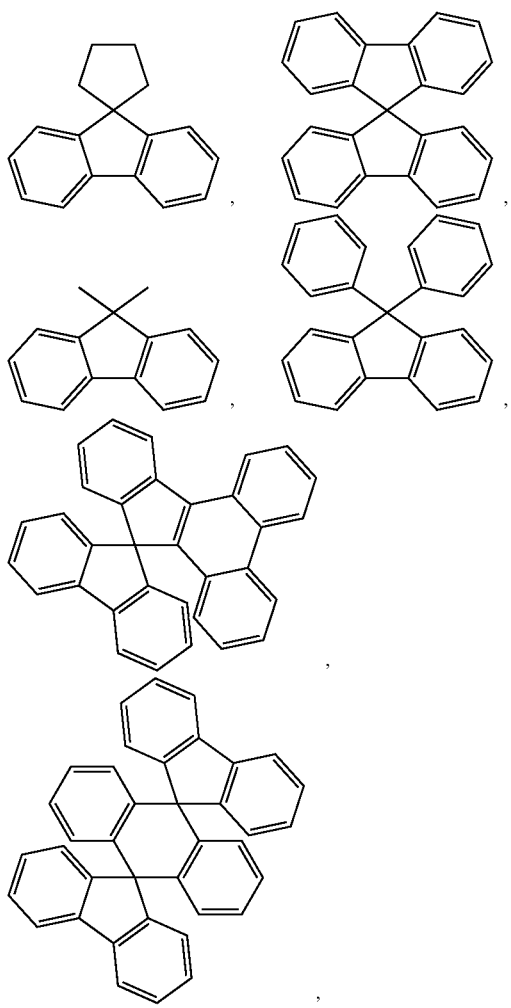

and the like, but is not limited thereto.

In the present specification, a heterocyclic group includes one or more of an atom other than carbon, that is, a heteroatom, and specifically, the heteroatom may include one or more atoms selected from the group consisting of O, N, Se, and S, and the like. The number of carbon atoms of the heterocyclic group is not particularly limited, but is preferably 2 to 60. Examples of the heterocyclic group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

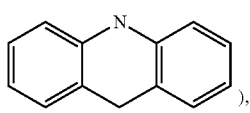), a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group; a benzosilole group; a dibenzosilole group; a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

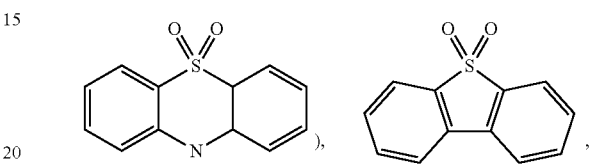

and the like.

In the present specification, the fused structure may be a structure in which an aromatic hydrocarbon ring is fused with the corresponding substituent. Examples of a fused ring of benzimidazole include

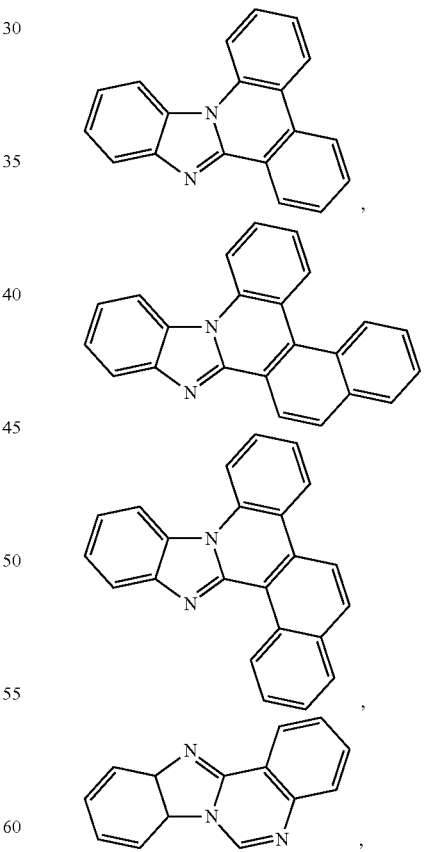

and the like, but are not limited thereto.

In the present specification, the "adjacent" group may mean a substituent substituted with an atom directly linked to an atom in which the corresponding substituent is substituted, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

According to an exemplary embodiment of the present application, $L_2$ is a direct bond; or a substituted or unsubstituted $C_6$ to $C_{20}$ arylene group.

According to an exemplary embodiment of the present application, $L_2$ is a direct bond.

According to an exemplary embodiment of the present application, $L_2$ is a substituted or unsubstituted phenylene group.

According to an exemplary embodiment of the present application, $L_2$ is a substituted or unsubstituted biphenylene group.

According to an exemplary embodiment of the present application, $L_2$ is a substituted or unsubstituted naphthylene group.

According to an exemplary embodiment of the present application, $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; a substituted or unsubstituted carbazole group; or any one of Chemical Formulae 6 to 10, when $L_1$ is Chemical Formulae 2 to 4, and $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; any one of Chemical Formulae 6 to 10, when $L_1$ is Chemical Formula 5.

According to an exemplary embodiment of the present application, $Ar_3$ is a substituted or unsubstituted $C_4$ to $C_{20}$ heteroaryl group including S or O.

According to an exemplary embodiment of the present application, the substituted or unsubstituted heteroaryl group including S or O of $Ar_3$ is a substituted or unsubstituted furan group; or a substituted or unsubstituted thiophene group.

According to an exemplary embodiment of the present application, the substituted or unsubstituted heteroaryl group including S or O of $Ar_3$ is a substituted or unsubstituted dibenzofuran group; or a substituted or unsubstituted dibenzothiophene group.

According to an exemplary embodiment of the present application, $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted carbazole group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formulae 2 to 4, $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formula 5, and the "substituted or unsubstituted" means being unsubstituted or substituted with at least one selected from deuterium; a halogen group; a cyano group; a $C_1$ to $C_{10}$ alkyl group; and a $C_6$ to $C_{10}$ aryl group.

According to an exemplary embodiment of the present application, $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted carbazole group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formulae 2 to 4, $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formula 5, and the "substituted or unsubstituted" means being unsubstituted or substituted with a cyano group; a methyl group; an ethyl group; a phenyl group; or a biphenyl group.

According to an exemplary embodiment of the present application, $Ar_3$ is a phenyl group substituted with a cyano group; a fluorenyl group unsubstituted or substituted with a cyano group, an alkyl group, or an aryl group; a benzofluorenyl group unsubstituted or substituted with an alkyl group or an aryl group; a spirobifluorenyl group; a spirofluoreneindenophenanthrene group; a dispirofluoreneanthracenefluorene group; a triphenylene group; a carbazole group; a pyrimidyl group; a pyridazinyl group; a triazinyl group unsubstituted or substituted with a phenyl group; a benzocarbazolyl group; a benzimidazole group; a benzoxazole group; a benzothiazole group; a dibenzofuran group; a dibenzothiophene group; a benzonaphthofuran group; or a benzonaphthothiophene group, when $L_1$ is Chemical Formulae 2 to 4, and $Ar_3$ is a phenyl group substituted with a cyano group; a fluorenyl group unsubstituted or substituted with a cyano group, an alkyl group, or an aryl group; a benzofluorenyl group unsubstituted or substituted with an alkyl group or an aryl group; a spirobifluorenyl group; a spirofluoreneindenophenanthrene group; a dispirofluoreneanthracenefluorene group; a triphenylene group; a pyrimidyl group; a pyridazinyl group; a triazinyl group unsubstituted or substituted with a phenyl group; a benzocarbazolyl group; a benzimidazole group; a benzoxazole group; a benzothiazole group; a dibenzofuran group; a dibenzothiophene group; a benzonaphthofuran group; or a benzonaphthothiophene group, when $L_1$ is Chemical Formula 5.

According to an exemplary embodiment of the present application, $Ar_3$ is a phenyl group substituted with a cyano group.

According to an exemplary embodiment of the present application, $Ar_3$ is a fluorenyl group.

According to an exemplary embodiment of the present application, $Ar_3$ is a fluorenyl group substituted with a cyano group.

According to an exemplary embodiment of the present application, $Ar_3$ is a benzofluorenyl group substituted with an aryl group.

According to an exemplary embodiment of the present application, $Ar_3$ is a benzofluorenyl group substituted with a phenyl group.

According to an exemplary embodiment of the present application, $Ar_3$ is a dimethylfluorenyl group.

According to an exemplary embodiment of the present application, $Ar_3$ is a spirobifluorenyl group.

According to an exemplary embodiment of the present application, $Ar_3$ is a spirofluoreneindenophenanthrene group.

According to an exemplary embodiment of the present application, $Ar_3$ is a dispirofluoreneanthracenefluorene group.

According to an exemplary embodiment of the present application, $Ar_3$ is a dimethylfluorenyl group substituted with a cyano group.

According to an exemplary embodiment of the present application, $Ar_3$ is a triphenylene group.

According to an exemplary embodiment of the present application, $Ar_3$ is a pyrimidyl group.

According to an exemplary embodiment of the present application, $Ar_3$ is a pyrimidyl group substituted with an aryl group.

According to an exemplary embodiment of the present application, $Ar_3$ is a pyrimidyl group substituted with a phenyl group, a biphenyl group, a phenanthrene group, or a fluorenyl group.

According to an exemplary embodiment of the present application, $Ar_3$ is a pyridazinyl group.

According to an exemplary embodiment of the present application, $Ar_3$ is a pyridazinyl group substituted with an aryl group.

According to an exemplary embodiment of the present application, $Ar_3$ is a pyridazinyl group substituted with a phenyl group.

According to an exemplary embodiment of the present application, $Ar_3$ is a triazinyl group.

According to an exemplary embodiment of the present application, $Ar_3$ is a benzimidazole group.

According to an exemplary embodiment of the present application, $Ar_3$ is a benzimidazole group substituted with an alkyl group or an aryl group.

According to an exemplary embodiment of the present application, $Ar_3$ is a benzimidazole group substituted with a methyl group.

According to an exemplary embodiment of the present application, $Ar_3$ is a benzimidazole group substituted with a phenyl group.

According to an exemplary embodiment of the present application, $Ar_3$ is a benzoxazole group.

According to an exemplary embodiment of the present application, $Ar_3$ is a benzothiazole group.

According to an exemplary embodiment of the present application, $Ar_3$ is a benzocarbazole group.

According to an exemplary embodiment of the present application, $Ar_3$ is a dibenzothiophene group.

According to an exemplary embodiment of the present application, $Ar_3$ is a dibenzofuran group.

According to an exemplary embodiment of the present application, $Ar_3$ is a benzonaphthothiophene group.

According to an exemplary embodiment of the present application, $Ar_3$ is a benzonaphthofuran group.

According to an exemplary embodiment of the present application, Chemical Formula 6 is represented by any one of the following Chemical Formulae 6-1-1 to 6-1-3.

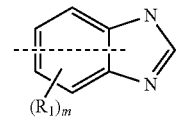

[Chemical Formula 6-1-1]

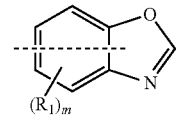

[Chemical Formula 6-1-2]

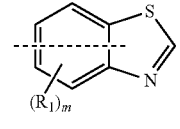

[Chemical Formula 6-1-3]

In Chemical Formulae 6-1-1 to 6-1-3, $R_1$ and m are the same as those described above.

According to an exemplary embodiment of the present application, Chemical Formula 6 is represented by any one of the following Chemical Formulae 6-2-1 to 6-2-3.

[Chemical Formula 6-2-1]
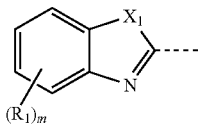

[Chemical Formula 6-2-2]
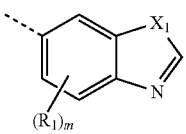

[Chemical Formula 6-2-3]
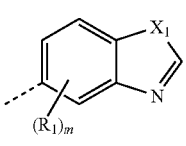

In Chemical Formulae 6-2-1 to 6-2-3, $X_1$, $R_1$, and m are the same as those described above.

According to an exemplary embodiment of the present application, Chemical Formula 7 is represented by any one of the following Chemical Formulae 7-1 to 7-6.

[Chemical Formula 7-1]
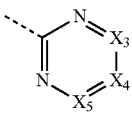

[Chemical Formula 7-2]
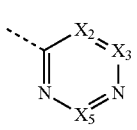

[Chemical Formula 7-3]
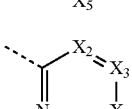

[Chemical Formula 7-4]
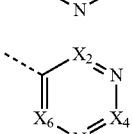

[Chemical Formula 7-5]
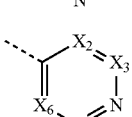

[Chemical Formula 7-6]
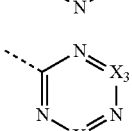

In Chemical Formulae 7-1 to 7-6, $X_2$ to $X_6$ are the same as CR' described above.

According to an exemplary embodiment of the present application, Chemical Formula 8 is represented by any one of the following Chemical Formulae 8-1 to 8-3.

[Chemical Formula 8-1]
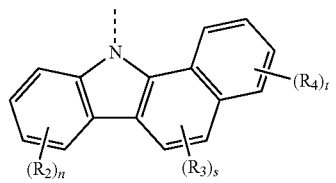

[Chemical Formula 8-2]
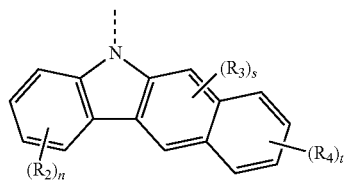

[Chemical Formula 8-3]
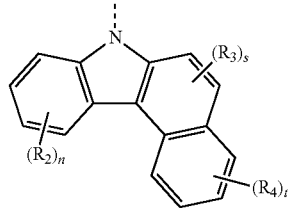

In Chemical Formulae 8-1 to 8-3, $R_2$ to $R_4$, n, s, and t are the same as those described above.

According to an exemplary embodiment of the present application, Chemical Formula 9 is represented by any one of the following Chemical Formulae 9-1 to 9-4.

[Chemical Formula 9-1]
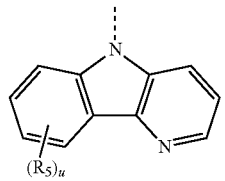

[Chemical Formula 9-2]
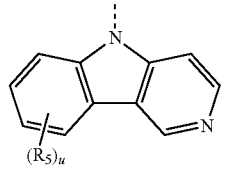

[Chemical Formula 9-3]
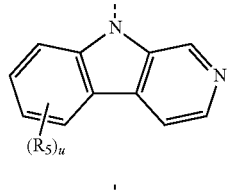

[Chemical Formula 9-4]
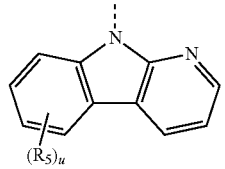

In Chemical Formulae 9-1 to 9-4, $R_5$ and u are the same as those described above.

According to an exemplary embodiment of the present application, Chemical Formula 10 is represented by the following Chemical Formula 10-1 or 10-2.

[Chemical Formula 10-1]

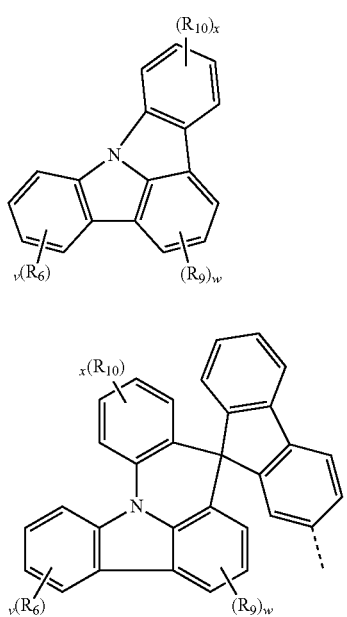

[Chemical Formula 10-2]

In Chemical Formulae 10-1 and 10-2, $R_6$, $R_9$, $R_{10}$, v, w, and x are the same as those described above, and " ------ " means a moiety bonded to $L_2$ of Chemical Formula 1, and the bonding moiety of Chemical Formula 10-1 is $R_6$, $R_9$, or $R_{10}$.

According to an exemplary embodiment of the present application, $Ar_1$ and $Ar_2$ are the same as or different from each other, and are each independently a substituted or unsubstituted $C_6$ to $C_{20}$ aryl group.

According to an exemplary embodiment of the present application, $Ar_1$ and $Ar_2$ are the same as or different from each other, and are each independently a substituted or unsubstituted phenyl group; a substituted or unsubstituted biphenyl group; or a substituted or unsubstituted naphthyl group.

According to an exemplary embodiment of the present application, $Ar_1$ and $Ar_2$ are a phenyl group.

According to an exemplary embodiment of the present application, $S_1$ to $S_4$ are the same as or different from each other, and are each independently hydrogen; deuterium; a halogen group; a $C_1$ to $C_{10}$ alkyl group; a $C_6$ to $C_{10}$ aryl group; or a $C_2$ to $C_{10}$ heterocyclic group.

According to an exemplary embodiment of the present application, $S_1$ to $S_4$ are hydrogen.

According to an exemplary embodiment of the present application, $R_1$ to $R_4$ are hydrogen.

According to an exemplary embodiment of the present application, $R_1$ to $R_6$, $R_9$, and $R_{10}$ are hydrogen.

According to an exemplary embodiment of the present application, the compound represented by Chemical Formula 1 is any one selected from the following structural formulae.

Compound 1-1

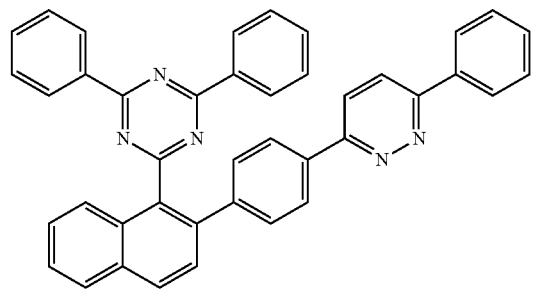

Compound 1-2

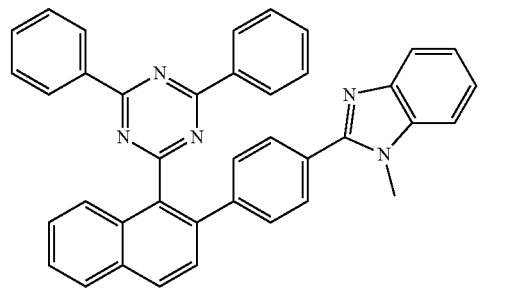

Compound 1-3

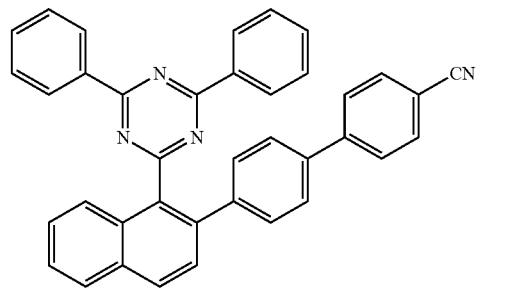

Compound 1-4

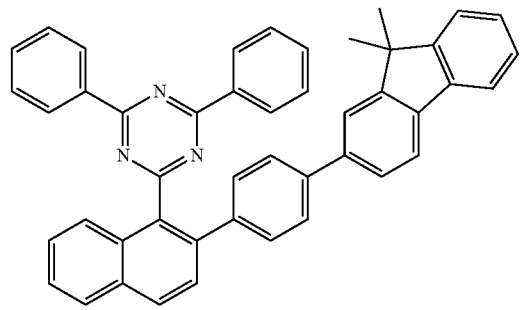

Compound 1-5

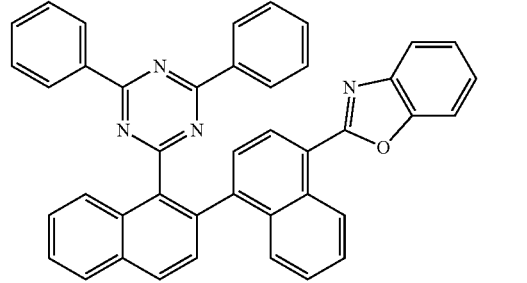

Compound 1-6
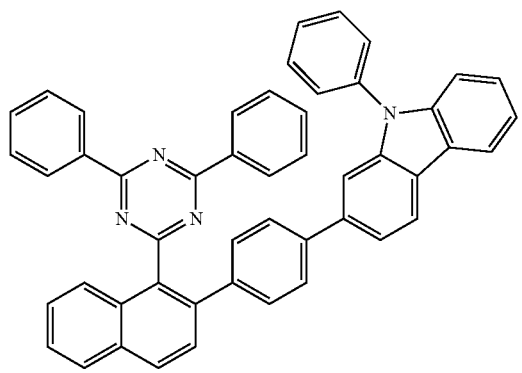
Compound 1-7
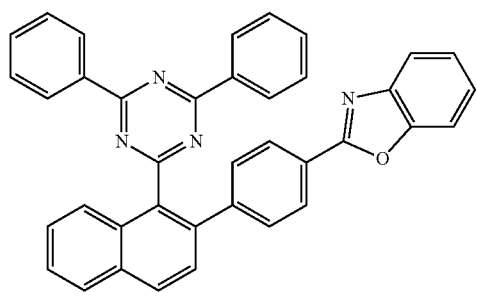
Compound 1-8
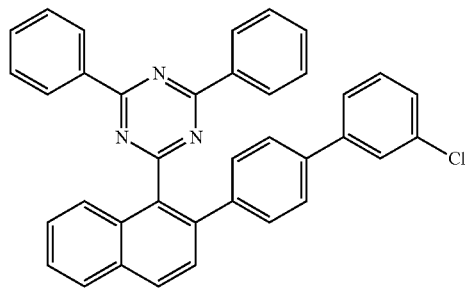
Compound 1-9
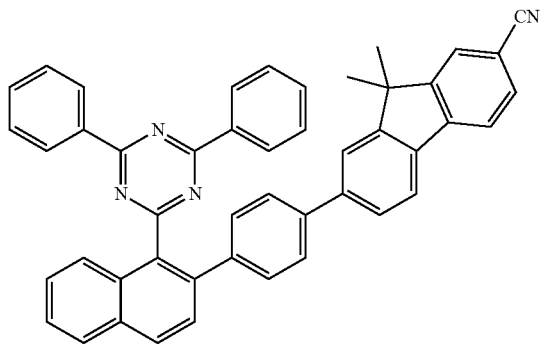
Compound 1-10
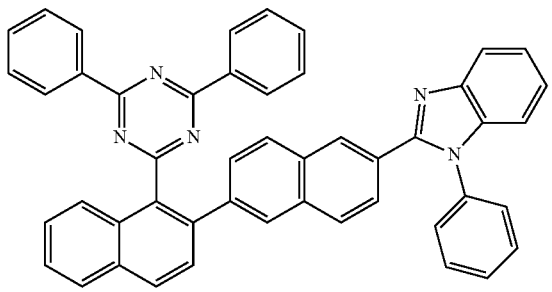
Compound 1-11
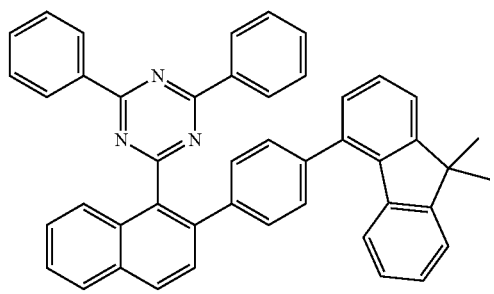
Compound 1-12
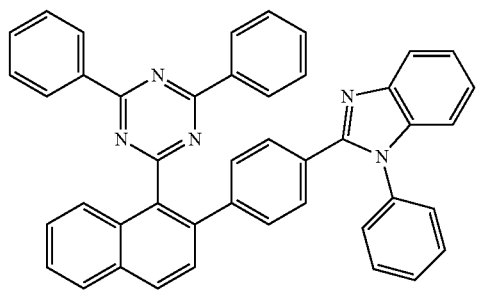
Compound 1-13
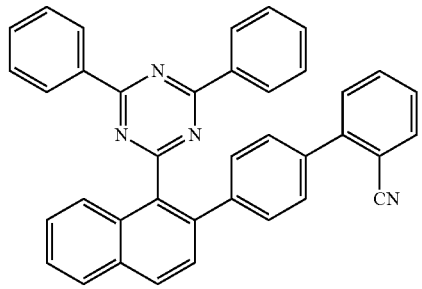
Compound 1-14
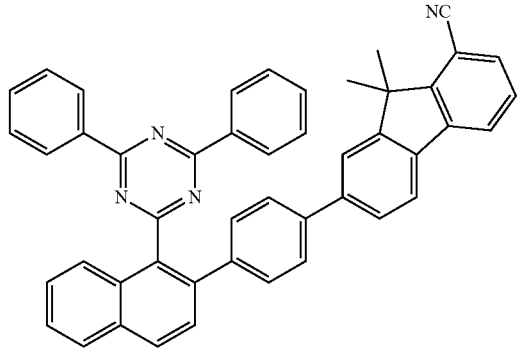

Compound 1-15
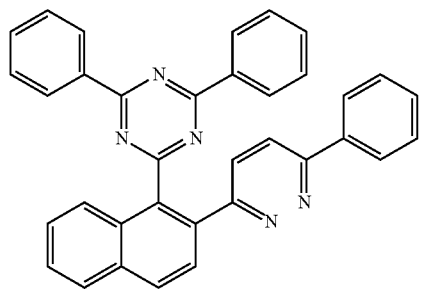
Compound 1-16
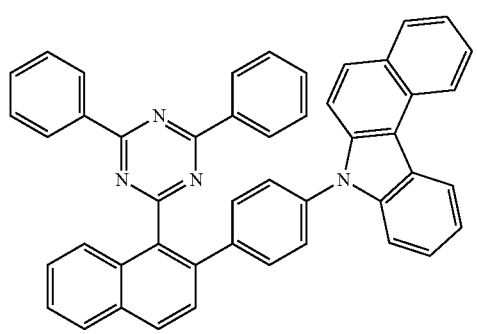
Compound 1-17
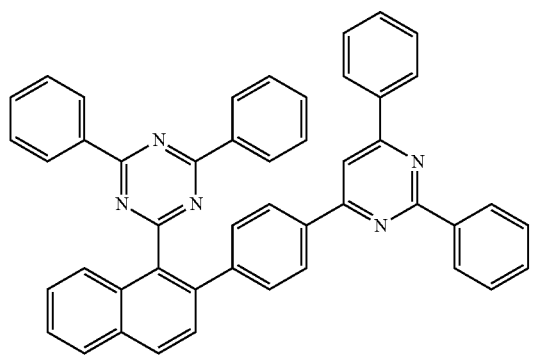
Compound 1-18
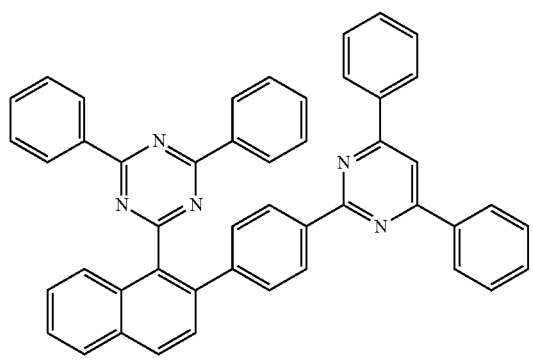
Compound 1-19
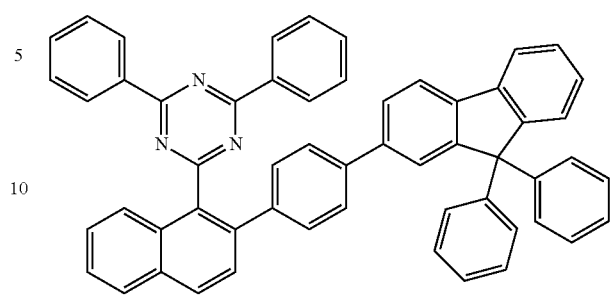
Compound 1-20
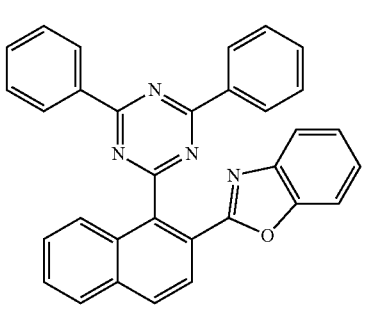
Compound 1-21
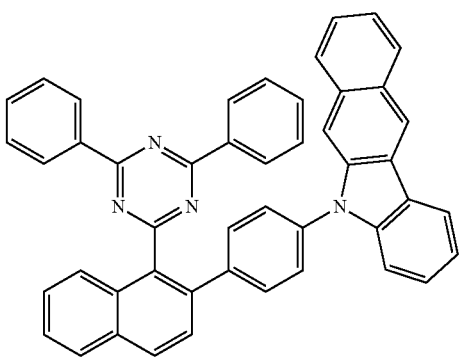
Compound 1-22
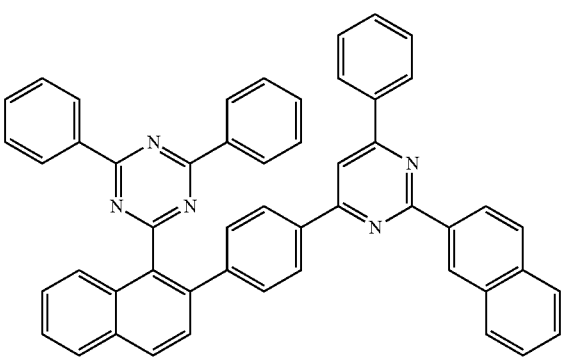

Compound 1-23
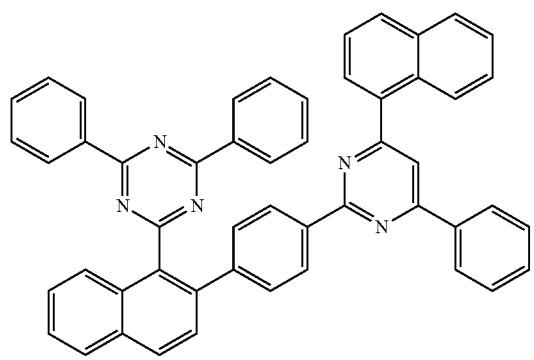
Compound 1-27
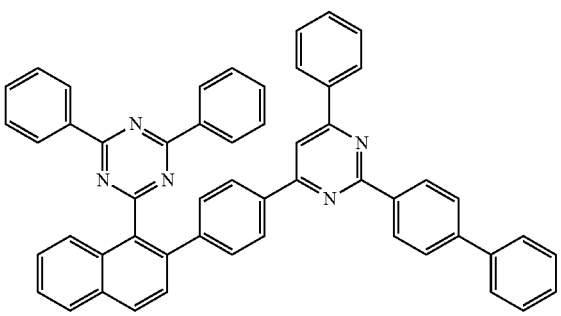
Compound 1-24
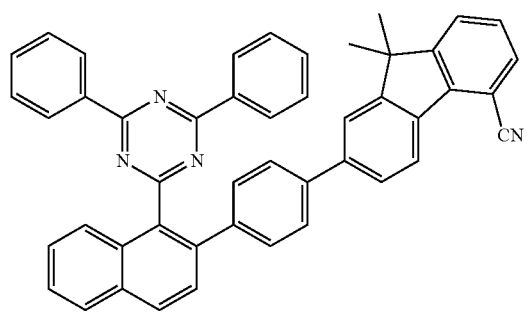
Compound 1-28
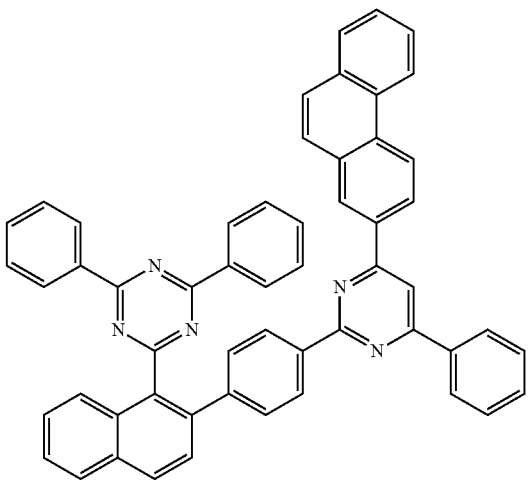
Compound 1-25
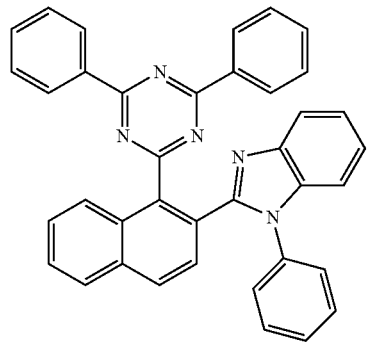
Compound 1-29
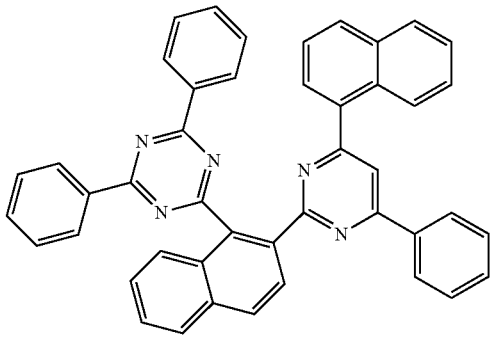
Compound 1-26
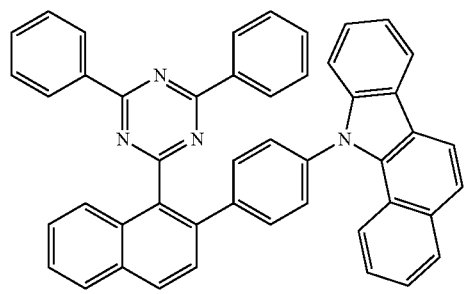
Compound 1-30
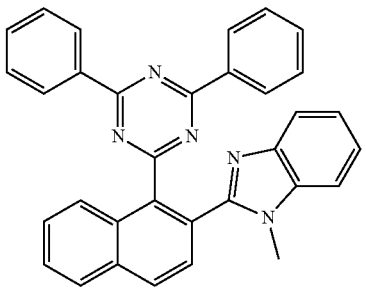

Compound 1-31
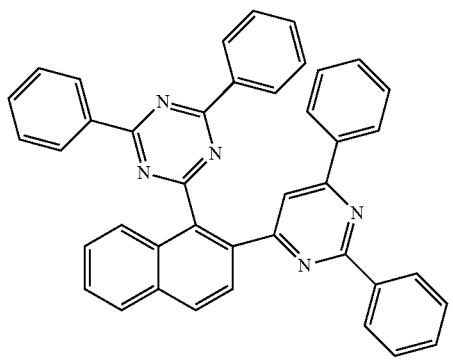
Compound 1-32
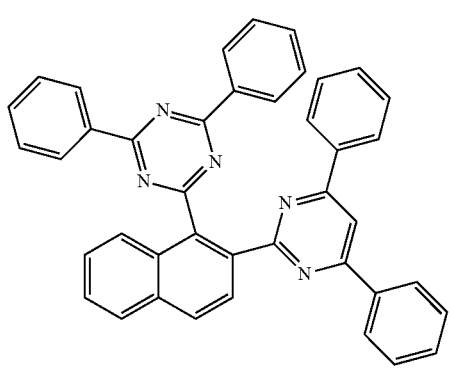
Compound 1-33
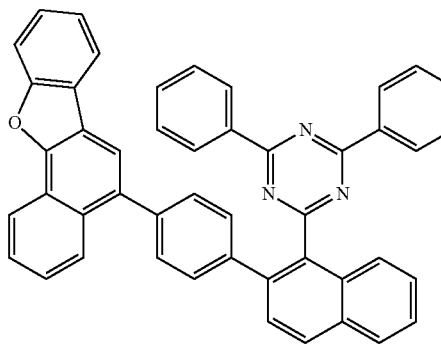
Compound 1-34
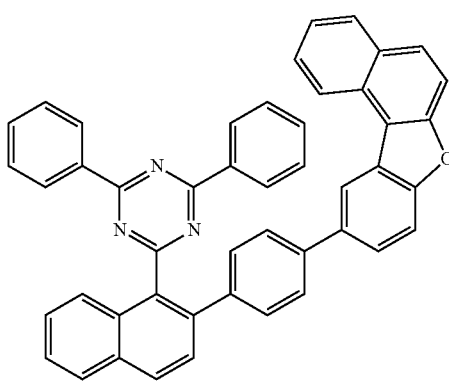
Compound 1-35
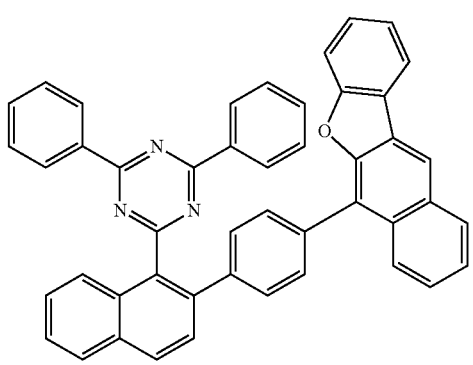
Compound 1-36
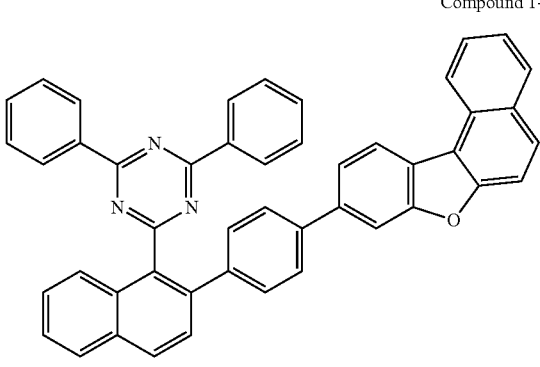
Compound 1-37
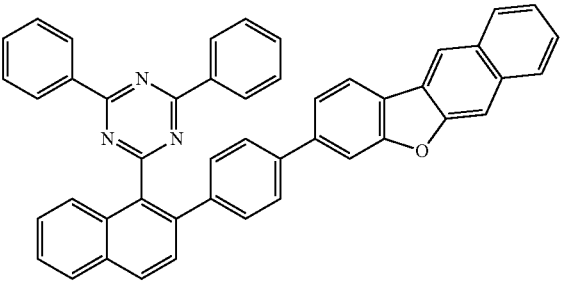
Compound 1-38
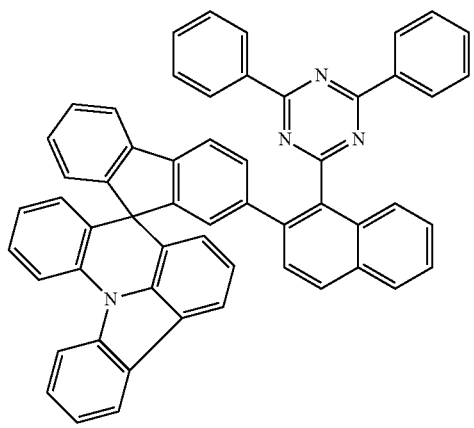

Compound 1-39
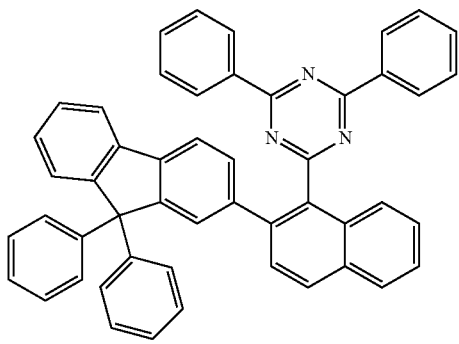
Compound 1-40
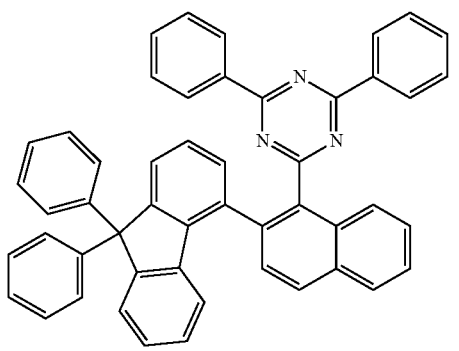
Compound 1-41
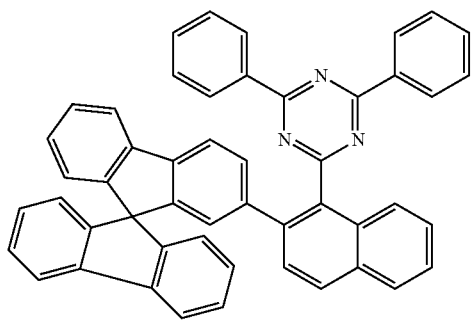
Compound 1-42
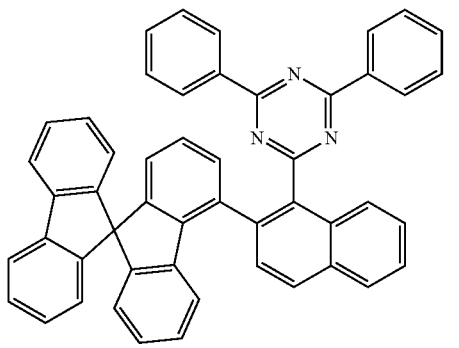
Compound 1-43
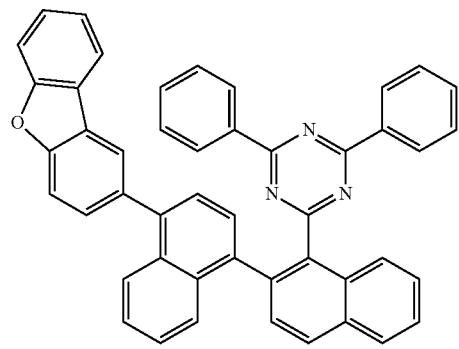
Compound 1-44
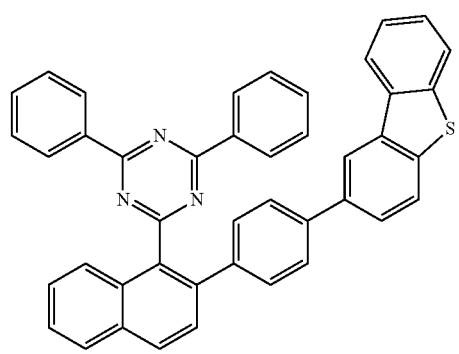
Compound 1-45
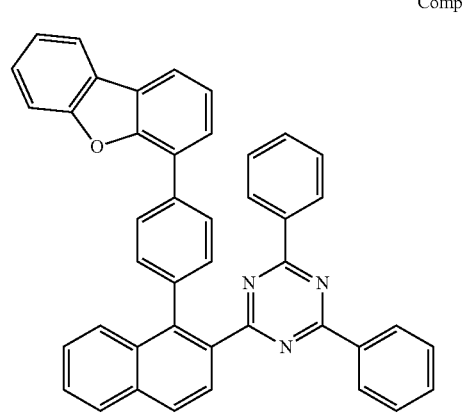
Compound 1-46
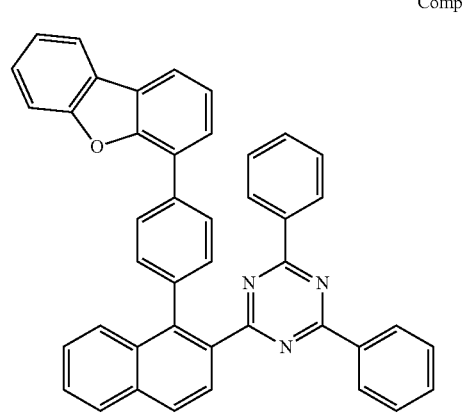

Compound 1-47
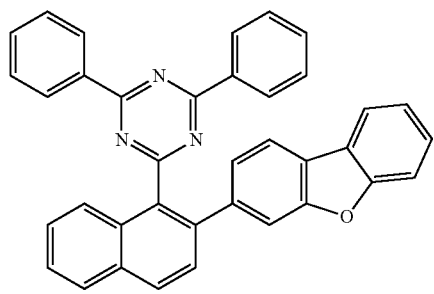
Compound 1-48
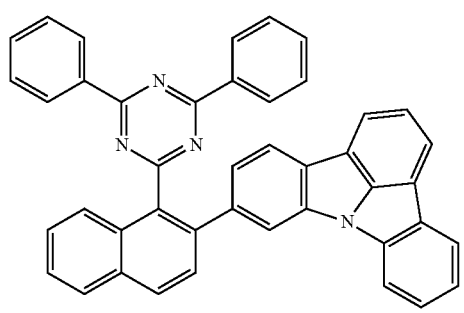
Compound 1-49
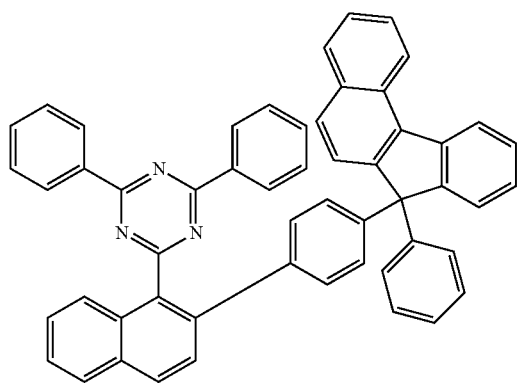
Compound 1-50
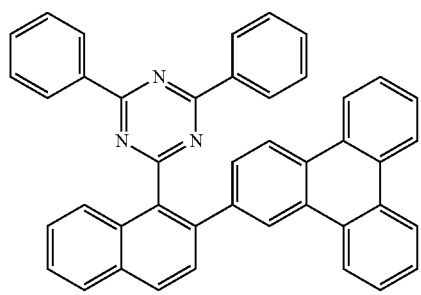
Compound 1-51
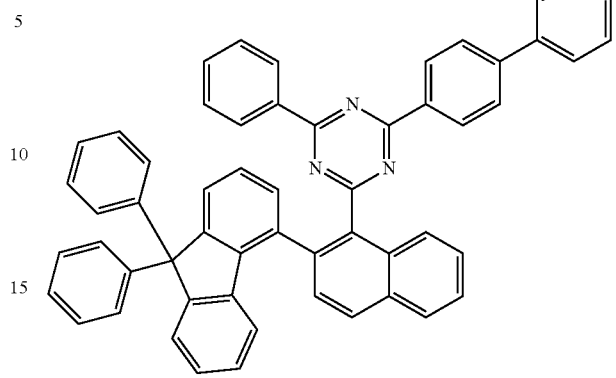
Compound 1-52
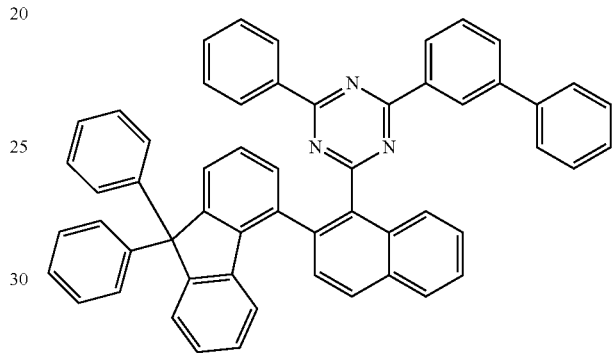
Compound 1-53
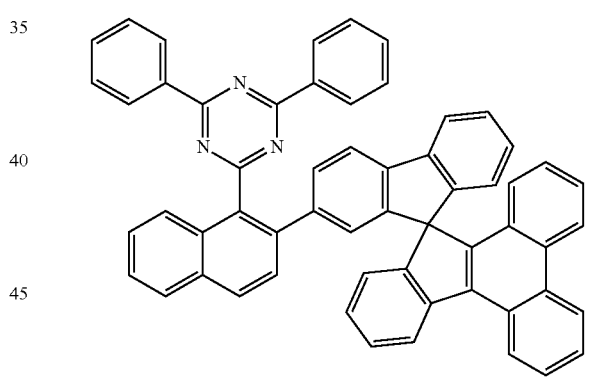
Compound 1-54
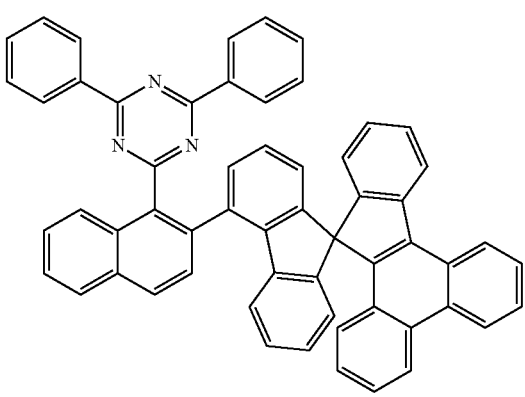

Compound 1-55
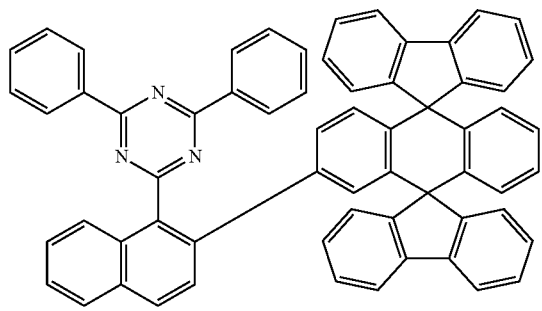
Compound 1-56
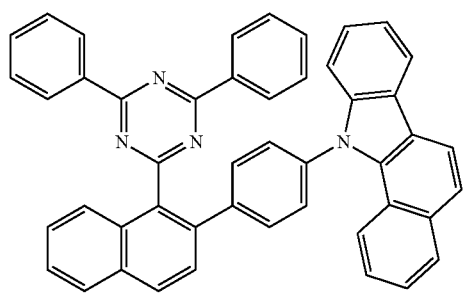
Compound 1-57
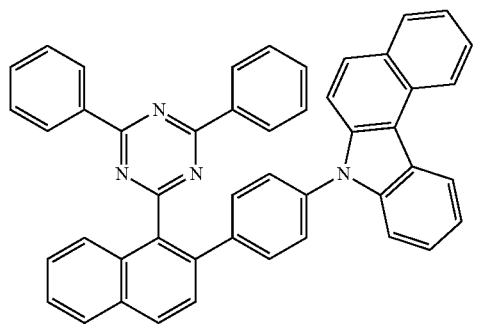
Compound 2-1
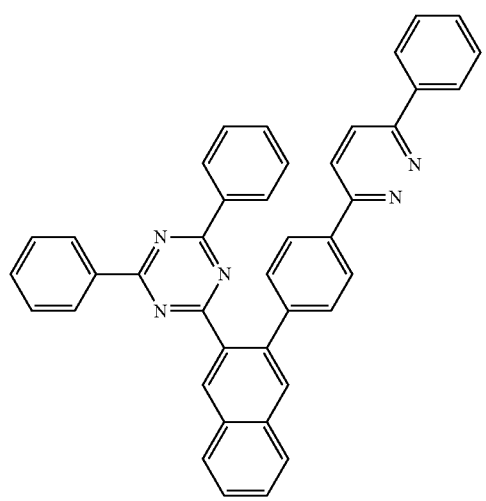
Compound 2-2
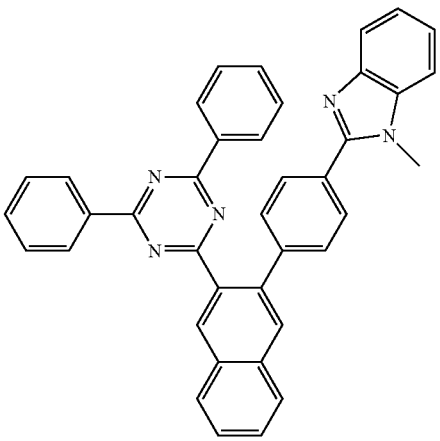
Compound 2-3
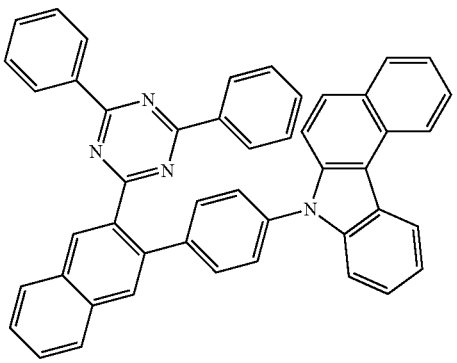
Compound 2-4
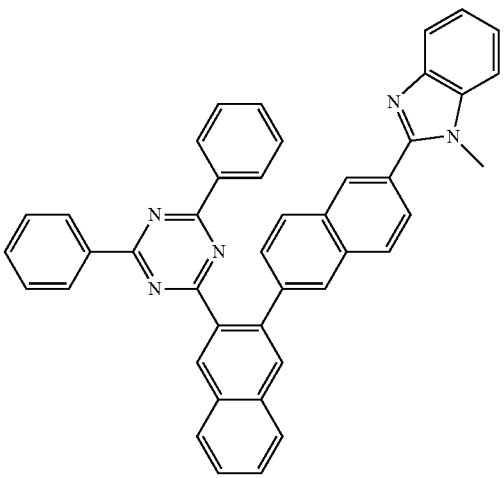

-continued
Compound 2-5
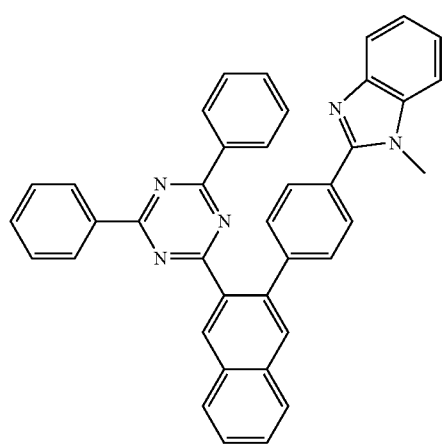
Compound 2-6
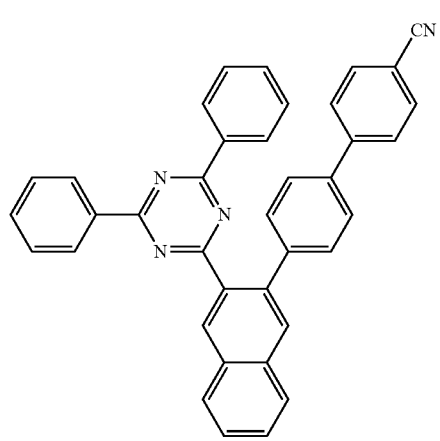
Compound 2-7
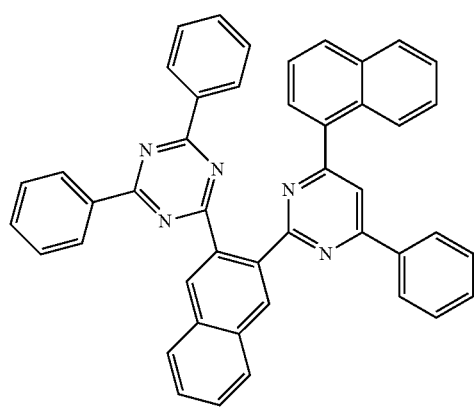
-continued
Compound 2-8
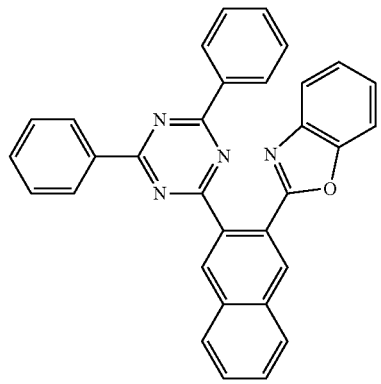
Compound 2-9
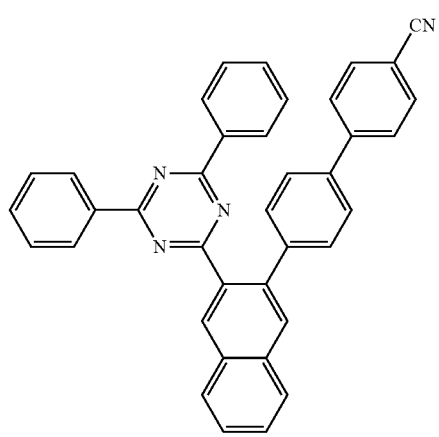
Compound 2-10
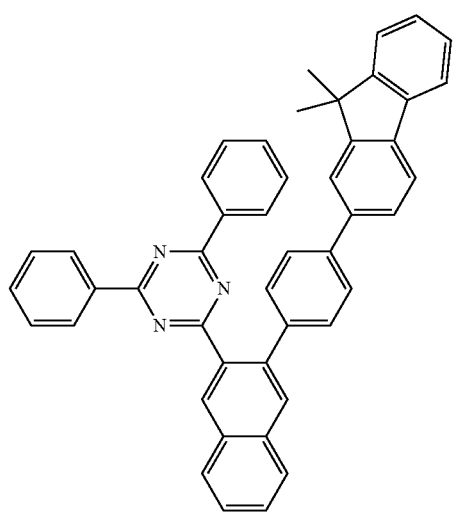

Compound 2-11
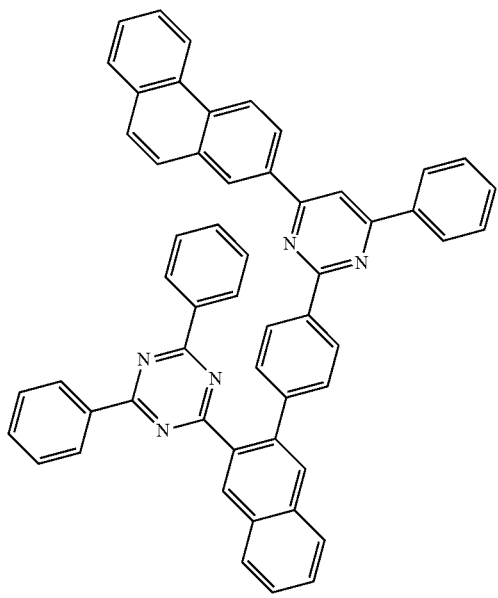
Compound 2-12
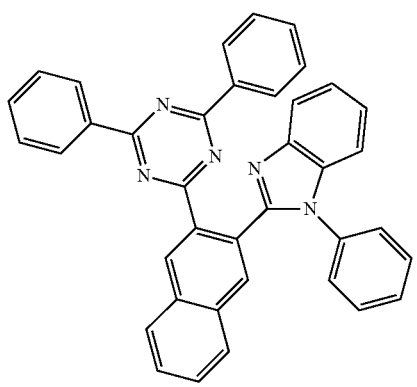
Compound 2-13
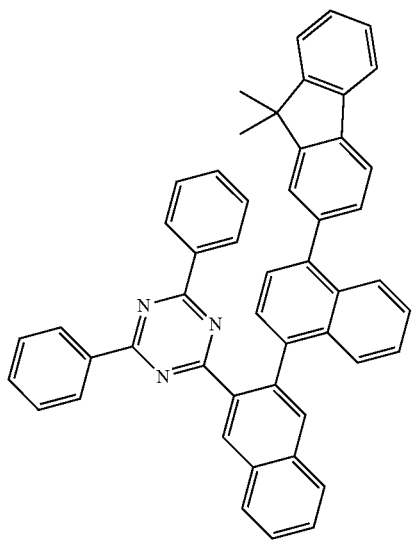
Compound 2-14
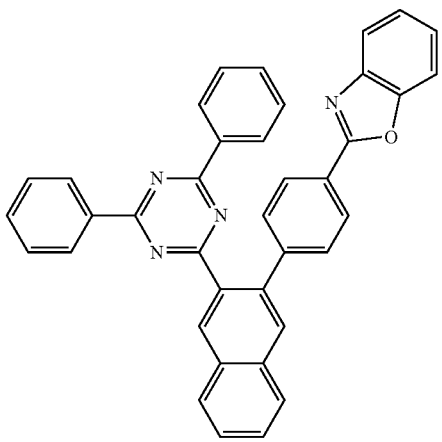
Compound 2-15
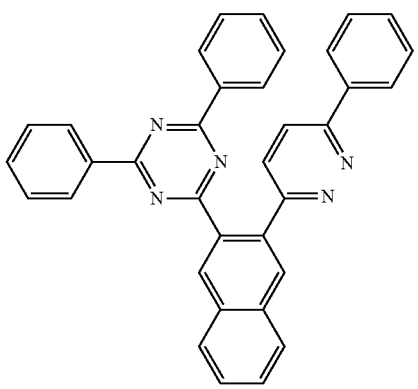
Compound 2-16
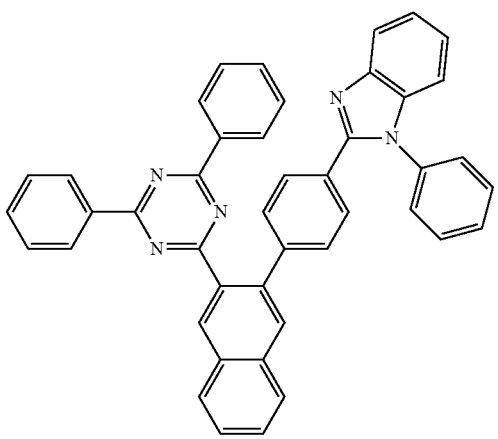

Compound 2-17
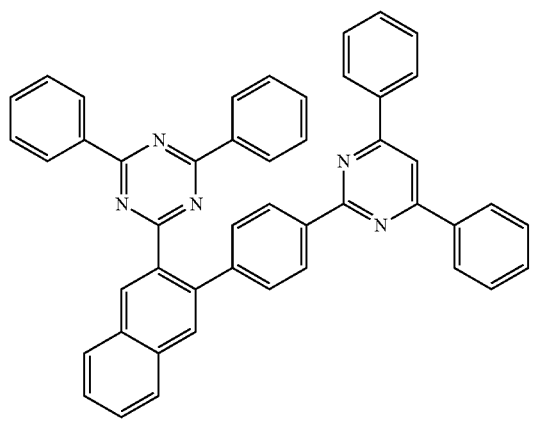
Compound 2-18
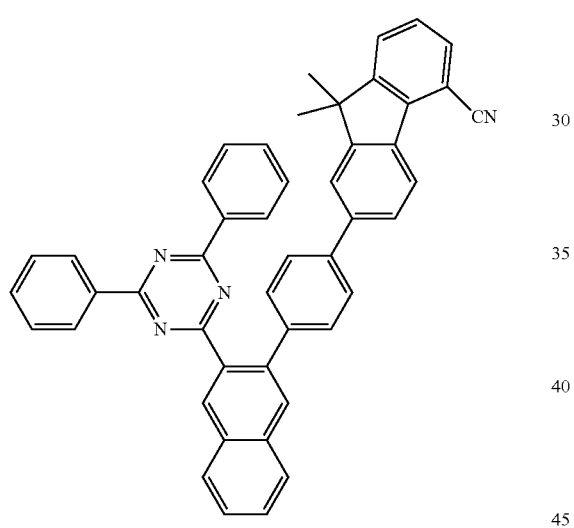
Compound 2-39
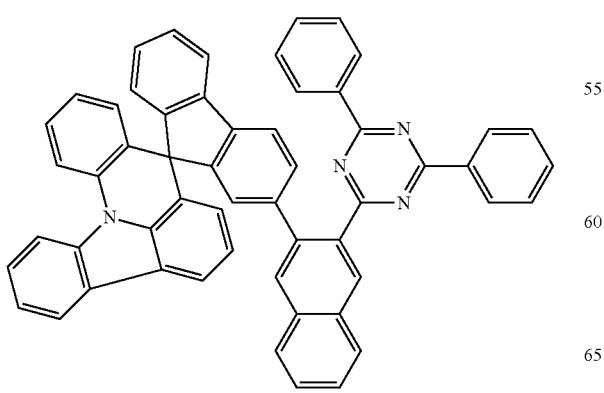
Compound 2-19
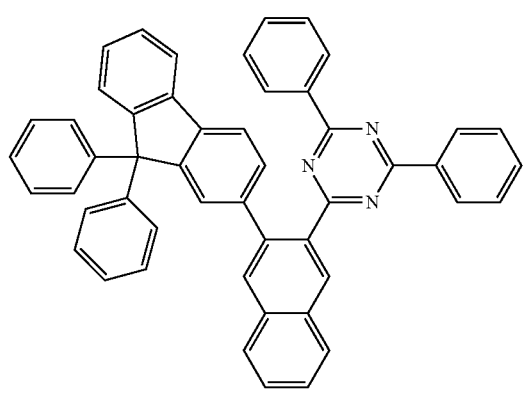
Compound 2-20
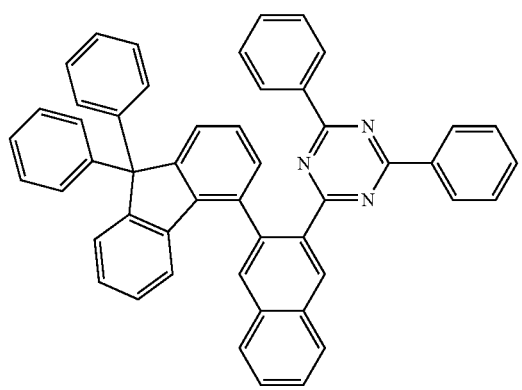
Compound 2-21
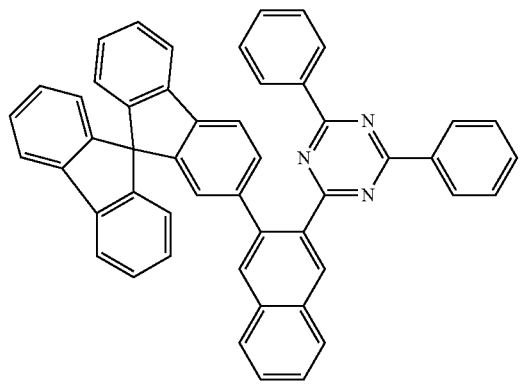
Compound 2-22
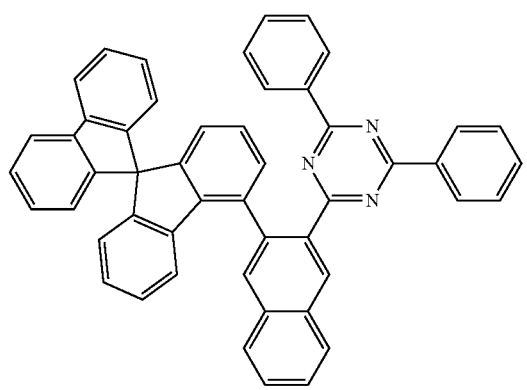

Compound 2-23
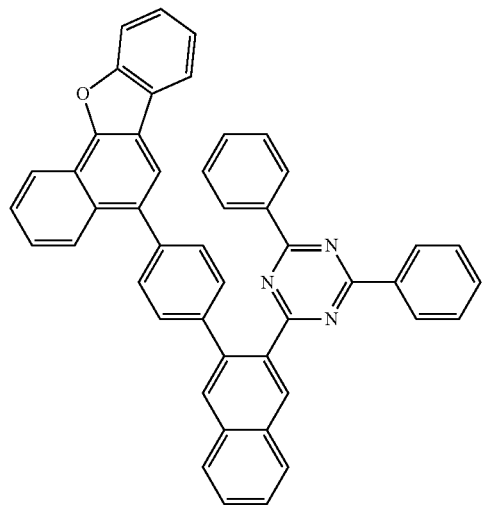
Compound 2-24
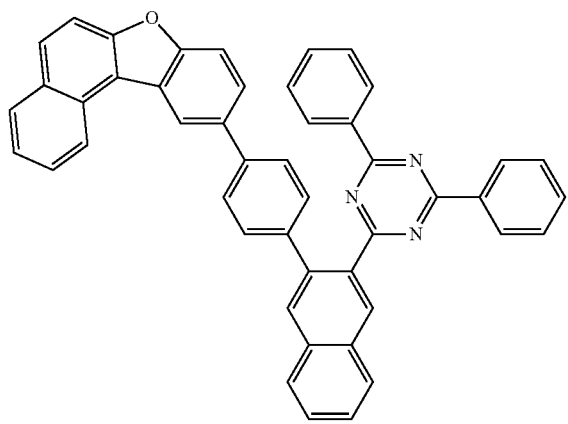
Compound 2-25
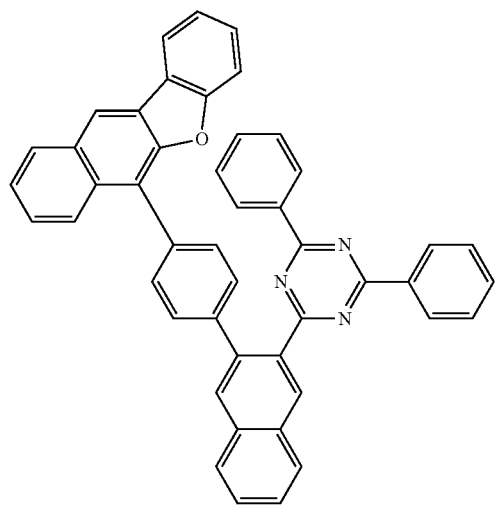
Compound 2-26
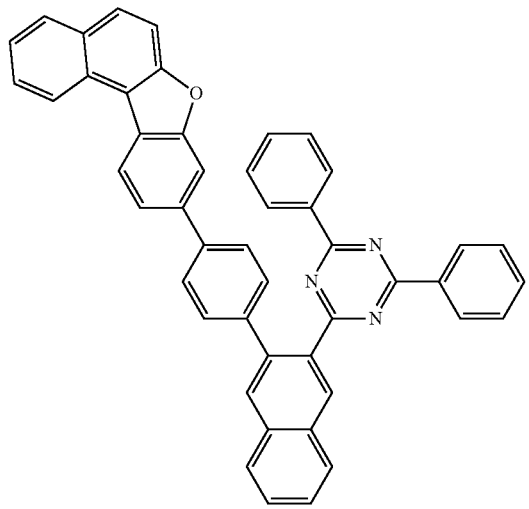
Compound 2-27
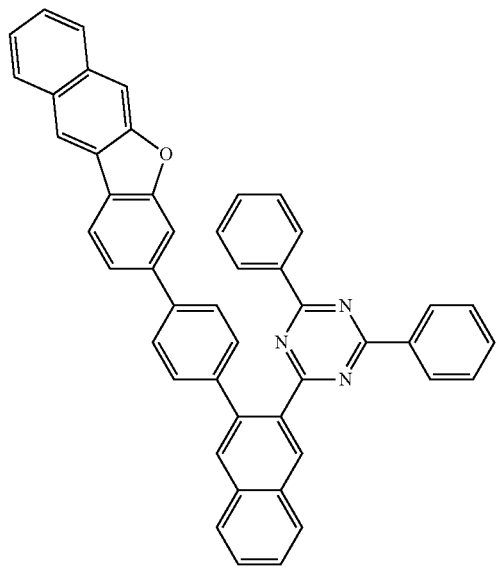
Compound 2-28
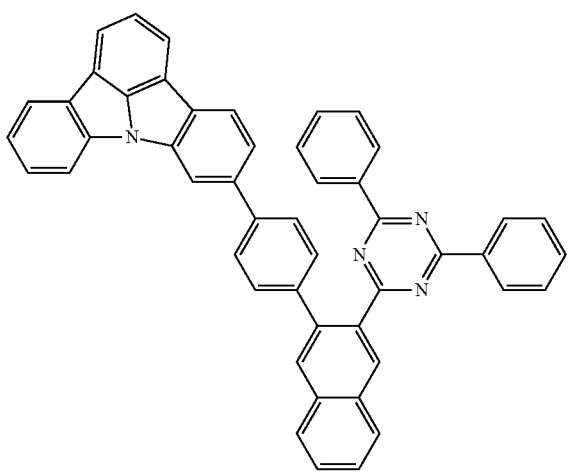

Compound 2-29
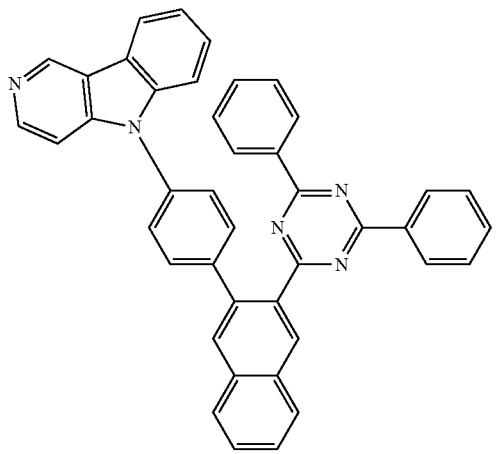
Compound 2-30
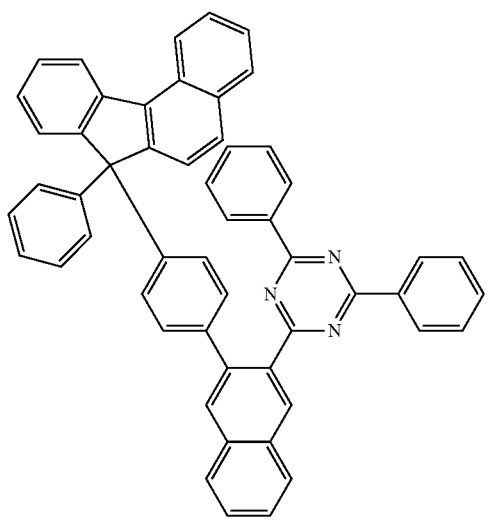
Compound 2-31
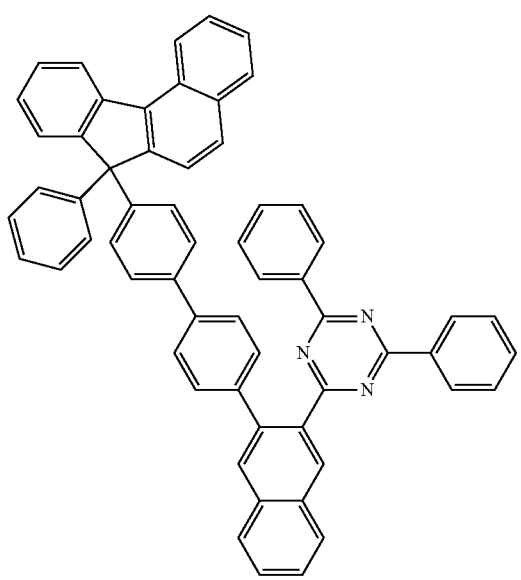
Compound 2-32
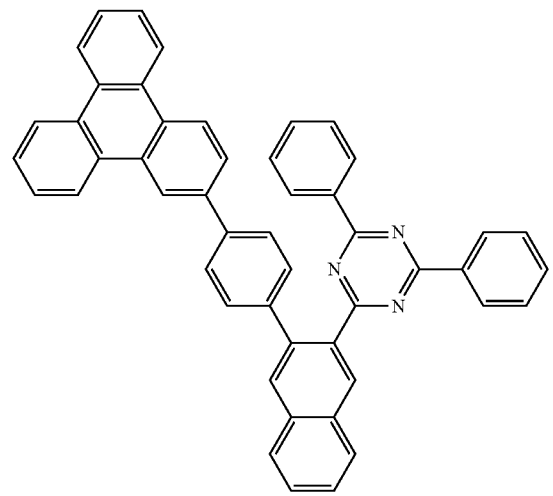
Compound 2-33
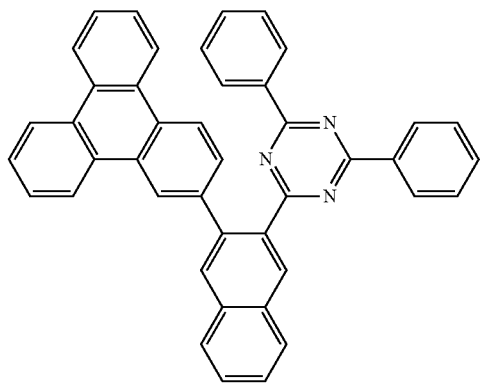
Compound 2-34
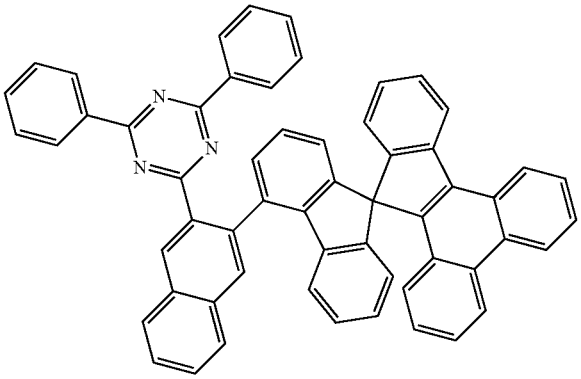

Compound 2-35
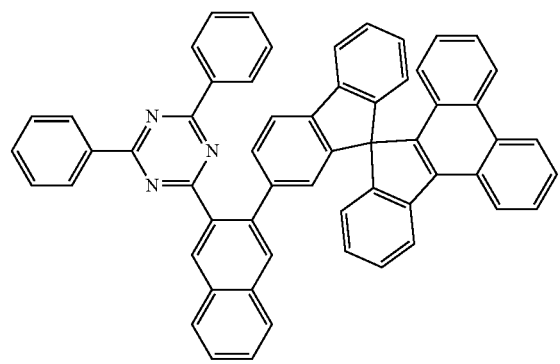
Compound 2-36
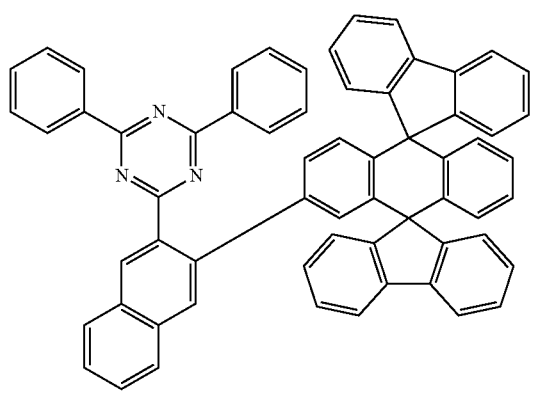
Compound 2-37
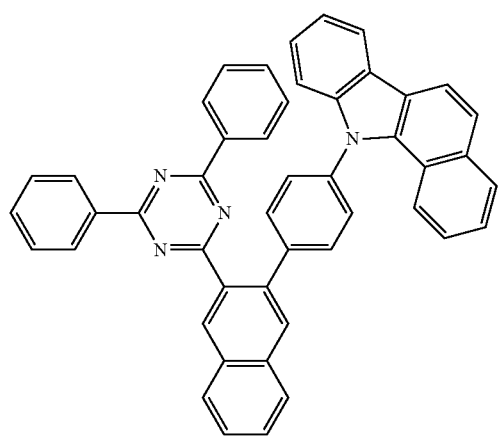
Compound 2-38
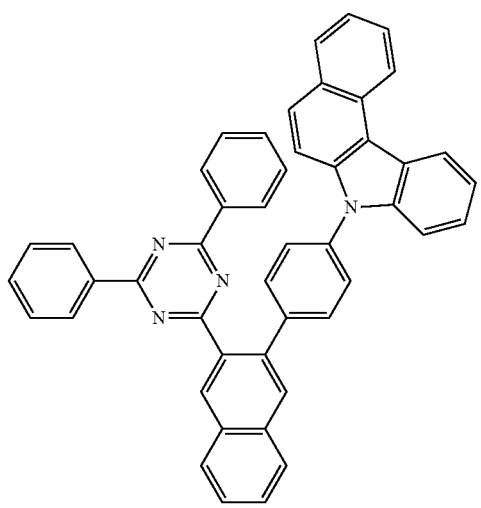
Compound 3-1
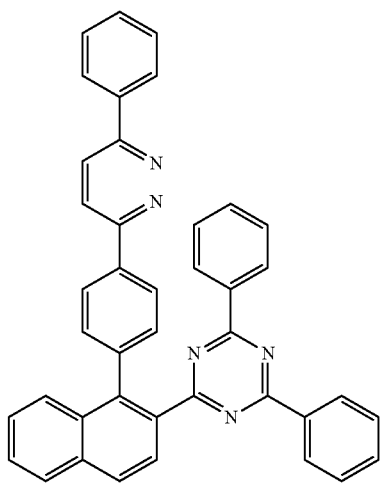
Compound 3-2
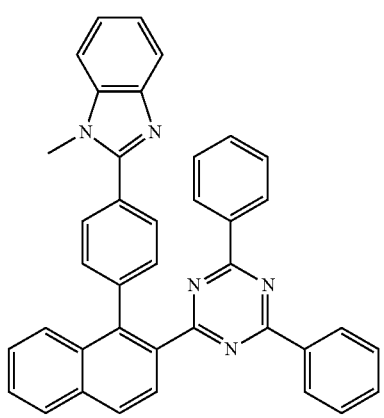

Compound 3-3
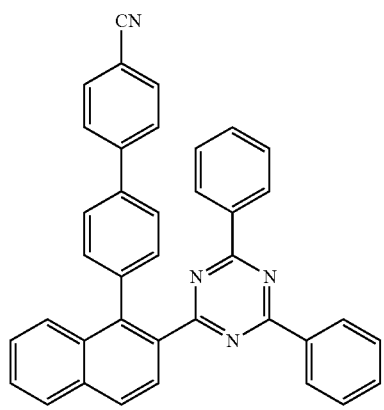
Compound 3-4
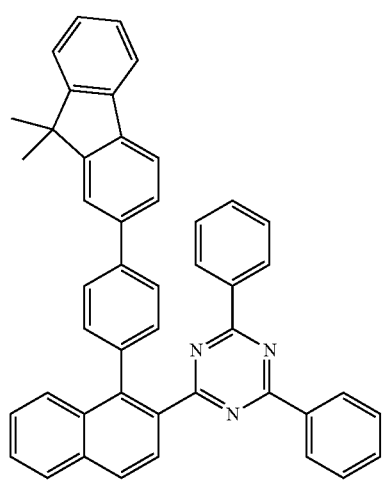
Compound 3-5
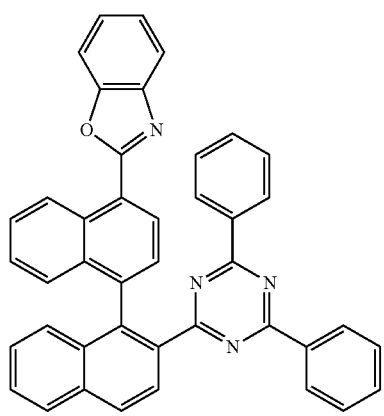
Compound 3-6
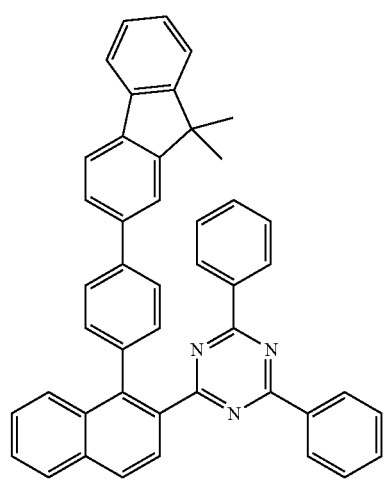
Compound 3-7
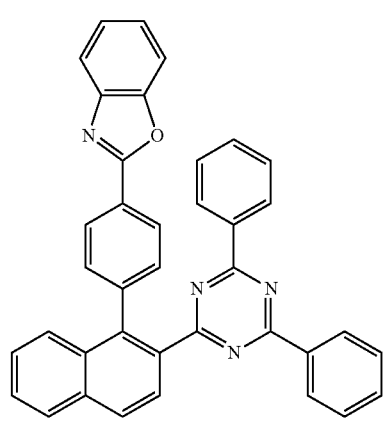
Compound 3-8
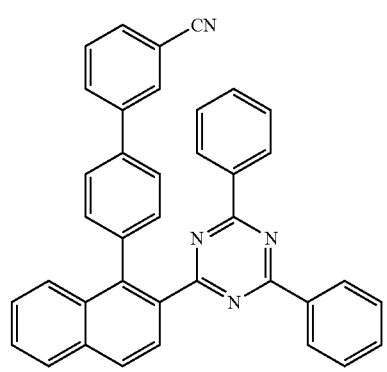

Compound 3-9
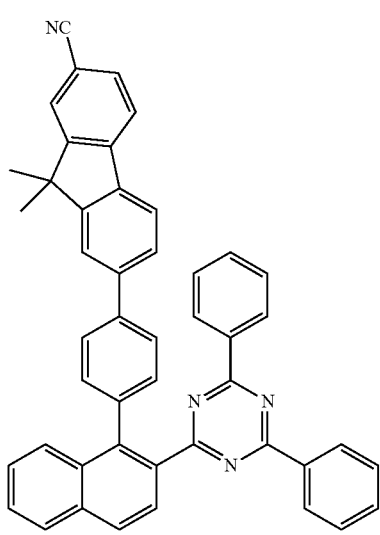
Compound 3-10
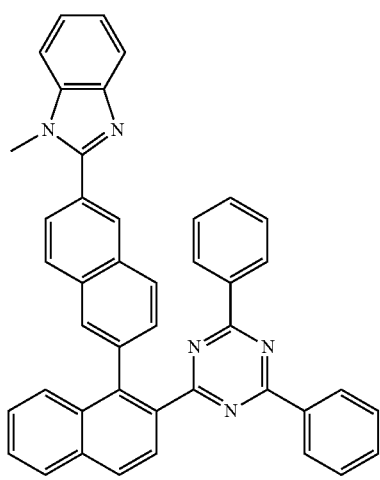
Compound 3-11
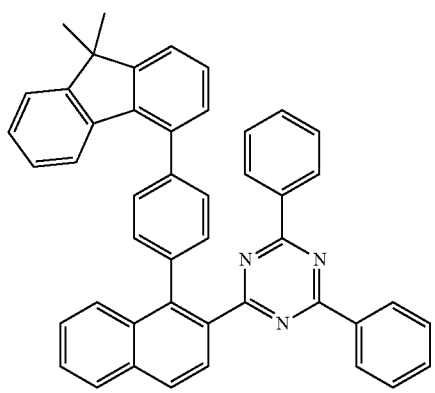
Compound 3-12
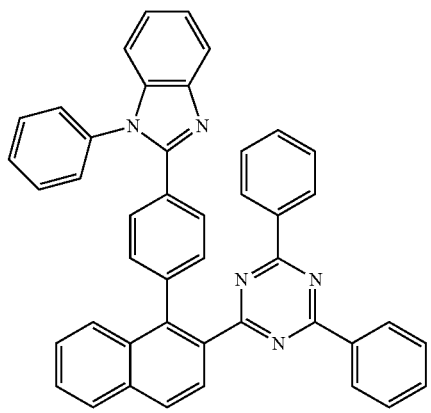
Compound 3-13
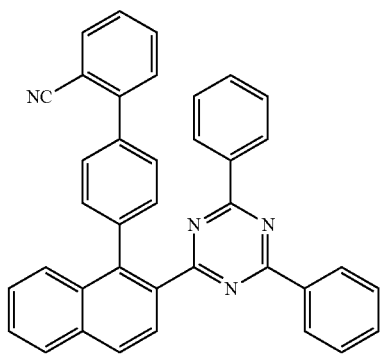
Compound 3-14
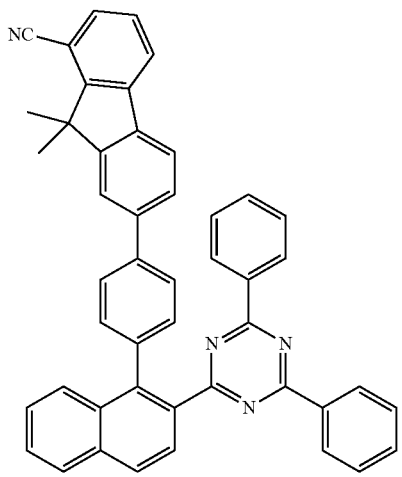
Compound 3-15
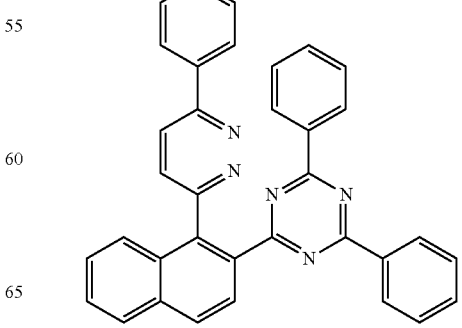

Compound 3-16
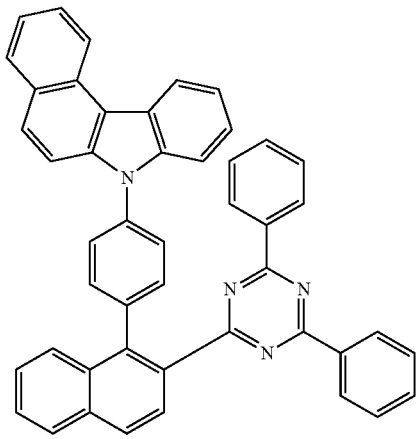
Compound 3-17
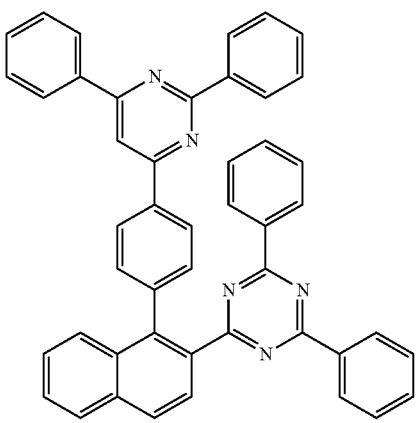
Compound 3-18
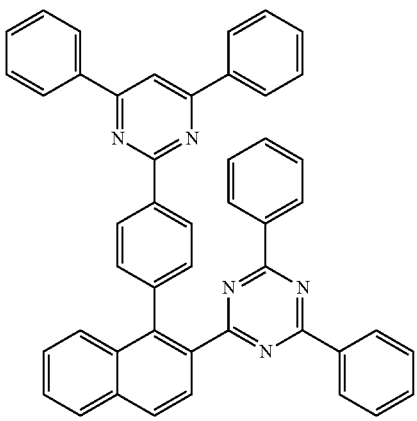
Compound 3-19
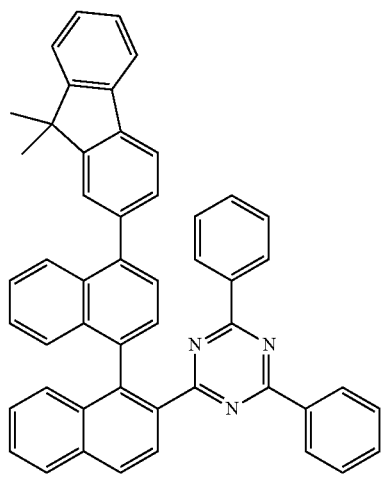
Compound 3-20
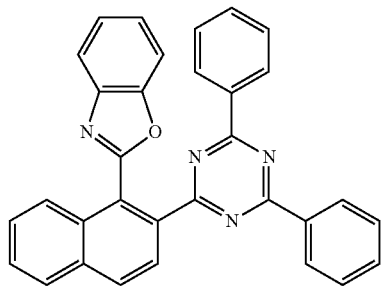
Compound 3-21
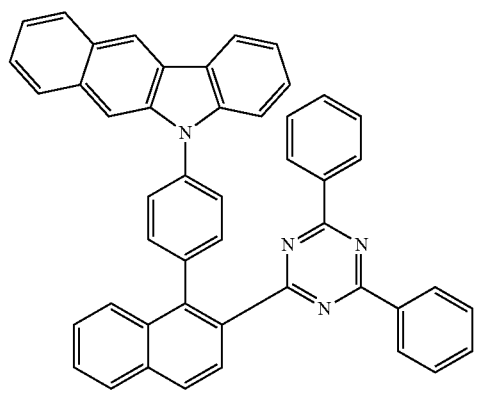
Compound 3-22
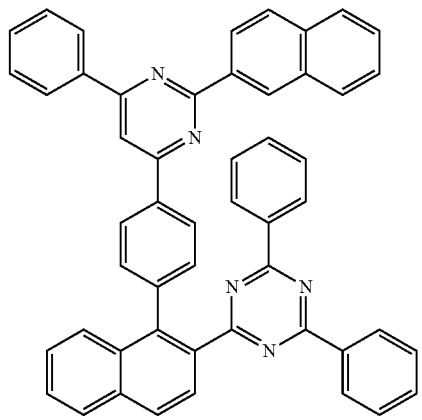

Compound 3-23
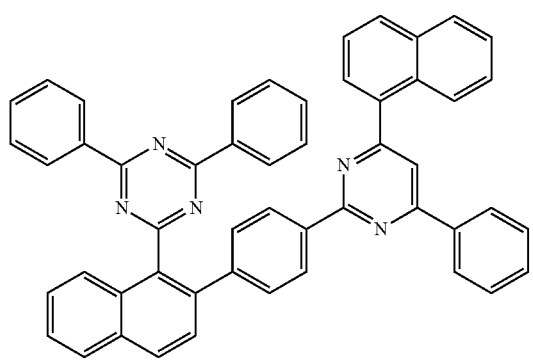
Compound 3-24
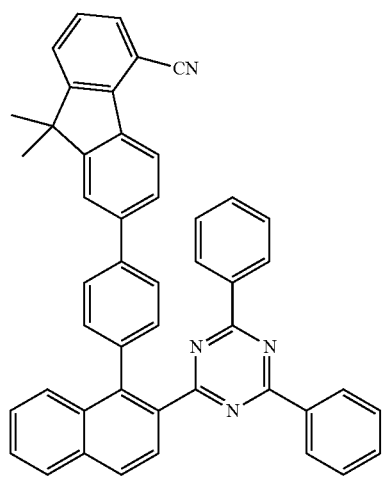
Compound 3-25
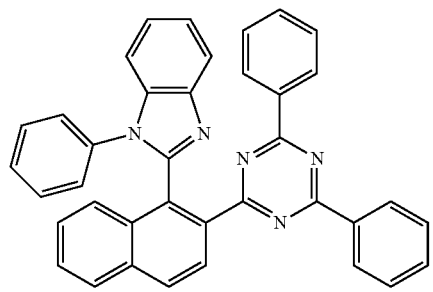
Compound 3-26
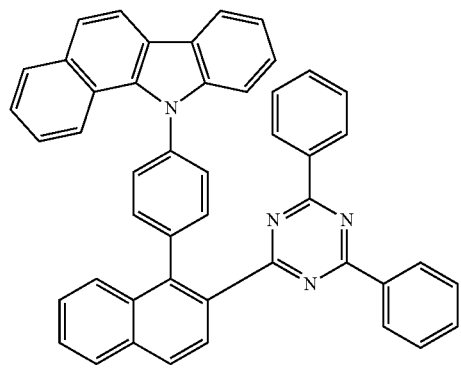
Compound 3-27
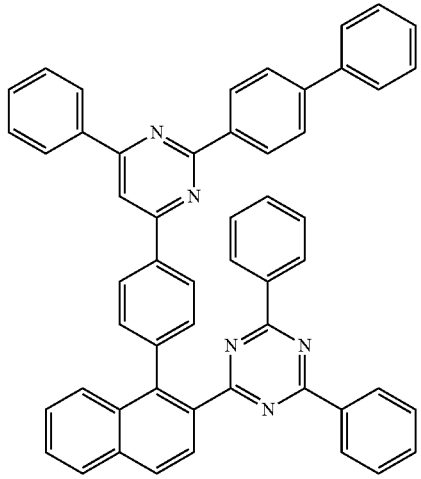
Compound 3-28
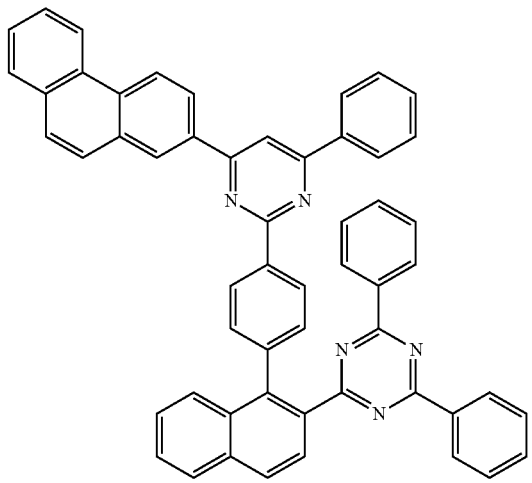
Compound 3-29
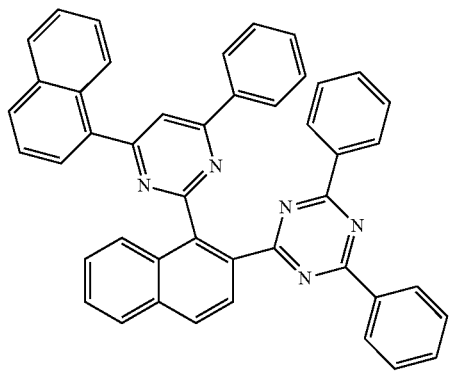

Compound 3-30
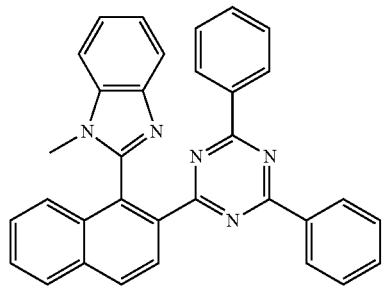
Compound 3-31
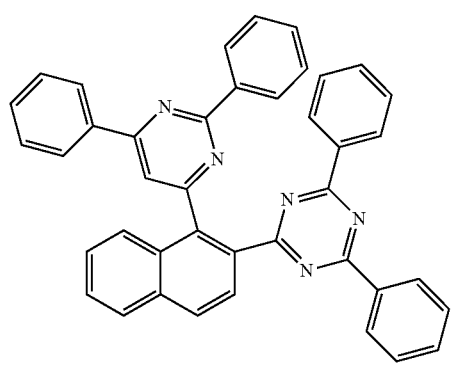
Compound 3-32
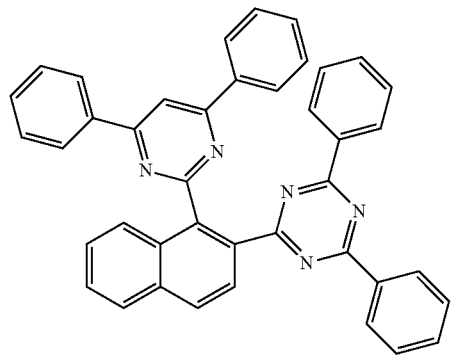
Compound 3-33
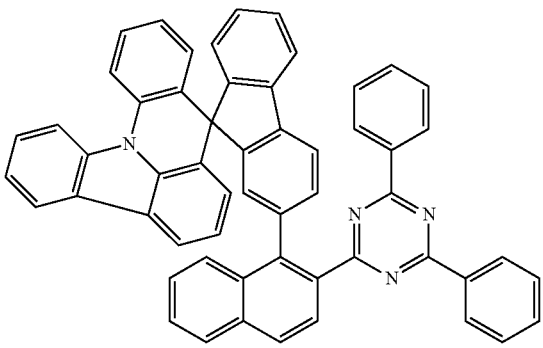
Compound 3-34
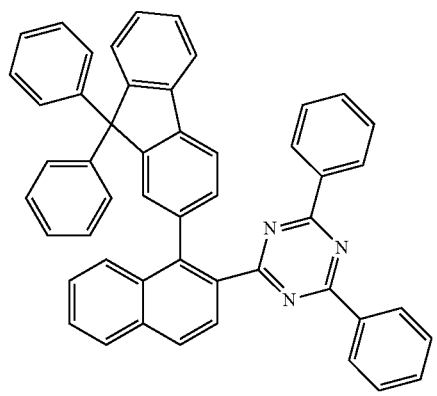
Compound 3-35
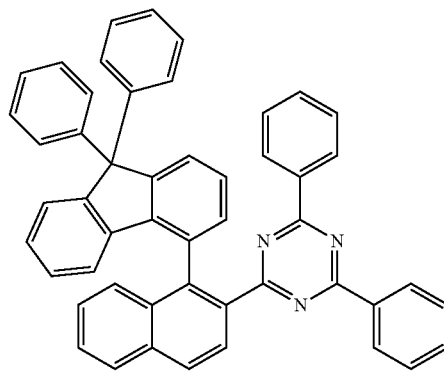
Compound 3-36
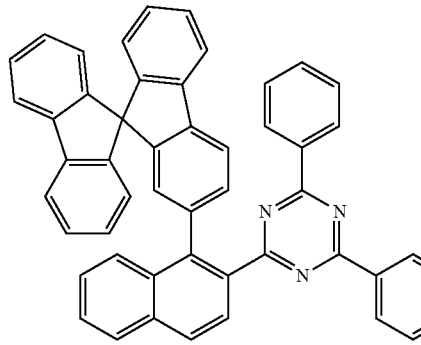
Compound 3-37
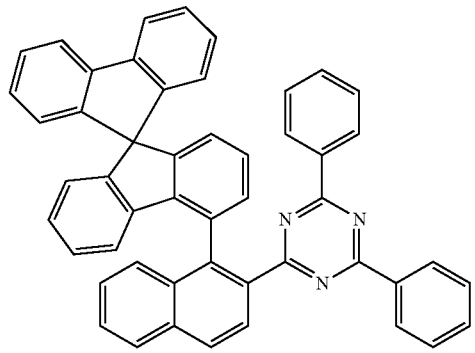

Compound 3-38
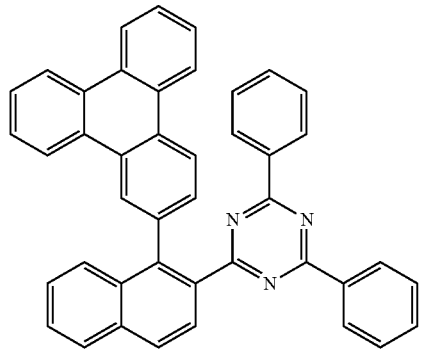
Compound 3-41
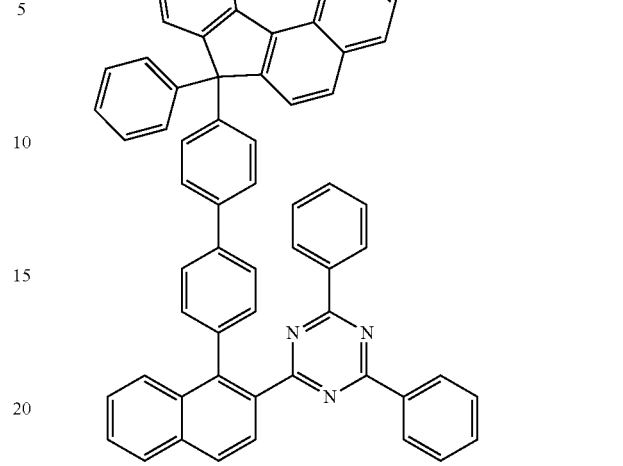
Compound 3-39
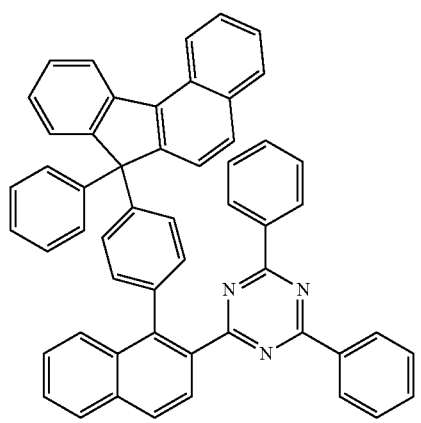
Compound 3-42
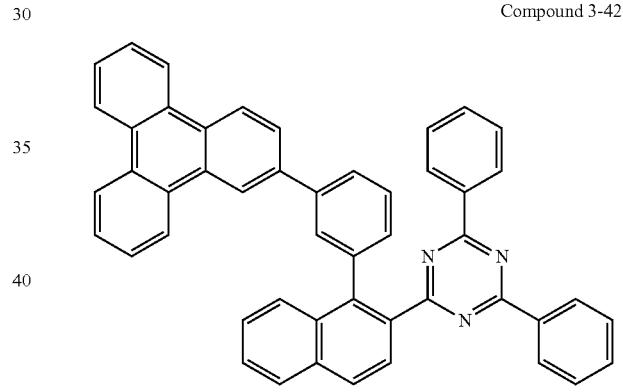
Compound 3-40
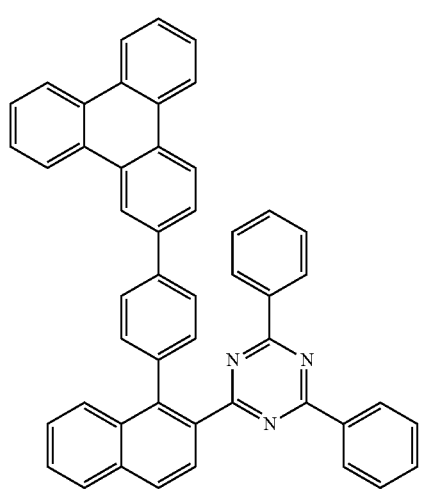
Compound 3-43
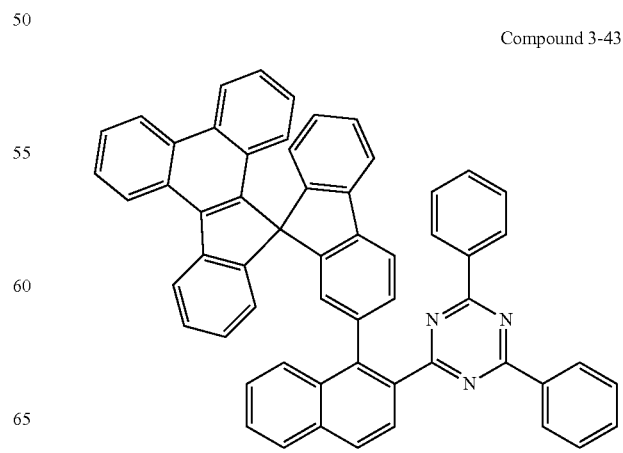

Compound 3-44
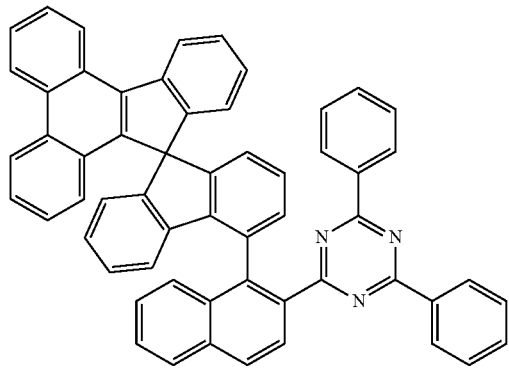
Compound 3-47
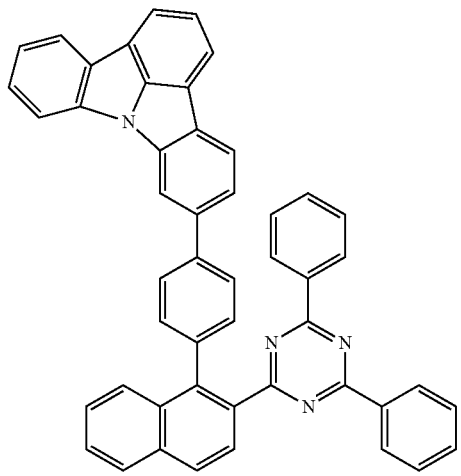
Compound 3-45
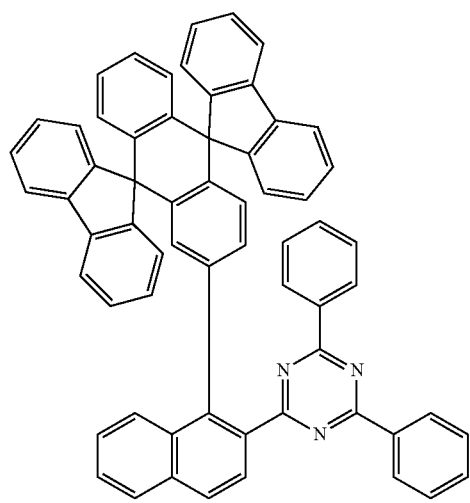
Compound 3-48
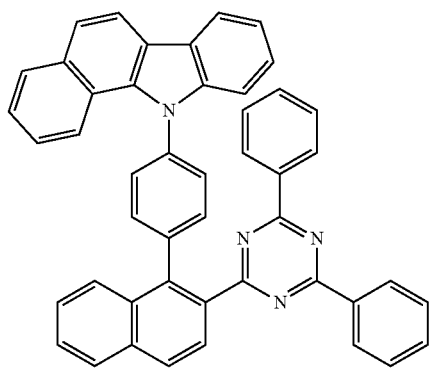
Compound 3-46
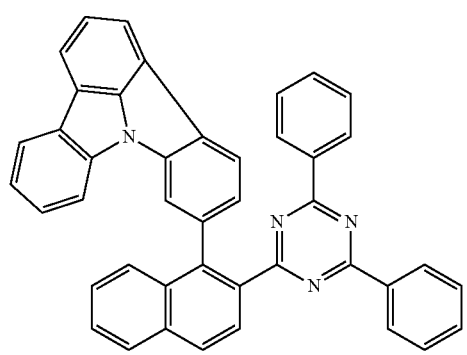
Compound 3-49
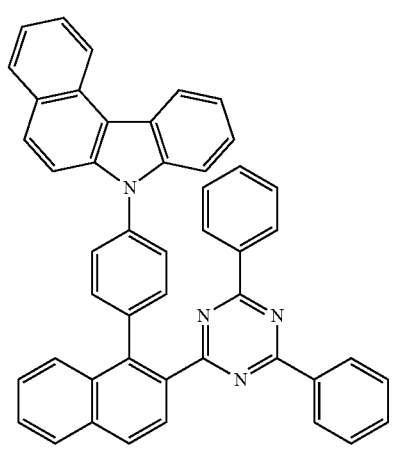

Compound 3-50
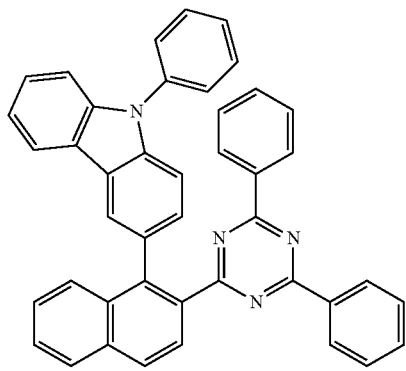
Compound 4-1
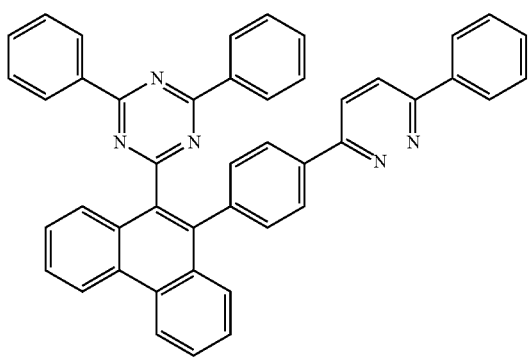
Compound 4-2
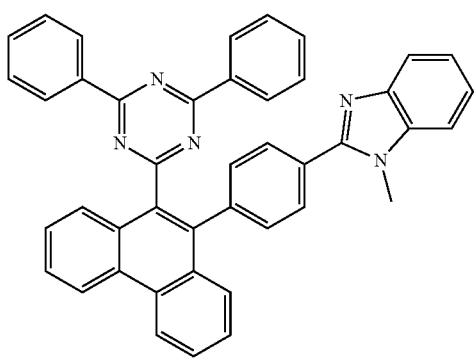
Compound 4-3
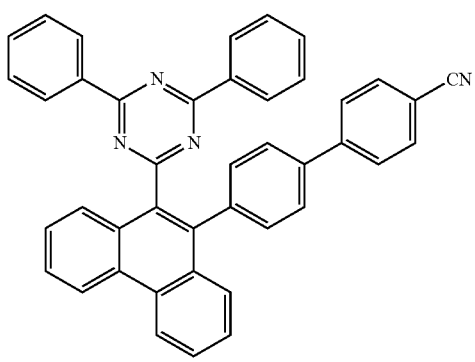
Compound 4-4
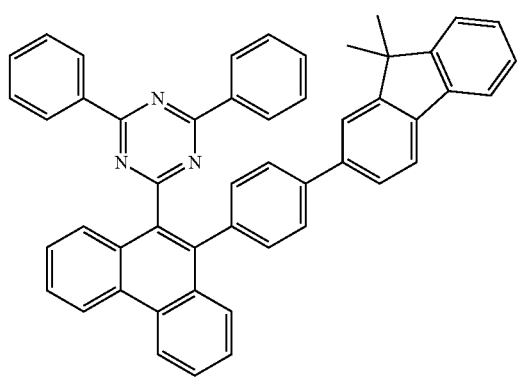
Compound 4-5
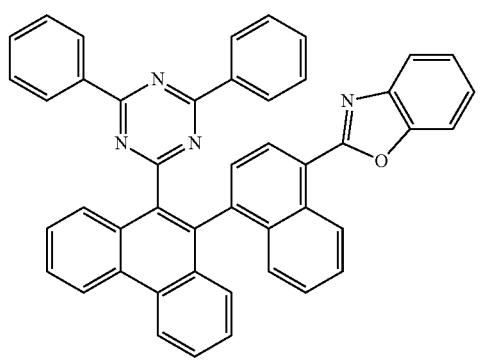
Compound 4-6
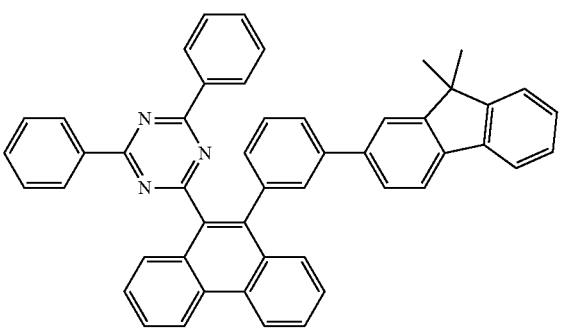
Compound 4-7
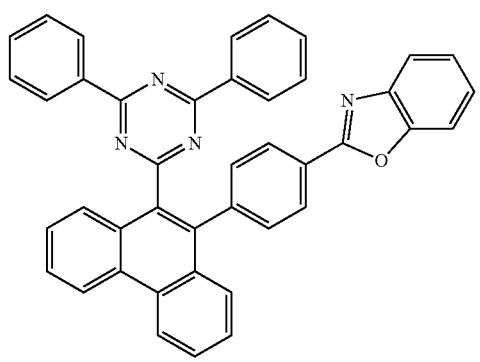

Compound 4-8
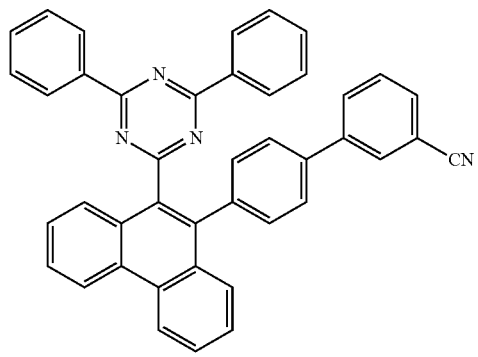
Compound 4-9
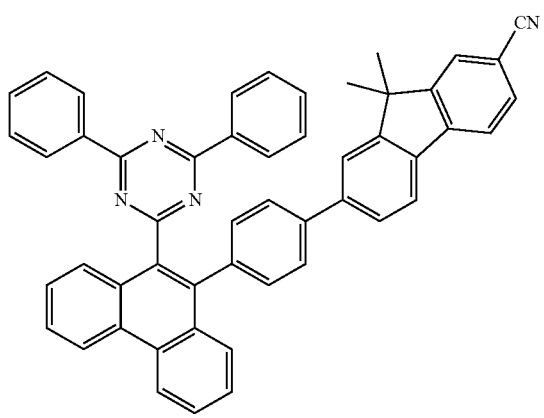
Compound 4-10
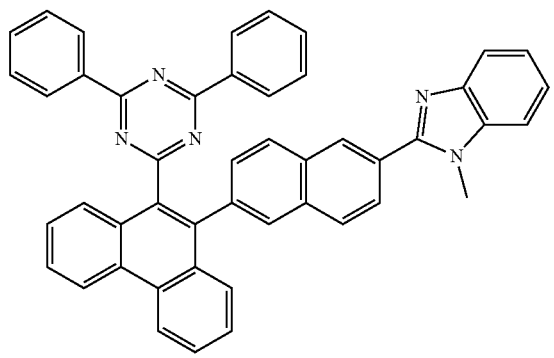
Compound 4-11
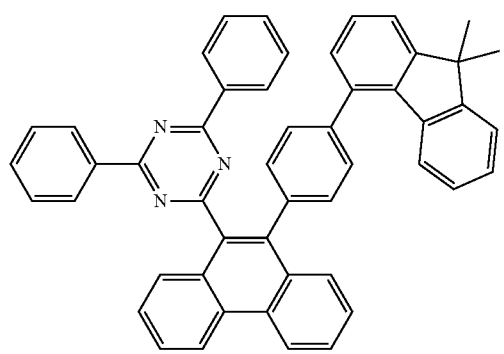
Compound 4-12
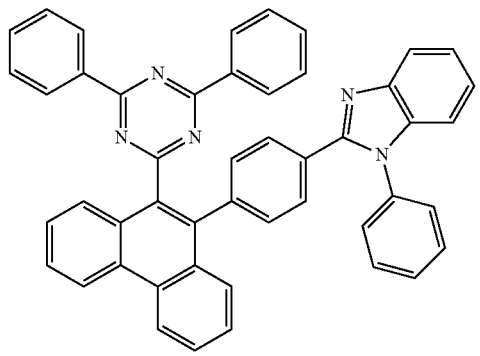
Compound 4-13
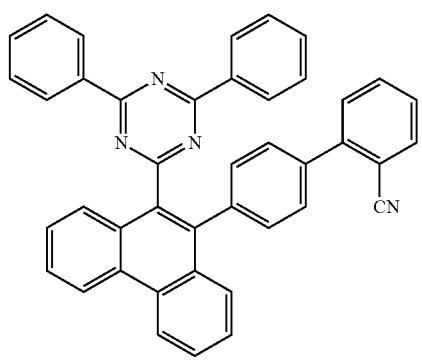
Compound 4-14
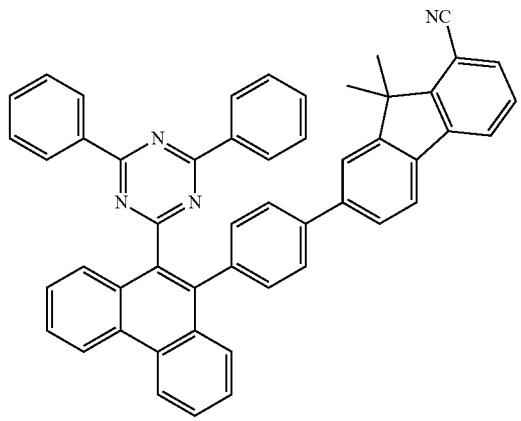
Compound 4-15
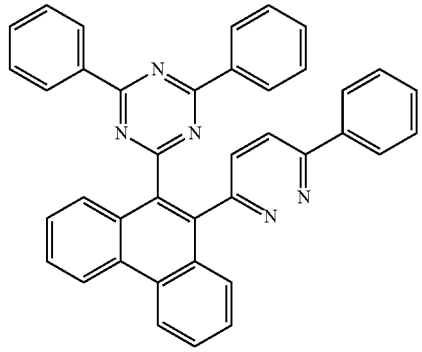

-continued
Compound 4-16
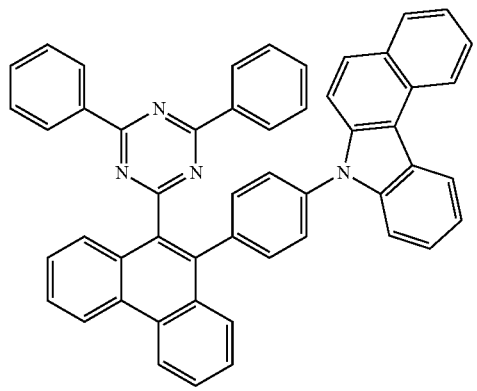
Compound 4-17
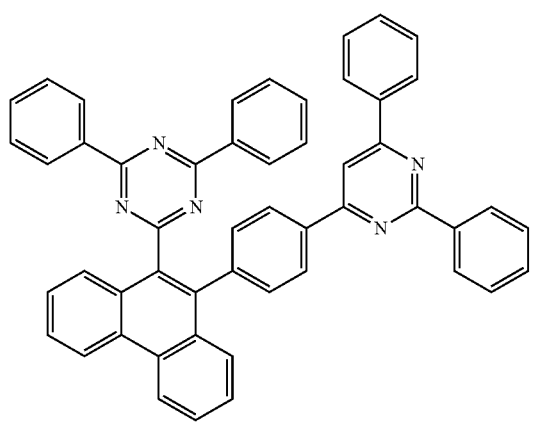
Compound 4-18
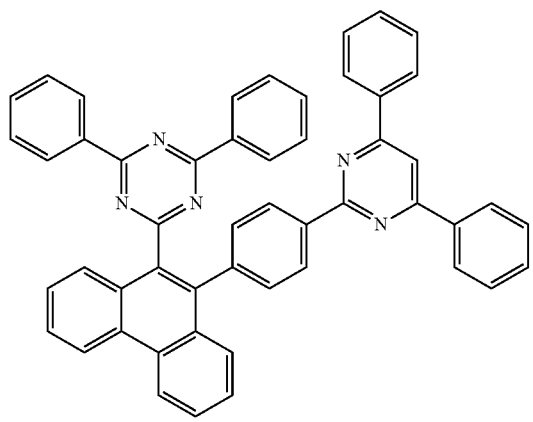
-continued
Compound 4-19
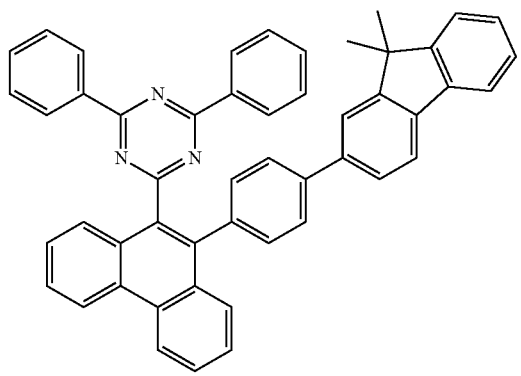
Compound 4-20
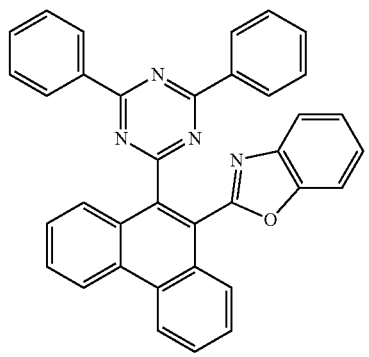
Compound 4-21
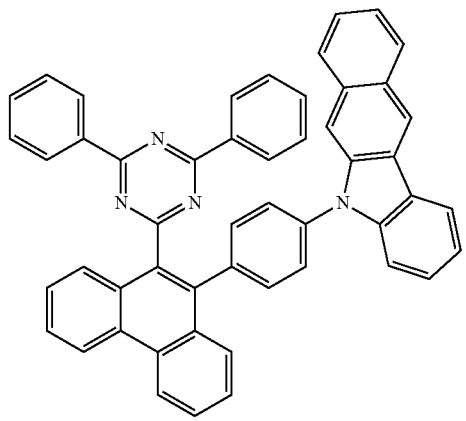
Compound 4-22
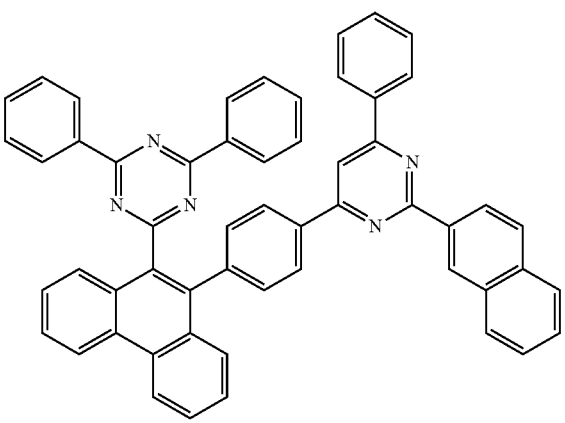

Compound 4-23
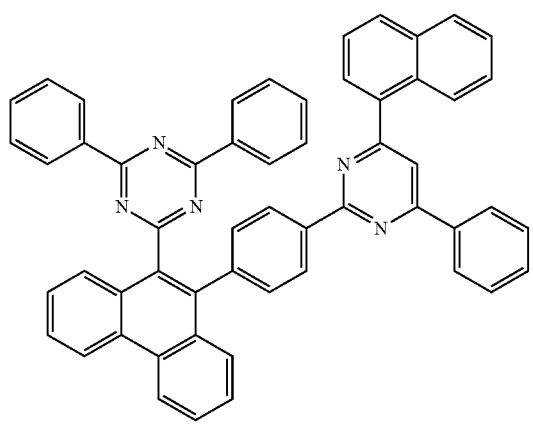
Compound 4-24
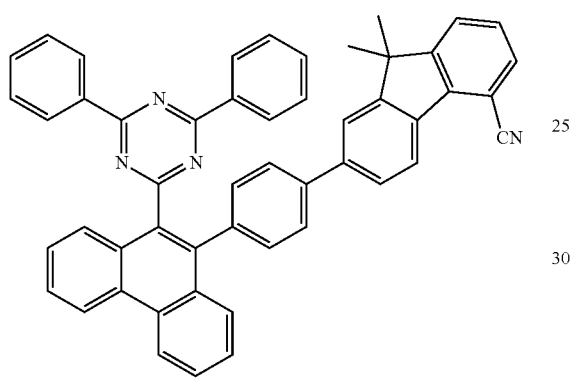
Compound 4-25
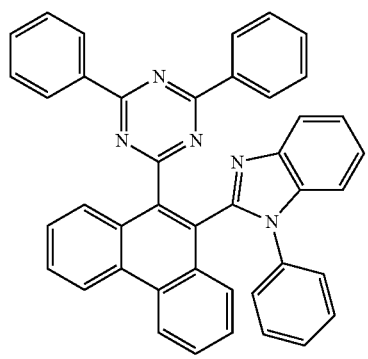
Compound 4-26
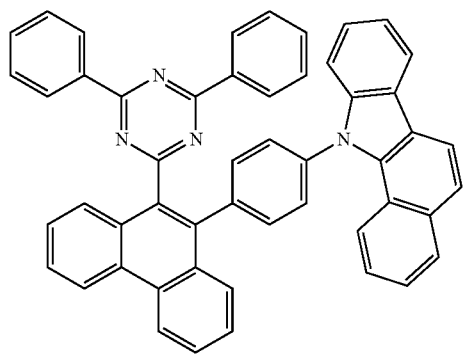
Compound 4-27
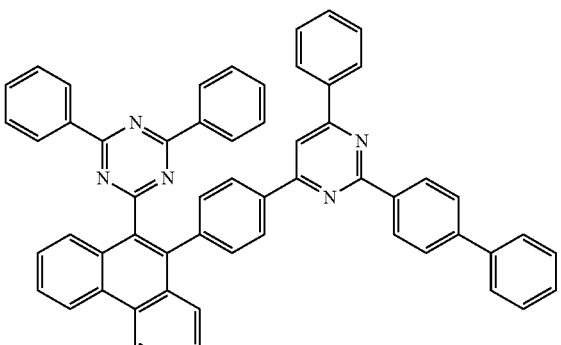
Compound 4-28
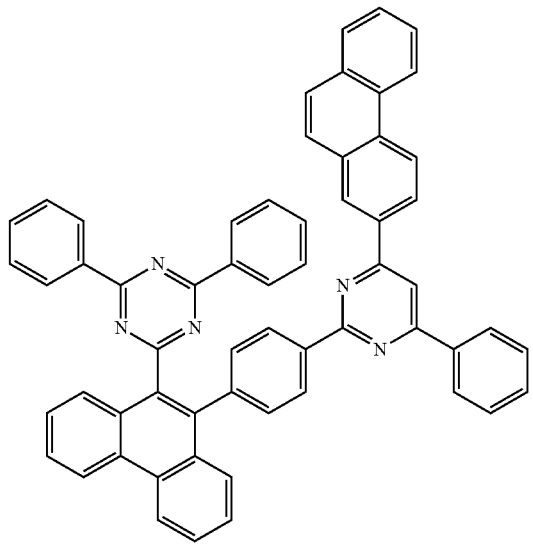
Compound 4-29
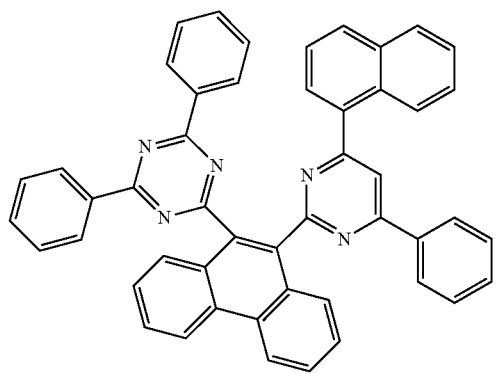

Compound 4-30
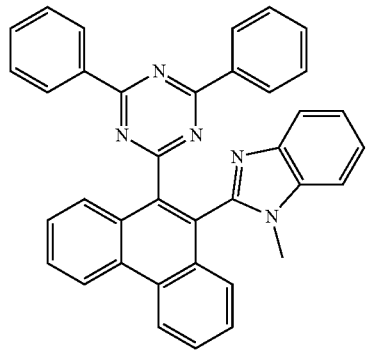
Compound 4-31
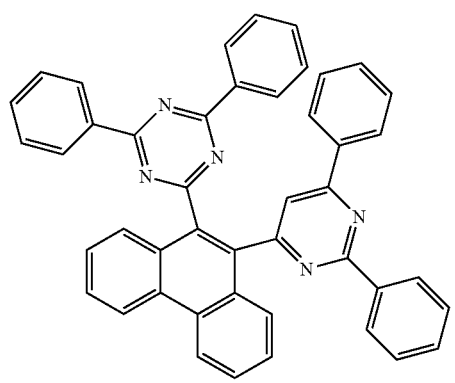
Compound 4-32
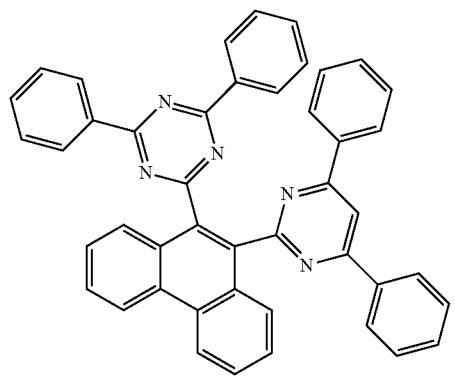
Compound 4-33
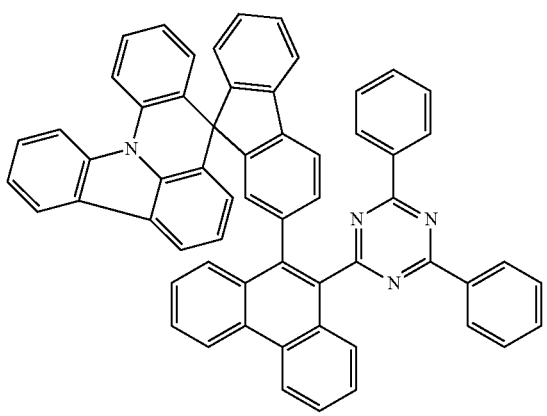
Compound 4-34
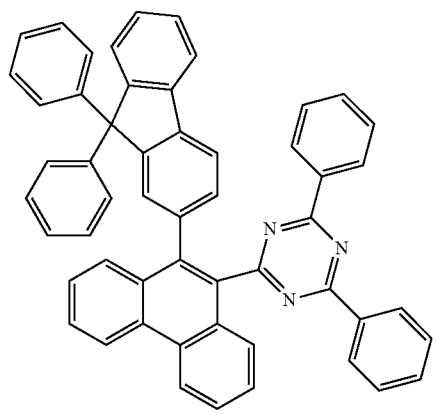
Compound 4-35
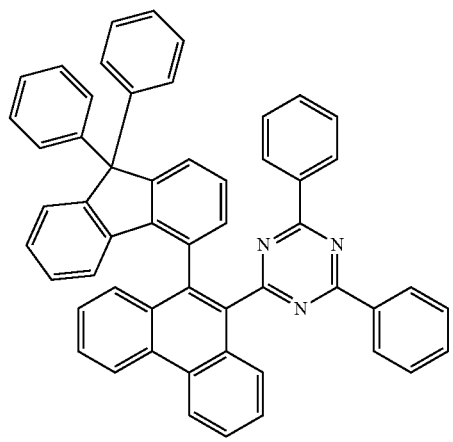
Compound 4-36
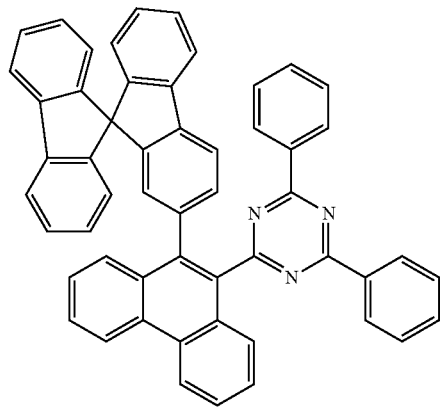

Compound 4-37
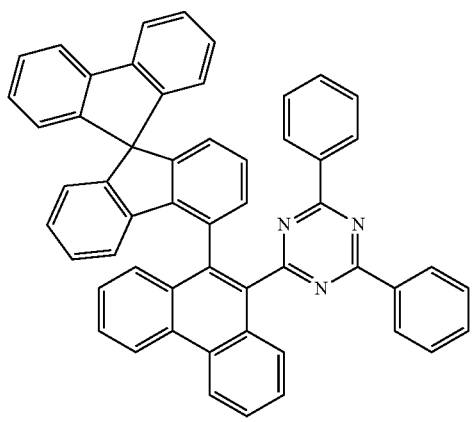
Compound 4-40
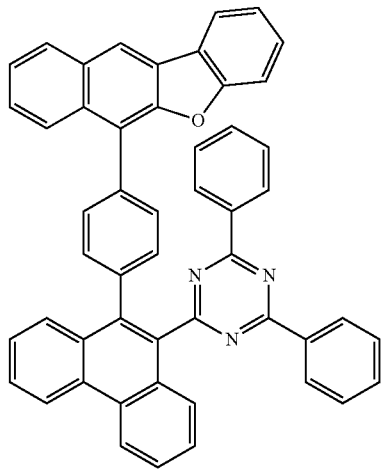
Compound 4-38
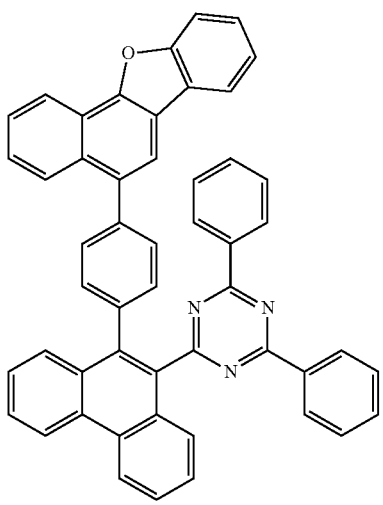
Compound 4-41
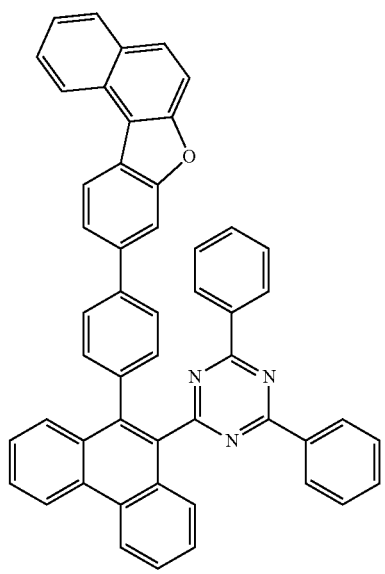
Compound 4-39
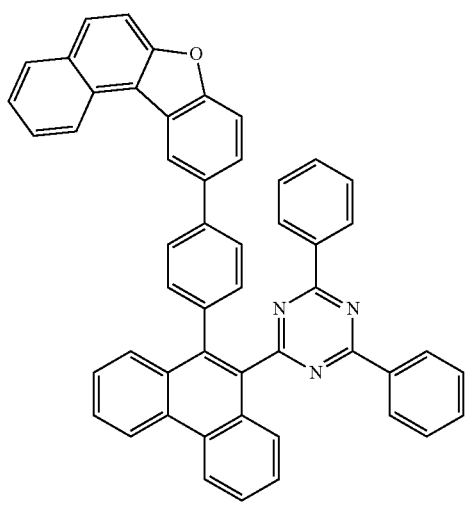
Compound 4-42
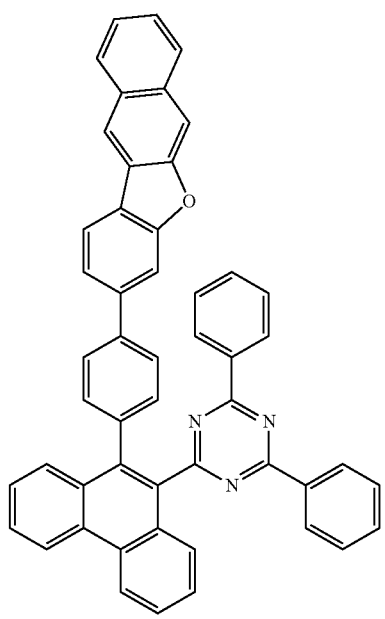

-continued
Compound 4-43
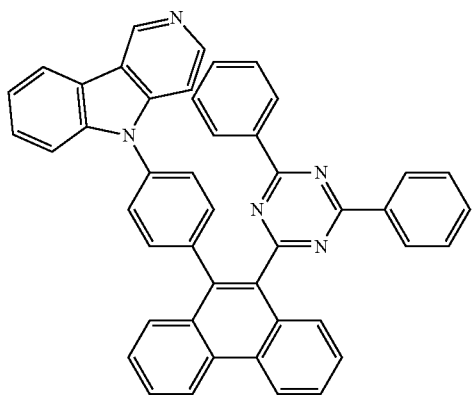
Compound 4-44
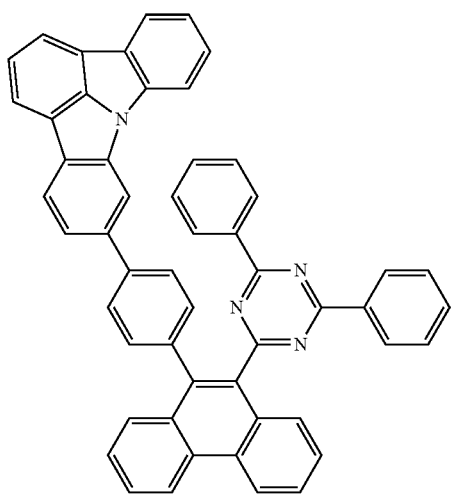
Compound 4-45
-continued
Compound 4-46
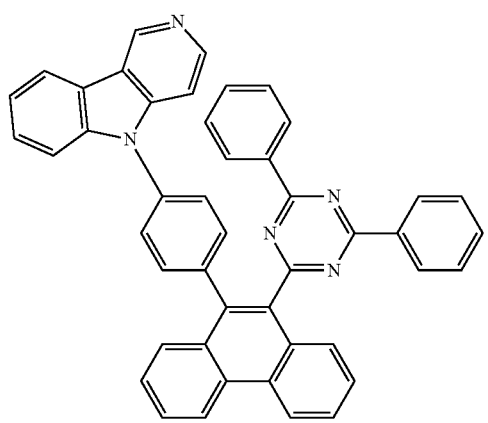
Compound 4-47
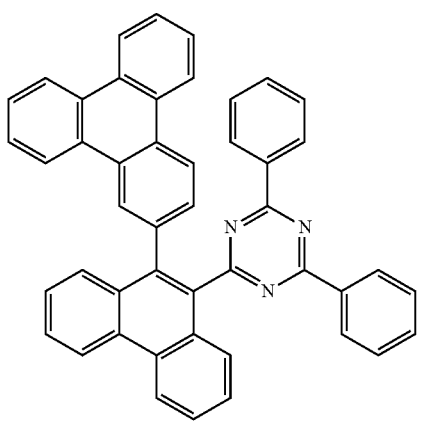
Compound 4-48
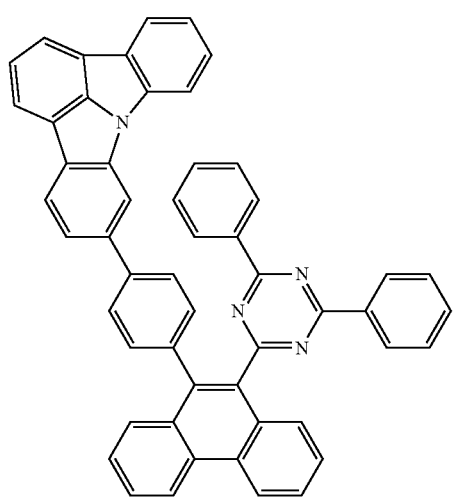

Compound 4-49
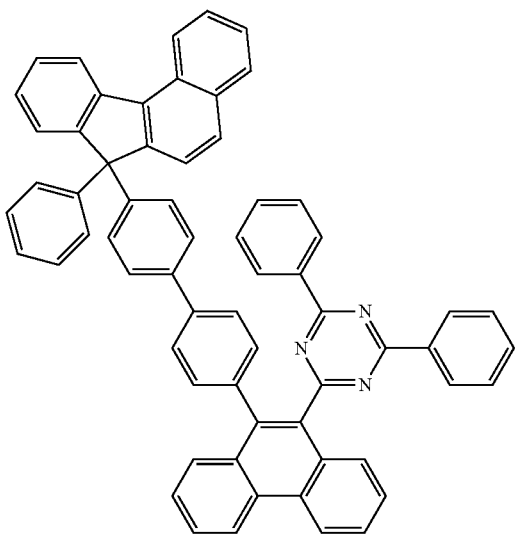
Compound 4-50
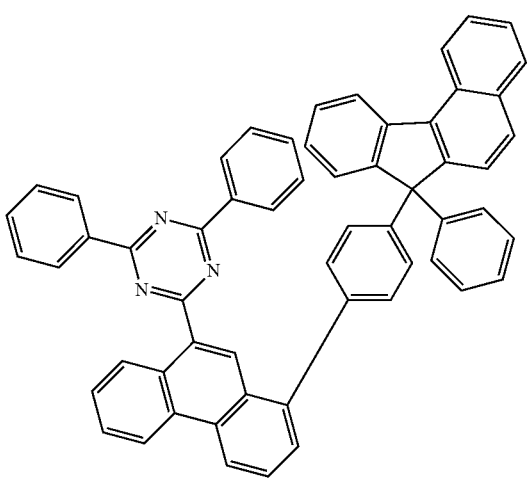
Compound 4-51
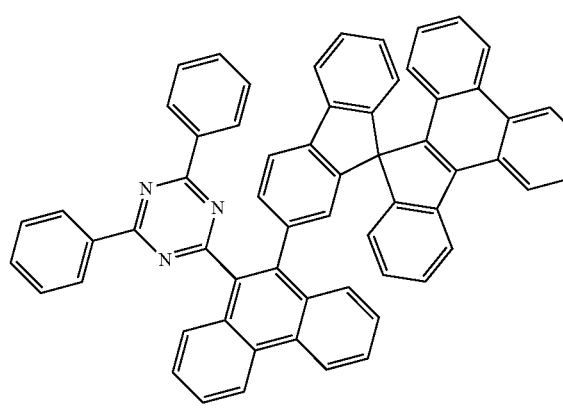
Compound 4-52
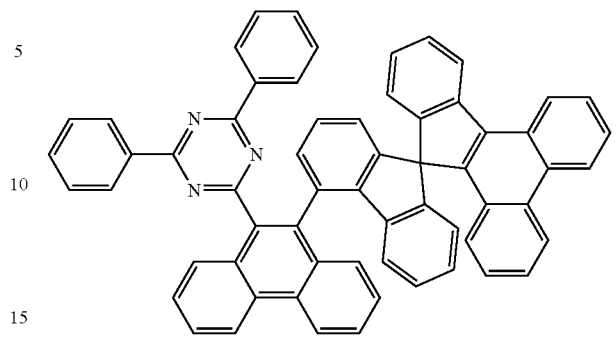
Compound 4-53
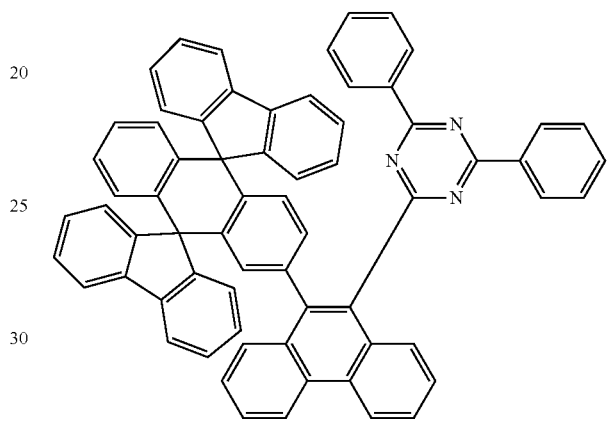
Compound 4-54
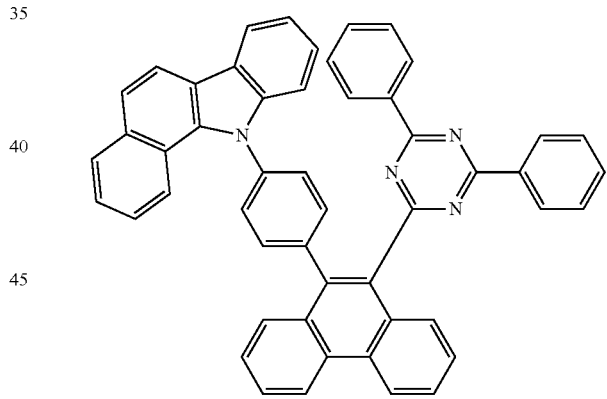
Compound 4-55
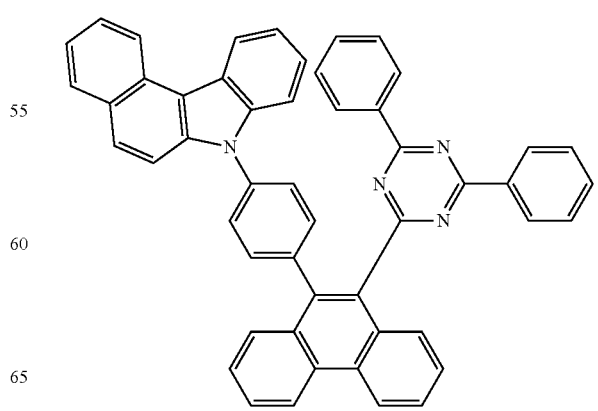

Compound 5-1
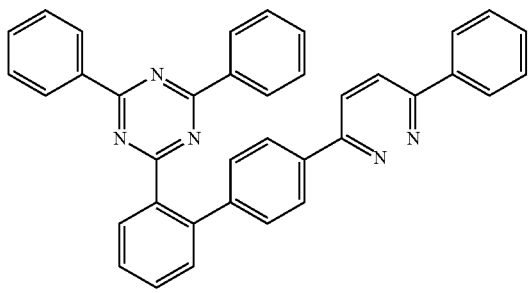
Compound 5-2
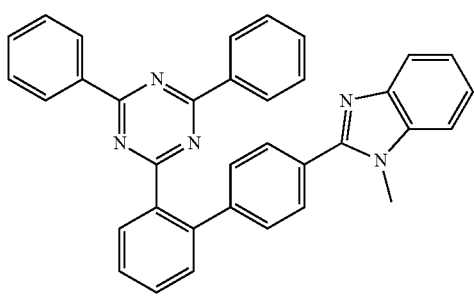
Compound 5-3
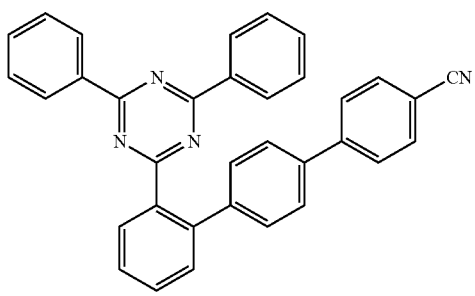
Compound 5-4
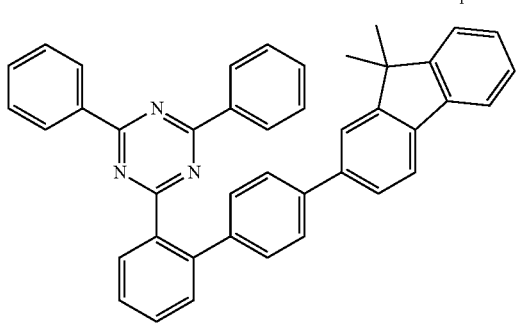
Compound 5-5
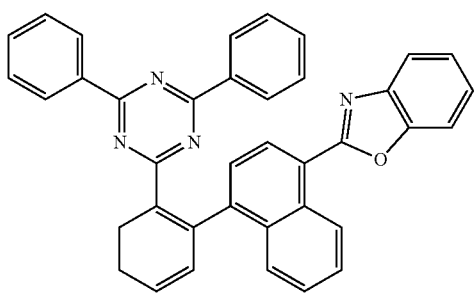
Compound 5-6
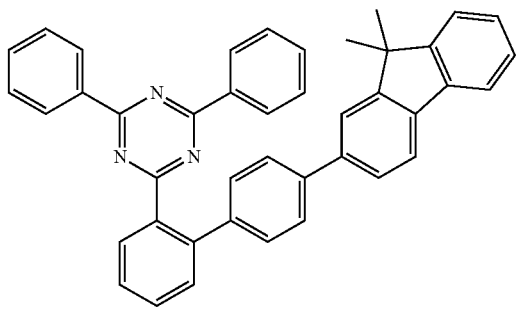
Compound 5-7
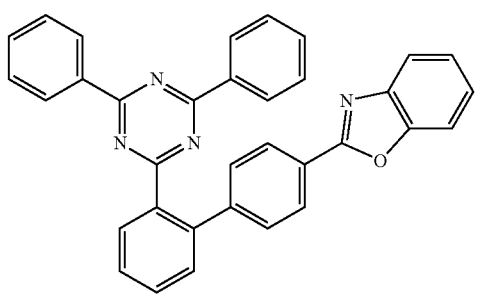
Compound 5-8
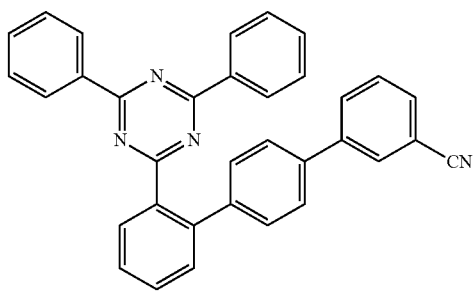
Compound 5-9
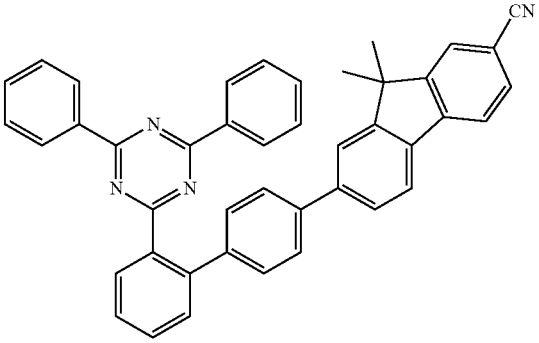
Compound 5-10
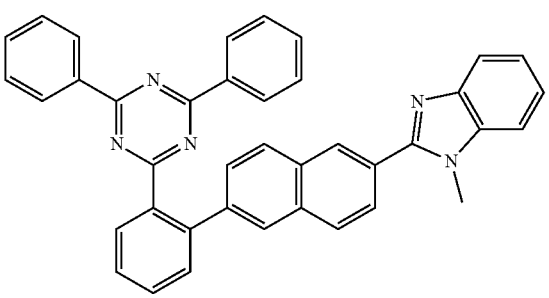

Compound 5-11
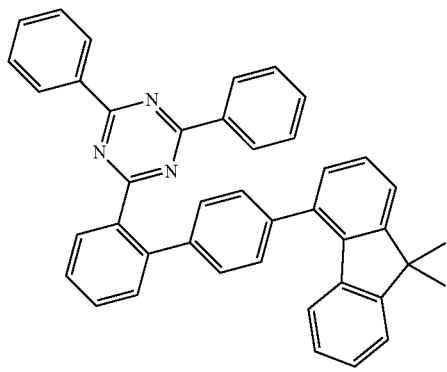
Compound 5-12
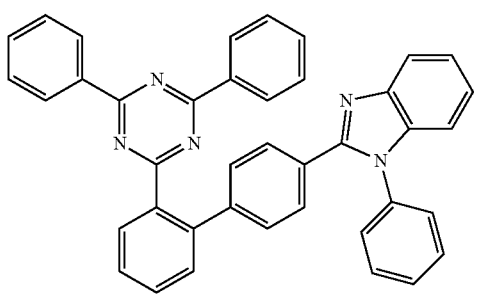
Compound 5-13
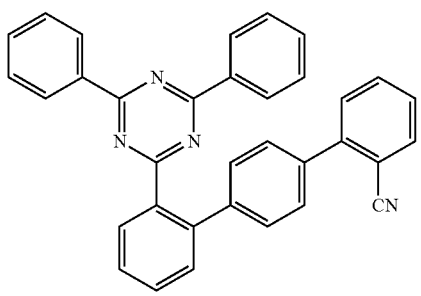
Compound 5-14
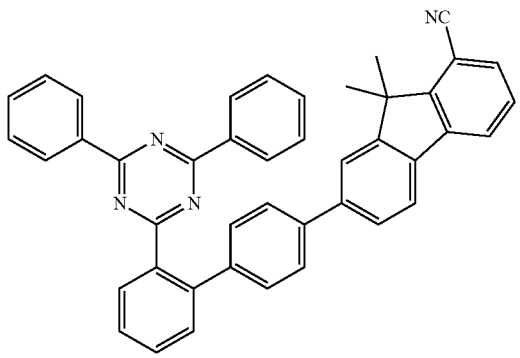
Compound 5-15
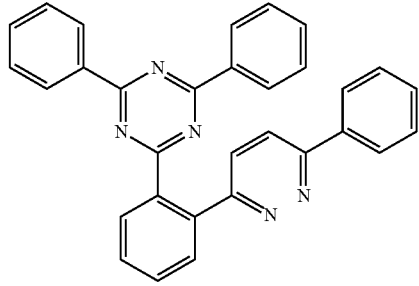
Compound 5-16
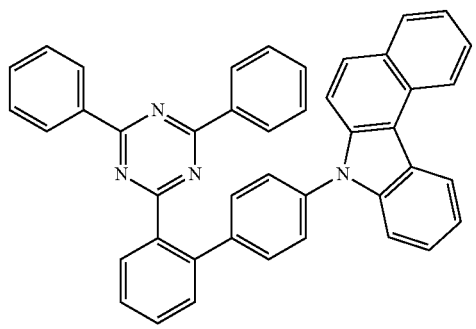
Compound 5-17
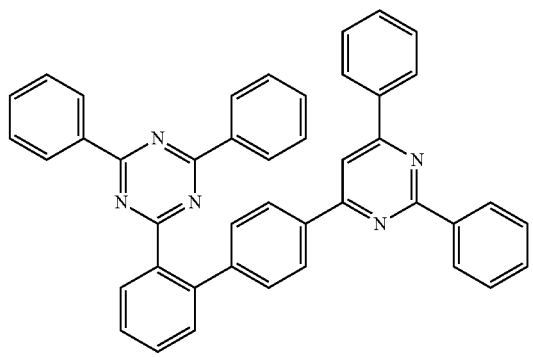
Compound 5-18
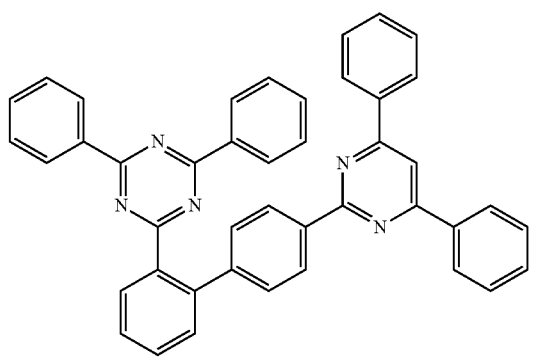

Compound 5-19
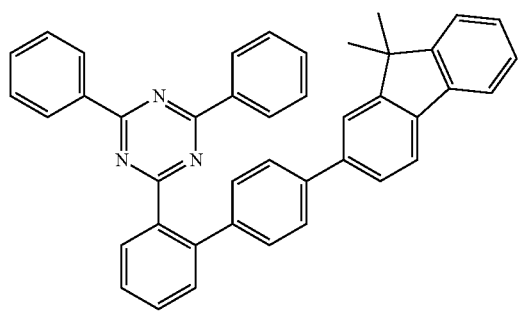
Compound 5-20
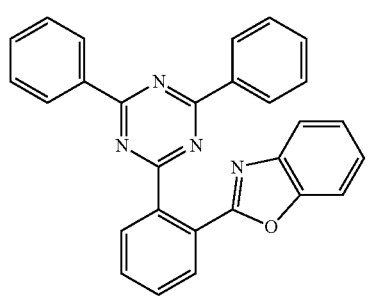
Compound 5-21
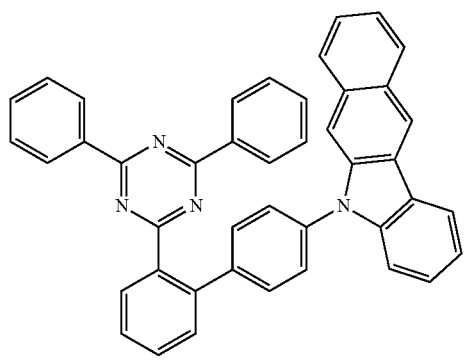
Compound 5-22
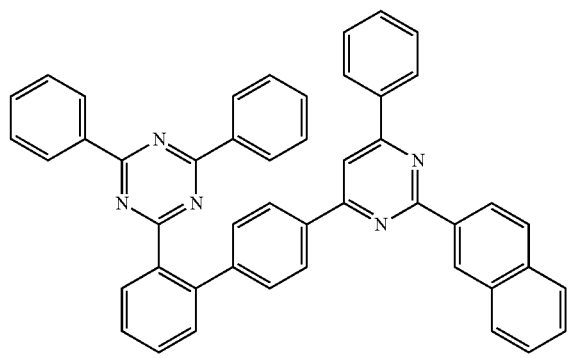
Compound 5-23
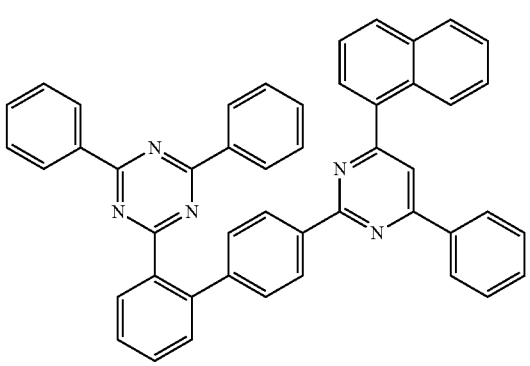
Compound 5-24
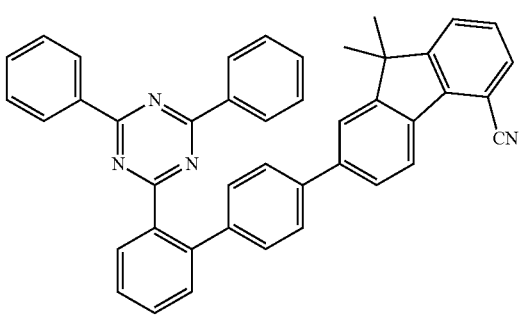
Compound 5-25
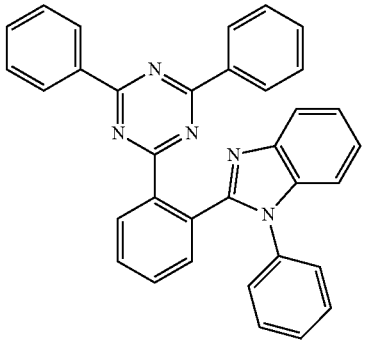
Compound 5-27
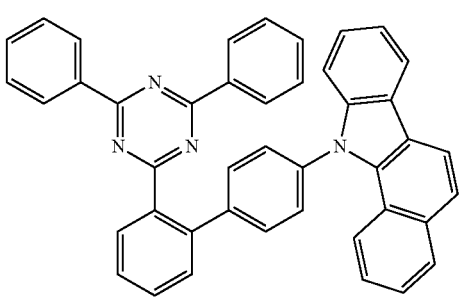

Compound 5-28
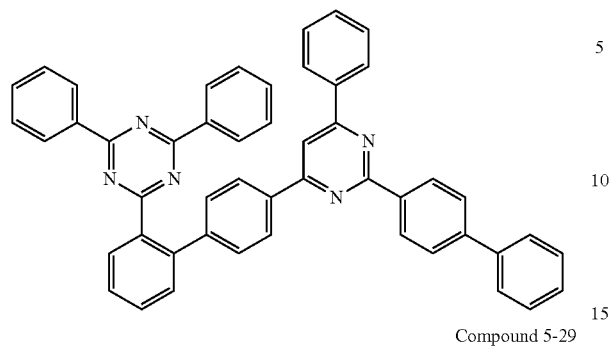
Compound 5-29
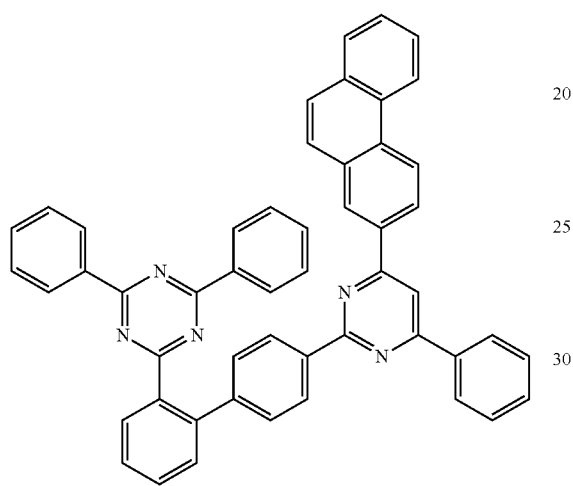
Compound 5-30
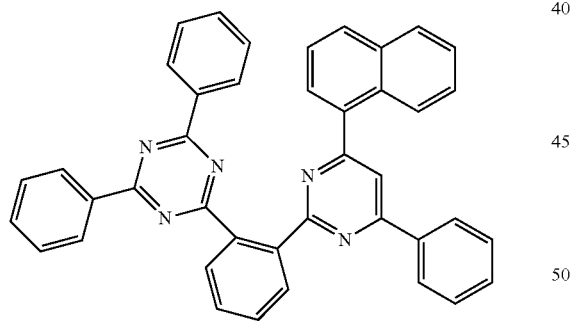
Compound 5-31
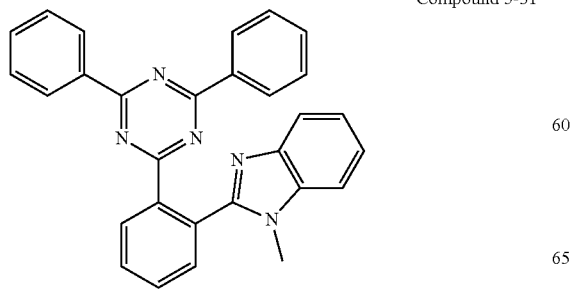
Compound 5-32
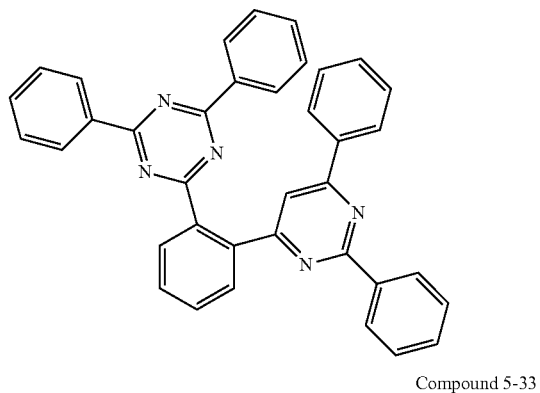
Compound 5-33
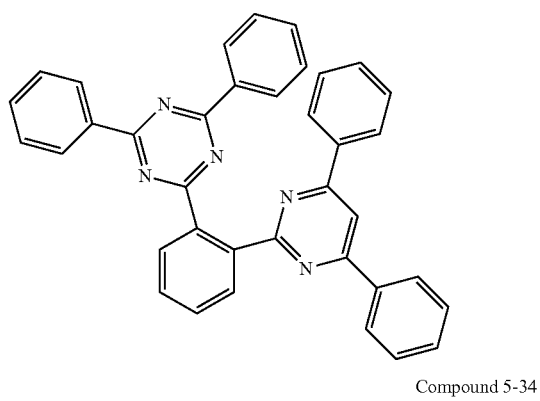
Compound 5-34
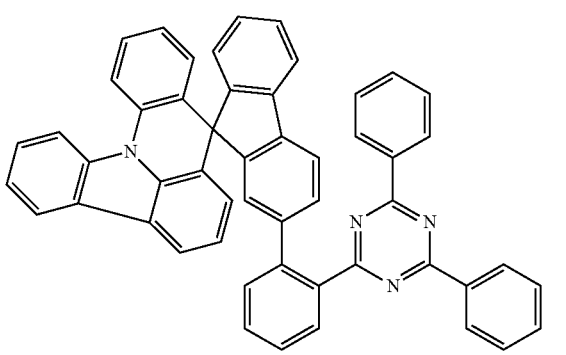
Compound 5-35
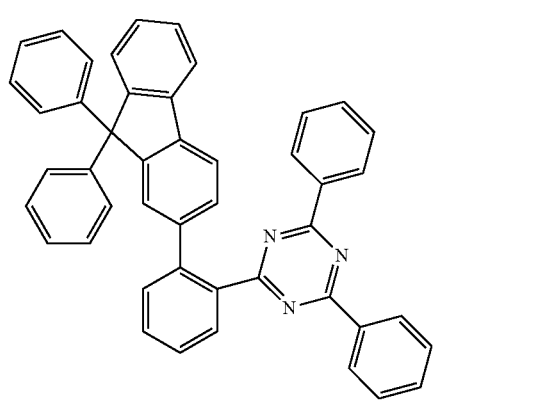

Compound 5-36
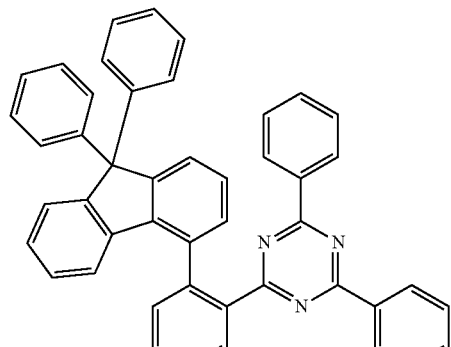
Compound 5-37
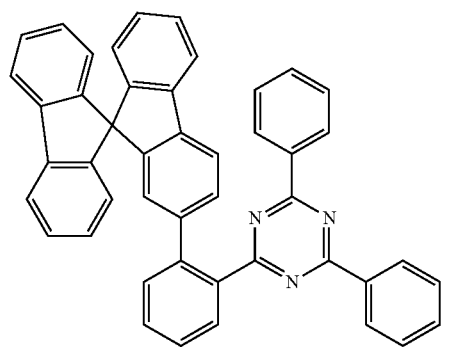
Compound 5-38
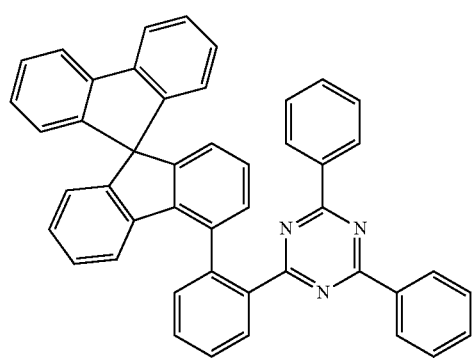
Compound 5-39
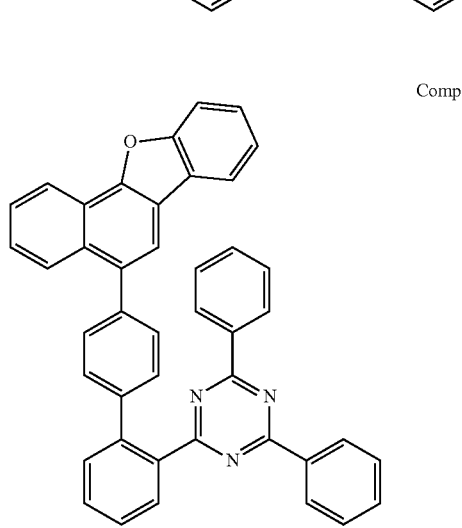
Compound 5-40
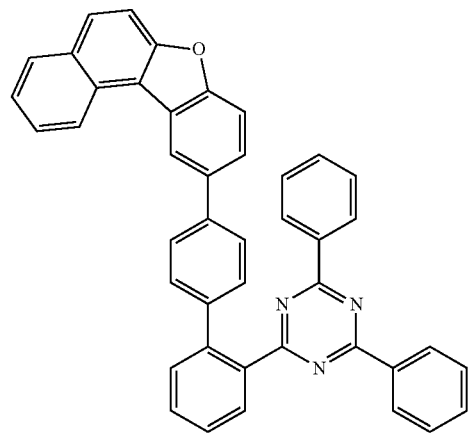
Compound 5-41
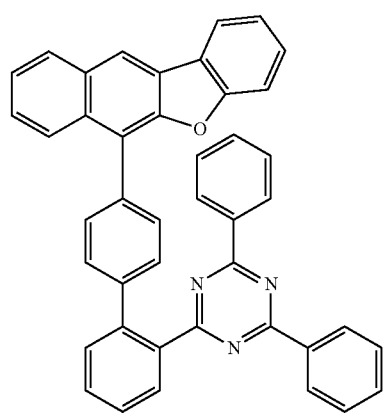
Compound 5-42
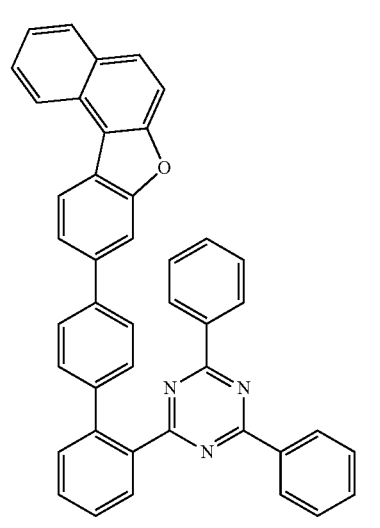

Compound 5-43
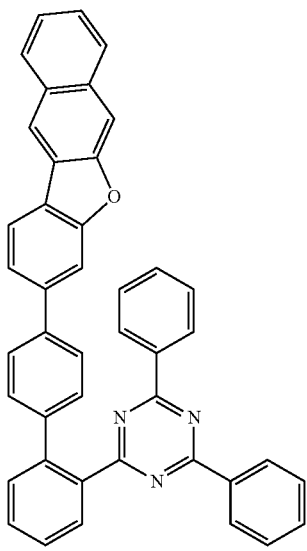
Compound 5-44
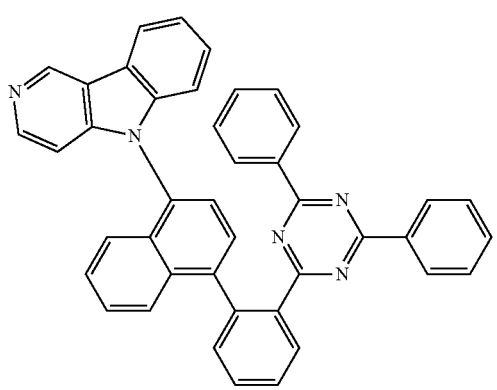
Compound 5-45
Compound 5-46
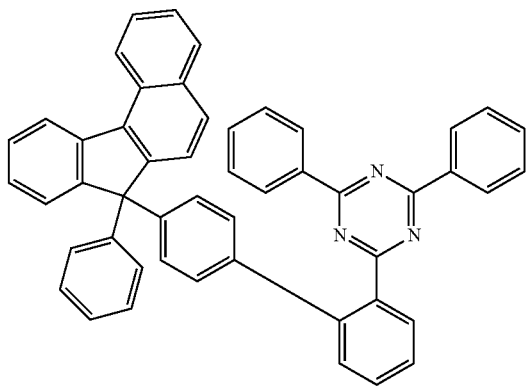
Compound 5-47
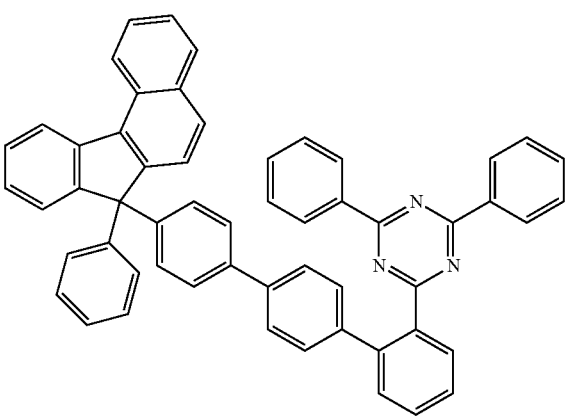
Compound 5-48
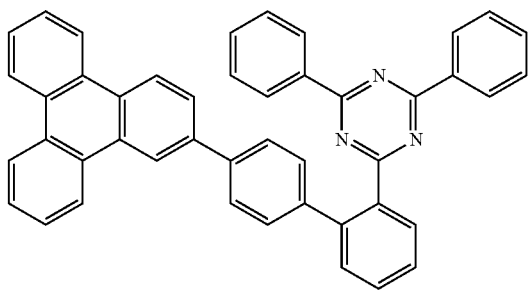
Compound 5-49
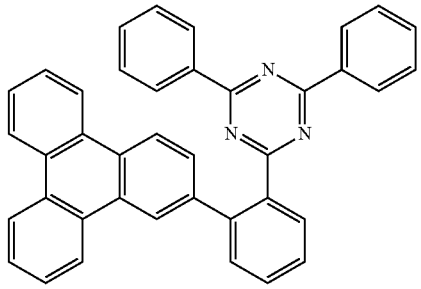

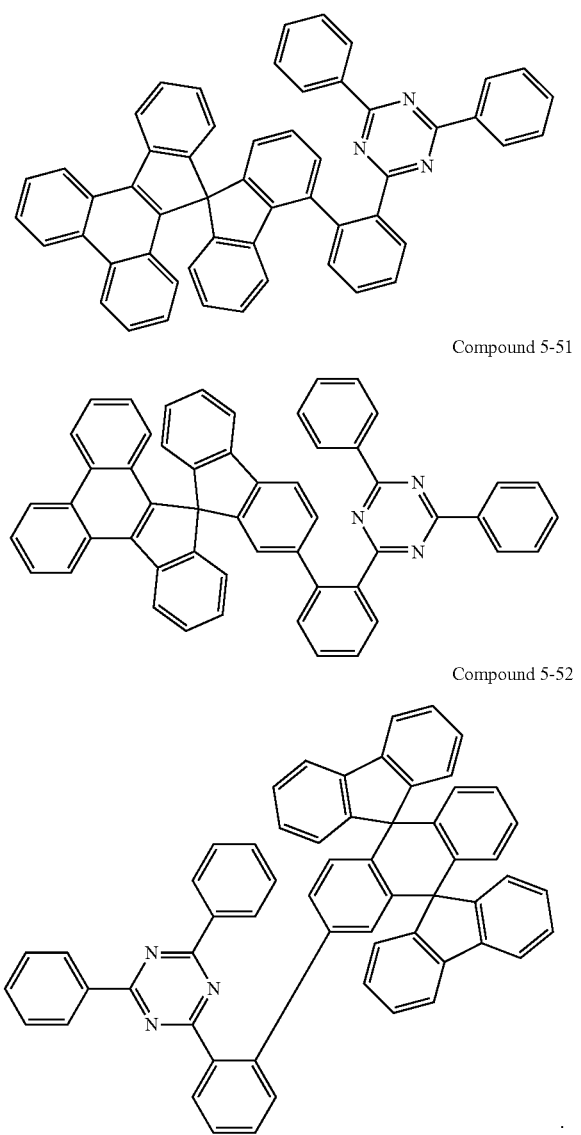

Compound 5-50

Compound 5-51

Compound 5-52

According to an exemplary embodiment of the present application, $Ar_4$ and $Ar_5$ are the same as or different from each other, and are each independently a substituted or unsubstituted $C_6$ to $C_{20}$ aryl group.

According to an exemplary embodiment of the present application, $Ar_4$ and $Ar_5$ are the same as or different from each other, and are each independently a substituted or unsubstituted phenyl group; a substituted or unsubstituted biphenyl group; or a substituted or unsubstituted naphthyl group.

According to an exemplary embodiment of the present application, $Ar_4$ and $Ar_5$ are the same as or different from each other, and are each independently a substituted or unsubstituted monocyclic aryl group.

According to an exemplary embodiment of the present application, $Ar_4$ and $Ar_5$ are the same as or different from each other, and are each independently a substituted or unsubstituted phenyl group; or a substituted or unsubstituted biphenyl group.

According to an exemplary embodiment of the present application, $Ar_4$ and $Ar_5$ are the same as or different from each other, and are each independently a phenyl group; or a biphenyl group.

According to an exemplary embodiment of the present application, $L_3$ is a direct bond; or a substituted or unsubstituted $C_6$ to $C_{20}$ arylene group.

According to an exemplary embodiment of the present application, $L_3$ is a direct bond; a substituted or unsubstituted phenylene group; a substituted or unsubstituted biphenylene group; or a substituted or unsubstituted naphthalene group.

According to an exemplary embodiment of the present application, $L_3$ is a direct bond; or a substituted or unsubstituted phenylene group.

According to an exemplary embodiment of the present application, $L_3$ is a direct bond; or a phenylene group.

According to an exemplary embodiment of the present application, $Ar_6$ is a substituted or unsubstituted $C_6$ to $C_{20}$ aryl group; or a substituted or unsubstituted $C_2$ to $C_{20}$ heterocyclic group.

According to an exemplary embodiment of the present application, $Ar_6$ is a substituted or unsubstituted spirofluoreneindoloacridine group; a substituted or unsubstituted indolocarbazole group; a substituted or unsubstituted benzocarbazole group; a substituted or unsubstituted carbazole group; a substituted or unsubstituted spirobifluorenyl group; or a substituted or unsubstituted fluorenyl group.

According to an exemplary embodiment of the present application, $Ar_6$ is a spirofluoreneindoloacridine group; an indolocarbazole group; a benzocarbazole group; a carbazole group; a spirobifluorenyl group; or a fluorenyl group which is unsubstituted or substituted with an aryl group.

According to an exemplary embodiment of the present application, $Ar_6$ is a spirofluoreneindoloacridine group; an indolocarbazole group; a benzocarbazole group; a carbazole group; a spirobifluorenyl group; or a fluorenyl group which is unsubstituted or substituted with a phenyl group.

According to an exemplary embodiment of the present application, $Ar_6$ is a spirofluoreneindoloacridine group; an indolocarbazole group; a benzocarbazole group; a carbazole group; a spirobifluorenyl group; or a dimethyl fluorenyl group.

According to an exemplary embodiment of the present application, the compound represented by Chemical Formula 11 is any one selected from the following structural formulae:

Compound 6-1

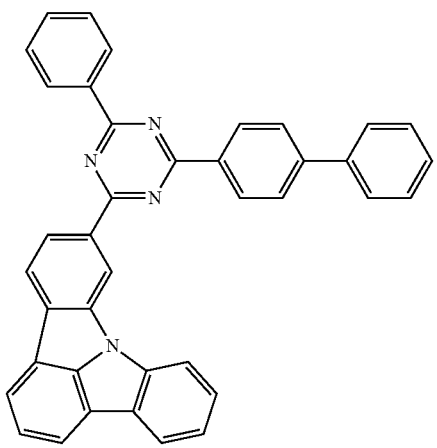

-continued
Compound 6-2
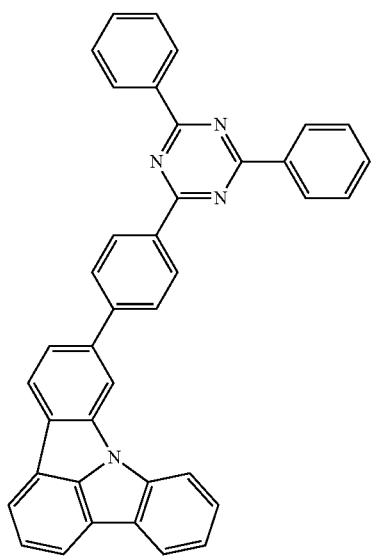
Compound 6-3
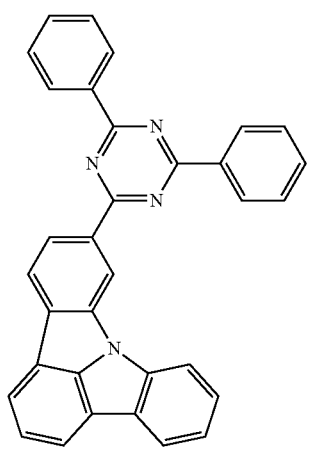
Compound 6-4
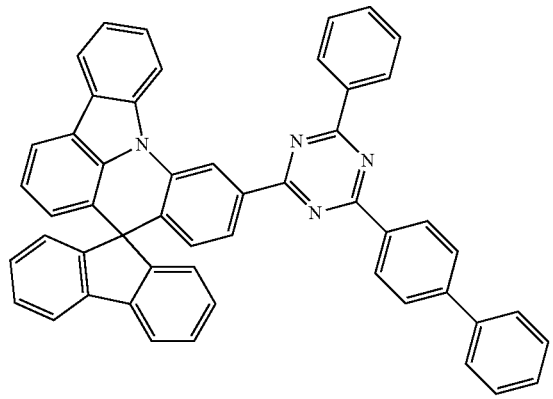
-continued
Compound 6-5
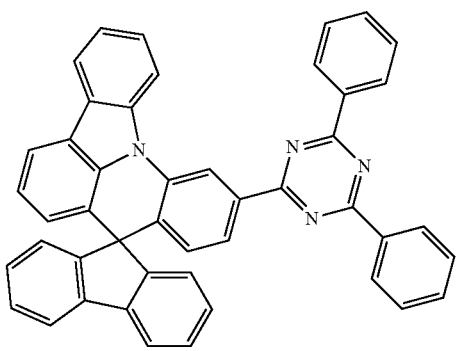
Compound 6-6
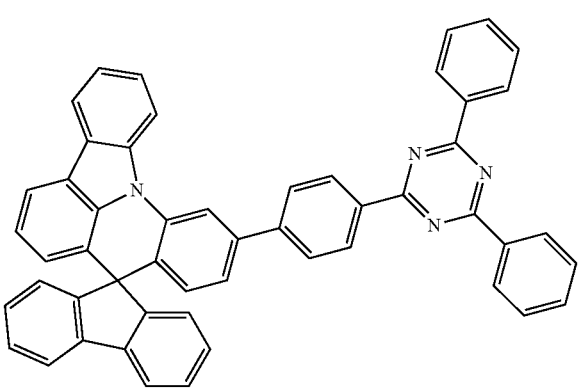
Compound 6-7
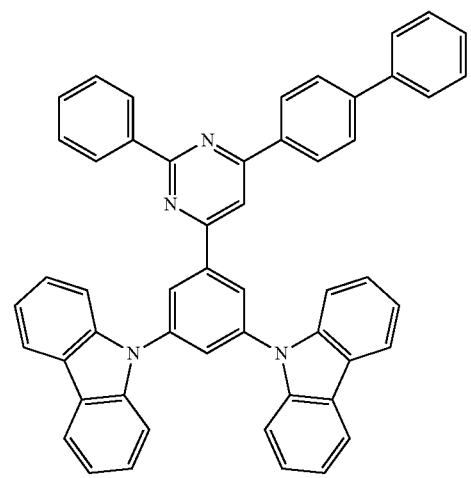

Compound 6-8
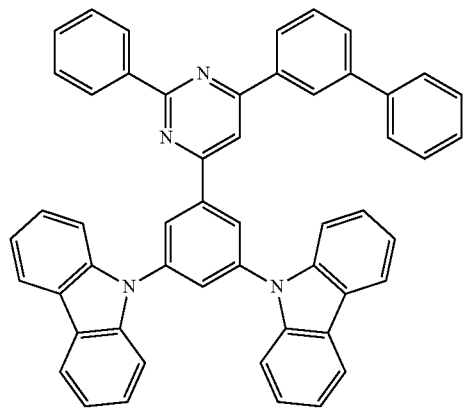
Compound 6-9
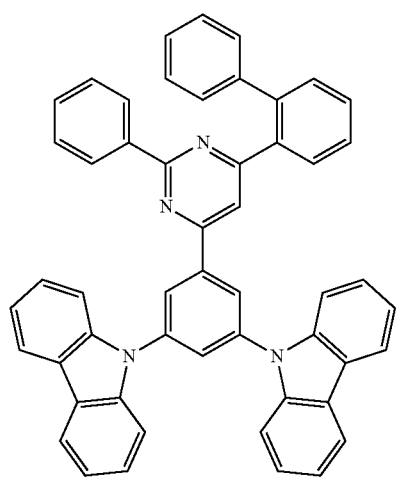
Compound 6-10
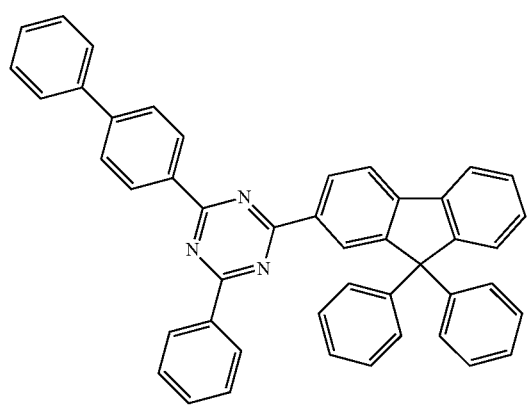
Compound 6-11
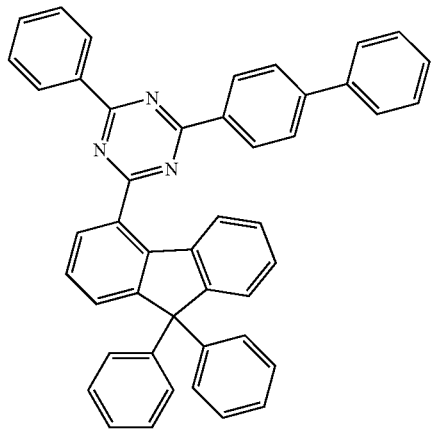
Compound 6-12
Compound 6-13
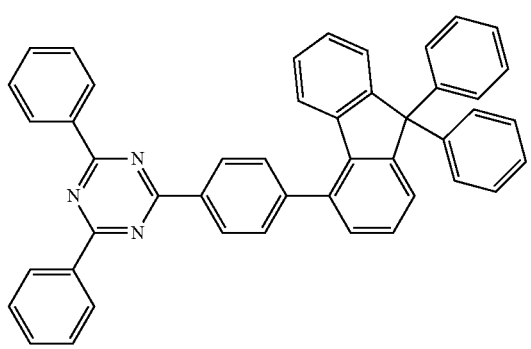
Compound 6-14
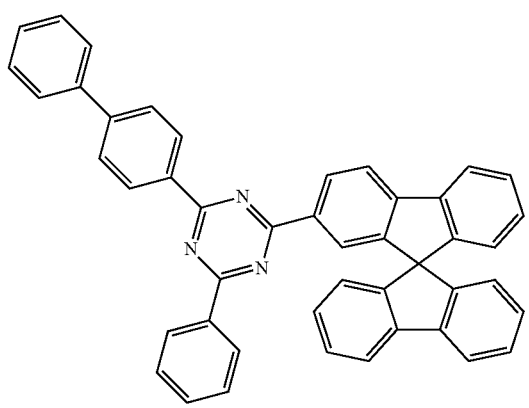

Compound 6-15
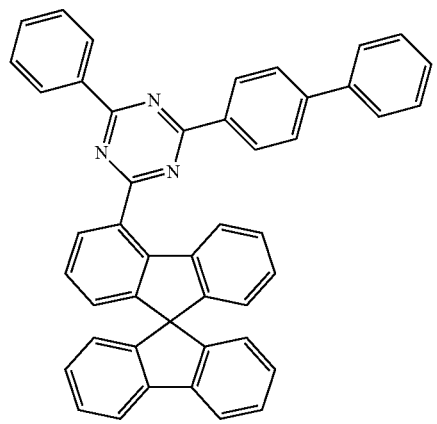
Compound 6-18
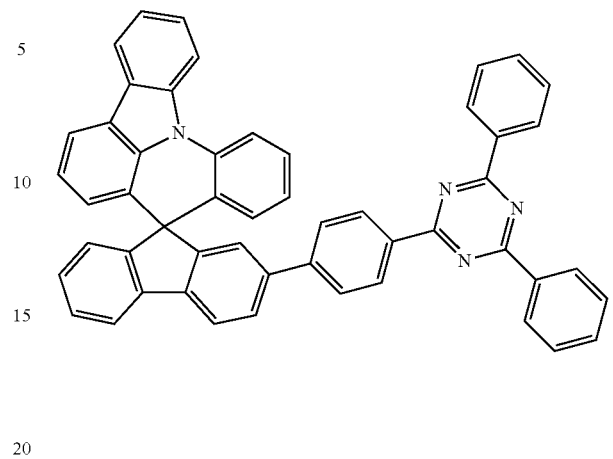
Compound 6-16
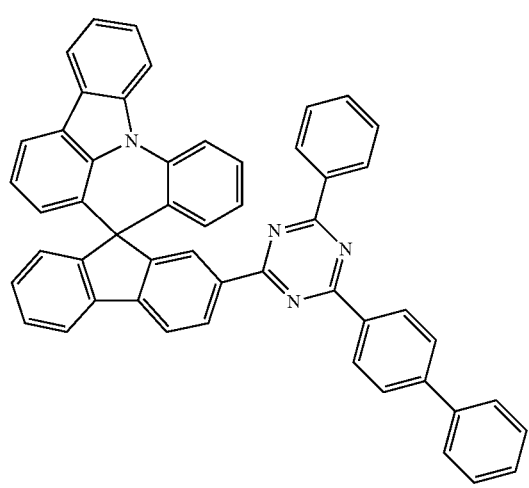
Compound 6-19
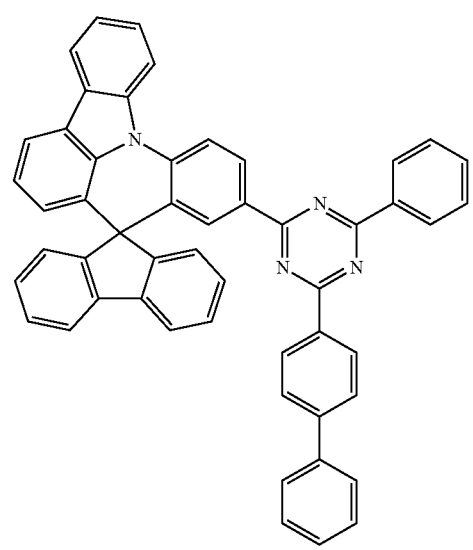
Compound 6-17
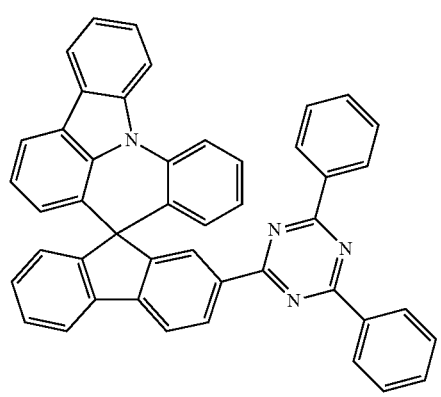
Compound 6-20
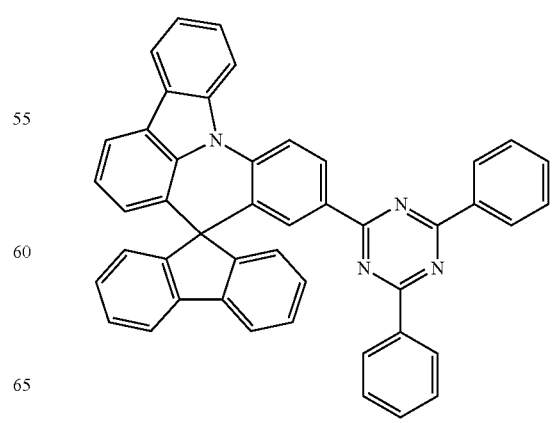

Compound 6-21
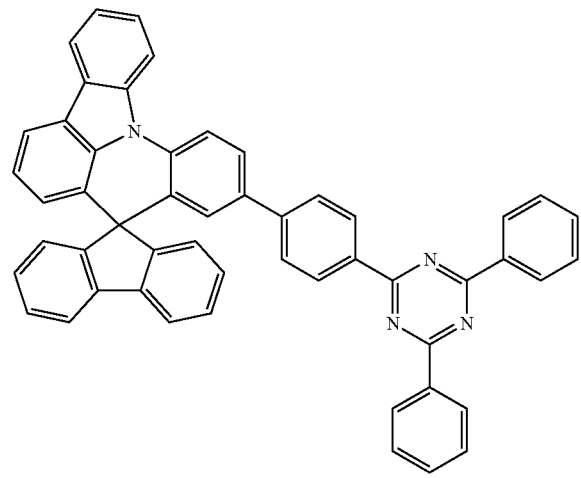
Compound 6-22
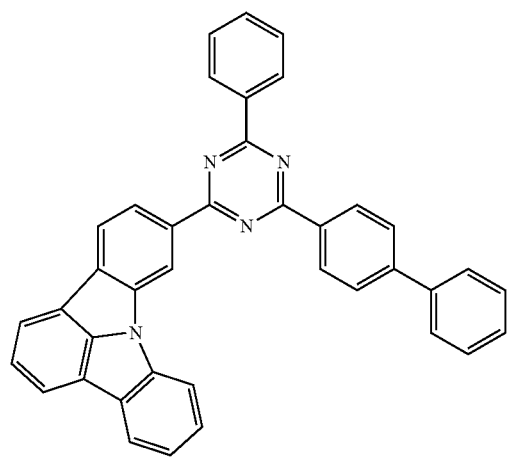
Compound 6-23
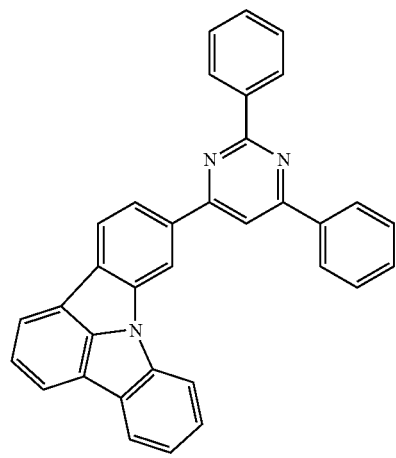
Compound 6-24
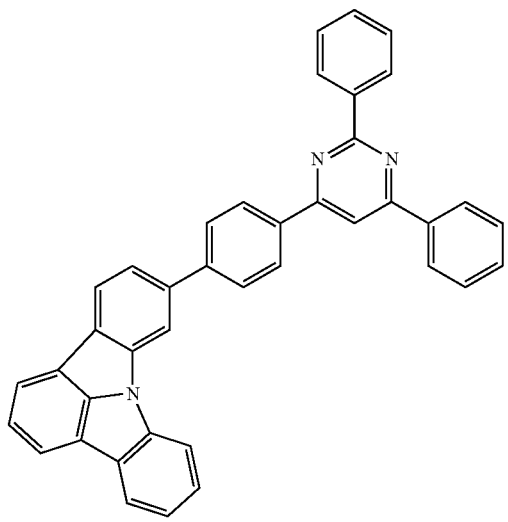
Compound 6-25
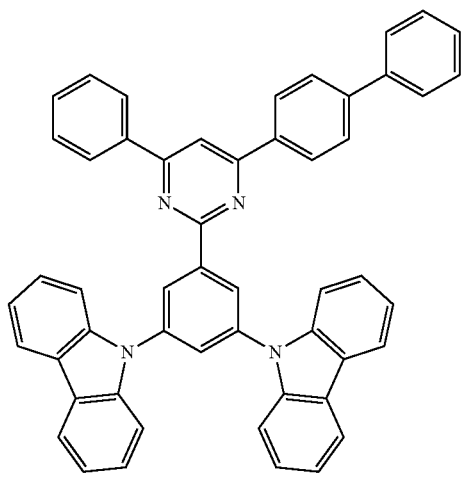
Compound 6-26
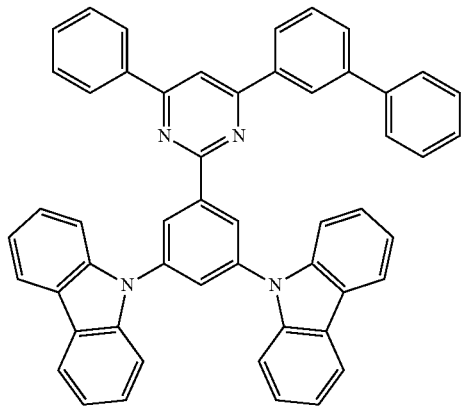

Compound 6-27
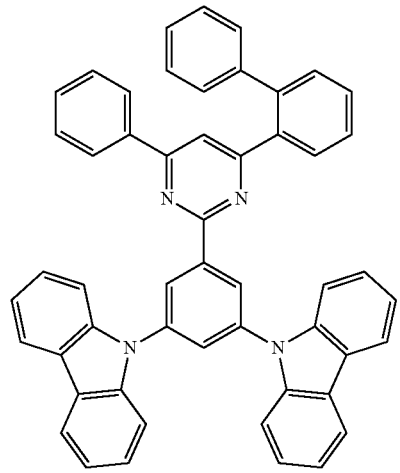
Compound 6-30
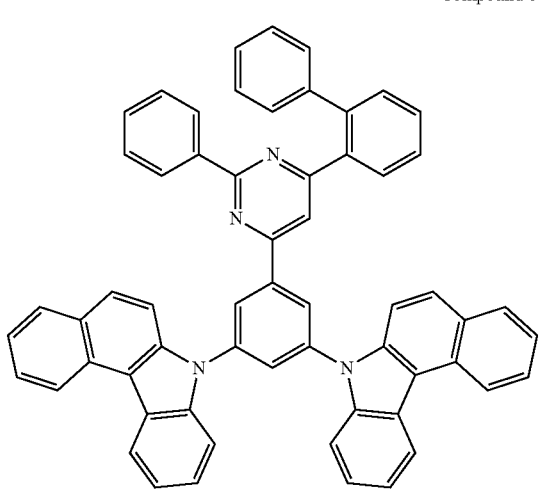
Compound 6-28
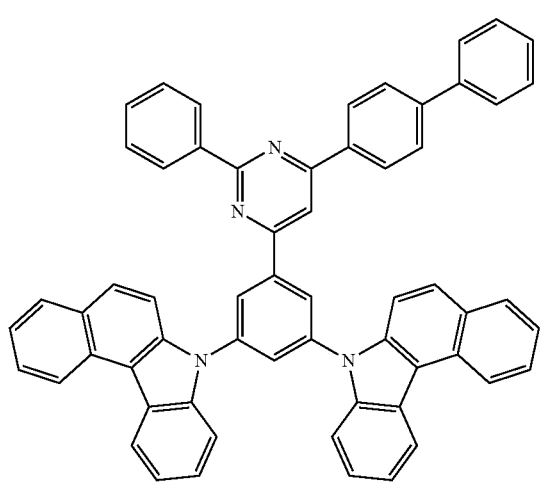
Compound 6-30
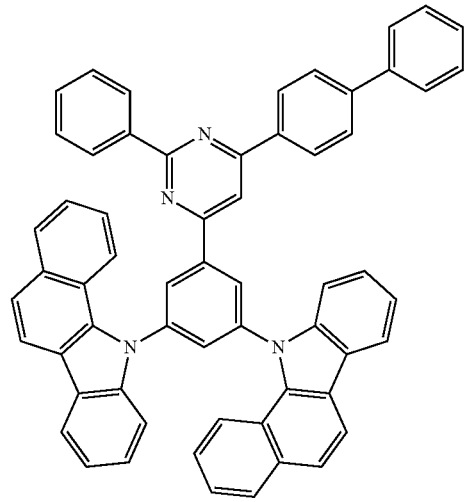
Compound 6-29
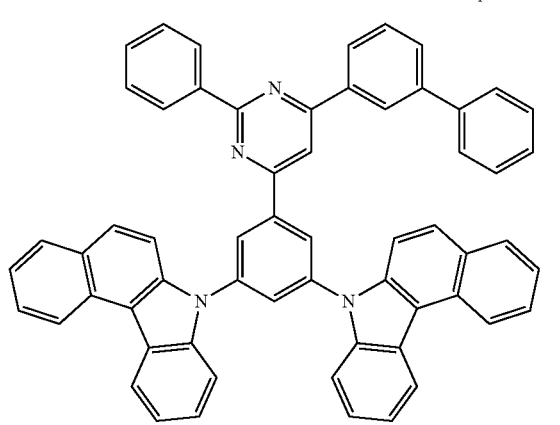
Compound 6-31
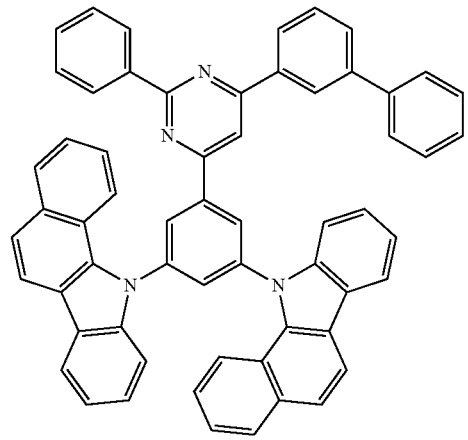

Compound 6-32
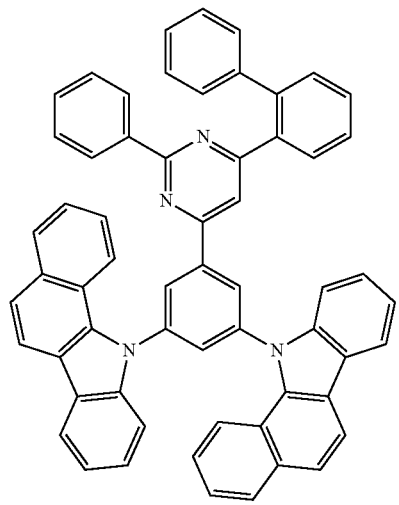
Compound 6-35
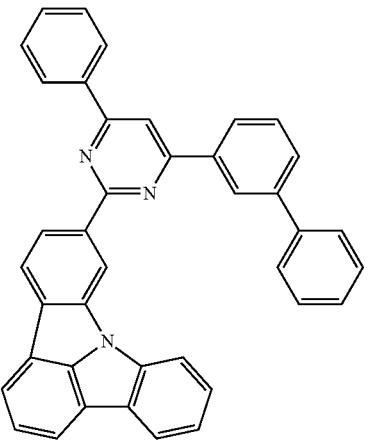
Compound 6-33
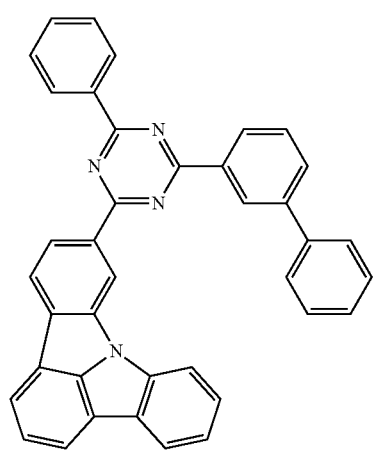
Compound 6-36
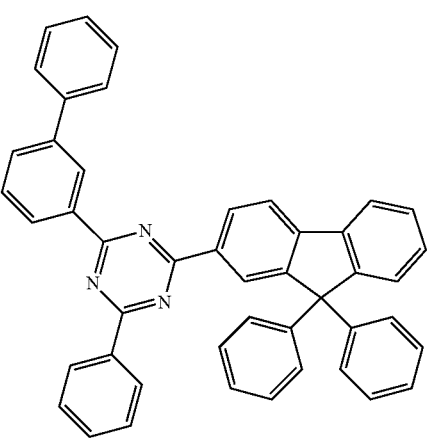
Compound 6-34
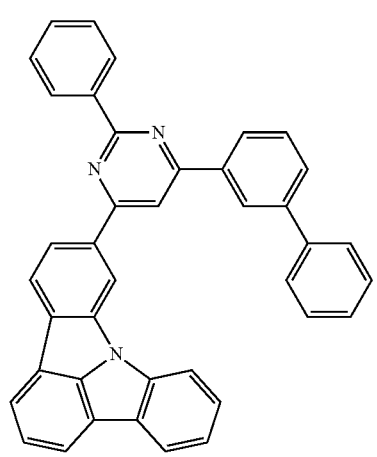
Compound 6-37
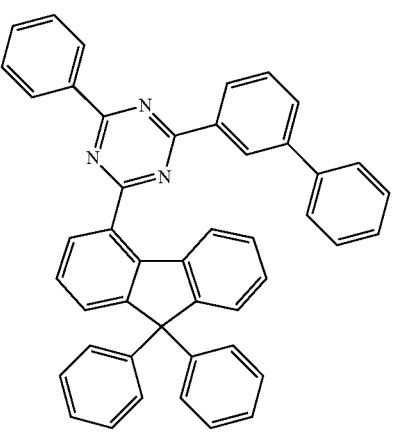

Compound 6-38

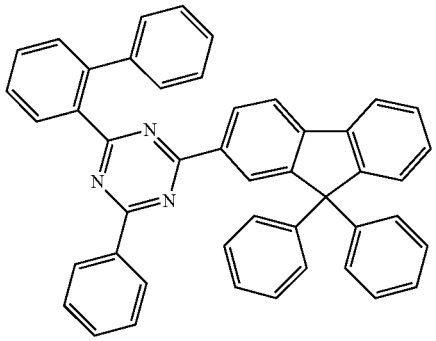

Compound 6-39

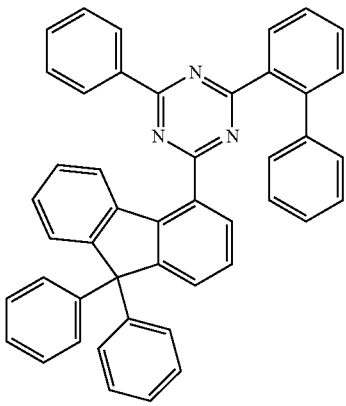

The organic light emitting device of the present specification may be manufactured by materials and methods known in the art, except for including an electron transport layer and an electron adjusting layer.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form an anode, forming an organic material layer including a hole injection layer, a hole transport layer, a light emitting layer, an electron adjusting layer, and an electron transport layer thereon, and then depositing a material, which may be used as a cathode, thereon by using a physical vapor deposition (PVD) method such as sputtering or e-beam evaporation. In addition to the method described above, an organic light emitting device may be made by sequentially depositing a cathode material, an organic material layer, and an anode material on a substrate.

The electron adjusting layer of the organic light emitting device of the present specification is provided between a light emitting layer and an electron transport layer.

The organic material layer of the organic light emitting device of the present specification may be composed of a multi-layered structure in which two or more organic material layers are stacked.

In an exemplary embodiment of the present specification, the organic light emitting device may further include one or two or more layers selected from the group consisting of a hole injection layer, a hole transport layer, an electron transport layer, an electron injection layer, an electron blocking layer, and a hole blocking layer.

In an exemplary embodiment of the present application, the organic material layer includes a light emitting layer, and the light emitting layer includes a compound of the following Chemical Formula A-1.

[Chemical Formula A-1]

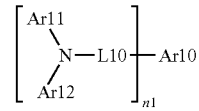

In Chemical Formula A-1,
n1 is an integer of 1 or more,
Ar10 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L10 is a direct bond; a substituted or unsubstituted arylene group; or a substituted or unsubstituted heteroarylene group,
Ar11 and Ar12 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heterocyclic group, or may combine with each other to form a substituted or unsubstituted ring, and
when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

According to an exemplary embodiment of the present specification, L10 is a direct bond.

According to an exemplary embodiment of the present specification, n1 is 2.

In an exemplary embodiment of the present specification, Ar10 is a divalent pyrene group which is unsubstituted or substituted with deuterium, a methyl group, an ethyl group, an isopropyl group, or a tert-butyl group; or a divalent chrysene group unsubstituted or substituted with deuterium, a methyl group, an ethyl group, or a tert-butyl group.

In an exemplary embodiment of the present specification, Ar10 is a divalent pyrene group unsubstituted or substituted with an alkyl group; or a divalent chrysene group unsubstituted or substituted with an alkyl group.

In an exemplary embodiment of the present specification, Ar10 is a divalent pyrene group unsubstituted or substituted with an alkyl group.

In an exemplary embodiment of the present specification, Ar10 is a divalent pyrene group.

According to an exemplary embodiment of the present specification, Ar11 and Ar12 are the same as or different from each other, and are each independently a substituted or unsubstituted aryl group having 6 to 30 carbon atoms.

According to an exemplary embodiment of the present specification, Ar11 and Ar12 are the same as or different from each other, and are each independently an aryl group unsubstituted or substituted with a silyl group substituted with an alkyl group, a cyano group, or an alkyl group.

According to an exemplary embodiment of the present specification, Ar11 and Ar12 are the same as or different from each other, and are each independently an aryl group unsubstituted or substituted with a silyl group substituted with a methyl group, an ethyl group, an isopropyl group, a tert-butyl group, a cyano group, or an alkyl group.

According to an exemplary embodiment of the present specification, Ar11 and Ar12 are the same as or different from each other, and are each independently an aryl group unsubstituted or substituted with silyl group substituted with an alkyl group.

According to an exemplary embodiment of the present specification, Ar11 and Ar12 are the same as or different from each other, and are each independently an aryl group unsubstituted or substituted with a trimethylsilyl group.

According to an exemplary embodiment of the present specification, Ar11 and Ar12 are the same as or different from each other, and are each independently a substituted or unsubstituted phenyl group; a substituted or unsubstituted biphenyl group; or a substituted or unsubstituted terphenyl group.

According to an exemplary embodiment of the present specification, Ar11 and Ar12 are the same as or different from each other, and are each independently a phenyl group unsubstituted or substituted with a methyl group, an ethyl group, an isopropyl group, a tert-butyl group, a cyano group, or a trimethylsilyl group.

According to an exemplary embodiment of the present specification, Ar11 and Ar12 are the same as or different from each other, and are each independently a phenyl group unsubstituted or substituted with a trimethylsilyl group.

According to an exemplary embodiment of the present specification, Ar11 and Ar12 are the same as or different from each other, and are each independently a substituted or unsubstituted heteroaryl group having 6 to 30 carbon atoms.

According to an exemplary embodiment of the present specification, Ar11 and Ar12 are the same as or different from each other, and are each independently a heteroaryl group unsubstituted or substituted with a methyl group, an ethyl group, a tert-butyl group, a nitrile group, a silyl group substituted with an alkyl group, or a phenyl group.

According to an exemplary embodiment of the present specification, Ar11 and Ar12 are the same as or different from each other, and are each independently a dibenzofuran group unsubstituted or substituted with a methyl group, an ethyl group, a tert-butyl group, a nitrile group, a trimethylsilyl group, or a phenyl group.

According to an exemplary embodiment of the present specification, Chemical Formula A-1 may be represented by the following compound.

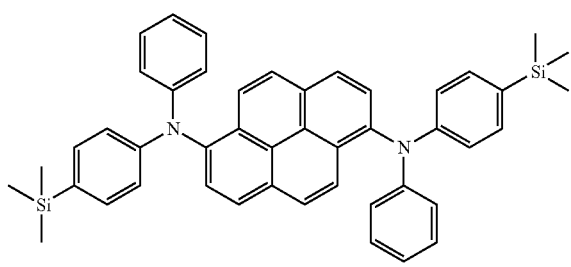

According to an exemplary embodiment of the present specification, the organic material layer includes a light emitting layer, and the light emitting layer includes a compound represented by the following Chemical Formula A-2.

[Chemical Formula A-2]

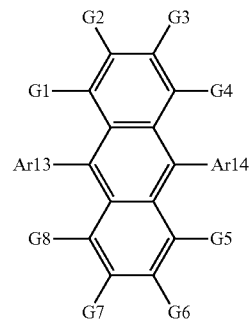

In Chemical Formula A-2,

Ar13 and Ar14 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula A-2 as a host of the light emitting layer.

According to an exemplary embodiment of the present specification, Ar13 and Ar14 are the same as or different from each other, and are each independently a substituted or unsubstituted polycyclic aryl group.

According to an exemplary embodiment of the present specification, Ar13 and Ar14 are the same as or different from each other, and are each independently a substituted or unsubstituted polycyclic aryl group having 10 to 30 carbon atoms.

According to an exemplary embodiment of the present specification, Ar13 and Ar14 are the same as or different from each other, and are each independently a substituted or unsubstituted naphthyl group.

According to an exemplary embodiment of the present specification, Ar13 and Ar14 are the same as or different from each other, and are each independently a substituted or unsubstituted 1-naphthyl group.

According to an exemplary embodiment of the present specification, Ar13 and Ar14 are a 1-naphthyl group.

According to an exemplary embodiment of the present specification, G1 to G8 are hydrogen.

According to an exemplary embodiment of the present specification, Chemical Formula A-2 may be represented by the following compound.

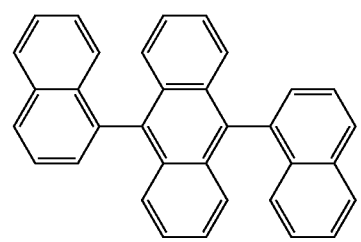 [SMILES: c1ccc2c(-c3c4ccccc4c(-c4cccc5ccccc45)c4ccccc34)cccc2c1]

According to an exemplary embodiment of the present specification, the organic material layer includes a light emitting layer, and the light emitting layer includes the compound represented by Chemical Formula A-1 as a dopant of the light emitting layer, and includes the compound represented by Chemical Formula A-2 as a host of the light emitting layer.

For example, the structure of the organic light emitting device of the present specification may have a structure as illustrated in FIG. 1, but is not limited thereto.

FIG. 1 illustrates the structure of an organic light emitting device in which a positive electrode 201, a light emitting layer 301, an electron adjusting layer 401, an electron transport layer 501, and a negative electrode 601 are sequentially stacked on a substrate 101. FIG. 1 is an exemplified structure according to an exemplary embodiment of the present specification, and the structure may further include other organic material layers.

When the organic light emitting device includes a plurality of organic material layers, the organic material layers may be formed of the same material or different materials.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2/Al$, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes transported from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a Spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an organic compound, a metal, or a metal compound.

Examples of the organic compound as the dopant material include an aromatic amine derivative, a styrylamine compound, a boron complex, a fluoranthene compound, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. In addition, as the metal or the metal compound, a typical metal or metal compound may be used, and specifically, a metal complex may be used. Examples of the metal complex include an iridium complex, a platinum complex, and the like, but are not limited thereto.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

In addition, the organic light emitting device according to the present specification may be a normal type in which a lower electrode is an anode and an upper electrode is a cathode, and may also be an inverted type in which a lower electrode is a cathode and an upper electrode is an anode.

The structure according to an exemplary embodiment of the present specification may be operated by a principle which is similar to the principle applied to an organic light emitting device, even in an organic electronic device including an organic solar cell, an organic photoconductor, an organic transistor, and the like.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

PREPARATION EXAMPLES

<Preparation Example 1> Synthesis of Compound 1-1

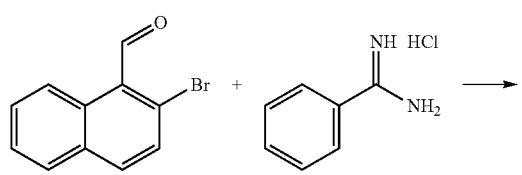

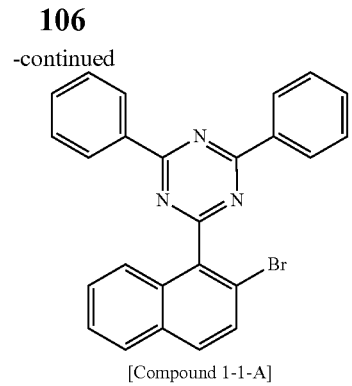

[Compound 1-1-A]

Under nitrogen flow, 2-bromo-1-naphthaldehyde (10 g, 42.54 mmol), benzimidamide hydrochloride (20 g, 127.6 mmol), and potassium phosphate (36 g, 170.2 mmol) were put into 150 mL of a dimethylacetamide (DMAc) solvent, and the resulting solution was heated and stirred for 18 hours. The reaction solution was cooled and then filtered, and then the filtered material was subjected to slurry purification using EtOH to obtain Compound 1-1-A (16 g, yield 86%).

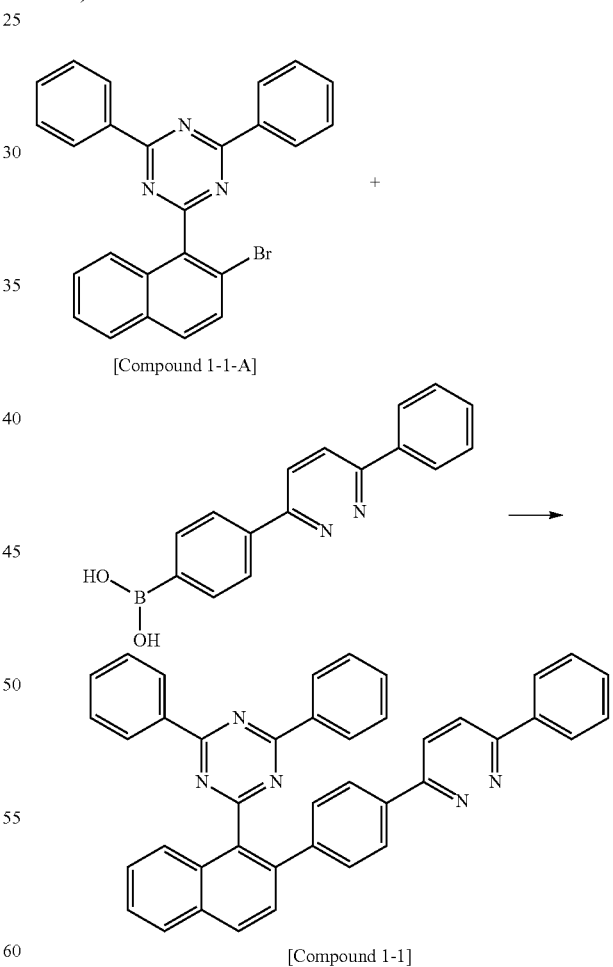

[Compound 1-1-A]

[Compound 1-1]

Under nitrogen flow, Compound 1-1-A (16 g, 36.5 mmol), (4-(6-phenylpyridazin-3-yl)phenyl)boronic acid (10.6 g, 38.3 mmol), tetrakis(triphenylphosphine)palladium(0) (1.3 g, 1.1 mmol), and potassium carbonate (10.1 g, 73 mmol) were put into a container, and the resulting mixture was heated and stirred for 6 hours. After the reaction was terminated, the temperature was lowered to normal temperature, and then a primary filtration was performed to remove impurities. The filtered material was put into water, extraction was performed by using chloroform to obtain an organic layer, and then the organic layer was dried over anhydrous magnesium sulfate. After distillation under reduced pressure, the residue was washed with ethanol to prepare Compound 1-1 (20 g, yield 93%).

MS: [M+H]⁺=590

<Preparation Example 2> Synthesis of Compound 1-3

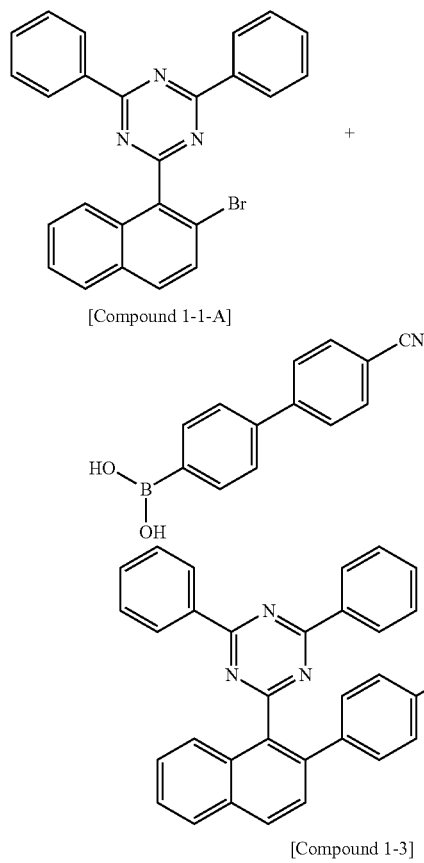

Under nitrogen flow, Compound 1-1-A (15 g, 34.2 mmol), (4'-cyano-[1,1'-biphenyl]-4-yl)boronic acid (8 g, 35.9 mmol), and potassium carbonate (9.5 g, 68.4 mmol) were put into a container, and the resulting mixture was heated and stirred. After reflux was performed, tetrakis(triphenyl-phosphine)palladium(0) (1.2 g, 1.0 mmol) was put thereinto, and the resulting mixture was additionally heated and stirred for 5 hours. After the reaction was terminated, the temperature was lowered to normal temperature, and then a primary filtration was performed to remove impurities. The filtered material was put into water, extraction was performed by using chloroform to obtain an organic layer, and then the organic layer was dried over anhydrous magnesium sulfate. After distillation under reduced pressure, the residue was washed with ethanol to prepare Compound 1-3 (16 g, yield 87%).

MS: [M+H]⁺=537

<Preparation Example 3> Synthesis of Compound 1-4

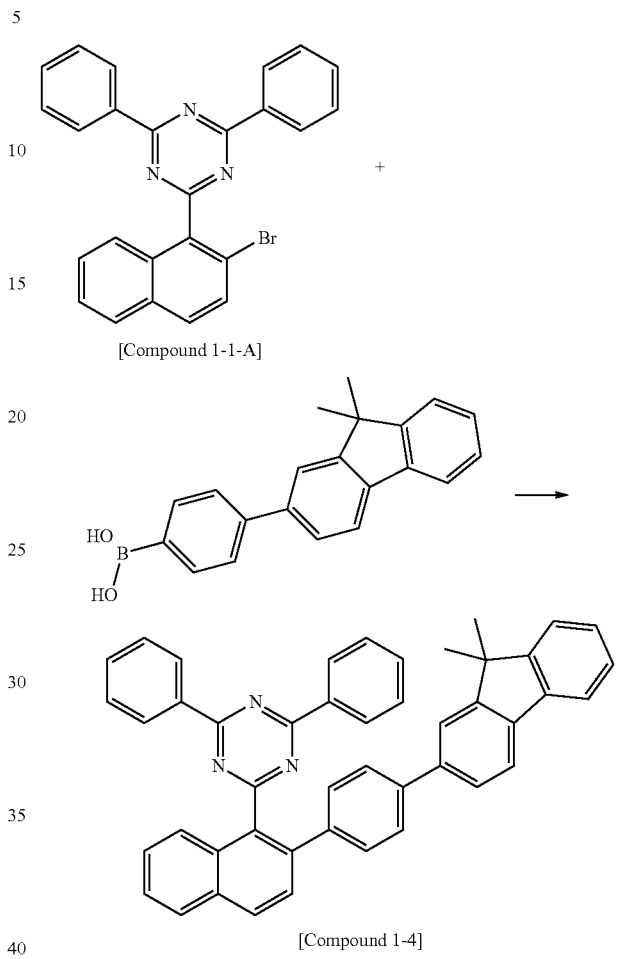

Compound 1-4 was obtained in the same manner as in the method for preparing Compound 1-1, except that (4-(9,9-dimethyl-9H-fluoren-2-yl)phenyl)boronic acid was used instead of (4-(6-phenylpyridazin-3-yl)phenyl)boronic acid.

MS: [M+H]⁺=628

<Preparation Example 4> Synthesis of Compound 1-6

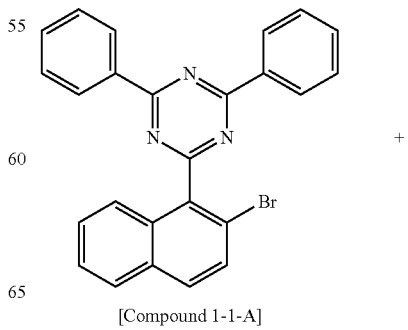

-continued

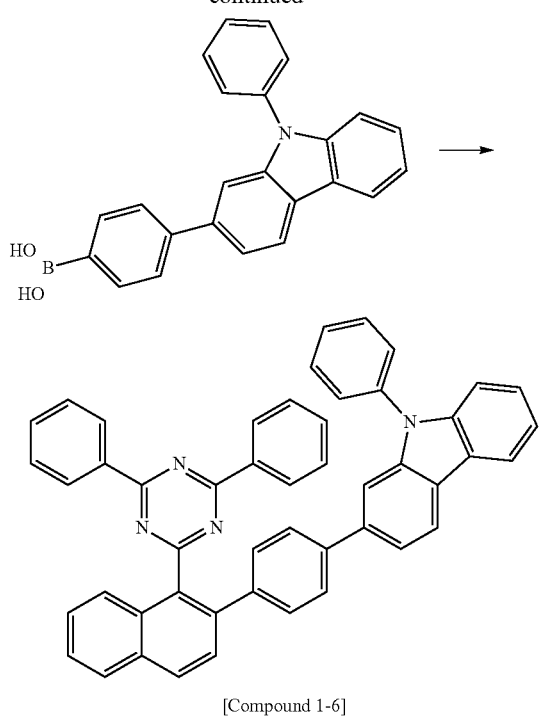

[Compound 1-6]

Compound 1-6 was obtained in the same manner as in the method for preparing Compound 1-1, except that (4-(9-phenyl-9H-carbazol-2-yl)phenyl)boronic acid was used instead of (4-(6-phenylpyridazin-3-yl)phenyl)boronic acid.

MS: [M+H]⁺=677

<Preparation Example 5> Synthesis of Compound 1-16

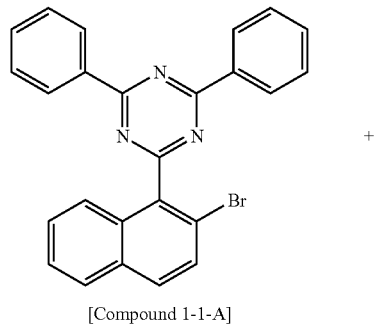

[Compound 1-1-A]

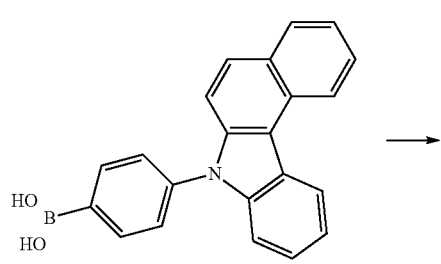

-continued

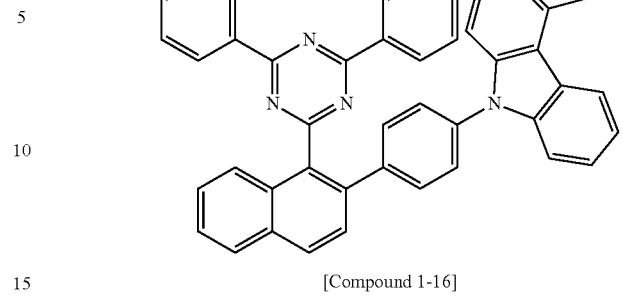

[Compound 1-16]

Compound 1-16 was obtained in the same manner as in the method for preparing Compound 1-1, except that (4-(7H-benzo[c]carbazol-7-yl)phenyl)boronic acid was used instead of (4-(6-phenylpyridazin-3-yl)phenyl)boronic acid.

MS: [M+H]⁺=651

<Preparation Example 6> Synthesis of Compound 1-19

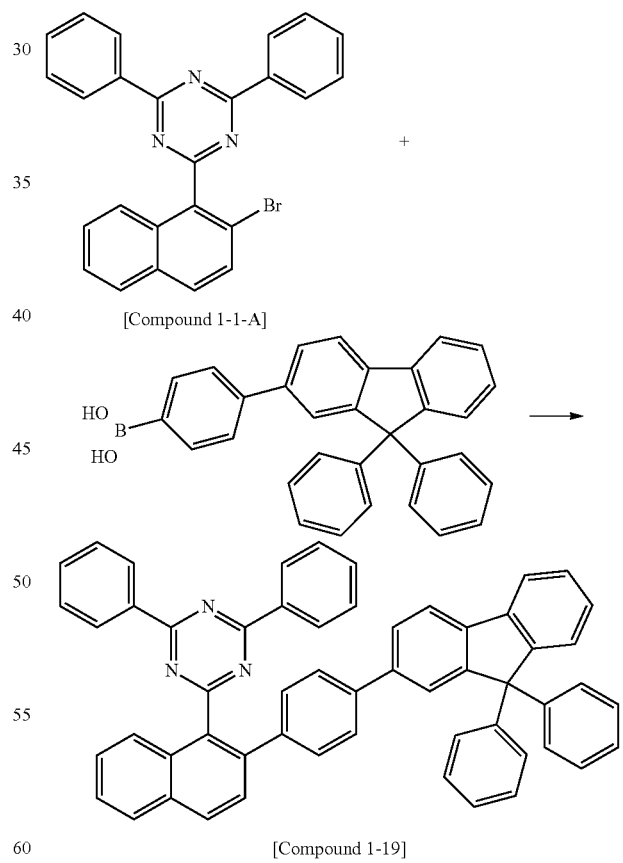

[Compound 1-19]

Compound 1-19 was obtained in the same manner as in the method for preparing Compound 1-1, except that (4-(9,9-diphenyl-9H-fluoren-2-yl)phenyl)boronic acid was used instead of (4-(6-phenylpyridazin-3-yl)phenyl)boronic acid.

MS: [M+H]⁺=752

<Preparation Example 7> Synthesis of Compound 1-27

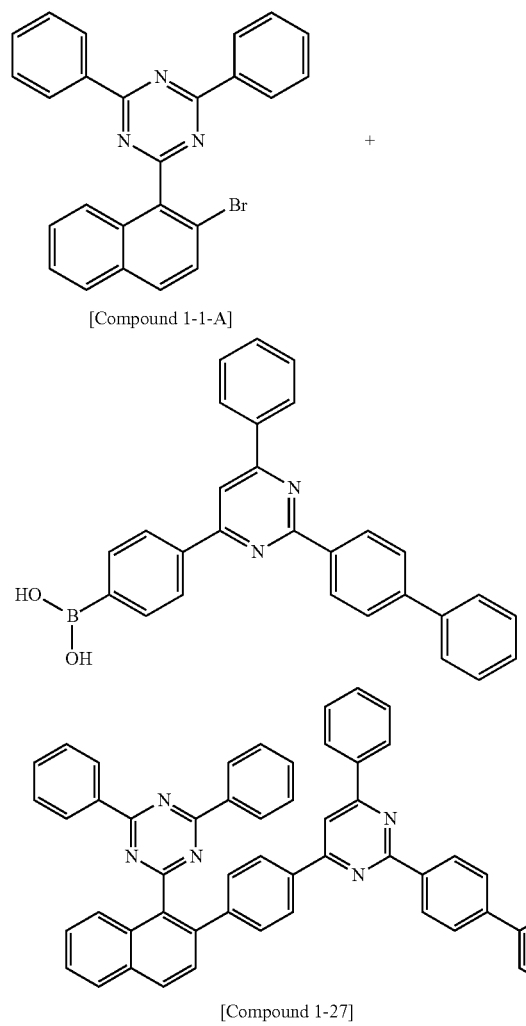

[Compound 1-1-A]

[Compound 1-27]

Compound 1-27 was obtained in the same manner as in the method for preparing Compound 1-1, except that (4-(2-([1,1'-biphenyl]-4-yl)-6-phenylpyrimidin-4-yl)phenyl)boronic acid was used instead of (4-(6-phenylpyridazin-3-yl)phenyl)boronic acid.
MS: [M+H]$^+$=742

<Preparation Example 8> Synthesis of Compound 1-36

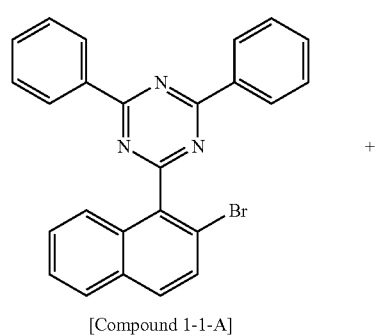

[Compound 1-1-A]

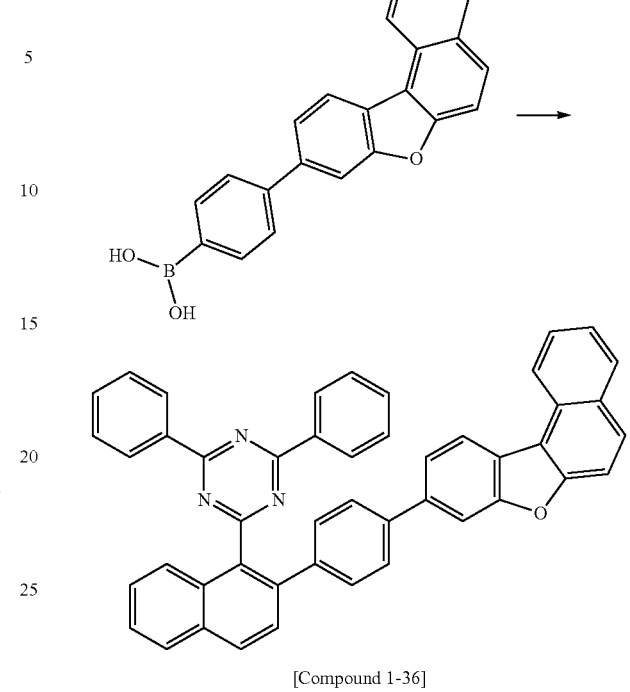

[Compound 1-36]

Compound 1-36 was obtained in the same manner as in the method for preparing Compound 1-1, except that (4-(naphtho[2,1-b]benzofuran-9-yl)phenyl)boronic acid was used instead of (4-(6-phenylpyridazin-3-yl)phenyl)boronic acid.
MS: [M+H]$^+$=652

<Preparation Example 9> Synthesis of Compound 1-38

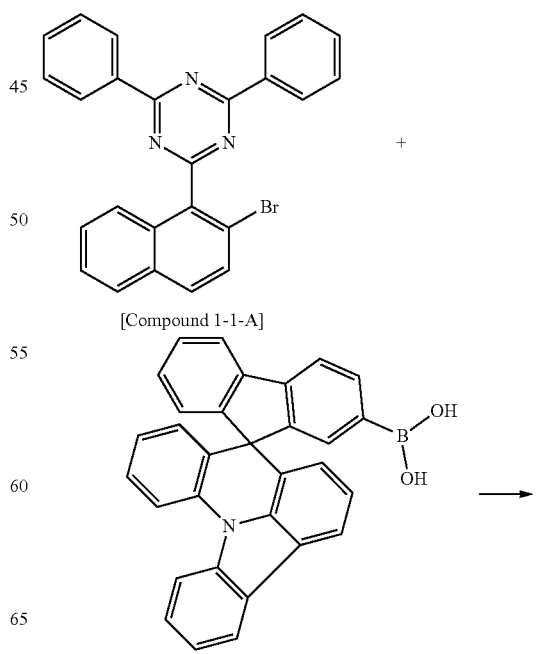

[Compound 1-1-A]

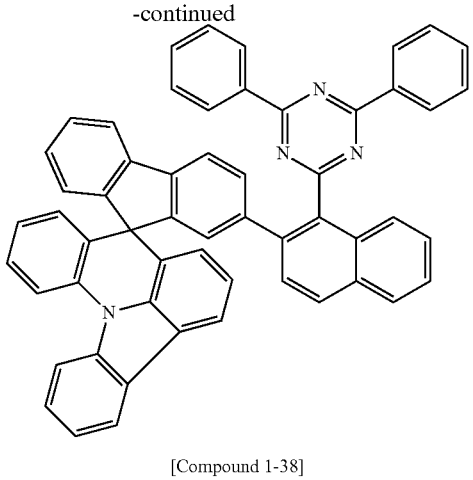

[Compound 1-38]

Compound 1-38 was obtained in the same manner as in the method for preparing Compound 1-1, except that spiro[fluoren-9,8'-indolo[3,2,1-de]acridin]-2-yl boronic acid was used instead of (4-(6-phenylpyridazin-3-yl)phenyl)boronic acid.

MS: [M+H]$^+$=763

<Preparation Example 10> Synthesis of Compound 1-39

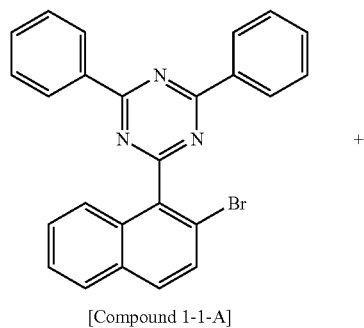

[Compound 1-1-A]

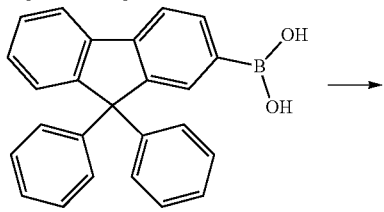

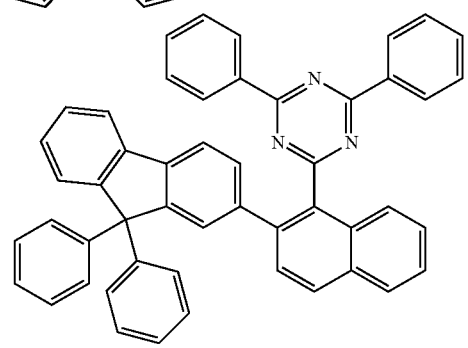

[Compound 1-39]

Compound 1-39 was obtained in the same manner as in the method for preparing Compound 1-1, except that (9,9-diphenyl-9H-fluoren-2-yl)boronic acid was used instead of (4-(6-phenylpyridazin-3-yl)phenyl)boronic acid.

MS: [M+H]$^+$=676

<Preparation Example 11> Synthesis of Compound 2-31

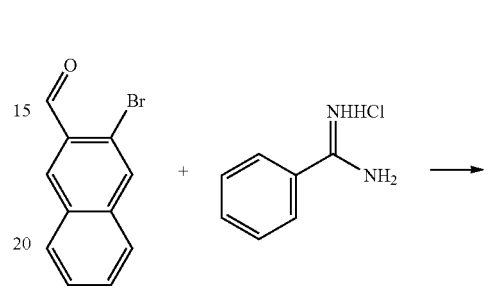

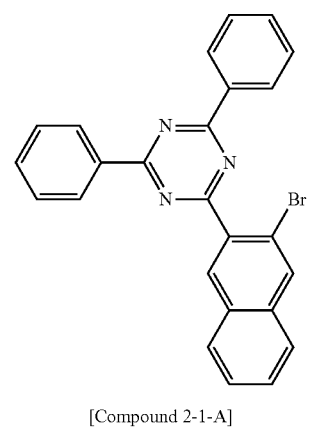

[Compound 2-1-A]

Compound 2-1-A was obtained in the same manner as in the method for preparing Compound 1-1-A, except that 3-bromo-2-naphthaldehyde was used instead of 2-bromo-1-naphthaldehyde.

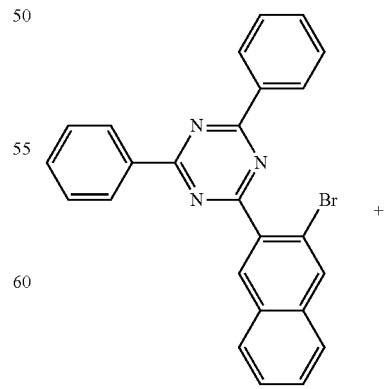

[Compound 2-1-A]

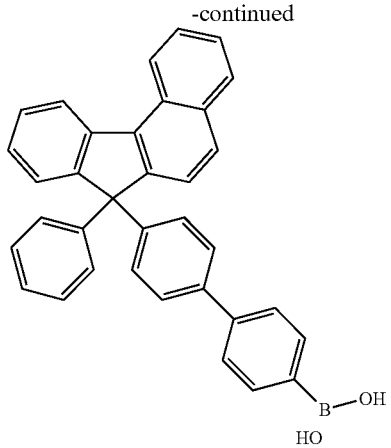

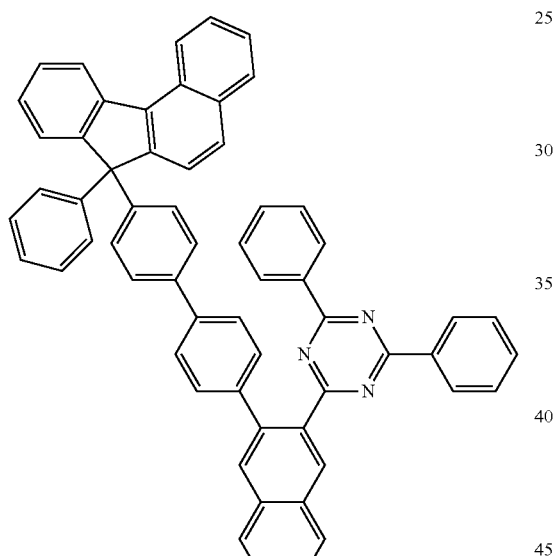

[Compound 2-31]

Compound 2-31 was obtained in the same manner as in the method for preparing Compound 1-1, except that [Compound 2-1-A] was used instead of [Compound 1-1-A], and (4'-(7-phenyl-7H-benzo[c]fluoren-7-yl)-[1,1'-biphenyl]-4-yl)boronic acid was used instead of (4-(6-phenylpyridazin-3-yl)phenyl)boronic acid.

MS: $[M+H]^+$=802

<Preparation Example 12> Synthesis of Compound 2-33

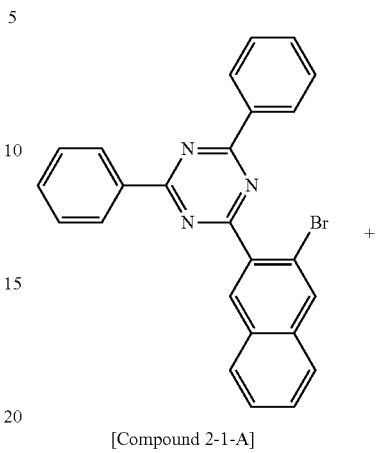

[Compound 2-1-A]

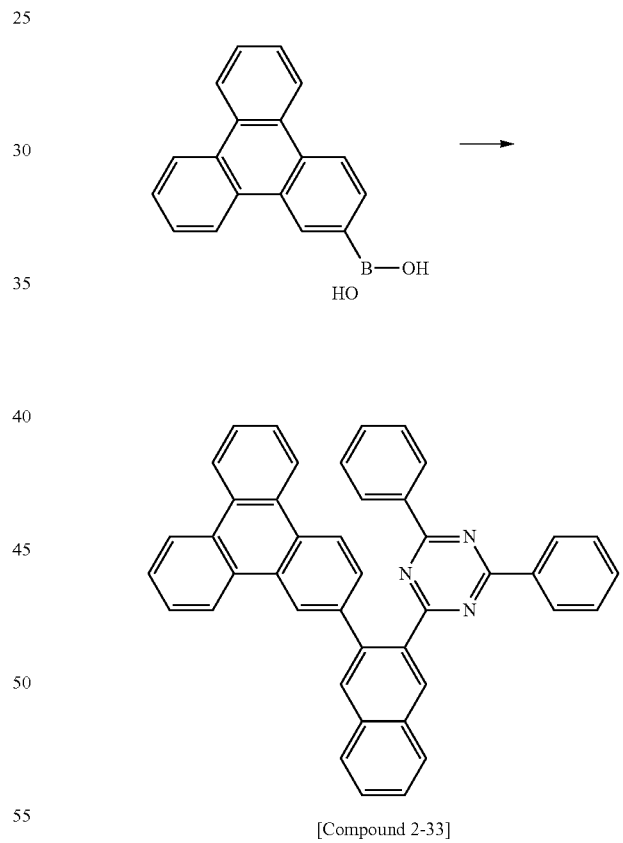

[Compound 2-33]

Compound 2-33 was obtained in the same manner as in the method for preparing Compound 1-1, except that [Compound 2-1-A] was used instead of [Compound 1-1-A], and triphenylene-2-yl boronic acid was used instead of (4-(6-phenylpyridazin-3-yl)phenyl)boronic acid.

MS: $[M+H]^+$=586

<Preparation Example 13> Synthesis of Compound 2-35

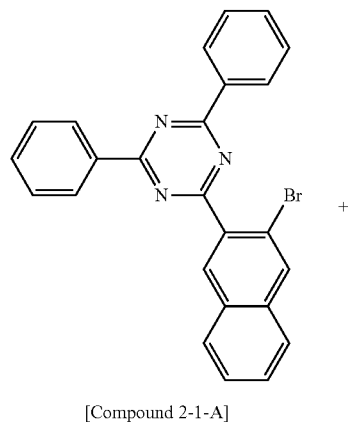

[Compound 2-1-A]

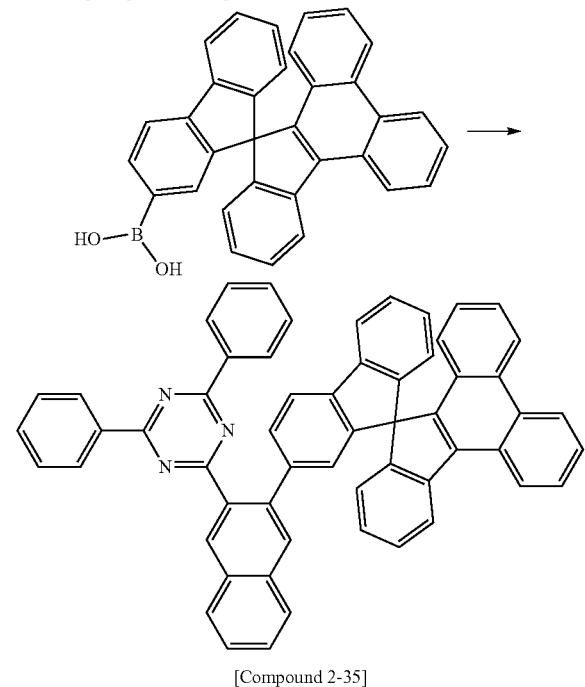

[Compound 2-35]

Compound 2-35 was obtained in the same manner as in the method for preparing Compound 1-1, except that [Compound 2-1-A] was used instead of [Compound 1-1-A], and spiro[fluoren-9,13'-indeno[1,2-yl]phenanthren]-2-yl]boronic acid was used instead of (4-(6-phenylpyridazin-3-yl)phenyl)boronic acid.

MS: [M+H]$^+$=774

<Preparation Example 14> Synthesis of Compound 3-16

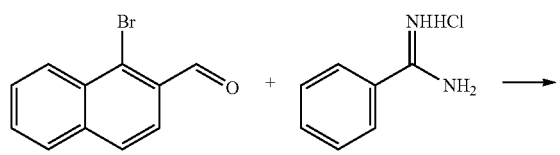

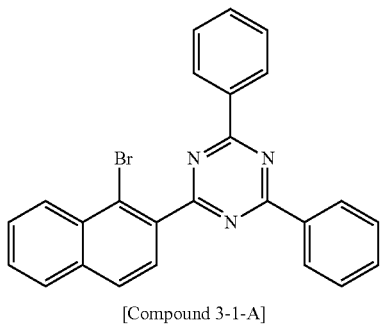

[Compound 3-1-A]

Compound 3-1-A was obtained in the same manner as in the method for preparing Compound 1-1-A, except that 1-bromo-2-naphthaldehyde was used instead of 2-bromo-1-naphthaldehyde.

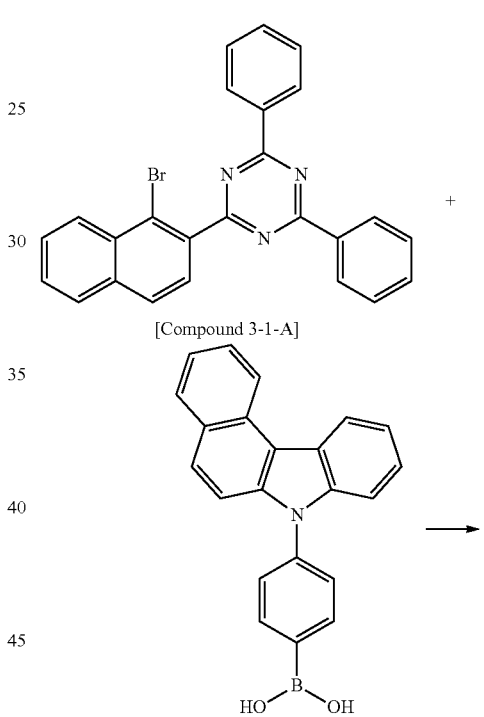

[Compound 3-1-A]

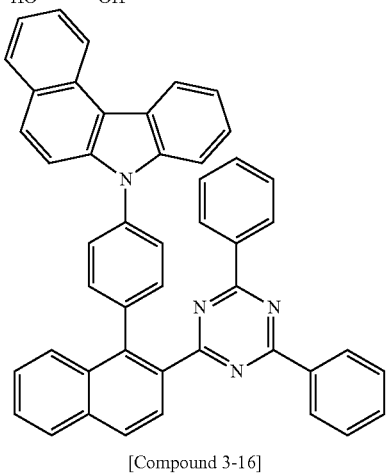

[Compound 3-16]

Compound 3-16 was obtained in the same manner as in the method for preparing Compound 1-1, except that [Compound 3-1-A] was used instead of [Compound 1-1-A], and (4-(7H-benzo[c]carbazol-7-yl)phenyl)boronic acid was used instead of (4-(6-phenylpyridazin-3-yl)phenyl)boronic acid.

MS: [M+H]$^+$=651

<Preparation Example 15> Synthesis of Compound 3-22

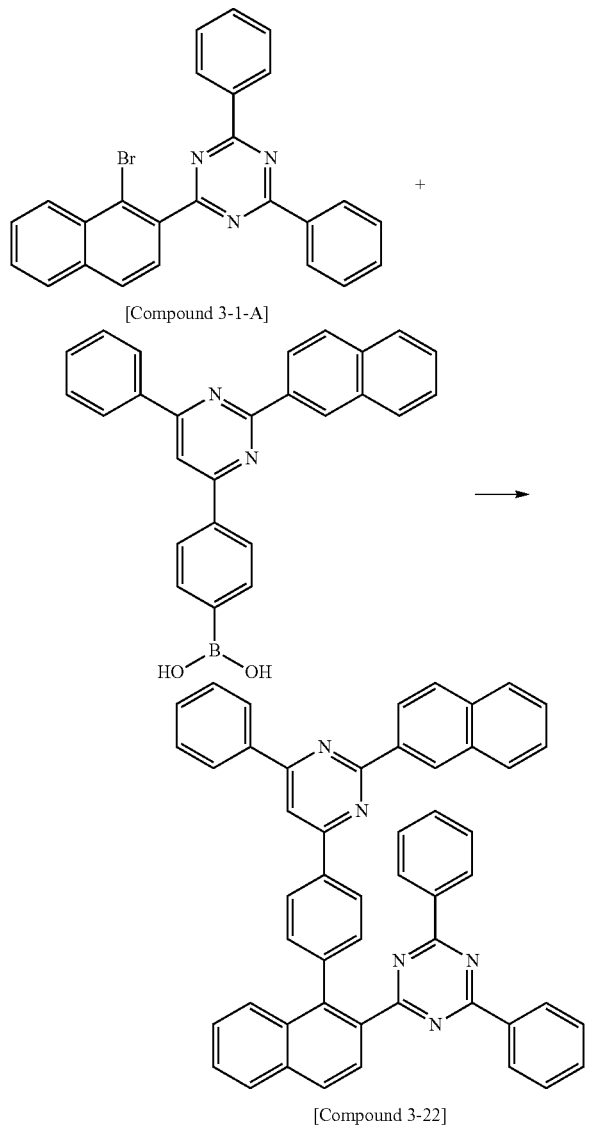

[Compound 3-22]

Compound 3-22 was obtained in the same manner as in the method for preparing Compound 1-1, except that [Compound 3-1-A] was used instead of [Compound 1-1-A], and (4-(2-(naphthalen-2-yl)-6-phenylpyrimidin-4-yl)phenyl)boronic acid was used instead of (4-(6-phenylpyridazin-3-yl)phenyl)boronic acid.

MS: [M+H]$^+$=716

<Preparation Example 16> Synthesis of Compound 3-33

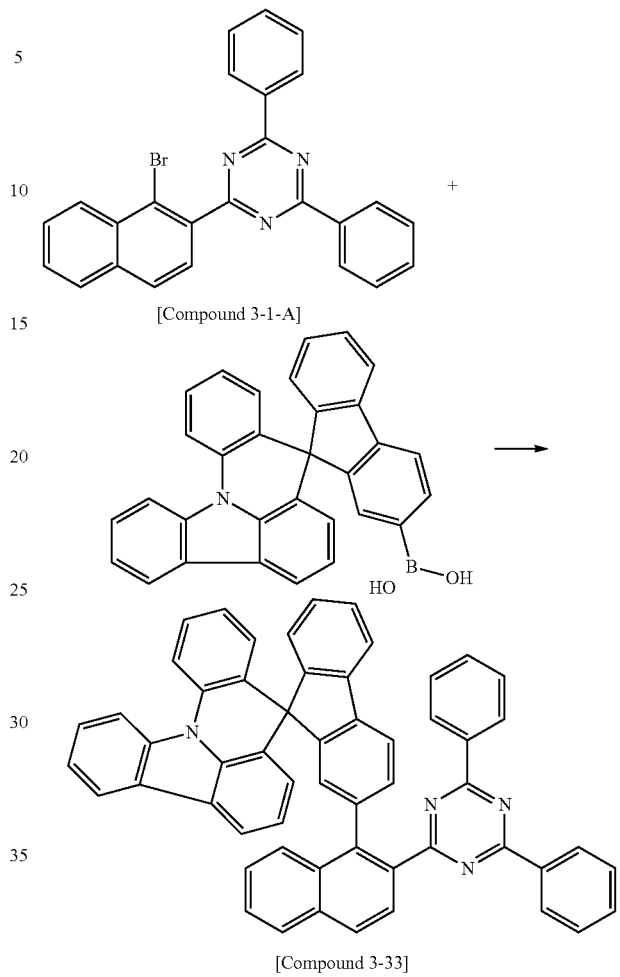

[Compound 3-33]

Compound 3-33 was obtained in the same manner as in the method for preparing Compound 1-1, except that [Compound 3-1-A] was used instead of [Compound 1-1-A], and spiro[fluoren-9,8'-indolo[3,2,1-de]acridin]-2-yl boronic acid was used instead of (4-(6-phenylpyridazin-3-yl)phenyl)boronic acid.

MS: [M+H]$^+$=763

<Preparation Example 17> Synthesis of Compound 3-34

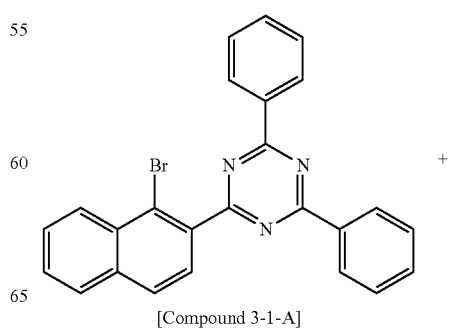

[Compound 3-1-A]

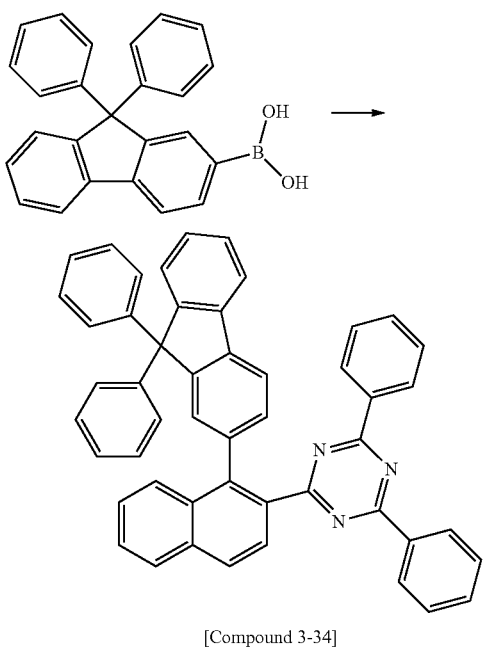

[Compound 3-34]

Compound 3-34 was obtained in the same manner as in the method for preparing Compound 1-1, except that [Compound 3-1-A] was used instead of [Compound 1-1-A], and (9,9-diphenyl-9H-fluoren-2-yl)boronic acid was used instead of (4-(6-phenylpyridazin-3-yl)phenyl)boronic acid.

MS: [M+H]$^+$=676

<Preparation Example 18> Synthesis of Compound 3-35

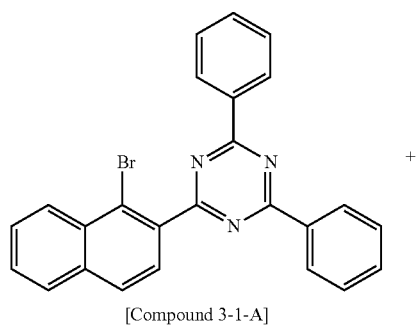

[Compound 3-1-A]

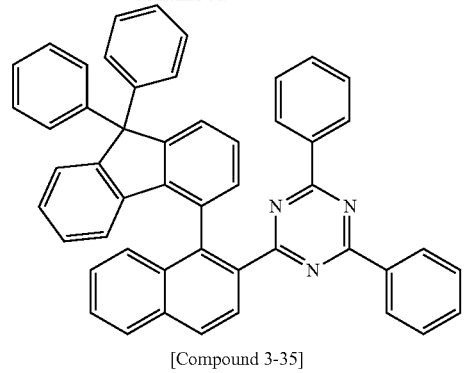

[Compound 3-35]

Compound 3-35 was obtained in the same manner as in the method for preparing Compound 1-1, except that [Compound 3-1-A] was used instead of [Compound 1-1-A], and (9,9-diphenyl-9H-fluoren-4-yl)boronic acid was used instead of (4-(6-phenylpyridazin-3-yl)phenyl)boronic acid.

MS: [M+H]$^+$=676

<Preparation Example 19> Synthesis of Compound 3-36

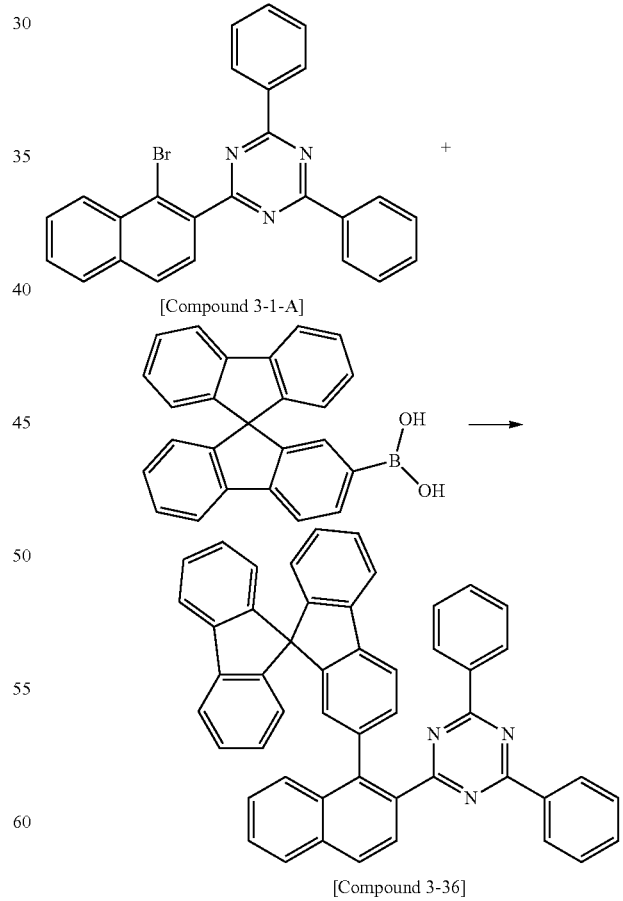

[Compound 3-1-A]

[Compound 3-36]

Compound 3-36 was obtained in the same manner as in the method for preparing Compound 1-1, except that [Compound 3-1-A] was used instead of [Compound 1-1-A], and 9,9'-spirobi[fluorene]-2-yl boronic acid was used instead of (4-(6-phenylpyridazin-3-yl)phenyl)boronic acid.

MS: [M+H]⁺=674

<Preparation Example 20> Synthesis of Compound 3-38

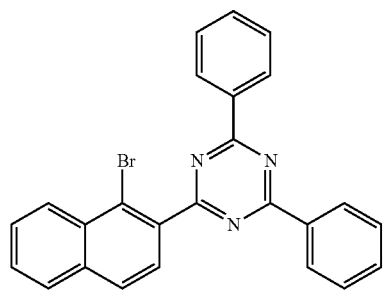
[Compound 3-1-A]

+

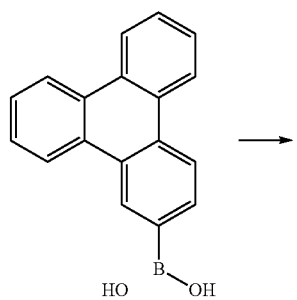

→

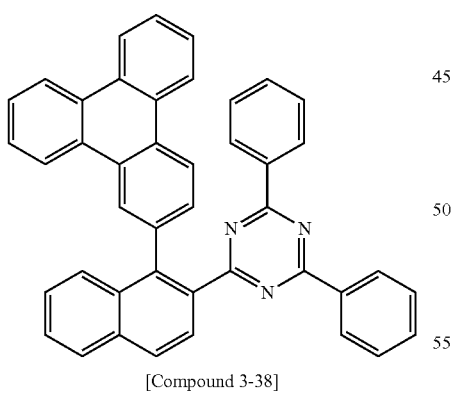
[Compound 3-38]

Compound 3-38 was obtained in the same manner as in the method for preparing Compound 1-1, except that [Compound 3-1-A] was used instead of [Compound 1-1-A], and triphenylene-2-yl boronic acid was used instead of (4-(6-phenylpyridazin-3-yl)phenyl)boronic acid.

MS: [M+H]+=586

<Preparation Example 21> Synthesis of Compound 3-39

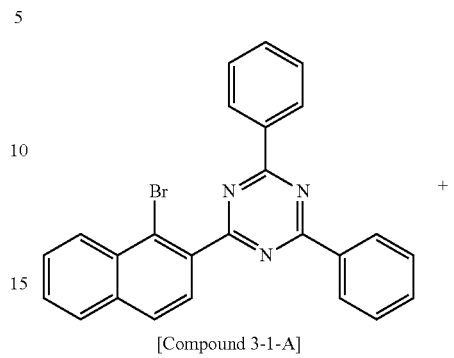
[Compound 3-1-A]

+

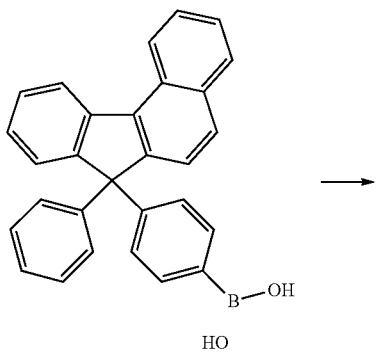

→

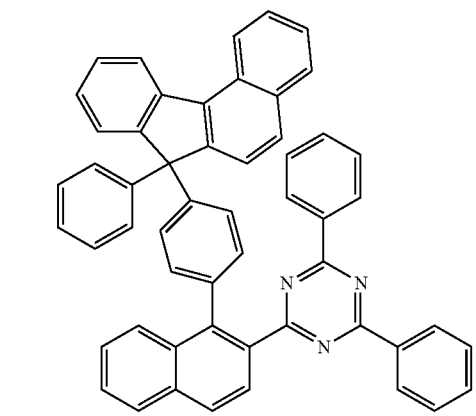
[Compound 3-39]

Compound 3-39 was obtained in the same manner as in the method for preparing Compound 1-1, except that [Compound 3-1-A] was used instead of [Compound 1-1-A], and (4-(7-phenyl-7H-benzo[c]fluoren-7-yl)phenyl)boronic acid was used instead of (4-(6-phenylpyridazin-3-yl)phenyl)boronic acid.

MS: [M+H]⁺=726

<Preparation Example 22> Synthesis of Compound 3-47

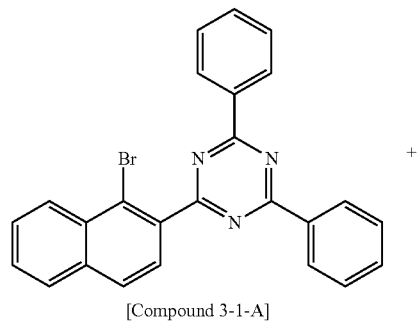

[Compound 3-1-A]

+

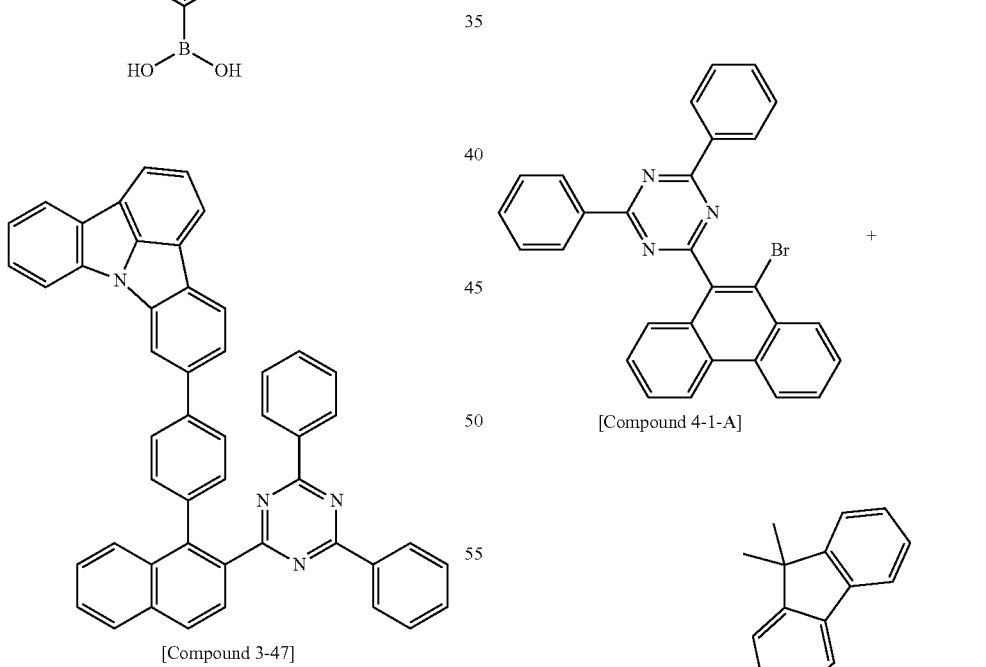

Compound 3-47 was obtained in the same manner as in the method for preparing Compound 1-1, except that [Compound 3-1-A] was used instead of [Compound 1-1-A], and (4-(indolo[3,2,1-jk]carbazol-10-yl)phenyl)boronic acid was used instead of (4-(6-phenylpyridazin-3-yl)phenyl)boronic acid.

MS: [M+H]⁺=675

<Preparation Example 23> Synthesis of Compound 4-4

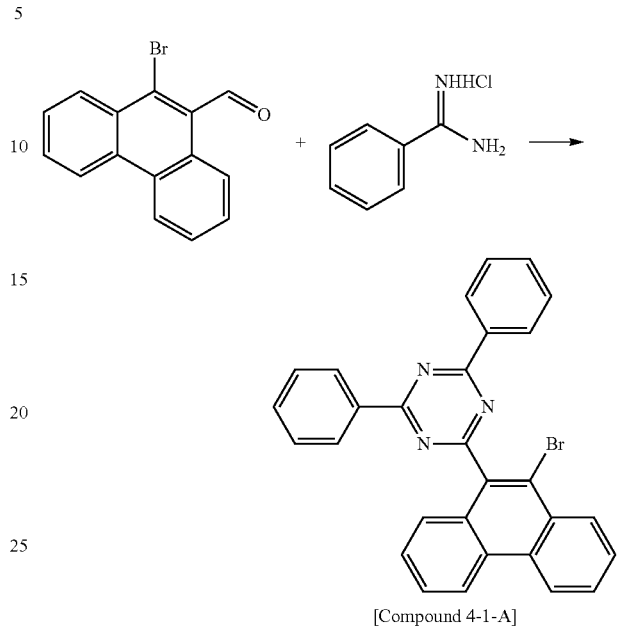

Compound 4-1-A was obtained in the same manner as in the method for preparing Compound 1-1-A, except that 10-bromophenanthrene-9-carbaldehyde was used instead of 2-bromo-1-naphthaldehyde.

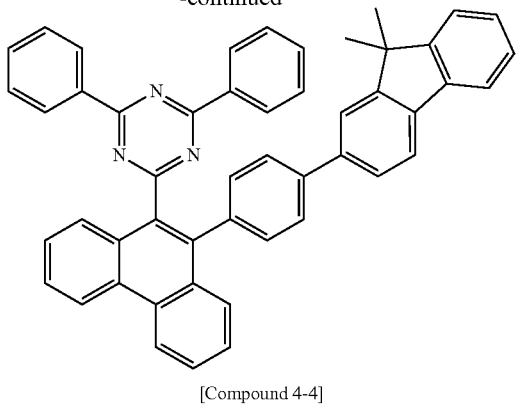

[Compound 4-4]

Compound 4-4 was obtained in the same manner as in the method for preparing Compound 1-1, except that [Compound 4-1-A] was used instead of [Compound 1-1-A], and (4-(9,9-dimethyl-9H-fluoren-2-yl)phenyl)boronic acid was used instead of (4-(6-phenylpyridazin-3-yl)phenyl)boronic acid.

MS: [M+H]$^+$=678

<Preparation Example 24> Synthesis of Compound 4-12

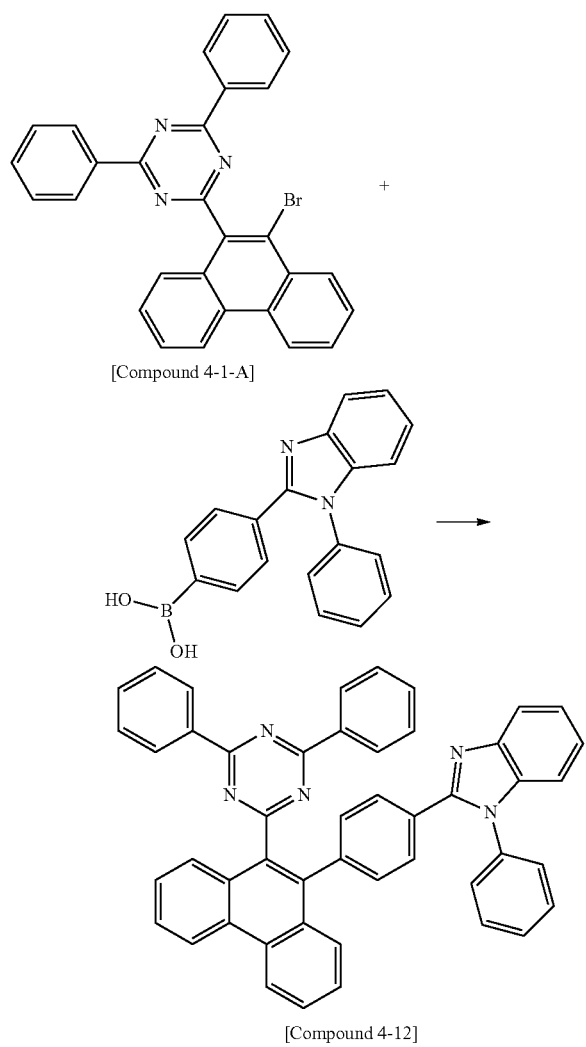

[Compound 4-1-A]

[Compound 4-12]

Compound 4-12 was obtained in the same manner as in the method for preparing Compound 1-1, except that [Compound 4-1-A] was used instead of [Compound 1-1-A], and (4-(1-phenyl-1H-benzo[d]imidazol-2-yl)phenyl)boronic acid was used instead of (4-(6-phenylpyridazin-3-yl)phenyl)boronic acid.

MS: [M+H]$^+$=678

<Preparation Example 25> Synthesis of Compound 4-3

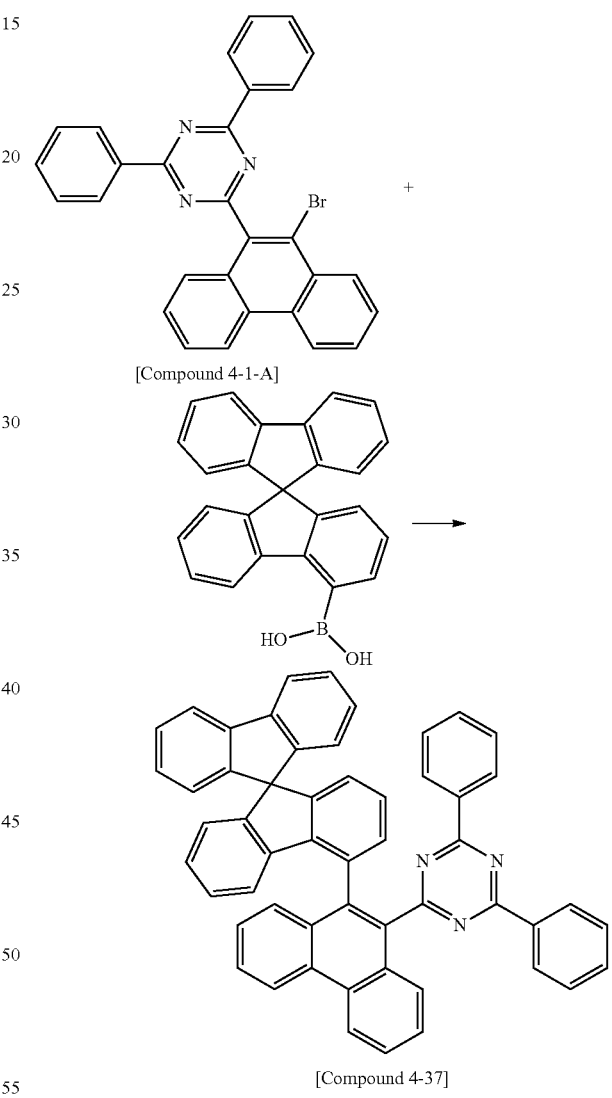

[Compound 4-1-A]

[Compound 4-37]

Compound 4-37 was obtained in the same manner as in the method for preparing Compound 1-1, except that [Compound 4-1-A] was used instead of [Compound 1-1-A], and 9,9'-spirobi[fluorene]-4-yl boronic acid was used instead of (4-(6-phenylpyridazin-3-yl)phenyl)boronic acid.

MS: [M+H]$^+$=724

<Preparation Example 26> Synthesis of Compound 4-51

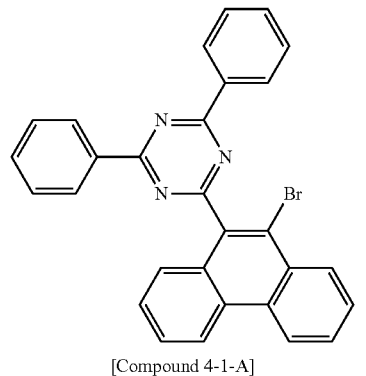

[Compound 4-1-A]

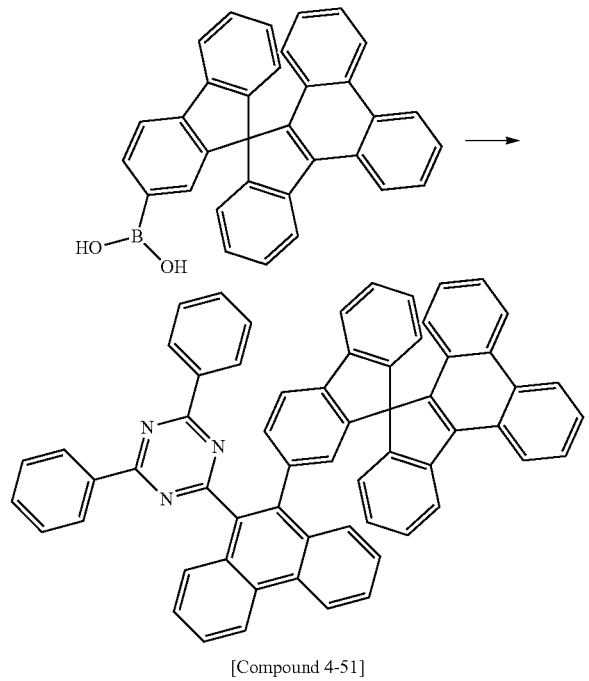

[Compound 4-51]

Compound 4-51 was obtained in the same manner as in the method for preparing Compound 1-1, except that [Compound 4-1-A] was used instead of [Compound 1-1-A], and spiro[fluoren-9,9'-indeno[2,1-1]phenanthren]-2-yl boronic acid was used instead of (4-(6-phenylpyridazin-3-yl)phenyl) boronic acid.

MS: [M+H]⁺=824

<Preparation Example 27> Synthesis of Compound 5-10

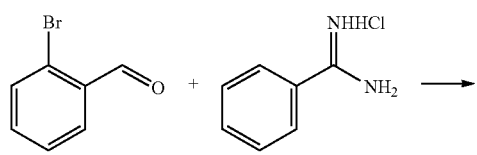

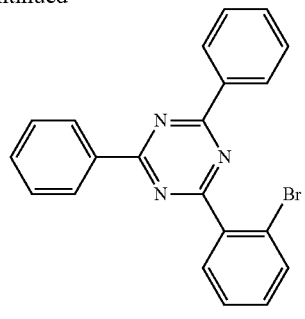

[Compound 5-1-A]

Compound 5-1-A was obtained in the same manner as in the method for preparing Compound 1-1-A, except that 2-bromobenzaldehyde was used instead of 2-bromo-1-naphthaldehyde.

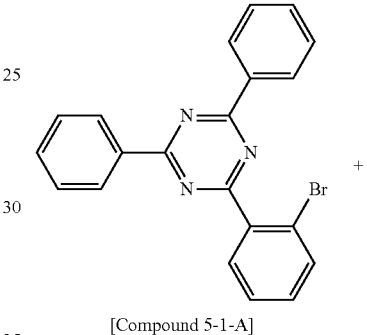

[Compound 5-1-A]

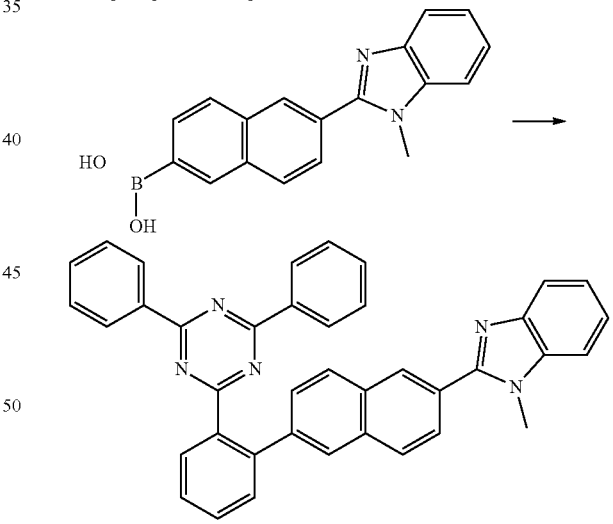

[Compound 5-10]

Compound 5-10 was obtained in the same manner as in the method for preparing Compound 1-1, except that [Compound 5-1-A] was used instead of [Compound 1-1-A], and (6-(1-methyl-1H-benzo[d]imidazol-2-yl)naphthalen-2-yl) boronic acid was used instead of (4-(6-phenylpyridazin-3-yl)phenyl)boronic acid.

MS: [M+H]⁺=566

<Preparation Example 28> Synthesis of Compound 5-28

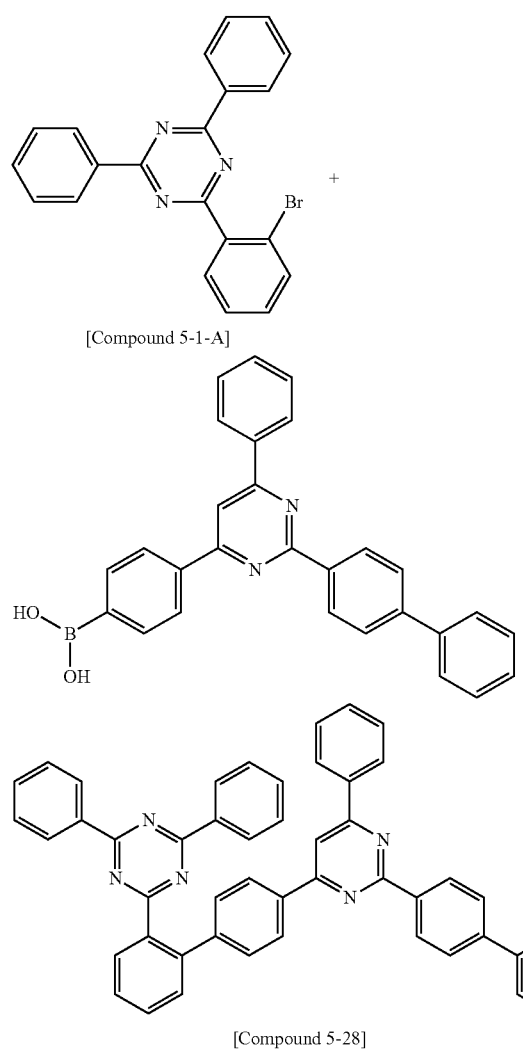

Compound 5-28 was obtained in the same manner as in the method for preparing Compound 1-1, except that [Compound 5-1-A] was used instead of [Compound 1-1-A], and (4-(2-([1,1'-biphenyl]-4-yl)-6-phenylpyrimidin-4-yl)phenyl)boronic acid was used instead of (4-(6-phenylpyridazin-3-yl)phenyl)boronic acid.

MS: $[M+H]^+=692$

<Preparation Example 29> Synthesis of Compound 5-52

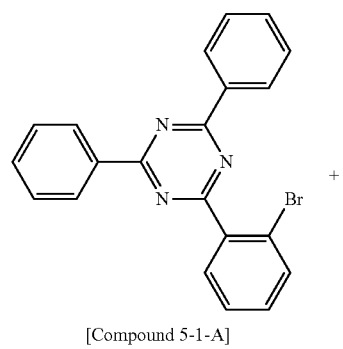

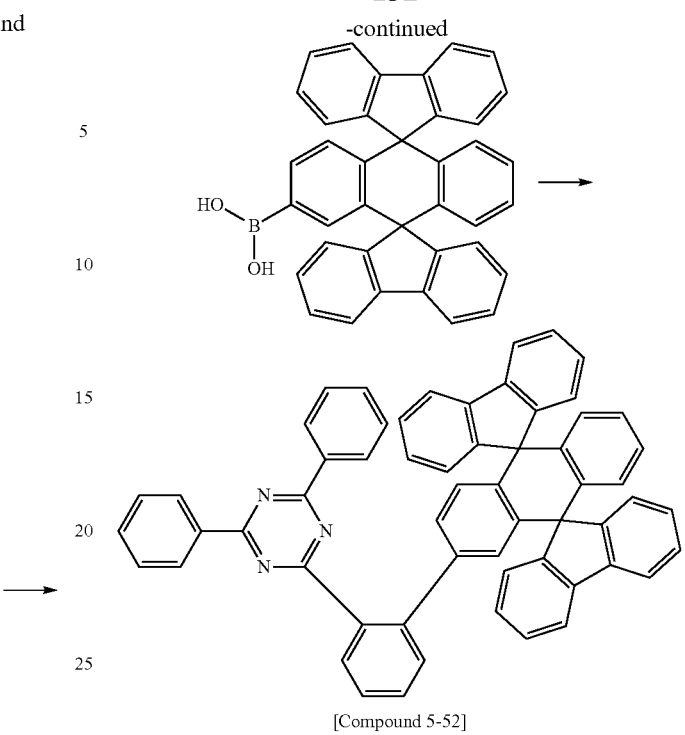

Compound 5-52 was obtained in the same manner as in the method for preparing Compound 1-1, except that [Compound 5-1-A] was used instead of [Compound 1-1-A], and dispiro[fluoren-9,9'-anthracen-10',9''-fluoren]-2'-yl boronic acid was used instead of (4-(6-phenylpyridazin-3-yl)phenyl) boronic acid.

MS: $[M+H]^+=788$

<Preparation Example 30> Synthesis of Compound 3-48

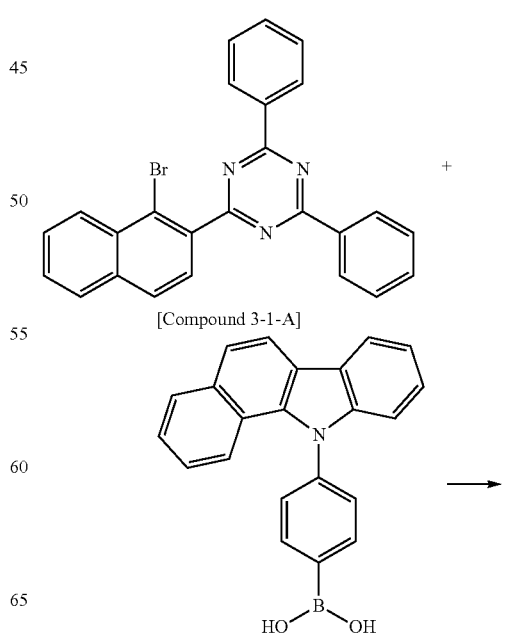

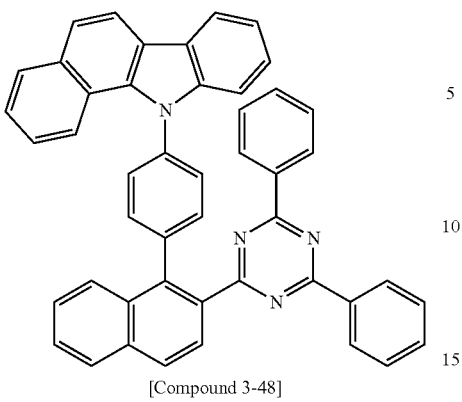

[Compound 3-48]

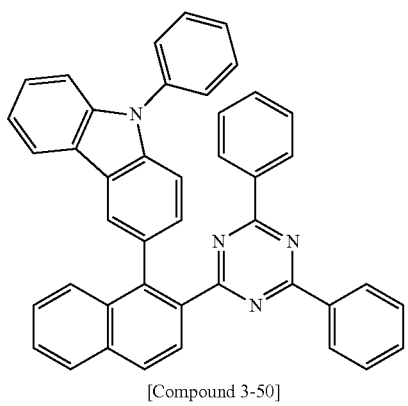

[Compound 3-50]

Compound 3-48 was obtained in the same manner as in the method for preparing Compound 1-1, except that [Compound 3-1-A] was used instead of [Compound 1-1-A], and (4-(11H-benzo[a]carbazol-11-yl)phenyl boronic acid was used instead of (4-(6-phenylpyridazin-3-yl)phenyl)boronic acid.

MS: [M+H]$^+$=651

<Preparation Example 31> Synthesis of Compound 3-50

Compound 3-50 was obtained in the same manner as in the method for preparing Compound 1-1, except that [Compound 3-1-A] was used instead of [Compound 1-1-A], and (9-phenyl-9H-carbazol-3-yl)boronic acid was used instead of (4-(6-phenylpyridazin-3-yl)phenyl)boronic acid.

MS: [M+H]$^+$=601

<Preparation Example 32> Synthesis of Compound 1-17

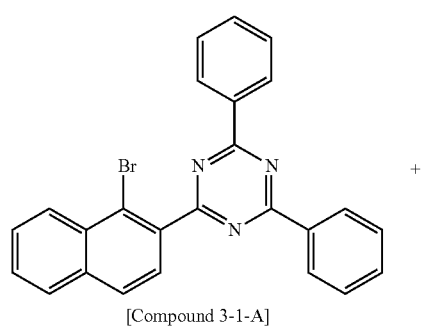

[Compound 3-1-A]

+

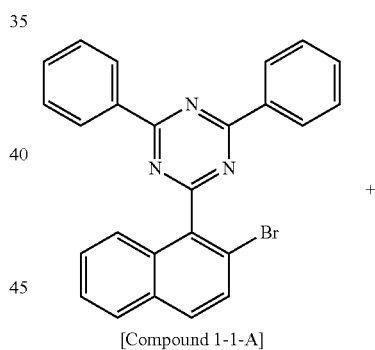

[Compound 1-1-A]

+

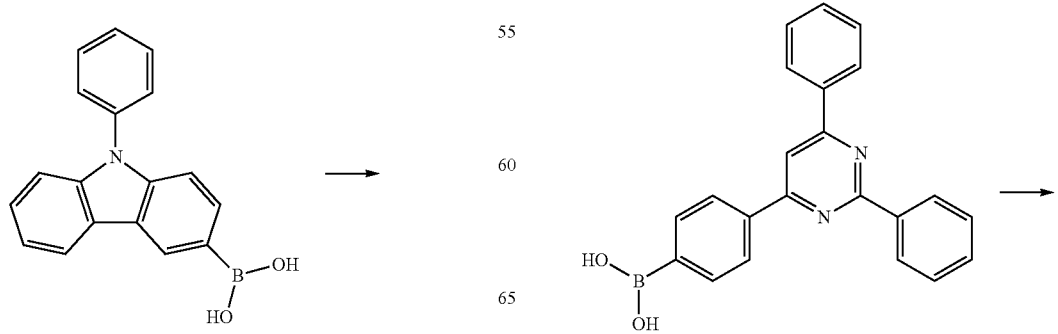

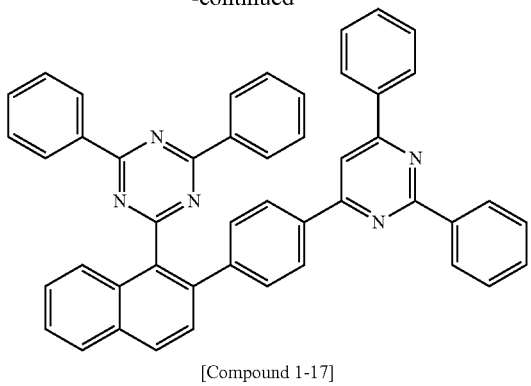

[Compound 1-17]

Compound 1-17 was obtained in the same manner as in the method for preparing Compound 1-1, except that (4-(2,6-diphenylpyrimidin-4-yl)phenyl)boronic acid was used instead of (4-(6-phenylpyridazin-3-yl)phenyl)boronic acid.

MS: [M+H]⁺=666

<Preparation Example 33> Synthesis of Compound 6-1

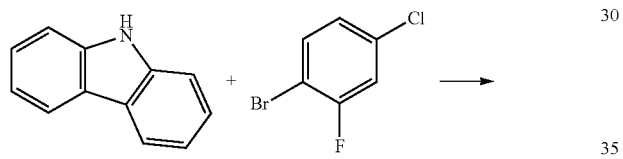

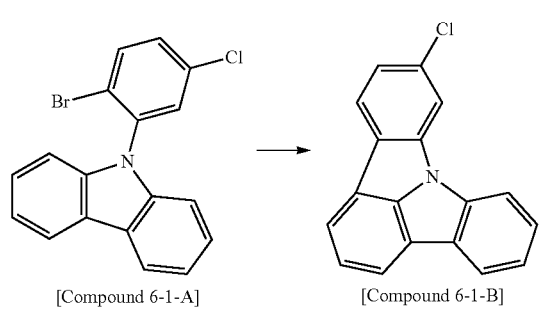

[Compound 6-1-A]   [Compound 6-1-B]

Under nitrogen flow, 9H-carbazole (10.0 g, 59.8 mmol), 1-bromo-4-chloro-2-fluorobenzene (12.5 g, 59.8 mmol), and sodium tert-butoxide (8.6 g, 89.7 mmol) were put into 240 mL of a dimethylacetamide (DMAc) solvent, and the resulting solution was heated and stirred for 16 hours. The reaction solution was cooled and then filtered, and then the filtered material was subjected to slurry purification using EtOH to obtain [Compound 6-1-A] (18.0 g, yield 86%).

Under nitrogen flow, [Compound 6-1-A] (18.0 g, 50.5 mmol), calcium chloride (10.5 g, 75.7 mmol), and tetrakis(triphenylphosphine)palladium(0) (1.7 g, 1.5 mmol) were put into 200 mL of a tetrahydrofuran solvent, and the resulting solution was heated and stirred for 1 hour. The reaction solution was cooled and then filtered, and then the filtered material was subjected to slurry purification using EtOH to obtain [Compound 6-1-B] (12.5 g, yield 90%).

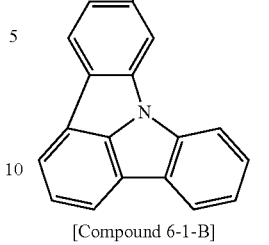

[Compound 6-1-B]

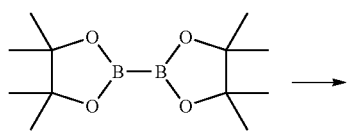

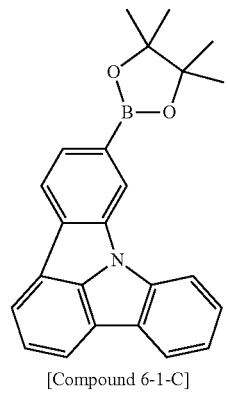

[Compound 6-1-C]

Under nitrogen flow, [Compound 6-1-B] (12.5 g, 45.3 mmol), 4,4,4',4',5,5,5',5'-octamethyl-2,2'-bi(1,3,2-dioxaborolane) (12.7 g, 49.9 mmol), and potassium acetate (9.4 g, 68.0 mmol) were put into 200 mL of a dioxane solvent, and the resulting solution was heated and stirred. After 30 minutes, bis(dibenzylideneacetone)palladium(0) (0.8 g, 1.4 mmol) and tricyclohexylphosphine (0.8 g, 2.7 mmol) were put thereinto, and the resulting mixture was heated and stirred for 3 hours. The reaction solution was cooled and then filtered to produce a solid, and then the solid was subjected to slurry purification using EtOH to obtain [Compound 6-1-C] (15.0 g, yield 90%).

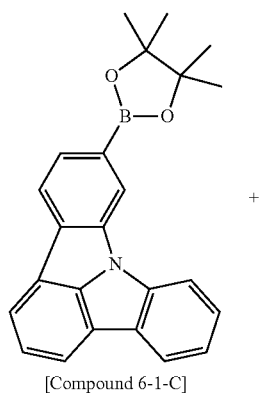

[Compound 6-1-C]

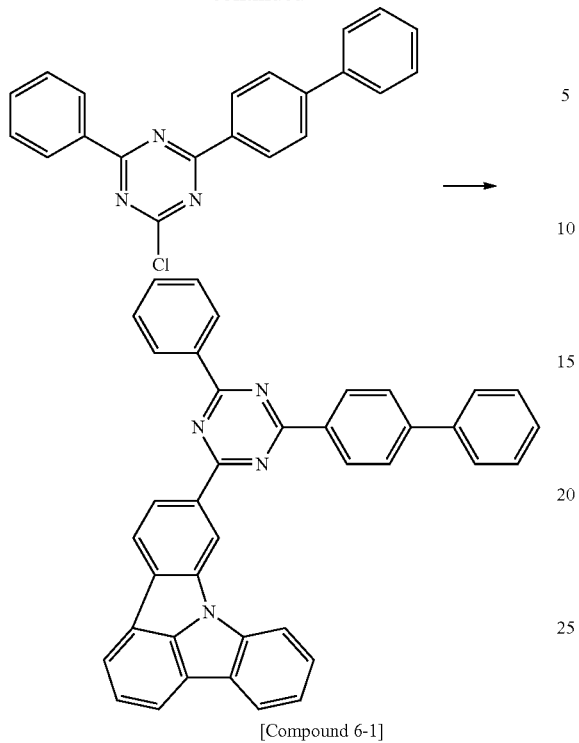

[Compound 6-1]

Under nitrogen flow, [Compound 6-1-C] (15.0 g, 40.8 mmol) and 2-([1,1'-biphenyl]-4-yl)-4-chloro-6-phenyl-1,3,5-triazine (14.0 g, 40.8 mmol) were put into 200 mL of a tetrahydrofuran solvent, an aqueous solution of calcium chloride (9.4 g, 68.0 mmol) was put to the solution, and the resulting solution was heated and stirred. After 30 minutes, tetrakis(triphenylphosphine)palladium(0) (1.4 g, 1.2 mmol) was put thereinto, and the resulting mixture was heated and stirred for 4 hours. The reaction solution was cooled and then filtered, and then the filtered material was subjected to slurry purification using EtOH to obtain [Compound 6-1] (20.0 g, yield 89%).

MS: [M+H]$^+$=549

<Preparation Example 34> Synthesis of Compound 6-2

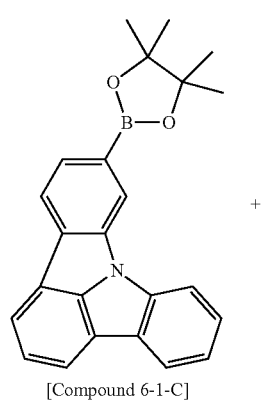

[Compound 6-1-C]

+

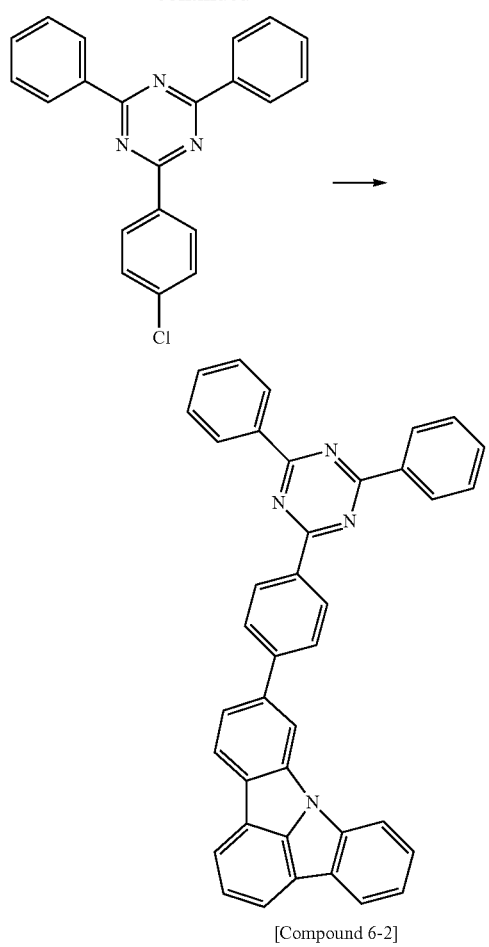

[Compound 6-2]

Compound 6-2 was obtained in the same manner as in the method for preparing [Compound 6-1], except that 2-(4-chlorophenyl)-4,6-diphenyl-1,3,5-triazine was used instead of 2-([1,1'-biphenyl]-4-yl)-4-chloro-6-phenyl-1,3,5-triazine.

MS: [M+H]$^+$=549

<Preparation Example 35> Synthesis of Compound 6-3

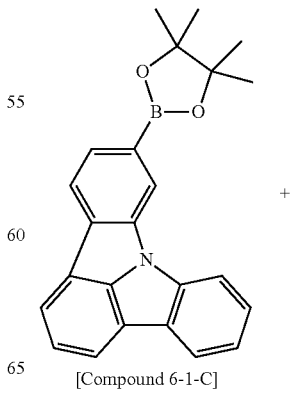

[Compound 6-1-C]

+

-continued

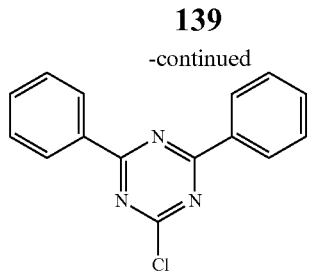

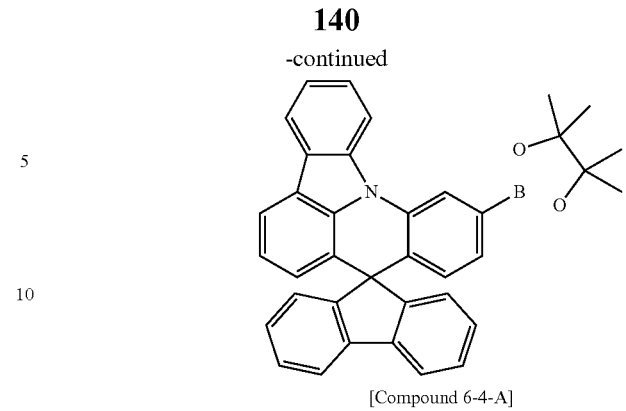

[Compound 6-4-A]

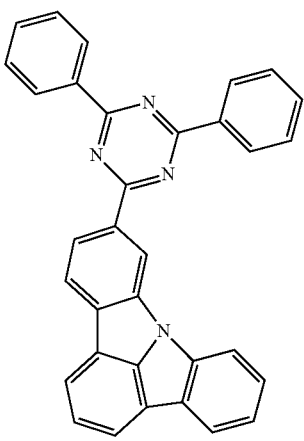

[Compound 6-3]

Under nitrogen flow, 11'-chlorospiro[fluoren-9,8'-indolo[3,2,1-de]acridine] (15.0 g, 34.1 mmol), 4,4,4',4',5,5,5',5'-octamethyl-2,2'-bi(1,3,2-dioxaborolane) (9.5 g, 37.5 mmol), and potassium acetate (6.6 g, 68.2 mmol) were into 200 mL of a dioxane solvent, and the resulting solution was heated and stirred. After 30 minutes, bis(dibenzylideneacetone)palladium(0) (0.59 g, 1.02 mmol) and tricyclohexylphosphine (0.55 g, 2.04 mmol) were put thereinto, and the resulting mixture was heated and stirred for 3 hours. The reaction solution was cooled and then filtered to produce a solid, and then the solid was subjected to slurry purification using EtOH to obtain [Compound 6-4-A] (17.0 g, yield 94%).

[Compound 6-3] was obtained in the same manner as in the method for preparing [Compound 6-1], except that 2-chloro-4,6-diphenyl-1,3,5-triazine was used instead of 2-([1,1'-biphenyl]-4-yl)-4-chloro-6-phenyl-1,3,5-triazine.

MS: [M+H]⁺=473

<Preparation Example 36> Synthesis of Compound 6-4

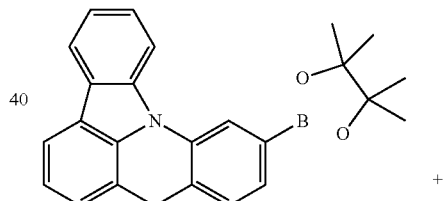

[Compound 6-4-A]

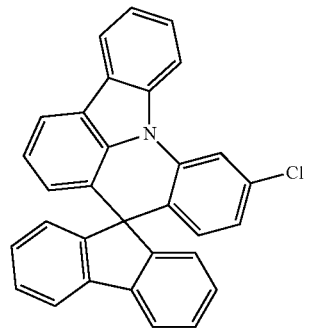

+

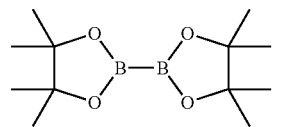

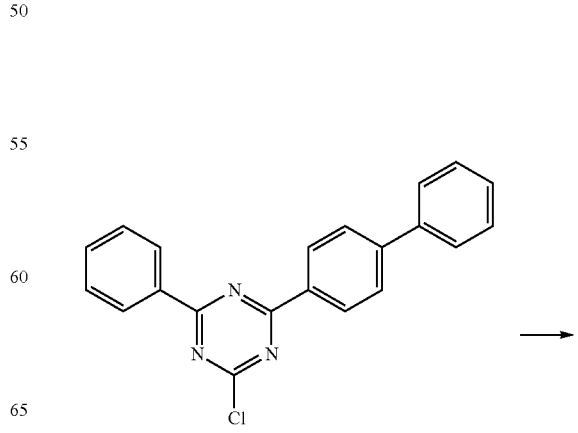

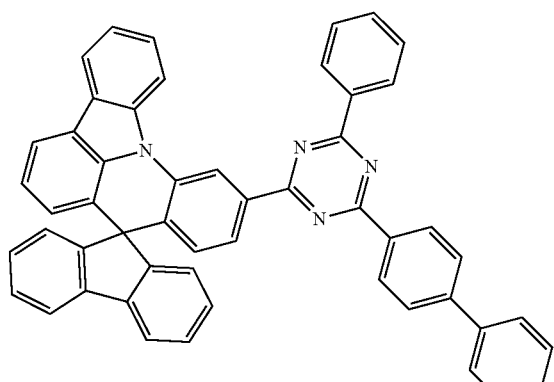

[Compound 6-4]

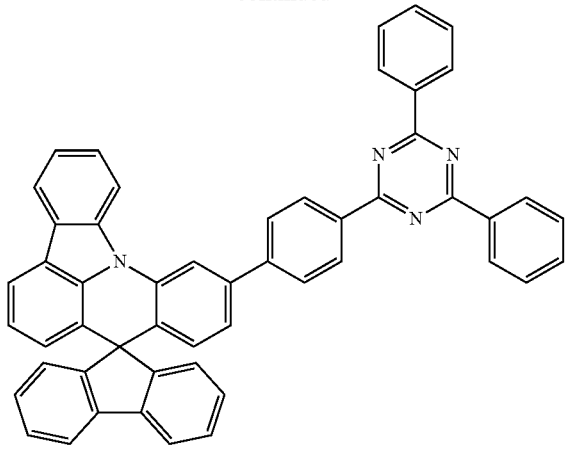

[Compound 6-6]

Under nitrogen flow, Compound 6-4-A (17.0 g, 32.0 mmol) and 2-([1,1'-biphenyl]-4-yl)-4-chloro-6-phenyl-1,3,5-triazine (11.0 g, 32.0 mmol) were put into 200 mL of a tetrahydrofuran solvent, an aqueous solution of calcium chloride (6.6 g, 48.0 mmol) was put to the solution, and the resulting solution was heated and stirred. After 30 minutes, tetrakis(triphenylphosphine)palladium(0) (1.1 g, 0.96 mmol) was put thereinto, and the resulting mixture was heated and stirred for 2 hours. The reaction solution was cooled and then filtered, and then the filtered material was subjected to slurry purification using EtOH to obtain [Compound 6-4] (19.0 g, yield 84%).

MS: [M+H]$^+$=713

<Preparation Example 37> Synthesis of Compound 6-6

[Compound 6-6] was obtained in the same manner as in the method for preparing Compound 6-4, except that 2-(4-chlorophenyl)-4,6-diphenyl-1,3,5-triazine was used instead of 2-([1,1'-biphenyl]-4-yl)-4-chloro-6-phenyl-1,3,5-triazine.

MS: [M+H]$^+$=713

<Preparation Example 38> Synthesis of Compound 6-7

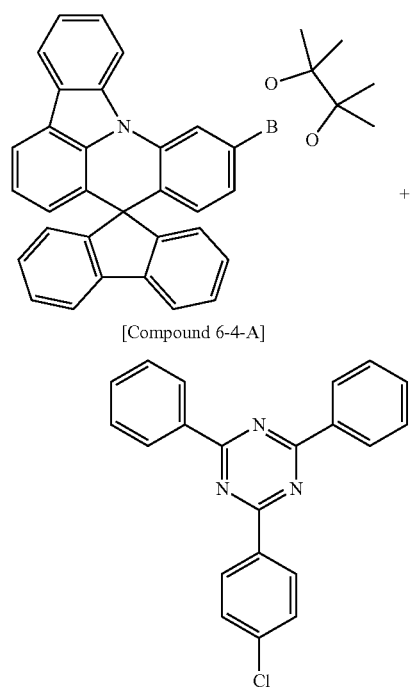

[Compound 6-4-A]

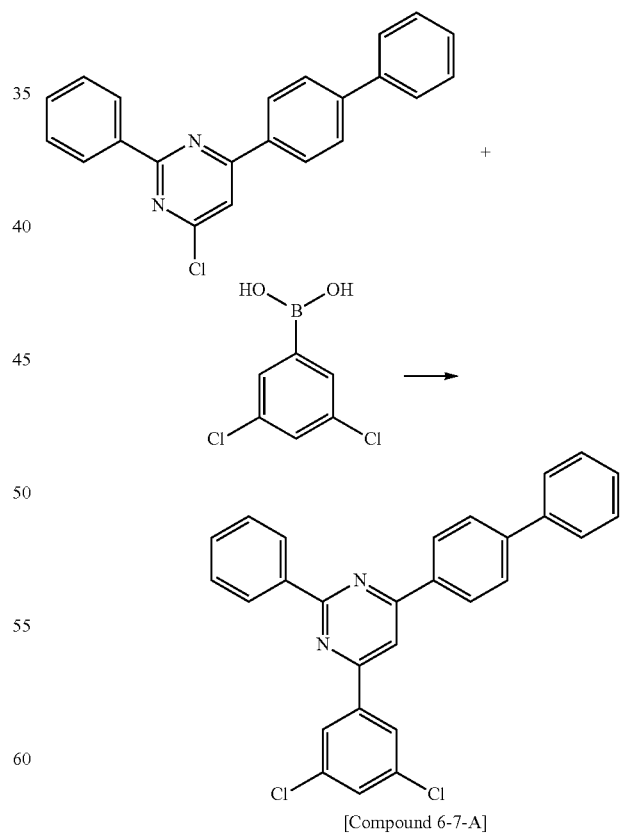

[Compound 6-7-A]

Under nitrogen flow, 4-([1,1'-biphenyl]-4-yl)-6-chloro-2-phenylpyrimidine (20 g, 58.3 mmol), (3,5-dichlorophenyl)boronic acid (11.7 g, 61.3 mmol), and an aqueous solution of calcium chloride (12.1 g, 87.5 mmol) were put into 250 mL of a tetrahydrofuran solvent, and the resulting solution was heated and stirred. After 30 minutes, tetrakis(triphenylphosphine)palladium(0) (2.0 g, 1.8 mmol) was put thereinto, and the resulting mixture was heated and stirred for 5 hours. The reaction solution was cooled and then filtered, and then the filtered material was subjected to slurry purification using EtOH to obtain [Compound 6-7-A] (24.0 g, yield 91%).

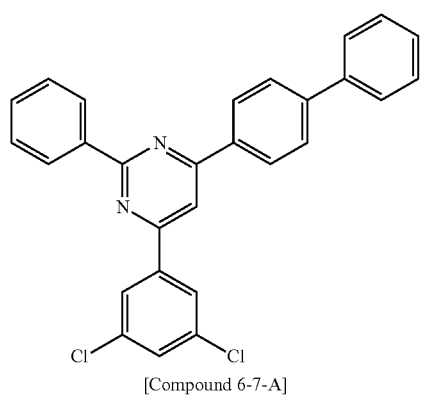
[Compound 6-7-A]

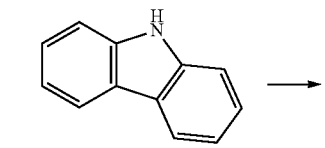

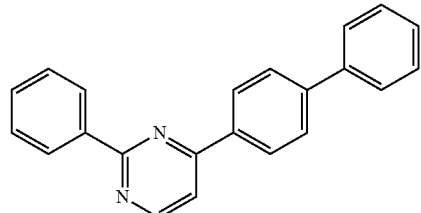
[Compound 6-7]

Under nitrogen flow, 4-([1,1'-biphenyl]-4-yl)-6-(3,5-dichlorophenyl)-2-phenylpyrimidine (24.0 g, 52.9 mmol), 9H-carbazole (18.6 g, 111.2 mmol), and sodium tert-butoxide (15.3 g, 158.8 mmol) were put into 240 mL of a xylene solvent, and the resulting solution was heated and stirred. Bis(tri-tert-butylphosphine)palladium(0) (0.54 g, 1.06 mmol) was put thereinto, and then the resulting mixture was heated and stirred for 12 hours. The reaction solution was cooled and then filtered, and then the filtered material was subjected to slurry purification using EtOH to obtain [Compound 6-7] (35 g, yield 92.6%).

MS: [M+H]⁺=715

<Preparation Example 39> Synthesis of Compound 6-8

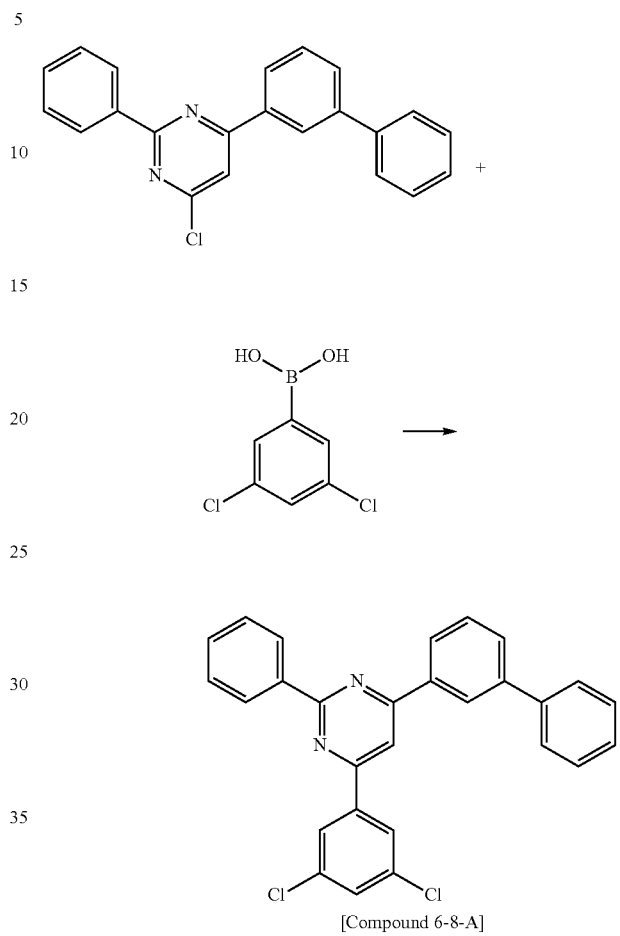
[Compound 6-8-A]

[Compound 6-8-A] was obtained in the same manner as in the method for preparing Compound 6-7-A, except that 4-([1,1'-biphenyl]-3-yl)-6-chloro-2-phenylpyrimidine was used instead of 4-([1,1'-biphenyl]-4-yl)-6-chloro-2-phenylpyrimidine.

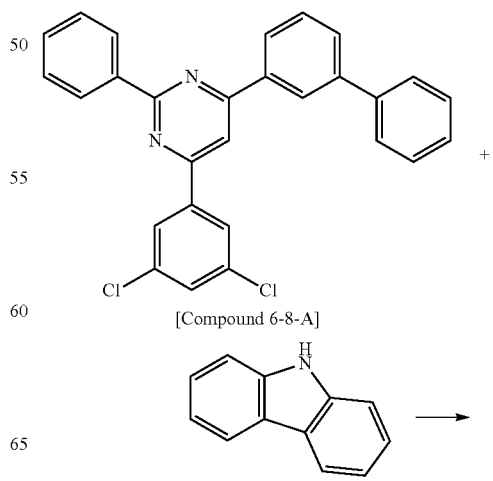
[Compound 6-8-A]

-continued

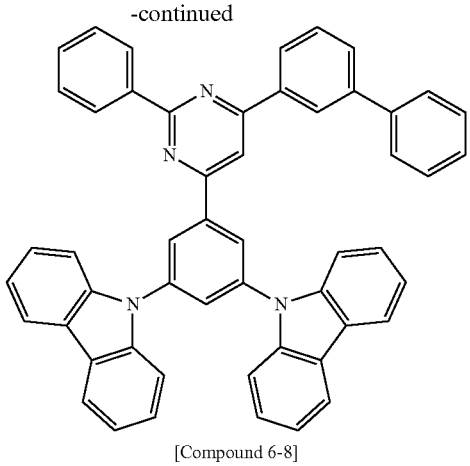

[Compound 6-8]

[Compound 6-8] (35 g, yield 89.9%) was obtained in the same manner as in the method for preparing Compound 6-7, except that [Compound 6-8-A] was used instead of [Compound 6-7-A].

MS: [M+H]⁺=715

<Preparation Example 40> Synthesis of Compound 6-10

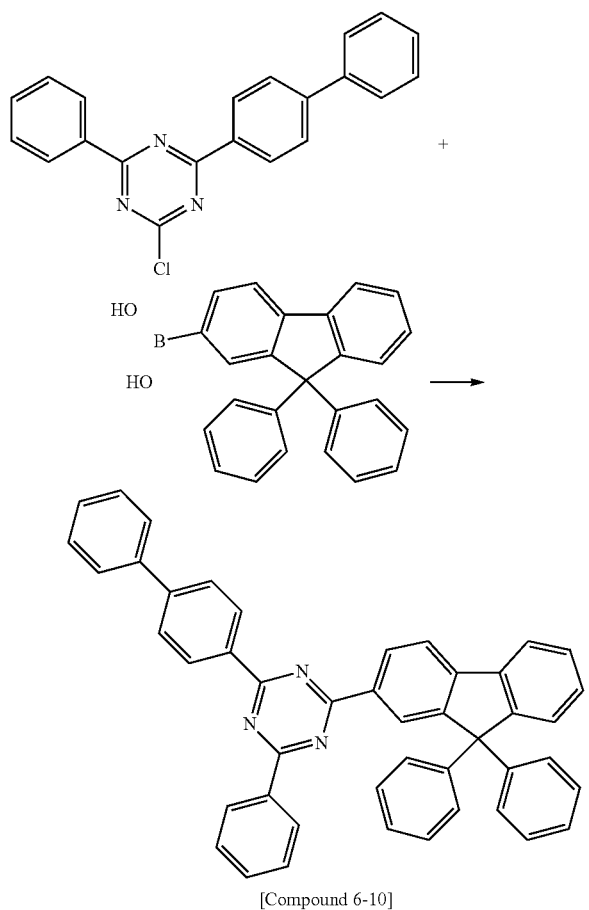

[Compound 6-10]

2-([1,1'-biphenyl]-4-yl)-4-chloro-6-phenyl-1,3,5-triazine (10 g, 29.1 mmol), (9,9-diphenyl-9H-fluoren-2-yl)boronic acid (11.1 g, 30.5 mmol), and calcium chloride (8.0 g, 58.2 mmol) were put into 120 mL of a tetrahydrofuran solvent, and the resulting solution was heated and stirred.

Tetrakis(triphenylphosphine)palladium(0) (1.0 g, 0.87 mmol) was put thereinto, and the resulting mixture was heated and stirred for 6 hours. The reaction solution was cooled and then filtered, and then the filtered material was subjected to slurry purification using EtOH to obtain [Compound 6-10] (16.5 g, yield 90.7%).

MS: [M+H]⁺=626

<Preparation Example 41> Synthesis of Compound 6-11

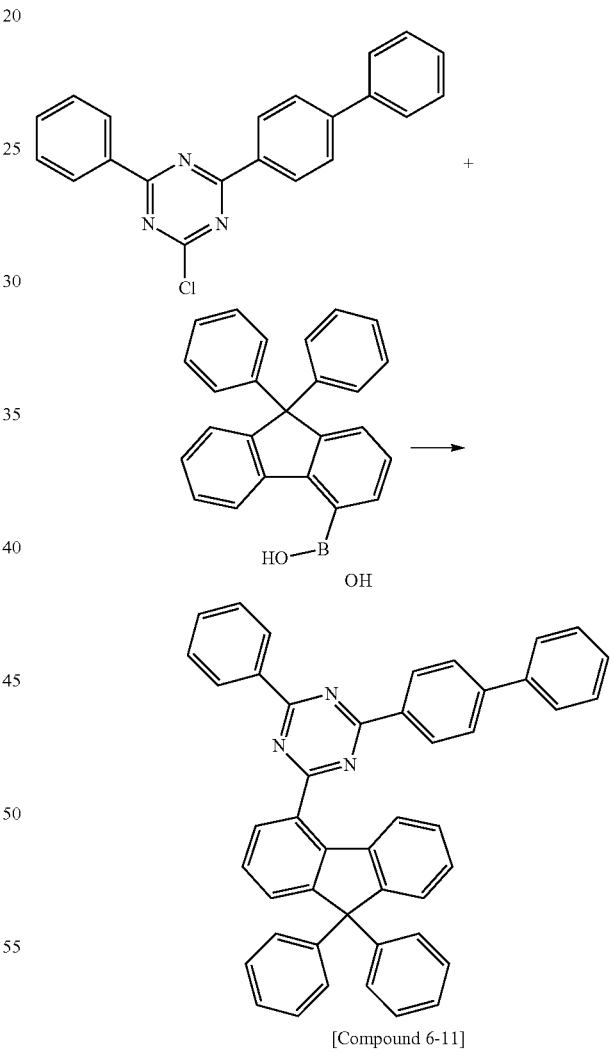

[Compound 6-11]

[Compound 6-11] (16.0 g, yield 88%) was obtained in the same manner as in the method for preparing [Compound 6-10], except that (9,9-diphenyl-9-H-fluoren-4-yl)boronic acid was used instead of (9,9-diphenyl-9H-fluoren-2-yl) boronic acid.

MS: [M+H]⁺=626

<Preparation Example 42> Synthesis of Compound 6-12

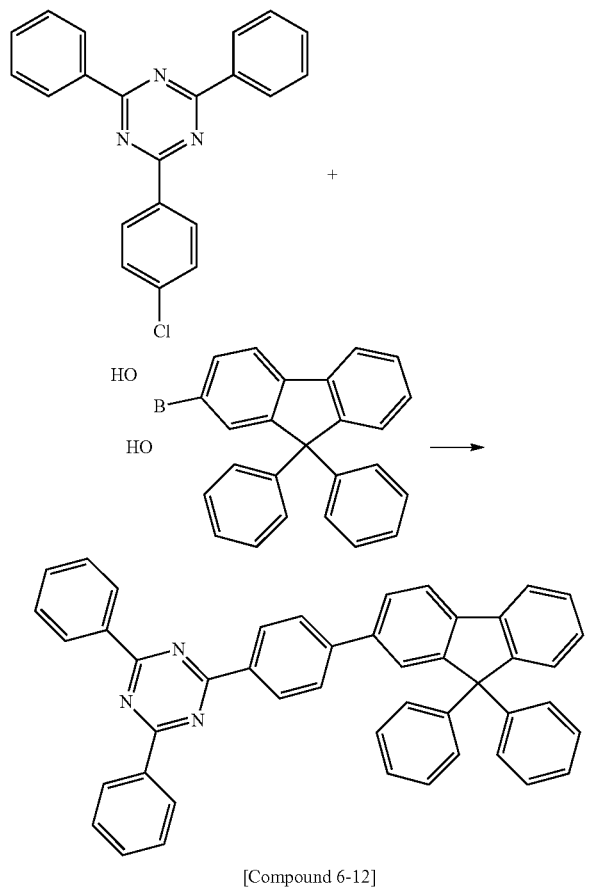

[Compound 6-12]

[Compound 6-12] (17.0 g, yield 93%) was obtained in the same manner as in the method for preparing [Compound 6-10], except that 2-(4-chlorophenyl)-4,6-diphenyl-1,3,5-triazine was used instead of (2-([1,1'-biphenyl]-4-yl)-4-chloro-6-phenyl-1,3,5-triazine.

MS: [M+H]⁺=626

<Preparation Example 43> Synthesis of Compound 6-13

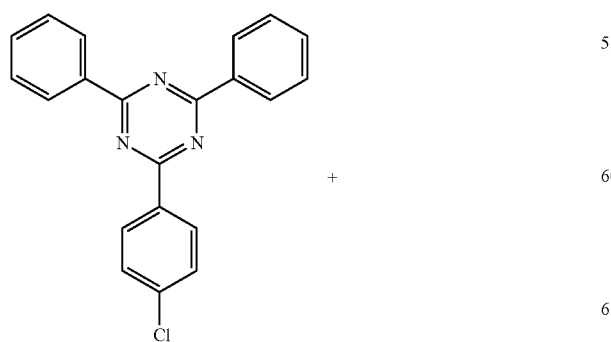

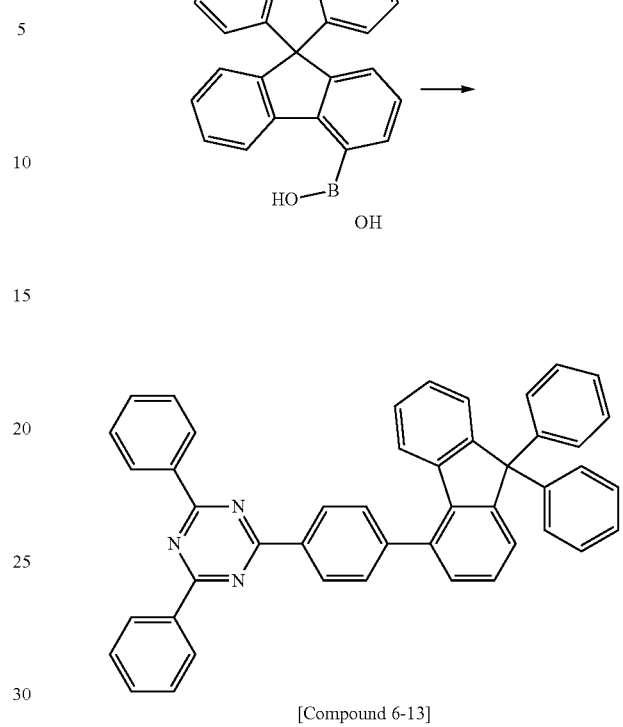

[Compound 6-13]

[Compound 6-13] (16.5 g, yield 90.7%) was obtained in the same manner as in the method for preparing [Compound 6-11], except that 2-(4-chlorophenyl)-4,6-diphenyl-1,3,5-triazine was used instead of (2-([1,1'-biphenyl]-4-yl)-4-chloro-6-phenyl-1,3,5-triazine.

MS: [M+H]⁺=626

<Preparation Example 44> Synthesis of Compound 6-17

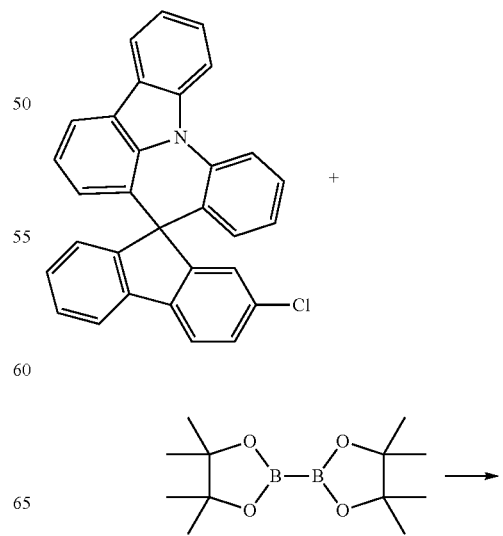

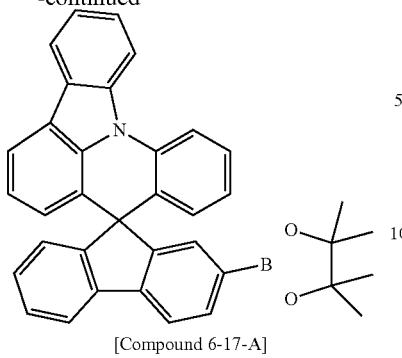

[Compound 6-17-A]

[Compound 6-17-A] (16.5 g, yield 91%) was obtained in the same manner as in the method for preparing [Compound 6-4-A], except that 2-chlorospiro[fluoren-9,8'-indolo[3,2,1-de]acridine] was used instead of 11'-chlorospiro[fluoren-9,8'-indolo[3,2,1-de]acridine].

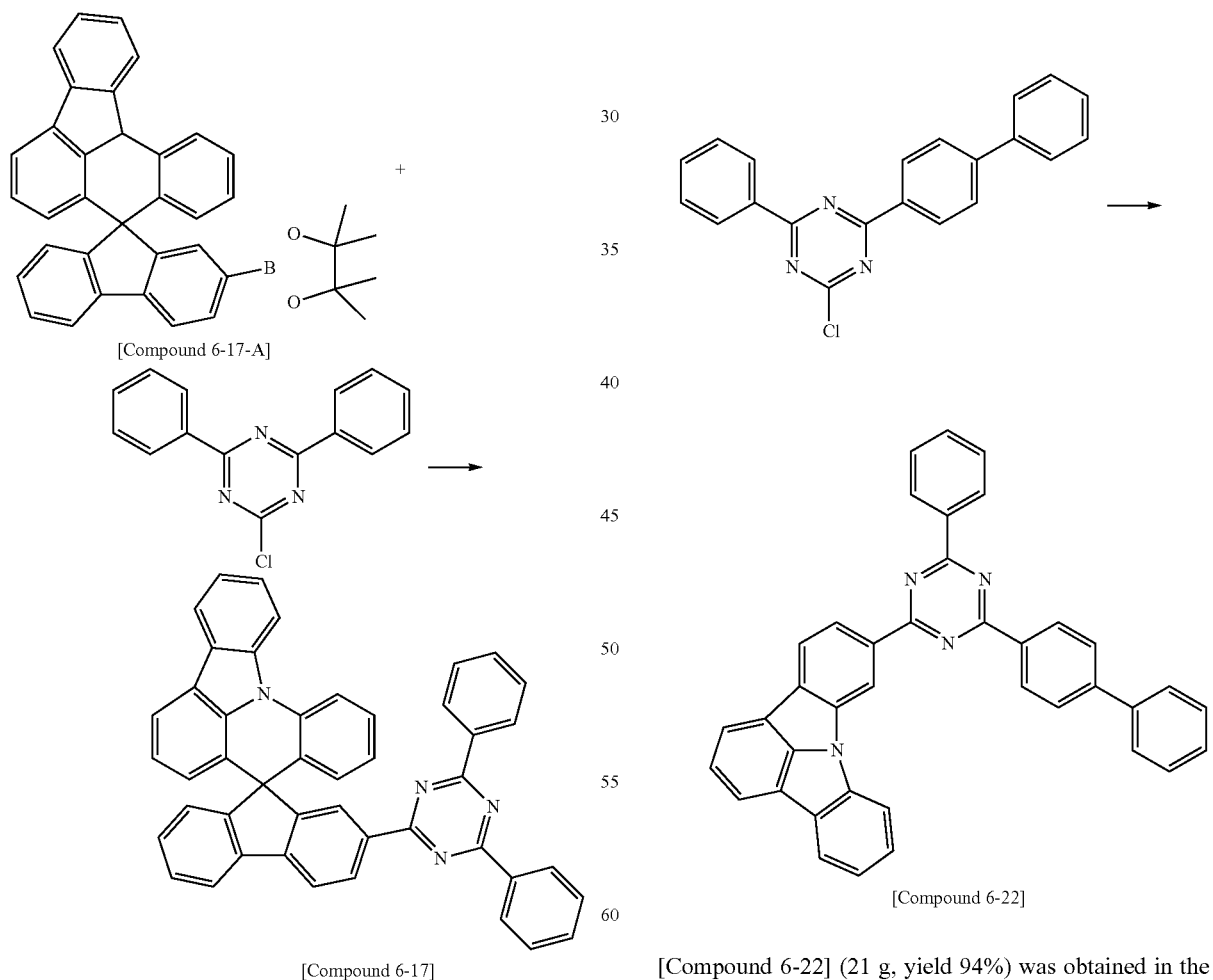

[Compound 6-17]

[Compound 6-17] (18.0 g, yield 88%) was obtained in the same manner as in the method for preparing [Compound 6-4], except that [Compound 6-17-A] was used instead of [Compound 6-4-A], and 2-chloro-4,6-diphenyl-1,3,5-triazine was used instead of 2-([1,1'-biphenyl]-4-yl)-4-chloro-6-phenyl-1,3,5-triazine.

MS: [M+H]⁺=637

<Preparation Example 45> Synthesis of Compound 6-22

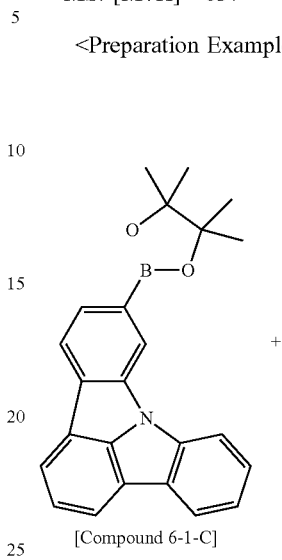

[Compound 6-22]

[Compound 6-22] (21 g, yield 94%) was obtained in the same manner as in the method for preparing [Compound 6-1], except that 4-([1,1'-biphenyl]-4-yl)-6-chloro-2-phenylpyrimidine was used instead of 2-([1,1'-biphenyl]-4-yl)-4-chloro-6-phenyl-1,3,5-triazine.

MS: [M+H]⁺=548

<Preparation Example 46> Synthesis of Compound 6-24

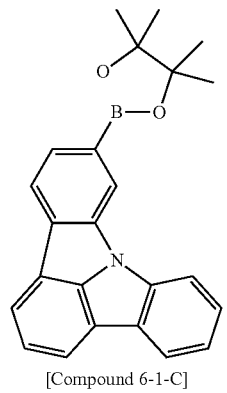
[Compound 6-1-C]

+

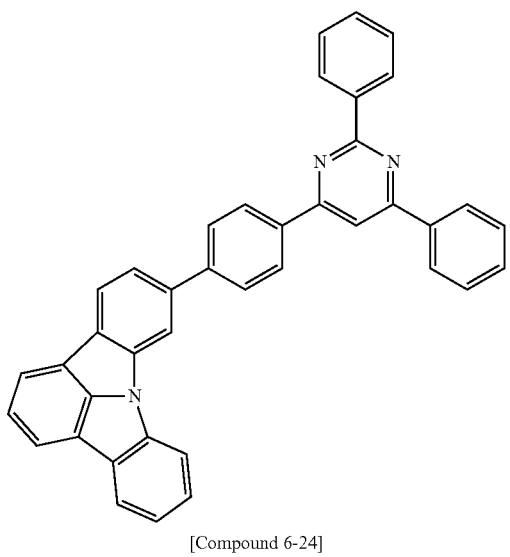

[Compound 6-24]

[Compound 6-24] (20.5 g, yield 91.7%) was obtained in the same manner as in the method for preparing [Compound 6-22], except that 4-(4-chlorophenyl)-2,6-diphenylpyrimidine was used instead of 4-([1,1'-biphenyl]-4-yl)-6-chloro-2-phenylpyrimidine.

MS: [M+H]$^+$=548

<Preparation Example 47> Synthesis of Compound 6-25

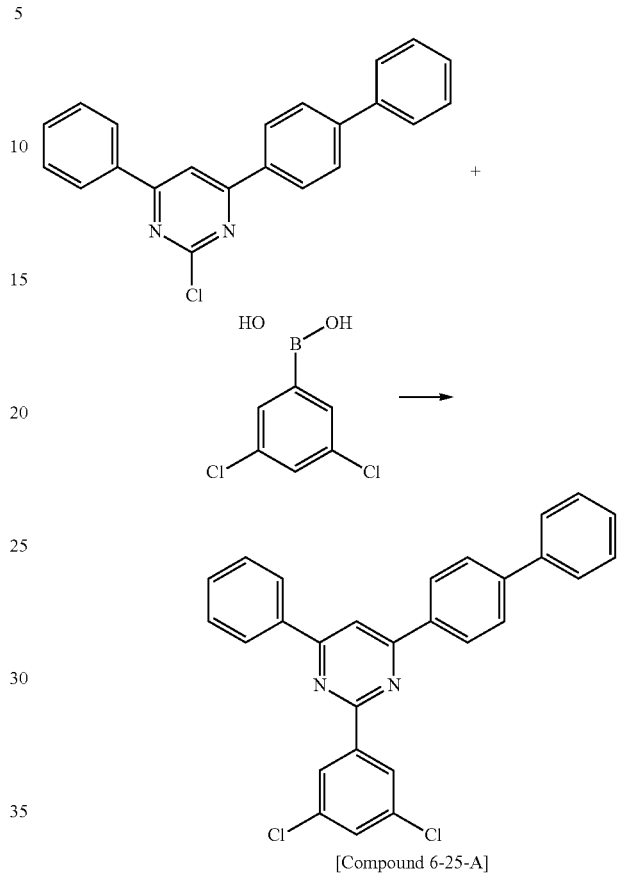
[Compound 6-25-A]

[Compound 6-25-A] was obtained in the same manner as in the method for preparing Compound 6-7-A, except that 4-([1,1'-biphenyl]-4-yl)-2-chloro-6-phenylpyrimidine was used instead of 4-([1,1'-biphenyl]-4-yl)-6-chloro-2-phenylpyrimidine.

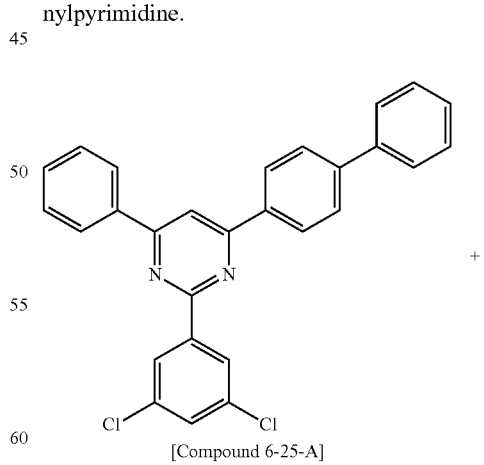
[Compound 6-25-A]

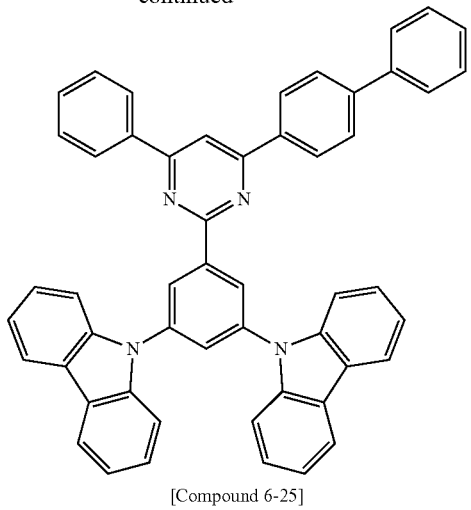

[Compound 6-25]

[Compound 6-25] (35 g, yield 89.9%) was obtained in the same manner as in the method for preparing Compound 6-7, except that [Compound 6-25-A] was used instead of [Compound 6-7-A].

MS: [M+H]$^+$=715

<Preparation Example 48> Synthesis of Compound 6-26

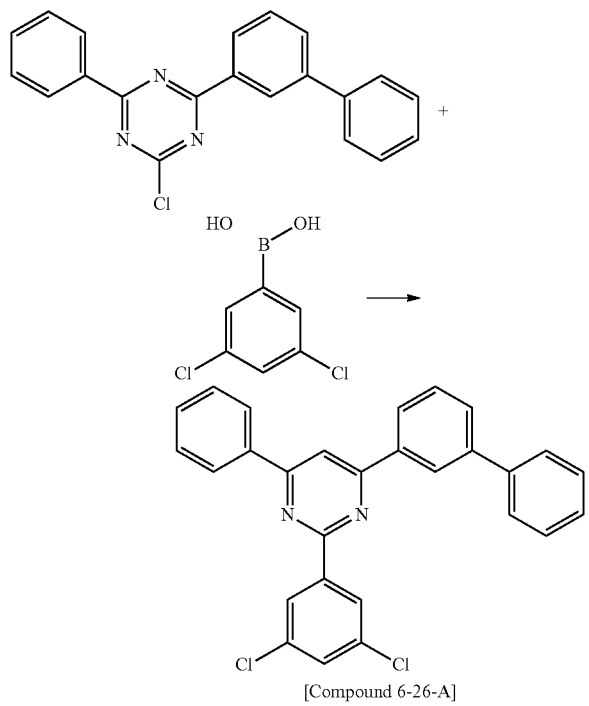

[Compound 6-26-A]

[Compound 6-26-A] was obtained in the same manner as in the method for preparing Compound 6-7-A, except that 4-([1,1'-biphenyl]-3-yl)-2-chloro-6-phenylpyrimidine was used instead of 4-([1,1'-biphenyl]-4-yl)-6-chloro-2-phenylpyrimidine.

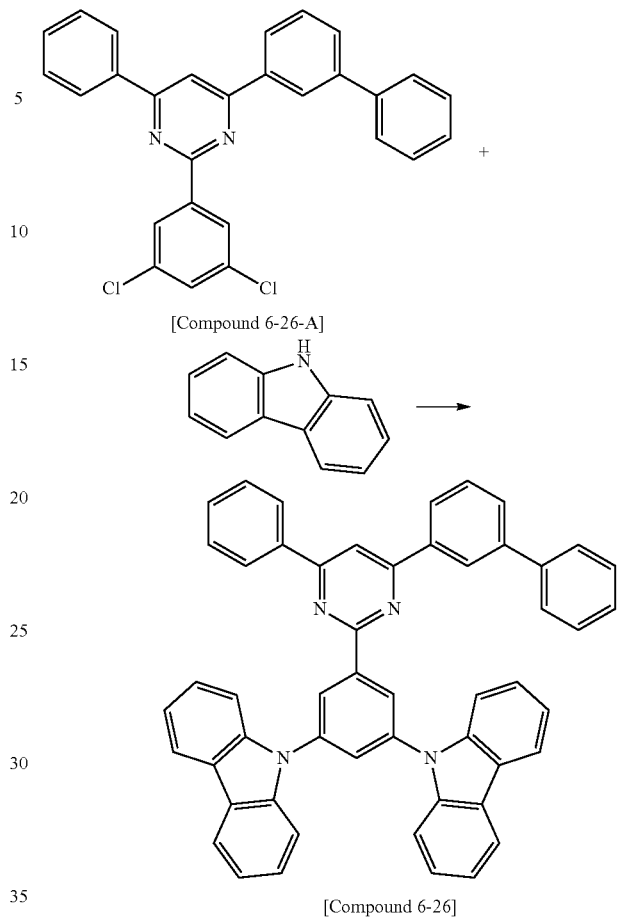

[Compound 6-26]

[Compound 6-26] (36.0 g, yield 95%) was obtained in the same manner as in the method for preparing Compound 6-7, except that [Compound 6-26-A] was used instead of [Compound 6-7-A].

MS: [M+H]$^+$=715

EXAMPLES

Example 1

A glass substrate (Corning 7059 glass) thinly coated with ITO (indium tin oxide) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material for transporting holes, was vacuum deposited thereon, and then a compound of a host H1 and a dopant D1 was vacuum deposited as a light emitting layer to have a thickness of 300 Å. Compound 1-3 prepared in Preparation Example 2 was deposited as an electron adjusting layer on the light emitting layer, and then Compound 6-1 prepared in Preparation Example 33 and lithium quinolate (LiQ) were vacuum deposited as an electron transport layer at a weight ratio of 2:1, thereby forming an electron injection and transport layer having a thickness of 250 Å.

Lithium fluoride (LiF) and aluminum were sequentially deposited on the electron injection and transport layer to have a thickness of 12 Å and 2,000 Å, respectively, thereby forming a negative electrode.

An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

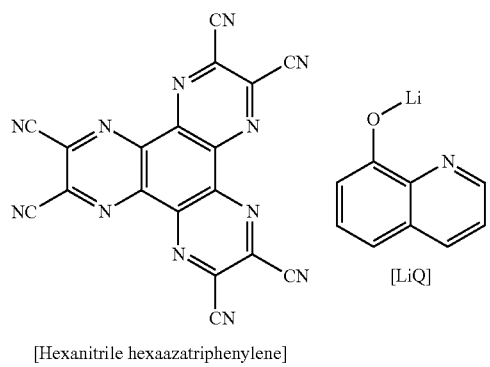

[Hexanitrile hexaazatriphenylene]     [LiQ]

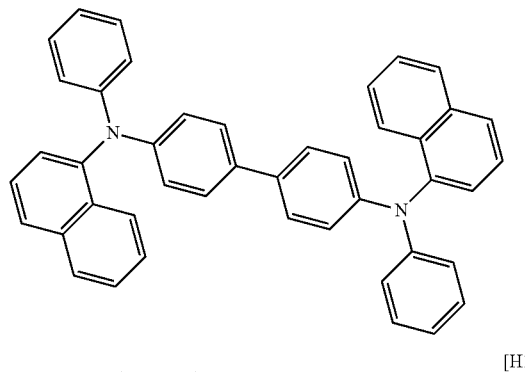

[H1]

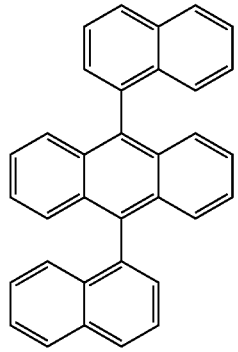

-continued

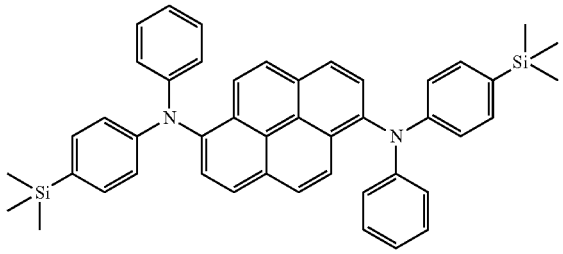

[D1]

Example 2

An experiment was performed in the same manner as in Example 1, except that as the electron adjusting layer, Compound 2-15 was used instead of Compound 1-3.

Example 3

An experiment was performed in the same manner as in Example 1, except that as the electron adjusting layer, Compound 3-33 was used instead of Compound 1-3, and as the electron transport layer, Compound 6-2 was used instead of Compound 6-1.

Example 4

An experiment was performed in the same manner as in Example 1, except that as the electron adjusting layer, Compound 3-33 was used instead of Compound 1-3, and as the electron transport layer, Compound 6-4 was used instead of Compound 6-1.

Example 5

An experiment was performed in the same manner as in Example 1, except that as the electron adjusting layer, Compound 3-33 was used instead of Compound 1-3, and as the electron transport layer, Compound 6-7 was used instead of Compound 6-1.

Example 6

An experiment was performed in the same manner as in Example 1, except that as the electron adjusting layer, Compound 3-33 was used instead of Compound 1-3, and as the electron transport layer, Compound 6-11 was used instead of Compound 6-1.

Example 7

An experiment was performed in the same manner as in Example 1, except that as the electron adjusting layer, Compound 3-34 was used instead of Compound 1-3, and as the electron transport layer, Compound 6-4 was used instead of Compound 6-1.

Example 8

An experiment was performed in the same manner as in Example 1, except that as the electron adjusting layer, Compound 3-34 was used instead of Compound 1-3, and as the electron transport layer, Compound 6-7 was used instead of Compound 6-1.

Example 9

An experiment was performed in the same manner as in Example 1, except that as the electron adjusting layer, Compound 3-36 was used instead of Compound 1-3, and as the electron transport layer, Compound 6-7 was used instead of Compound 6-1.

Example 10

An experiment was performed in the same manner as in Example 1, except that as the electron adjusting layer, Compound 3-36 was used instead of Compound 1-3, and as the electron transport layer, Compound 6-8 was used instead of Compound 6-1.

Example 11

An experiment was performed in the same manner as in Example 1, except that as the electron adjusting layer, Compound 3-36 was used instead of Compound 1-3, and as the electron transport layer, Compound 6-11 was used instead of Compound 6-1.

Example 12

An experiment was performed in the same manner as in Example 1, except that as the electron adjusting layer, Compound 3-38 was used instead of Compound 1-3, and as the electron transport layer, Compound 6-7 was used instead of Compound 6-1.

Example 13

An experiment was performed in the same manner as in Example 1, except that as the electron adjusting layer, Compound 3-39 was used instead of Compound 1-3, and as the electron transport layer, Compound 6-7 was used instead of Compound 6-1.

Example 14

An experiment was performed in the same manner as in Example 1, except that as the electron adjusting layer, Compound 4-19 was used instead of Compound 1-3, and as the electron transport layer, Compound 6-10 was used instead of Compound 6-1.

Example 15

An experiment was performed in the same manner as in Example 1, except that as the electron adjusting layer, Compound 5-27 was used instead of Compound 1-3, and as the electron transport layer, Compound 6-24 was used instead of Compound 6-1.

Comparative Example 1

An experiment was performed in the same manner as in Example 1, except that the compound for an electron adjusting layer was not used, and as the electron transport layer, Compound 6-2 was used.

Comparative Example 2

An experiment was performed in the same manner as in Example 1, except that the compound for an electron adjusting layer was not used, and as the electron transport layer, Compound 6-4 was used.

Comparative Example 3

An experiment was performed in the same manner as in Example 1, except that the compound for an electron adjusting layer was not used, and as the electron transport layer, Compound 6-7 was used.

Comparative Example 4

An experiment was performed in the same manner as in Example 1, except that as the electron adjusting layer, Compound [ET 1] was used instead of Compound 1-3, and as the electron transport layer, Compound 6-4 was used instead of Compound 6-1.

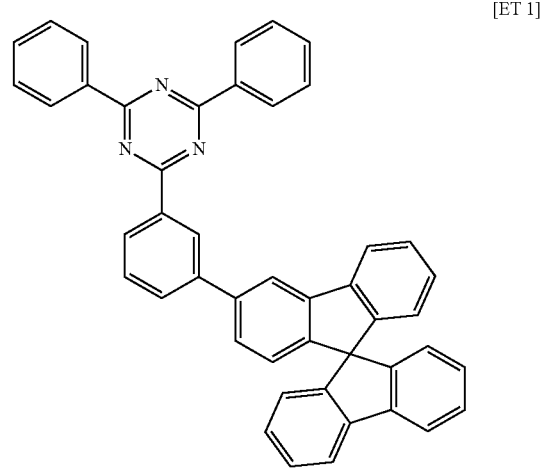 [SMILES: c1ccc(-c2nc(-c3ccccc3)nc(-c3cccc(-c4ccc5c(c4)-c4ccccc4C54c5ccccc5-c5ccccc54)c3)n2)cc1]

[ET 1]

Comparative Example 5

An experiment was performed in the same manner as in Example 1, except that as the electron adjusting layer, Compound [ET 1] was used instead of Compound 1-3, and as the electron transport layer, Compound 6-7 was used instead of Compound 6-1.

Comparative Example 6

An experiment was performed in the same manner as in Example 1, except that as the electron adjusting layer, Compound 3-33 was used instead of Compound 1-3, and as the electron transport layer, Compound [ET 2] was used instead of Compound 6-1.

[ET 2]

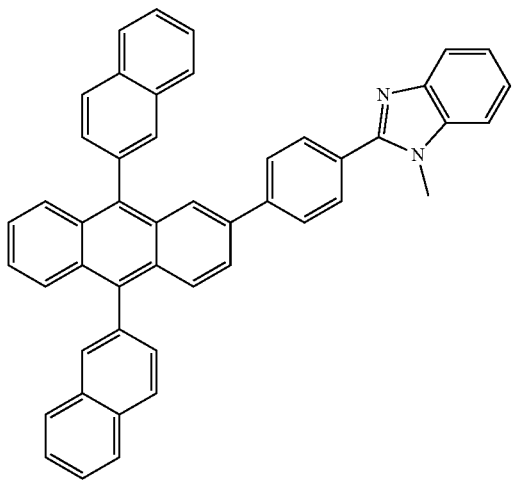

Comparative Example 7

An experiment was performed in the same manner as in Example 1, except that as the electron adjusting layer, Compound 3-36 was used instead of Compound 1-3, and as the electron transport layer, Compound [ET 3] was used instead of Compound 6-1.

[ET 3]

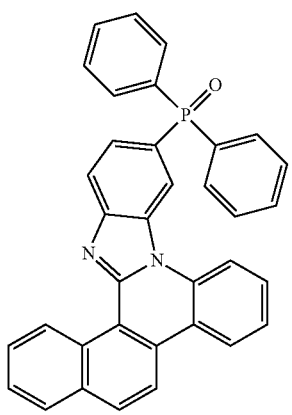

For the organic light emitting devices of Examples 1 to 15 and Comparative Examples 1 to 7, the driving voltage and the light emitting efficiency were measured at a current density of 10 mA/cm², and a time (LT98) for reaching a 98% value compared to the initial luminance was measured at a current density of 20 mA/cm². The results are shown in the following Table 1.

TABLE 1

| Example 10 mA/cm² | Compound (adjusting layer/transport layer) | Voltage (V) | Current efficiency (cd/A) | Color coordinate (x, y) | Life Time (98 at 20 mA/cm²) |
|---|---|---|---|---|---|
| Example 1 | 1-3/6-1 | 3.94 | 5.19 | (0.137, 0.127) | 40 |
| Example 2 | 2-15/6-1 | 4.05 | 5.07 | (0.137, 0.128) | 38 |
| Example 3 | 3-33/6-2 | 3.89 | 5.28 | (0.138, 0.127) | 44 |
| Example 4 | 3-33/6-4 | 3.91 | 5.30 | (0.137, 0.126) | 42 |
| Example 5 | 3-33/6-7 | 3.89 | 5.39 | (0.136, 0.127) | 44 |
| Example 6 | 3-33/6-11 | 3.93 | 5.26 | (0.136, 0.126) | 41 |
| Example 7 | 3-34/6-4 | 3.91 | 5.31 | (0.136, 0.126) | 40 |
| Example 8 | 3-34/6-7 | 3.90 | 5.40 | (0.136, 0.127) | 43 |
| Example 9 | 3-36/6-7 | 3.92 | 5.38 | (0.136, 0.126) | 40 |
| Example 10 | 3-36/6-8 | 3.91 | 5.35 | (0.137, 0.127) | 39 |
| Example 11 | 3-36/6-11 | 3.90 | 5.37 | (0.137, 0.127) | 37 |
| Example 12 | 3-38/6-7 | 4.00 | 5.20 | (0.136, 0.127) | 36 |
| Example 13 | 3-39/6-7 | 3.95 | 5.19 | (0.137, 0.126) | 38 |
| Example 14 | 4-19/6-10 | 4.06 | 5.09 | (0.137, 0.127) | 37 |
| Example 15 | 5-27/6-24 | 4.03 | 5.07 | (0.136, 0.127) | 36 |
| Comparative Example 1 | —/6-2 | 4.13 | 4.86 | (0.140, 0.129) | 26 |
| Comparative Example 2 | —/6-4 | 4.14 | 4.92 | (0.139, 0.130) | 23 |
| Comparative Example 3 | —/6-7 | 4.16 | 4.90 | (0.139, 0.130) | 28 |
| Comparative Example 4 | ET 1/6-4 | 4.08 | 4.94 | (0.140, 0.130) | 22 |
| Comparative Example 5 | ET 1/6-7 | 4.12 | 4.92 | (0.139, 0.130) | 26 |
| Comparative Example 6 | 3-33/ET 2 | 4.17 | 4.89 | (0.139, 0.130) | 25 |
| Comparative Example 7 | 3-36/ET 3 | 4.19 | 4.88 | (0.139, 0.130) | 27 |

EXPLANATION OF REFERENCE NUMERALS AND SYMBOLS

101: Substrate
201: Positive electrode
301: Light emitting layer
401: Electron adjusting layer
501: Electron transport layer
601: Negative electrode

The invention claimed is:
1. An organic light emitting device comprising:
a positive electrode;
a negative electrode provided to face the positive electrode; and
an organic material layer between the positive electrode and the negative electrode,
wherein the organic material layer comprises a light emitting layer,
the organic material layer further includes an electron adjusting layer and an electron transport layer provided between the light emitting layer and the negative electrode,
the electron adjusting layer includes a compound represented by the following Chemical Formula 1, and the electron transport layer includes a compound represented by the following Chemical Formula 11:

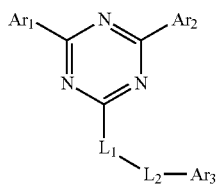

[Chemical Formula 1]

in Chemical Formula 1,
$Ar_1$ and $Ar_2$ are the same as or different from each other, and are each independently a substituted or unsubstituted aryl group; or a substituted or unsubstituted heterocyclic group, and
$L_1$ is represented by any one of the following Chemical Formulae 2 to 5,

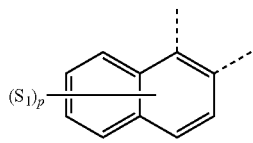

[Chemical Formula 2]

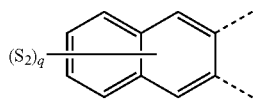

[Chemical Formula 3]

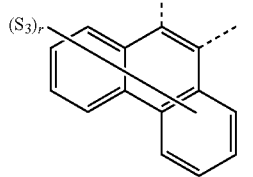

[Chemical Formula 4]

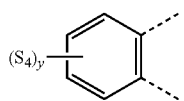

[Chemical Formula 5]

in Chemical Formulae 2 to 5,
a dotted line " ------ " is each a moiety bonded to a triazine group or $L_2$ of Chemical Formula 1,
$S_1$ to $S_4$ are the same as or different from each other, and are each independently hydrogen; deuterium; a halogen group; a substituted or unsubstituted alkyl group; a substituted or unsubstituted aryl group; or a substituted or unsubstituted heterocyclic group,
p and q are the same as or different from each other, and are each independently an integer of 0 to 6,
r is an integer of 0 to 8,
y is an integer of 0 to 4,
when p, q, r, and y are each an integer of 2 or more, a plurality of $S_1$ to $S_4$ are each the same as or different from each other,
$L_2$ is a direct bond; or a substituted or unsubstituted arylene group,
$Ar_3$ is represented by a substituted or unsubstituted aryl group; a substituted or unsubstituted heterocyclic group including S or O; a substituted or unsubstituted carbazole group; or any one of the following Chemical Formulae 6 to 10, when $L_1$ is Chemical Formulae 2 to 4,
$Ar_3$ is represented by a substituted or unsubstituted aryl group; a substituted or unsubstituted heterocyclic group including S or O; or any one of the following Chemical Formulae 6 to 10, when $L_1$ is Chemical Formula 5,

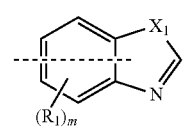

[Chemical Formula 6]

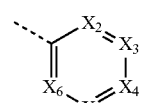

[Chemical Formula 7]

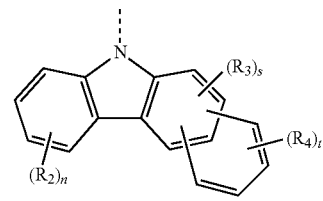

[Chemical Formula 8]

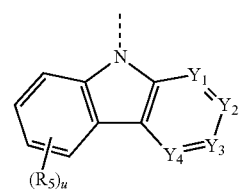

[Chemical Formula 9]

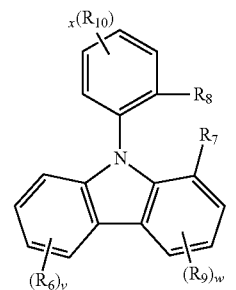

[Chemical Formula 10]

in Chemical Formulae 6 to 10,
$X_1$ is O, S, or NR,
at least two of $X_2$ to $X_6$ are N, and the others are each independently CR',
R and R' are the same as or different from each other, and are each independently hydrogen; deuterium; a halogen group; a substituted or unsubstituted alkyl group; or a substituted or unsubstituted aryl group,
$R_1$ to $R_6$, $R_9$, and $R_{10}$ are the same as or different from each other, and are each independently hydrogen; deuterium; a halogen group; a substituted or unsubstituted alkyl group; a substituted or unsubstituted aryl group; or a substituted or unsubstituted heterocyclic group,
at least one of $Y_1$ to $Y_4$ is N, and the others are CR",
R" is each independently hydrogen or deuterium,
$R_7$ and $R_8$ are directly bonded, or combine with each other to form a substituted or unsubstituted ring,
m, n, t, u, v, and x are each an integer of 0 to 4, w is an integer of 0 to 3, and when m, n, t, u, v, w, and x are each an integer of 2 or more, a plurality of $R_1$ to $R_6$, $R_9$, and $R_{10}$ are each the same as or different from each other, s is an integer of 0 to 2, and when s is 2, two $R_3$s are the same as or different from each other, " ------ " means a moiety bonded to $L_2$ of Chemical Formula 1, and the bonding moiety of Chemical Formula 10 is bonded to a ring formed by bonding $R_6$, $R_9$, $R_{10}$ or $R_7$, and $R_8$,

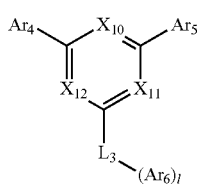

[Chemical Formula 11]

in Chemical Formula 11, at least two of $X_{10}$ to $X_{12}$ are N, and the other is each independently CR''', R''' is hydrogen; deuterium; a halogen group; a substituted or unsubstituted alkyl group; or a substituted or unsubstituted aryl group, $Ar_4$ to $Ar_6$ are the same as or different from each other, and are each independently a substituted or unsubstituted aryl group; or a substituted or unsubstituted heterocyclic group, $L_3$ is a direct bond; a substituted or unsubstituted arylene group; or a substituted or unsubstituted divalent heterocyclic group, and l is 1 or 2, and when l is 2, $Ar_6$s are the same as or different from each other.

2. The organic light emitting device of claim 1, wherein $L_2$ is a direct bond; or a substituted or unsubstituted $C_6$ to $C_{20}$ arylene group.

3. The organic light emitting device of claim 1, wherein $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; a substituted or unsubstituted carbazole group; or any one of Chemical Formulae 6 to 10, when $L_1$ is Chemical Formulae 2 to 4, and $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; any one of Chemical Formulae 6 to 10, when $L_1$ is Chemical Formula 5.

4. The organic light emitting device of claim 1, wherein $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted carbazole group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formulae 2 to 4, and $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formula 5.

5. The organic light emitting device of claim 1, wherein $Ar_1$ and $Ar_2$ are the same as or different from each other, and are each independently a substituted or unsubstituted $C_6$ to $C_{20}$ aryl group.

6. The organic light emitting device of claim 1, wherein $S_1$ to $S_4$ are hydrogen.

7. The organic light emitting device of claim 1, wherein $R_1$ to $R_6$, $R_9$, and $R_{10}$ are hydrogen.

8. The organic light emitting device of claim 1, wherein the compound represented by Chemical Formula 1 is any one selected from the following structural formulae:

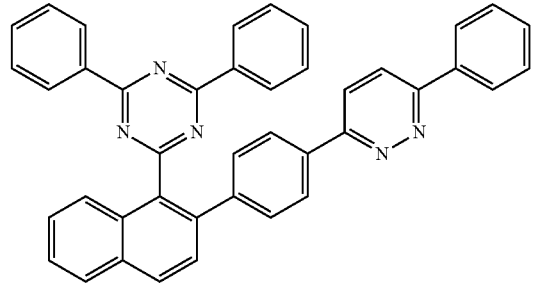

Compound 1-1

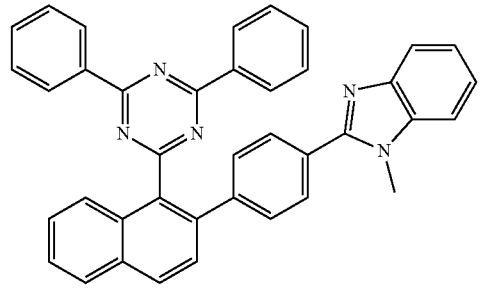

Compound 1-2

Compound 1-3
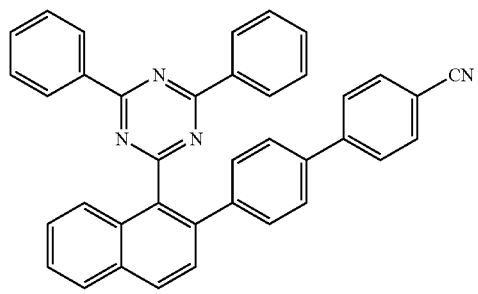
Compound 1-4
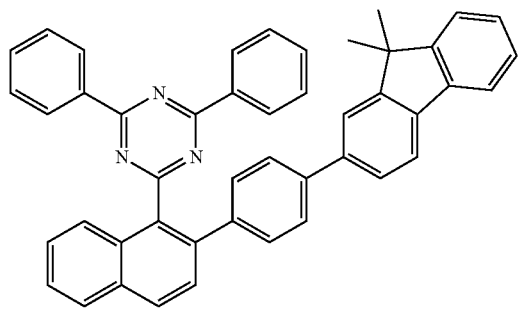
Compound 1-5
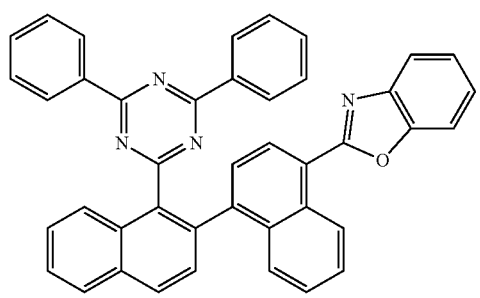
Compound 1-6
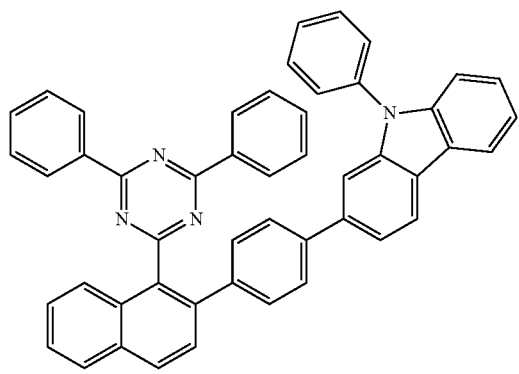
Compound 1-7
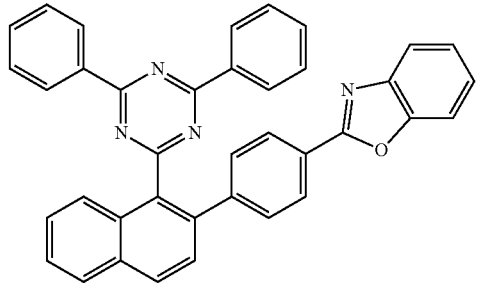
Compound 1-8
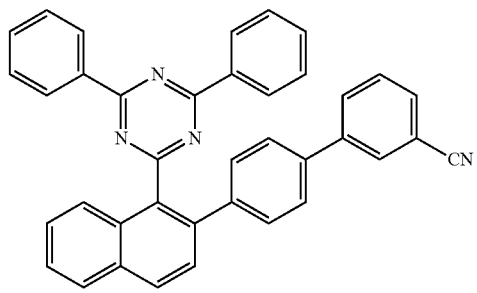
Compound 1-9
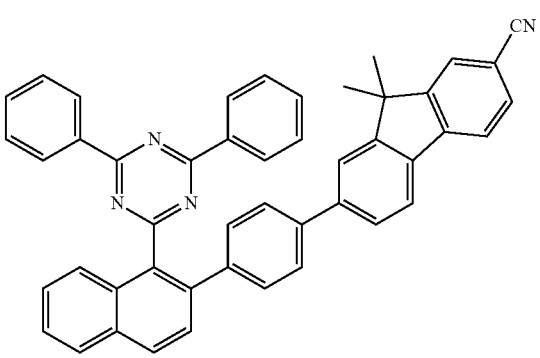
Compound 1-10
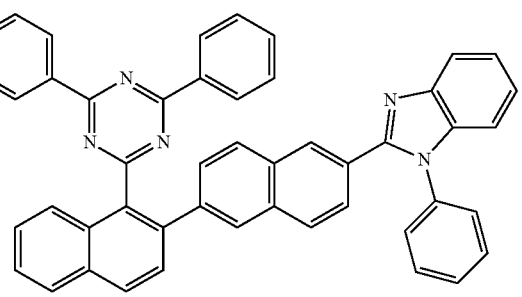
Compound 1-11
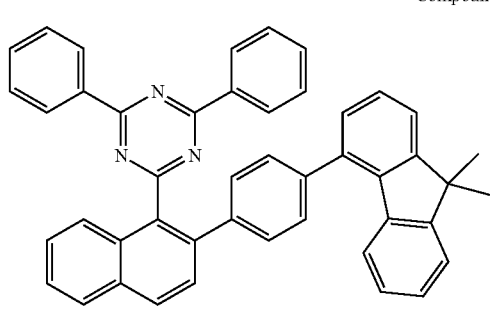

Compound 1-12
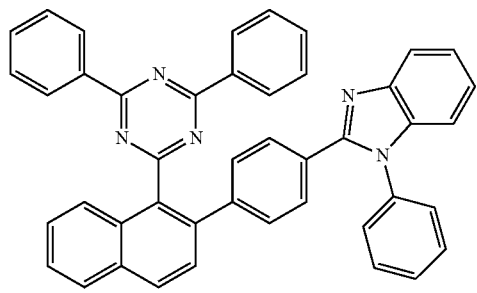
Compound 1-13
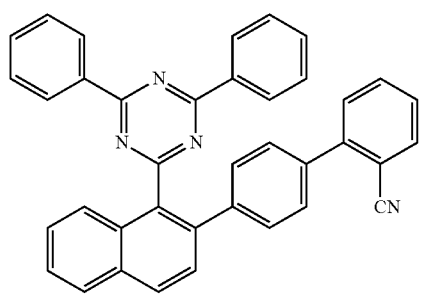
Compound 1-14
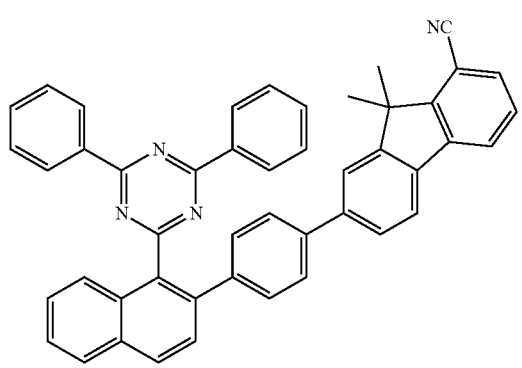
Compound 1-15
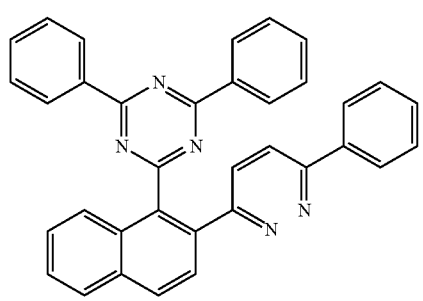
Compound 1-16
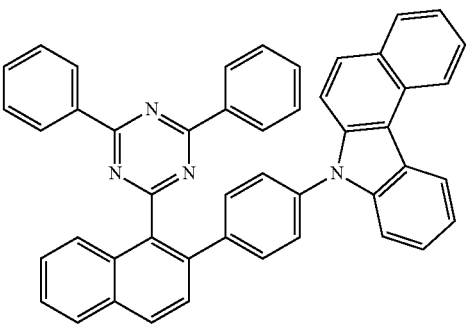
Compound 1-17
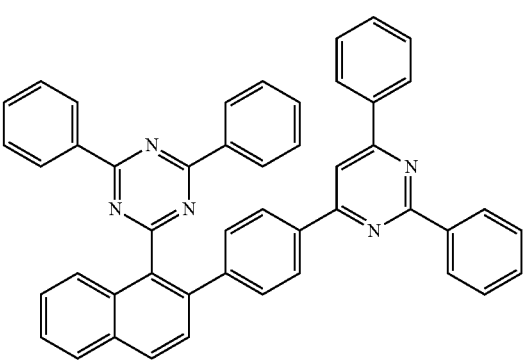
Compound 1-18
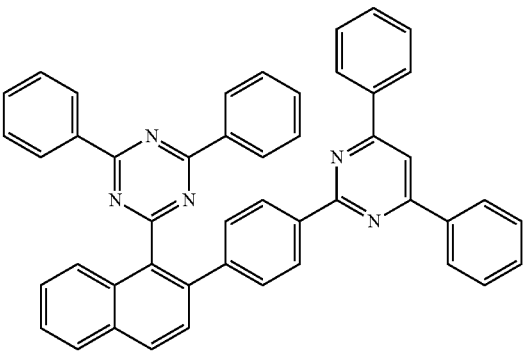
Compound 1-19
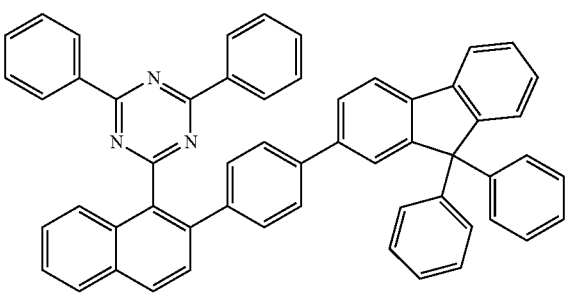

Compound 1-20
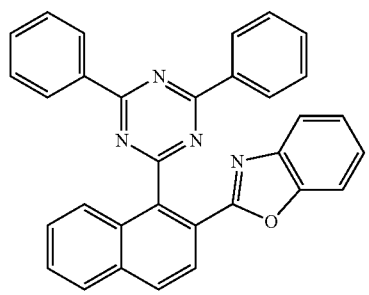
Compound 1-21
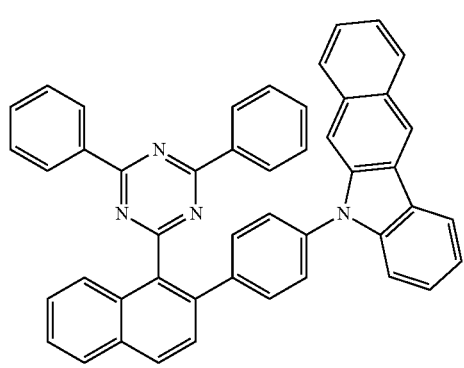
Compound 1-22
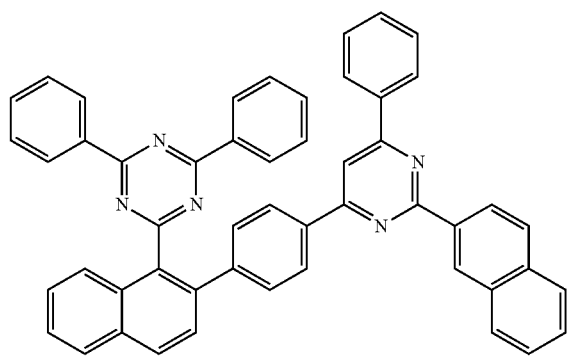
Compound 1-23
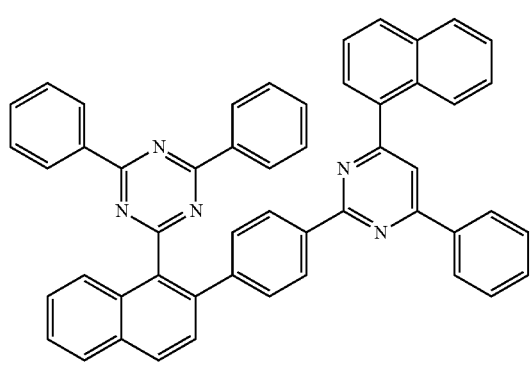
Compound 1-24
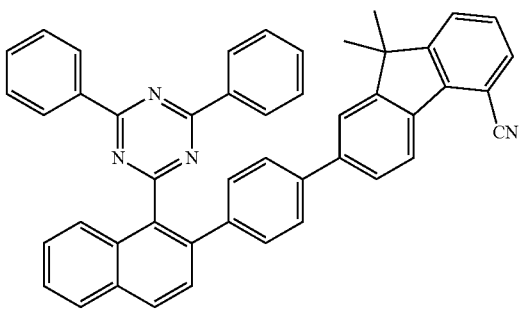
Compound 1-25
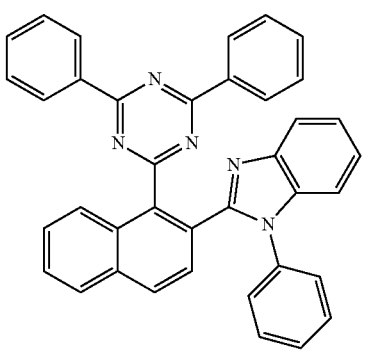
Compound 1-26
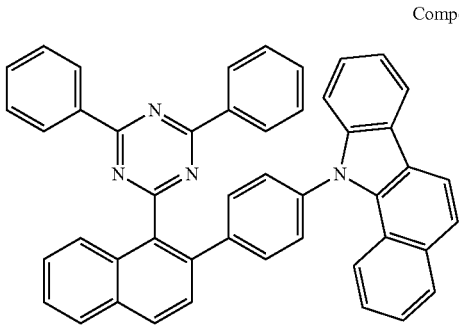
Compound 1-27
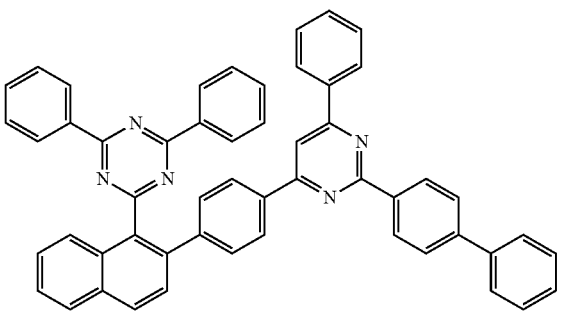

Compound 1-28
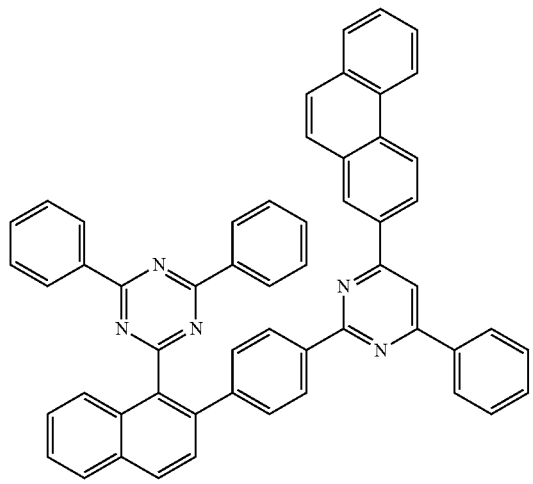
Compound 1-29
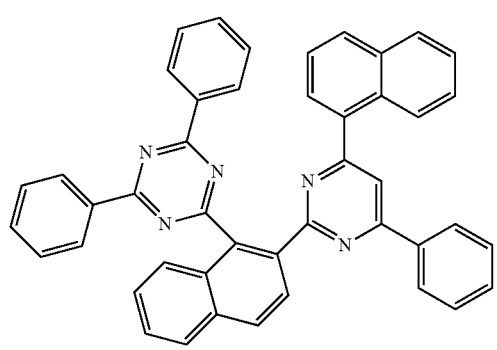
Compound 1-30
Compound 1-31
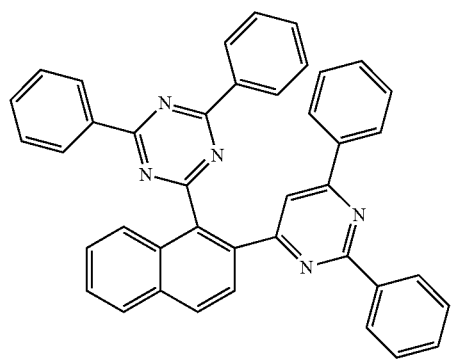
Compound 1-32
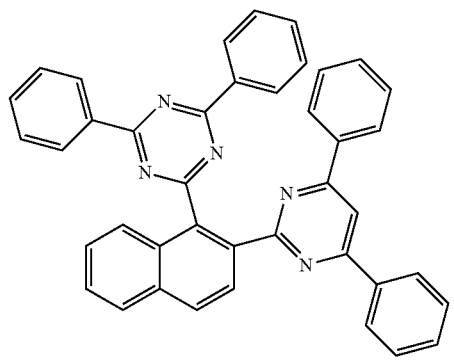
Compound 1-33
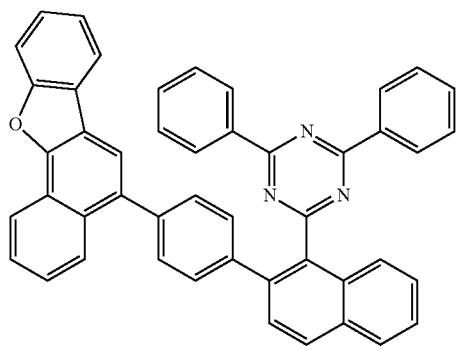
Compound 1-34
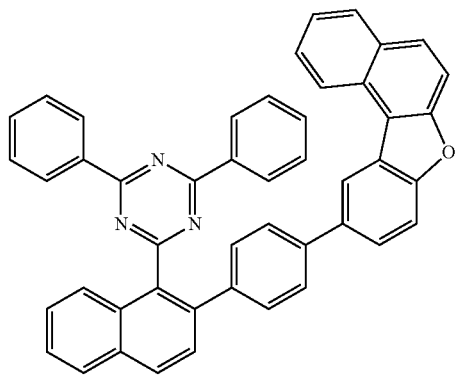
Compound 1-35
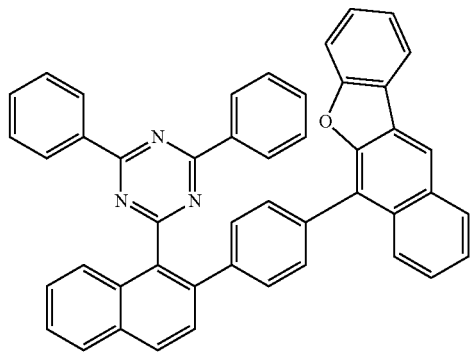

Compound 1-36
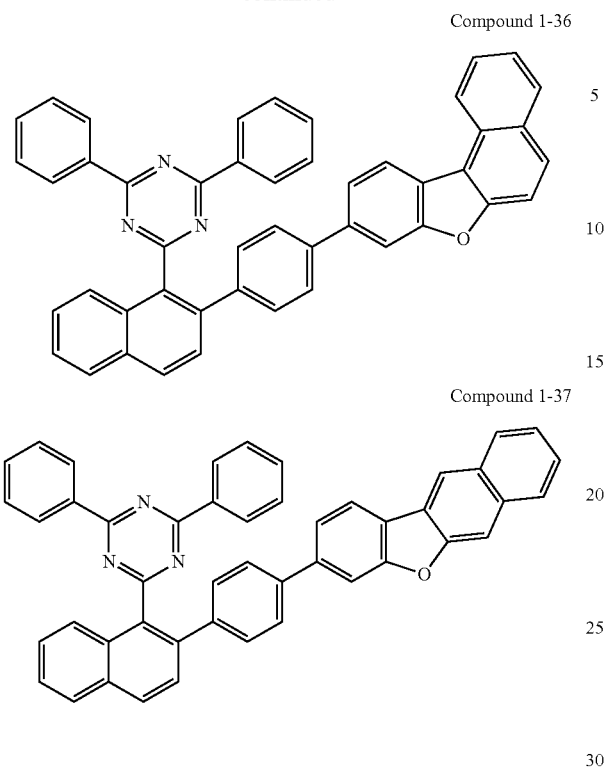
Compound 1-37
Compound 1-38
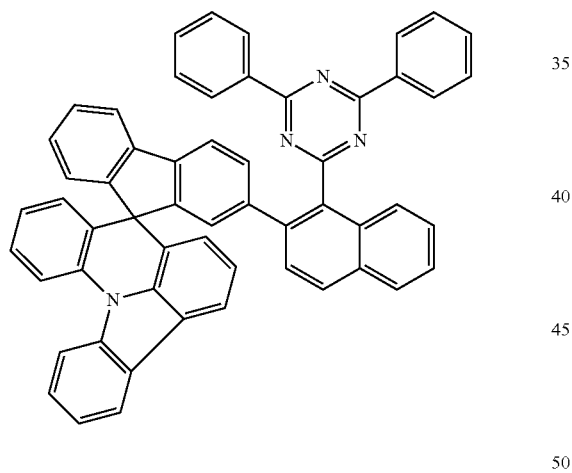
Compound 1-39
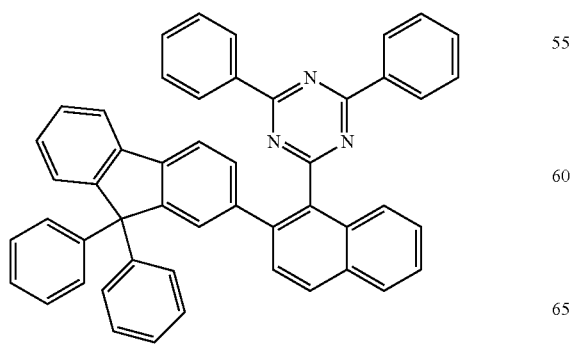
Compound 1-40
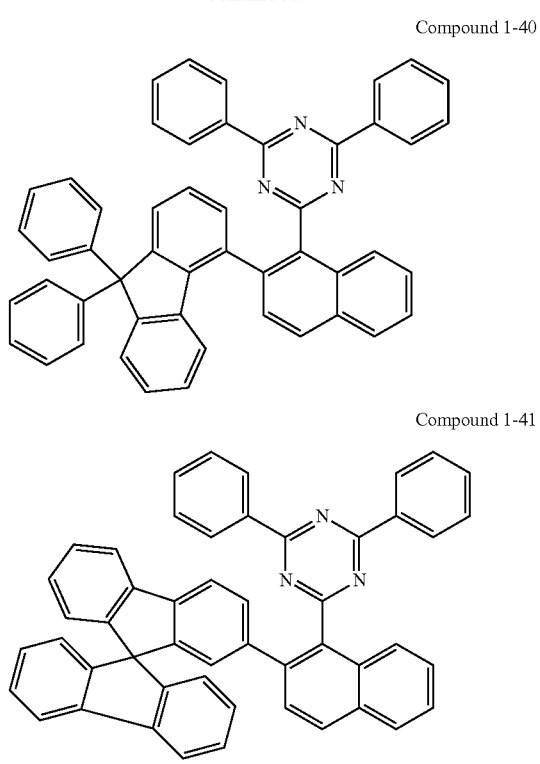
Compound 1-41
Compound 1-42
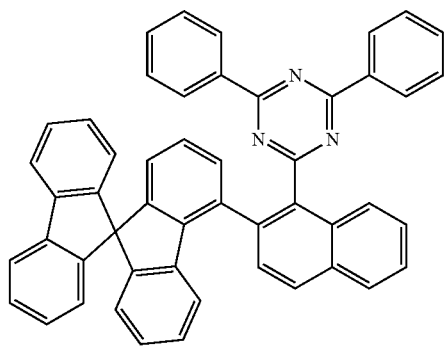
Compound 1-43
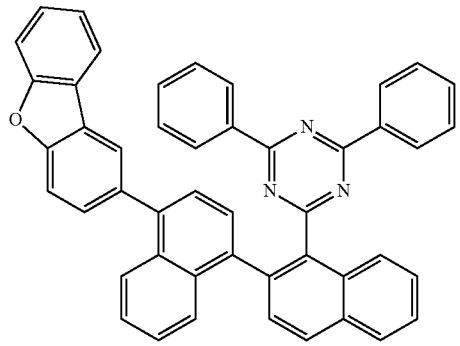

Compound 1-44
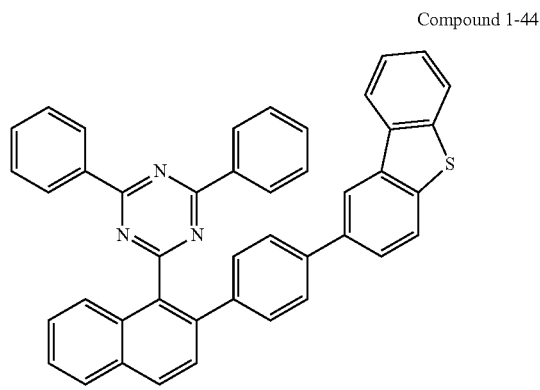
Compound 1-45
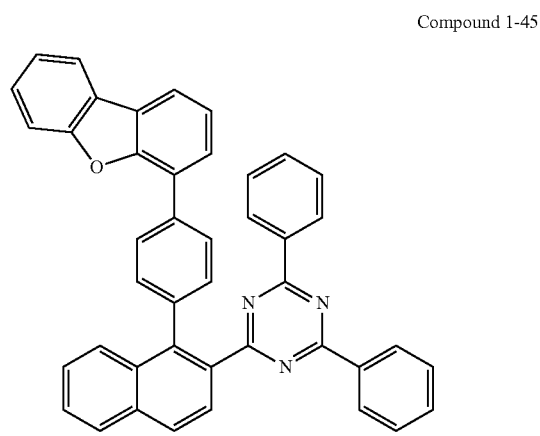
Compound 1-46
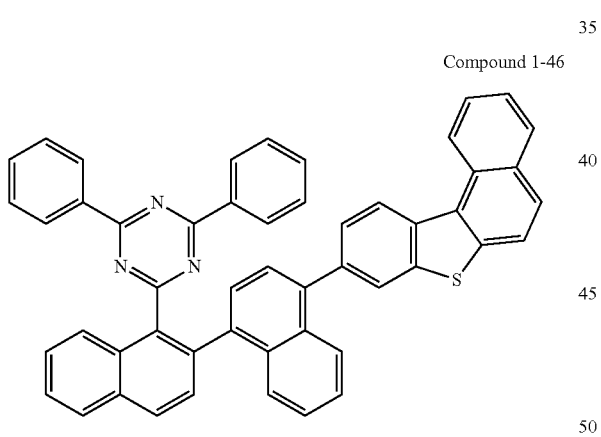
Compound 1-47
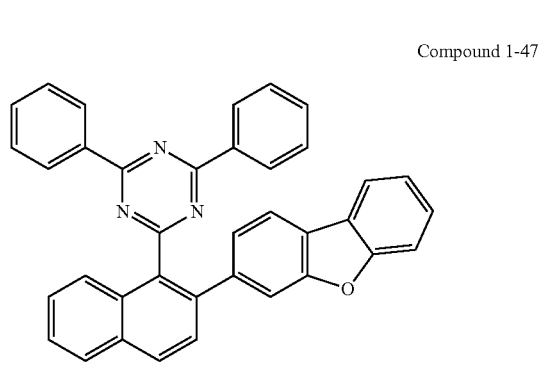
Compound 1-48
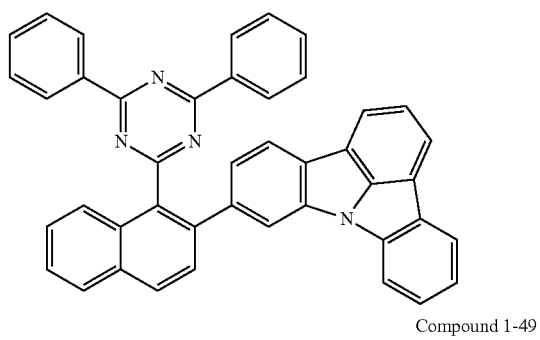
Compound 1-49
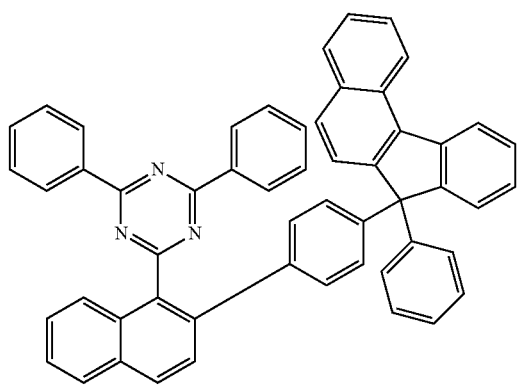
Compound 1-50
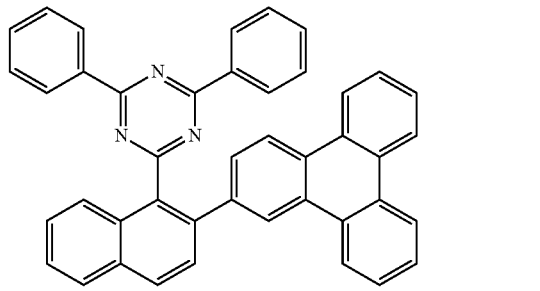
Compound 1-51
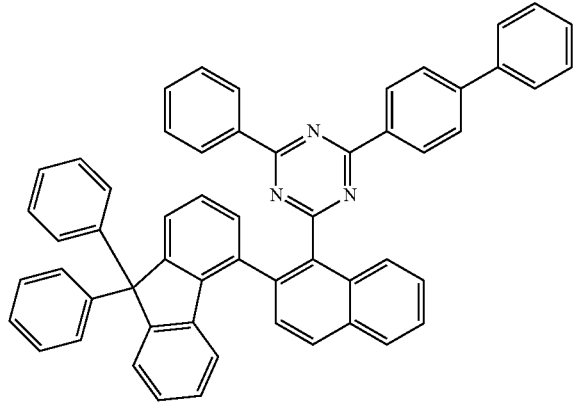

-continued
Compound 1-52
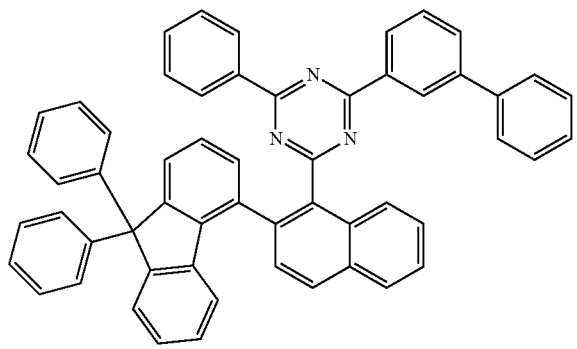
Compound 1-53
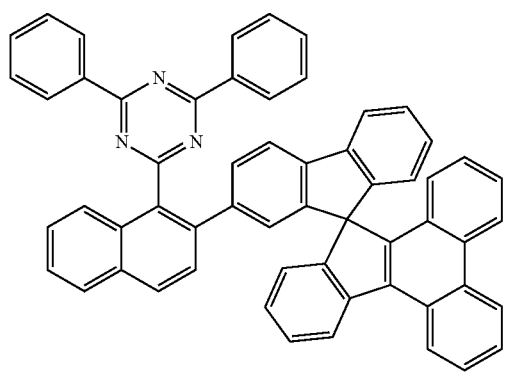
Compound 1-54
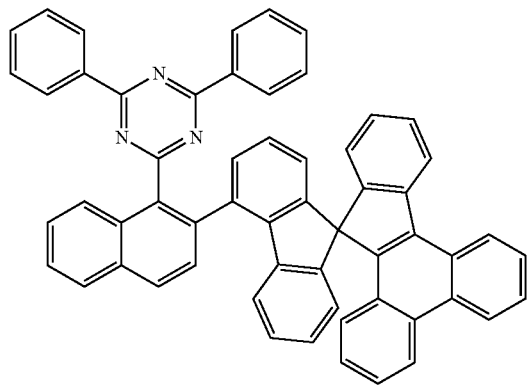
Compound 1-55
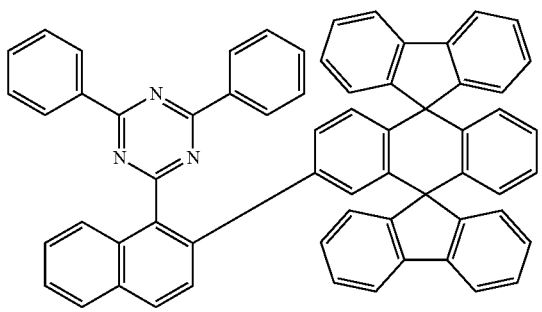
-continued
Compound 1-56
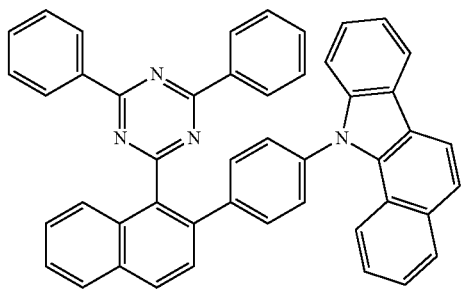
Compound 1-57
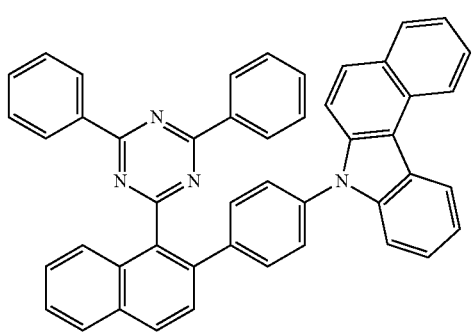
Compound 2-1
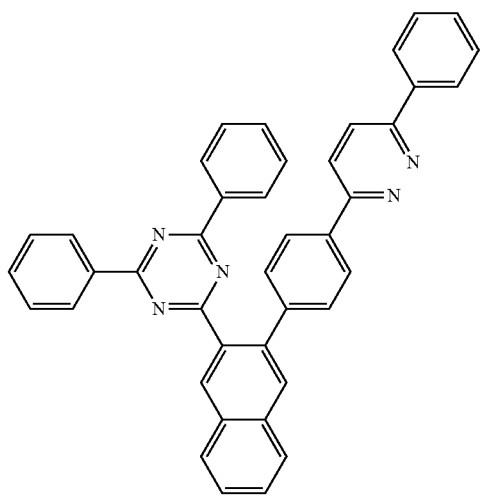
Compound 2-2
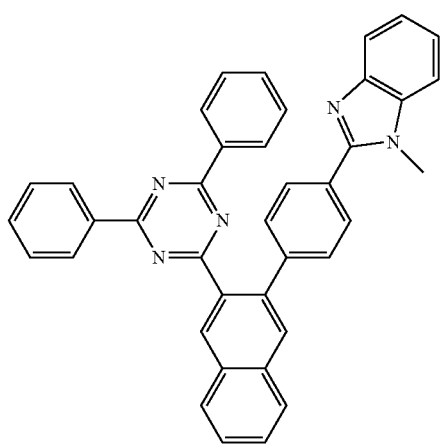

Compound 2-3
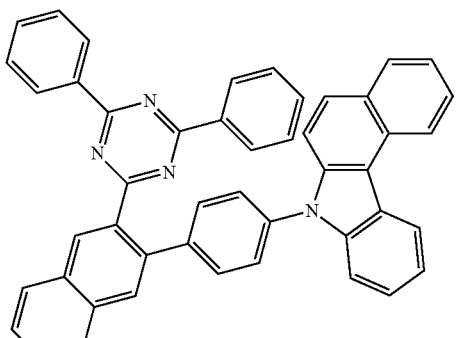
Compound 2-4
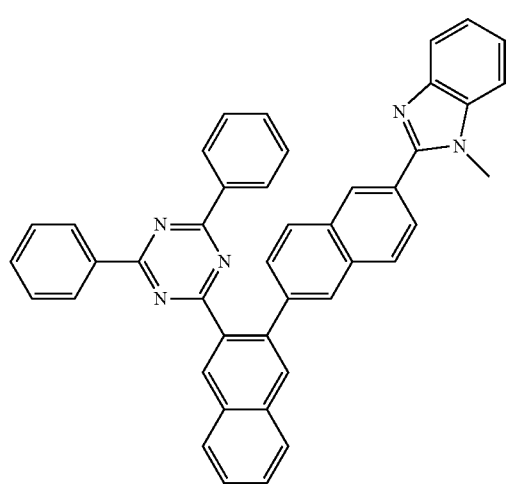
Compound 2-5
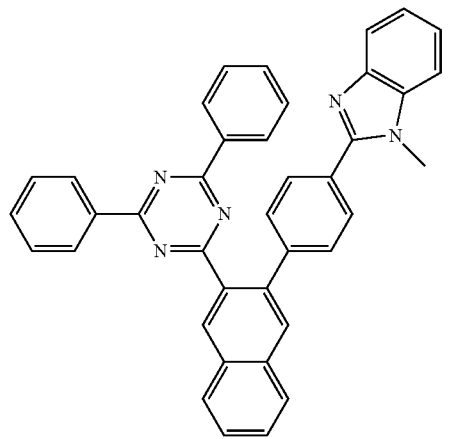
Compound 2-6
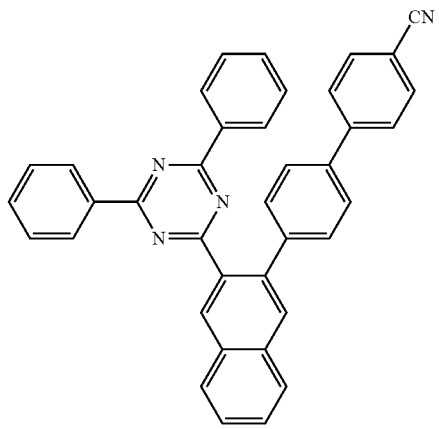
Compound 2-7
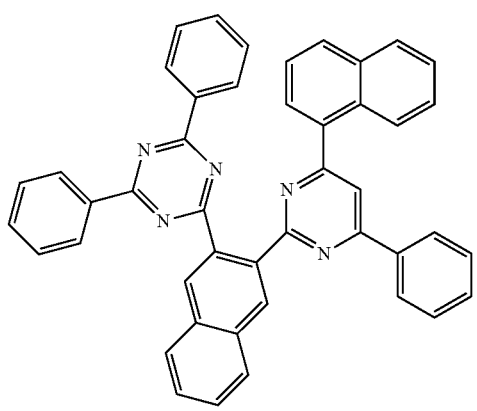
Compound 2-8
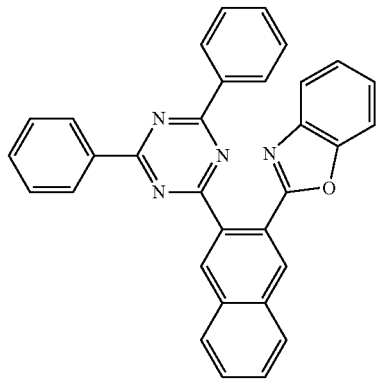

Compound 2-9
Compound 2-12
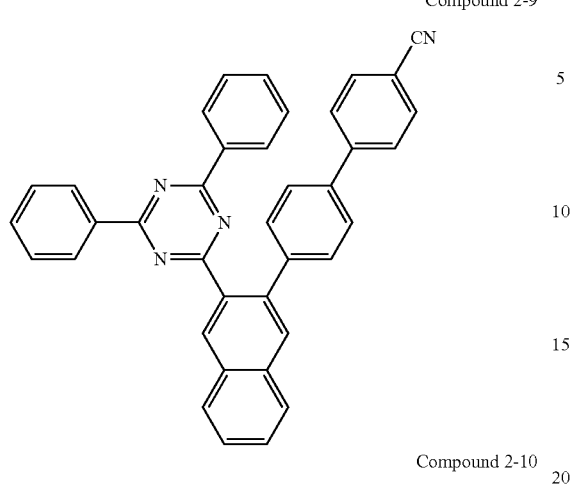
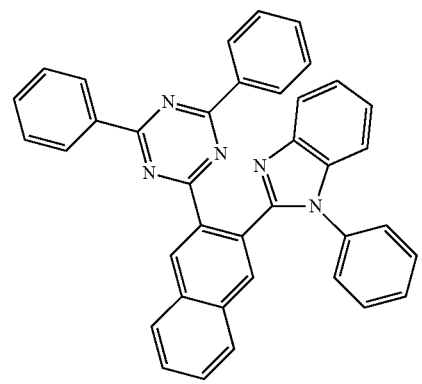
Compound 2-10
Compound 2-13
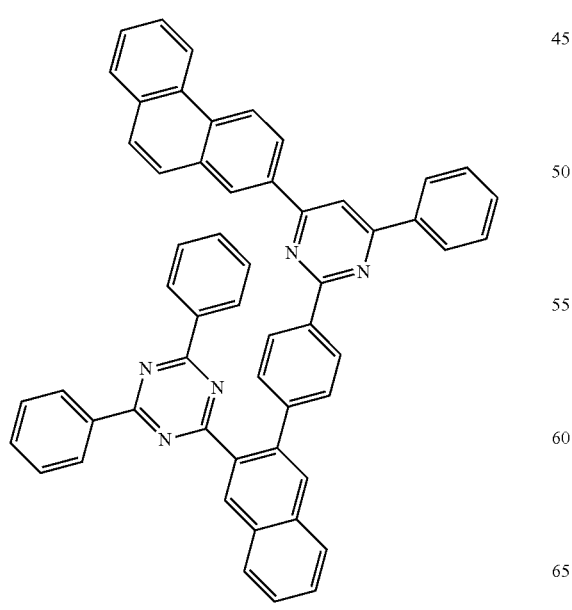
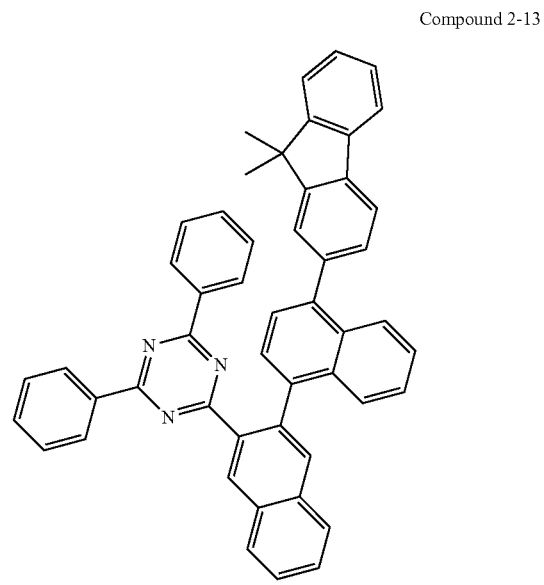
Compound 2-11
Compound 2-14

Compound 2-15
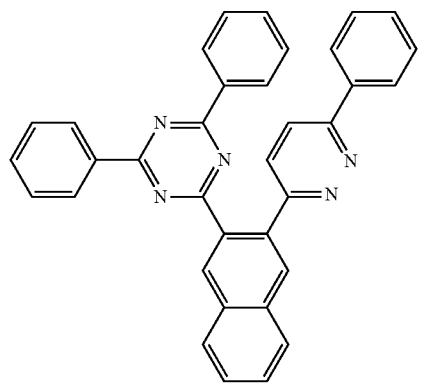
Compound 2-16
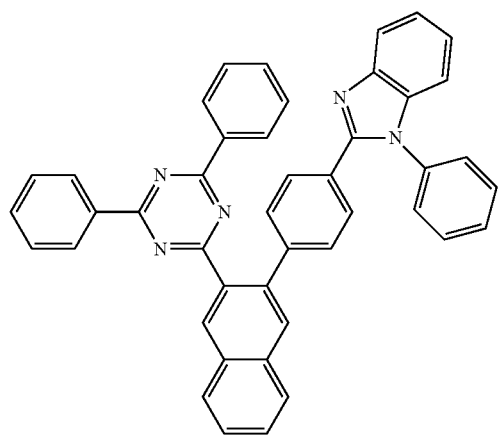
Compound 2-17
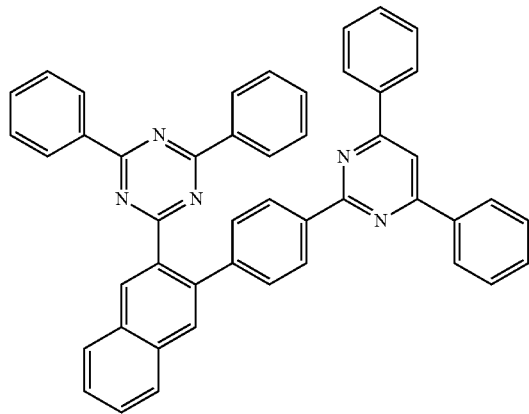
Compound 2-18
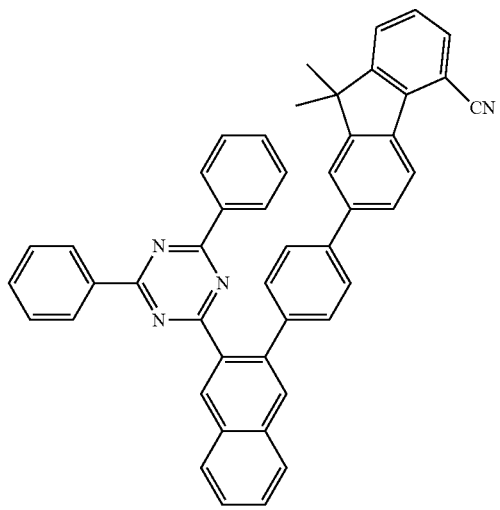
Compound 2-39
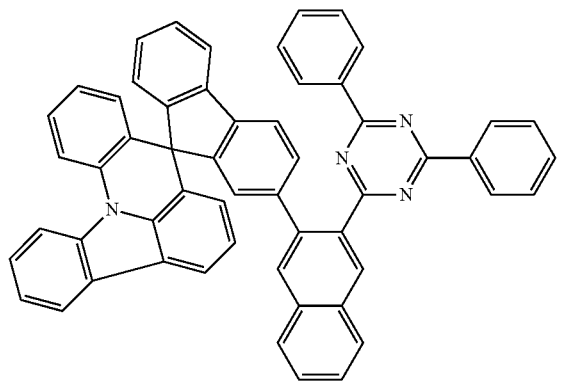
Compound 2-19
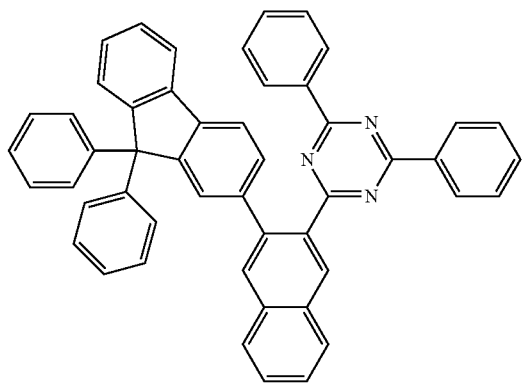

-continued
Compound 2-20
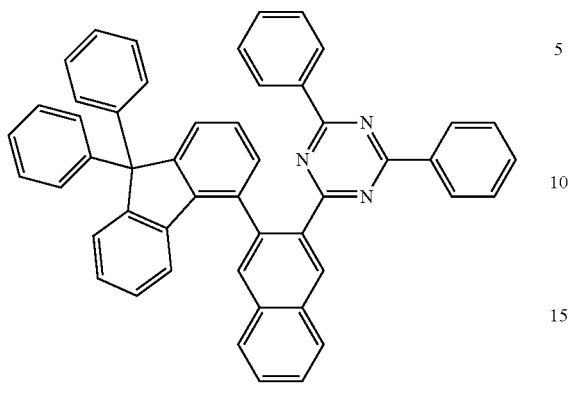
Compound 2-21
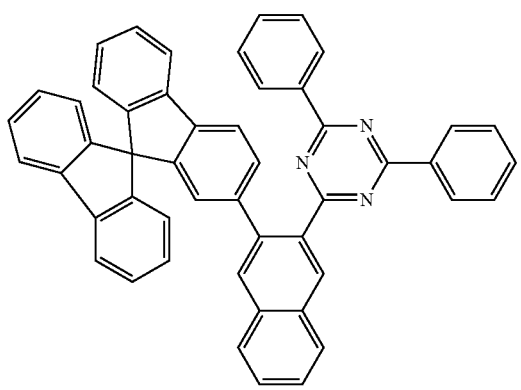
Compound 2-22
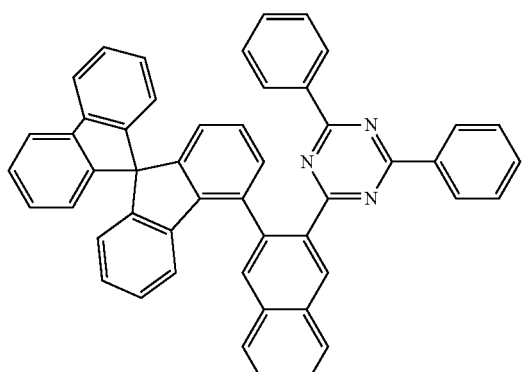
-continued
Compound 2-23
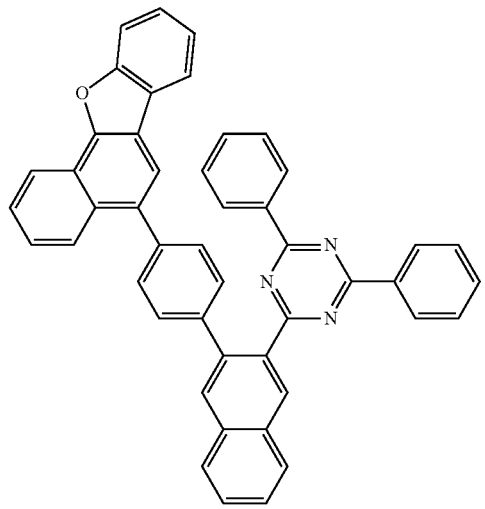
Compound 2-24
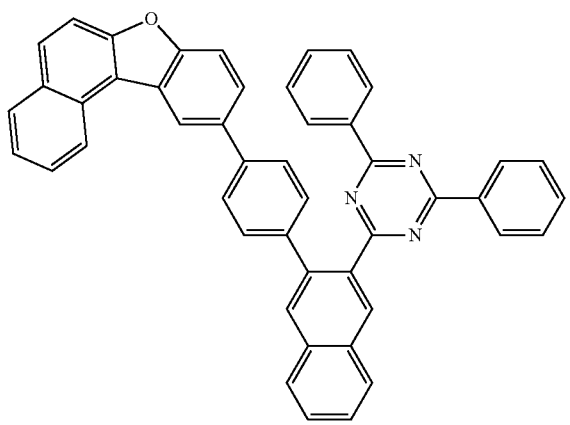
Compound 2-25
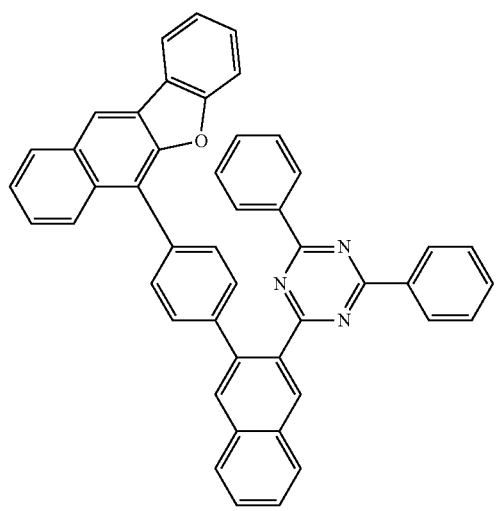

Compound 2-26
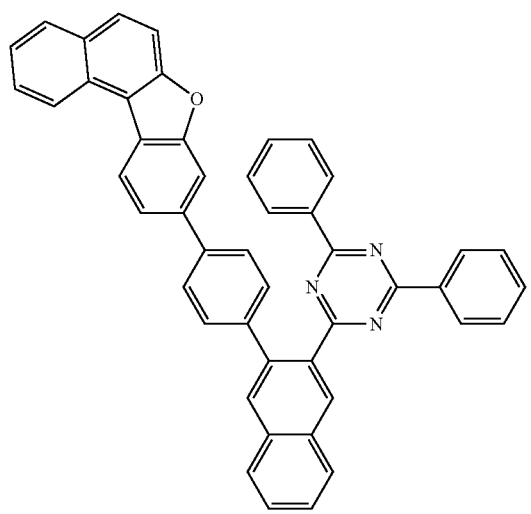
Compound 2-27
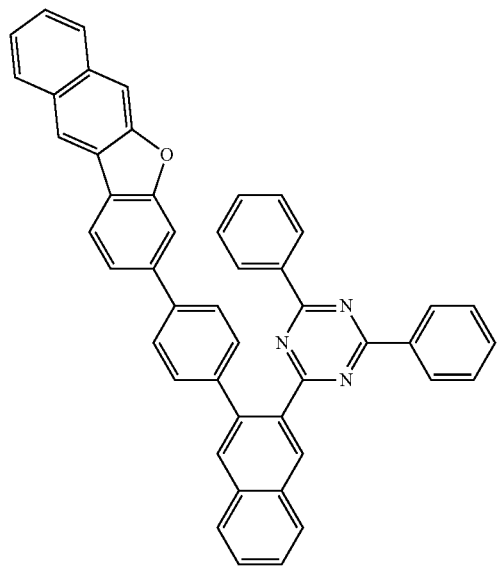
Compound 2-28
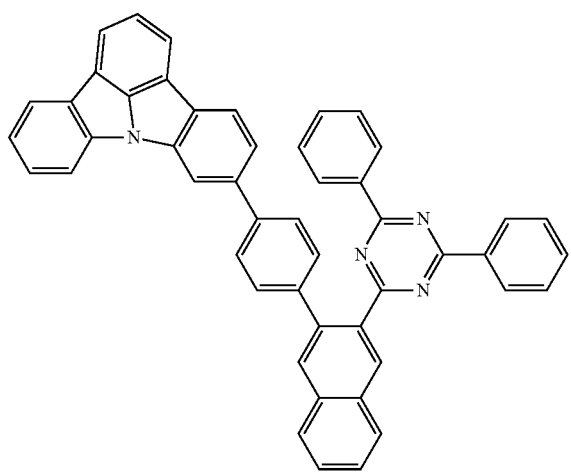
Compound 2-29
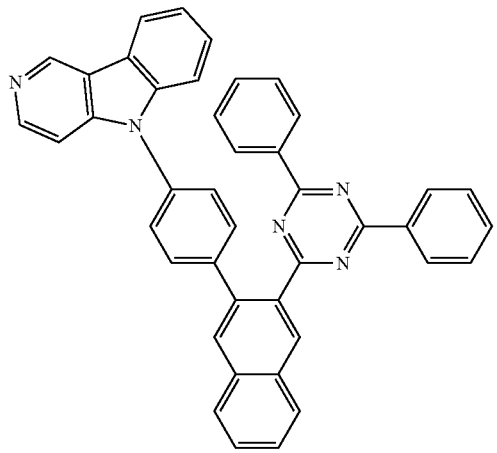
Compound 2-30
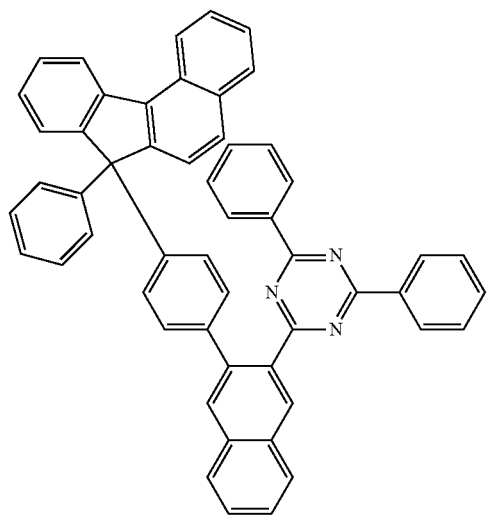
Compound 2-31

Compound 2-32
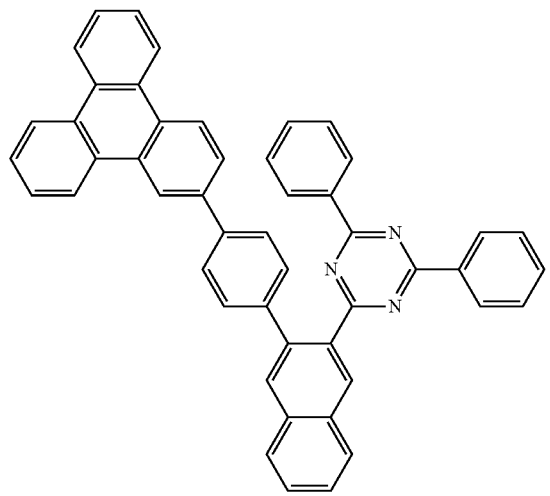
Compound 2-33
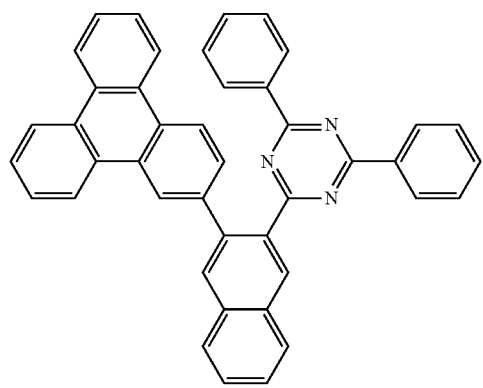
Compound 2-34
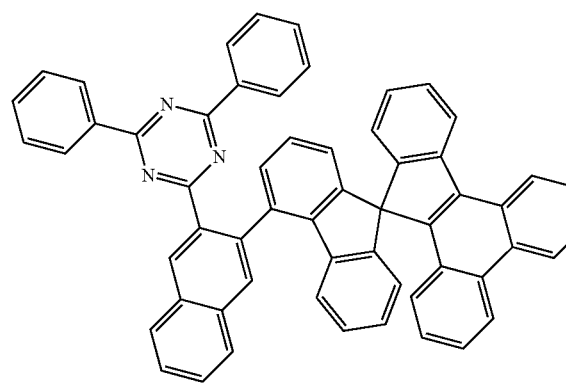
Compound 2-35
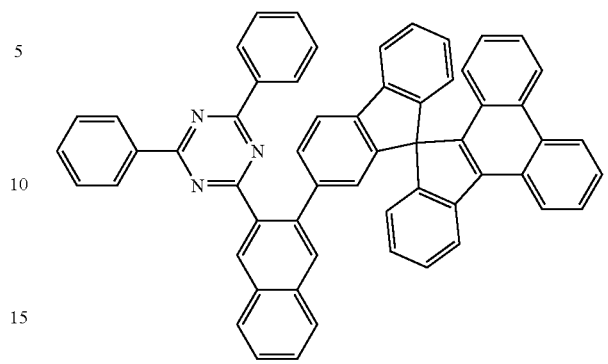
Compound 2-36
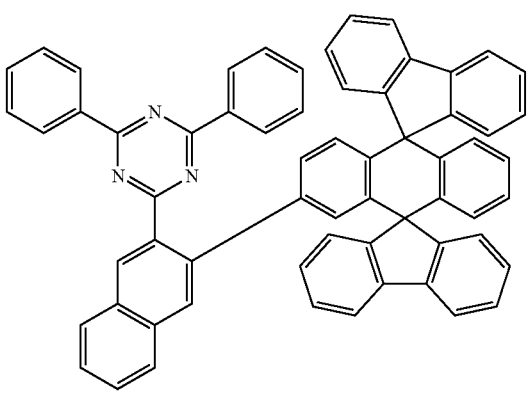
Compound 2-37
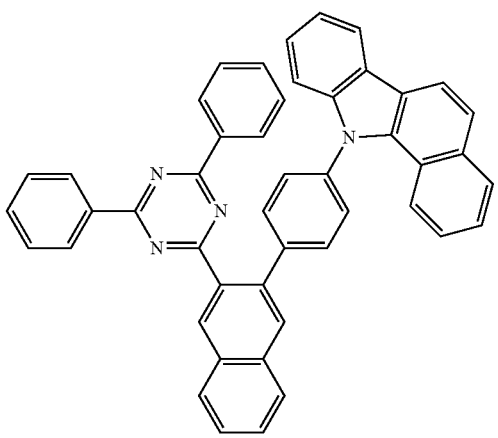

Compound 2-38
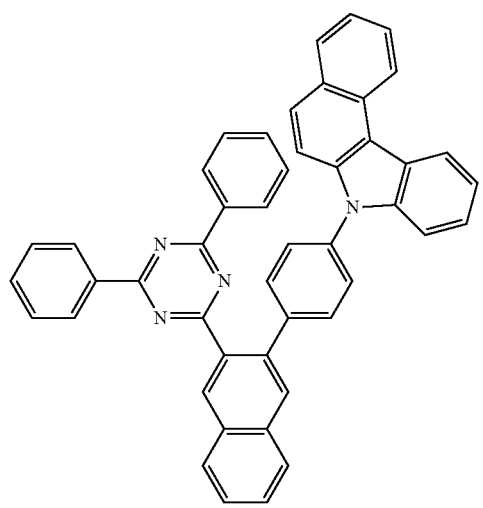
Compound 3-3
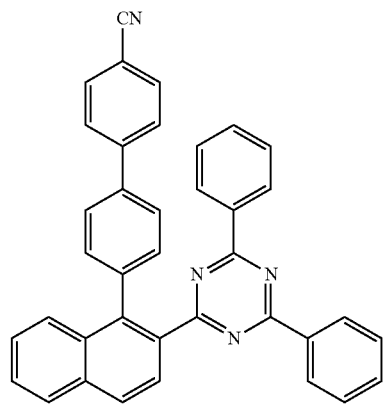
Compound 3-1
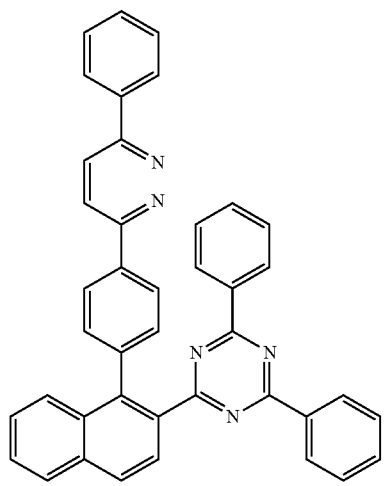
Compound 3-4
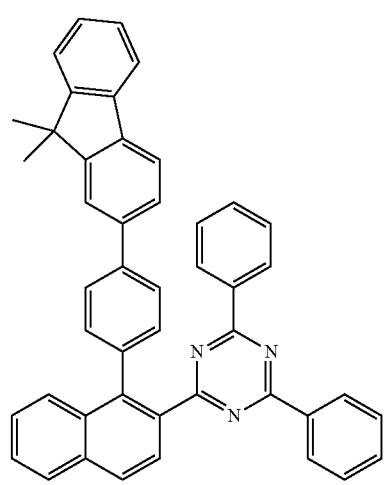
Compound 3-2
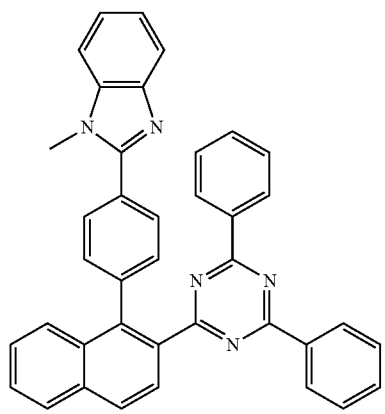
Compound 3-5
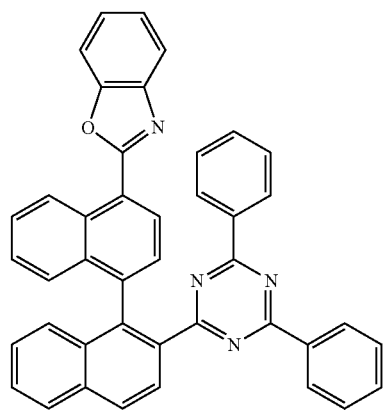

Compound 3-6
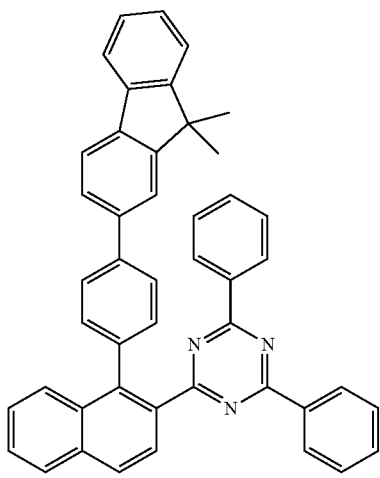
Compound 3-9
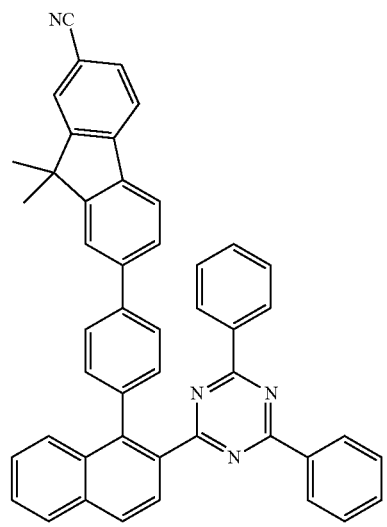
Compound 3-7
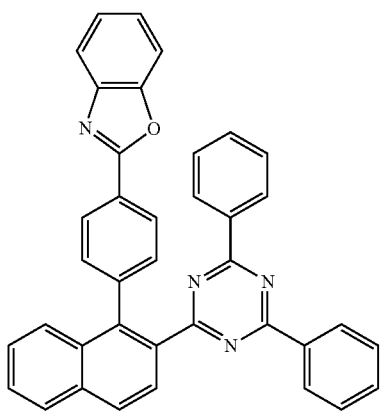
Compound 3-10
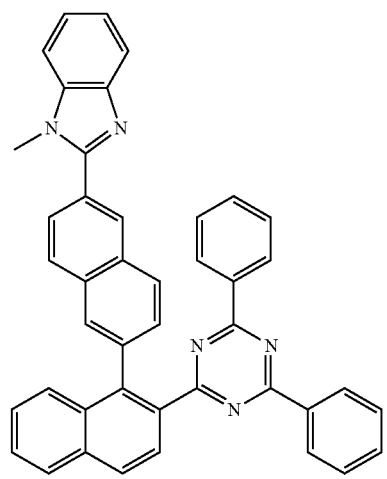
Compound 3-8
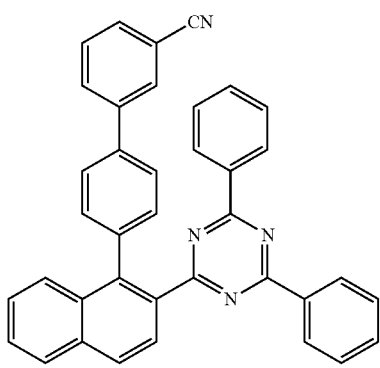
Compound 3-11
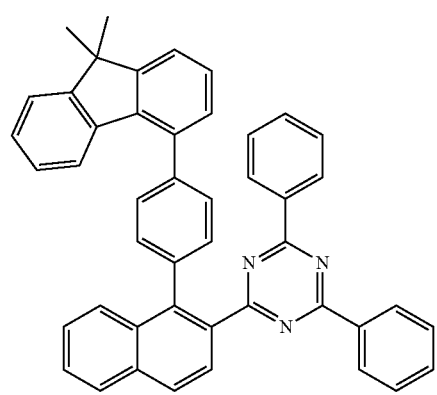

Compound 3-12
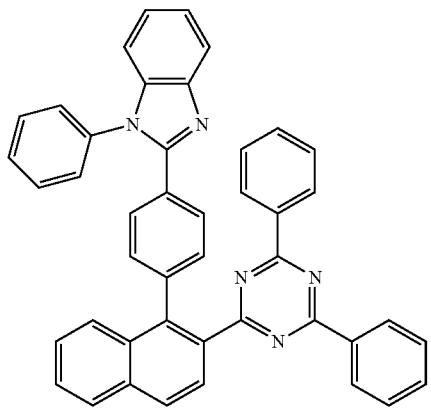
Compound 3-13
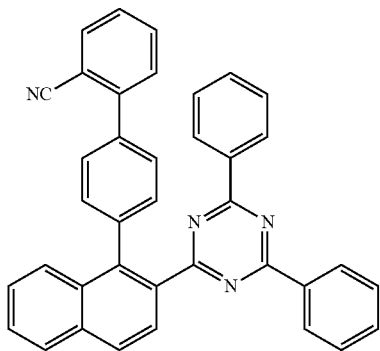
Compound 3-14
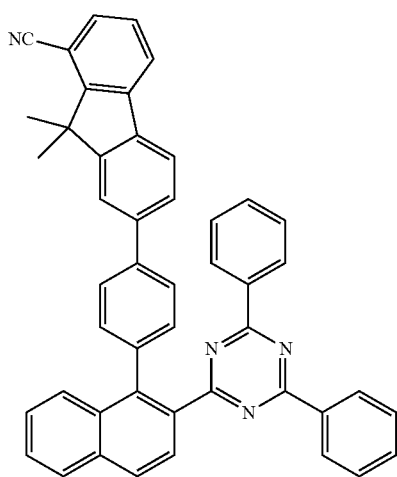
Compound 3-15
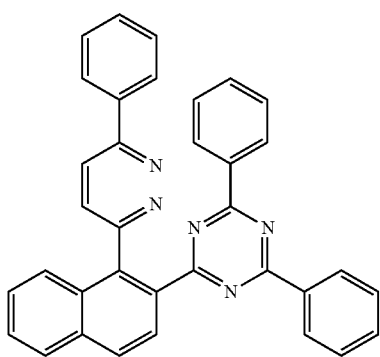
Compound 3-16
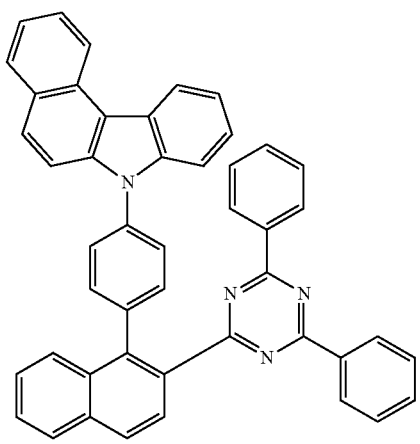
Compound 3-17
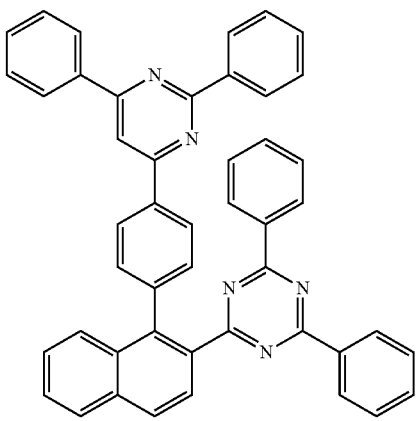
Compound 3-18
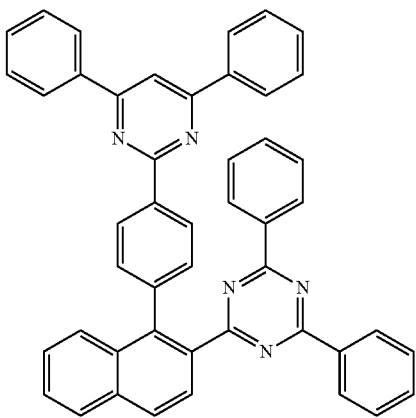

Compound 3-19
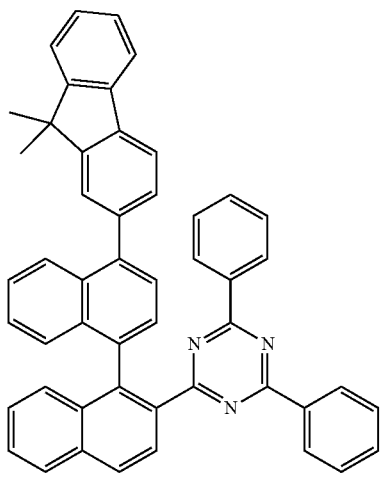
Compound 3-20
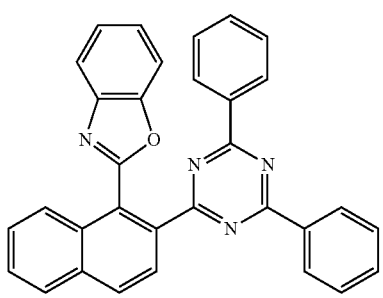
Compound 3-21
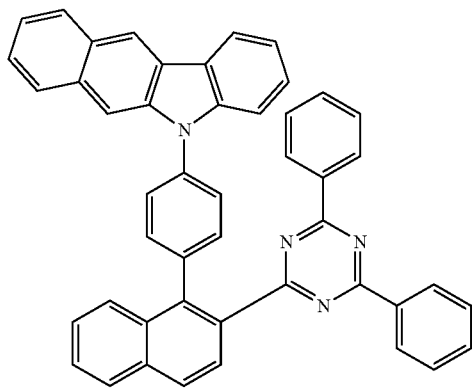
Compound 3-22
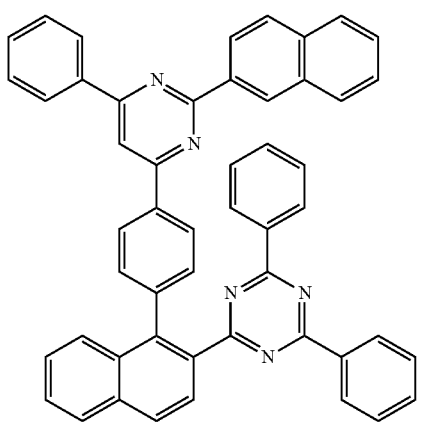
Compound 3-23
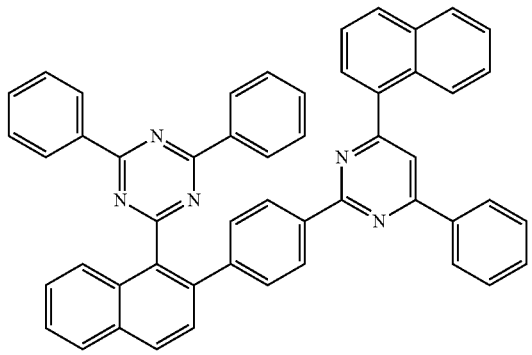
Compound 3-24
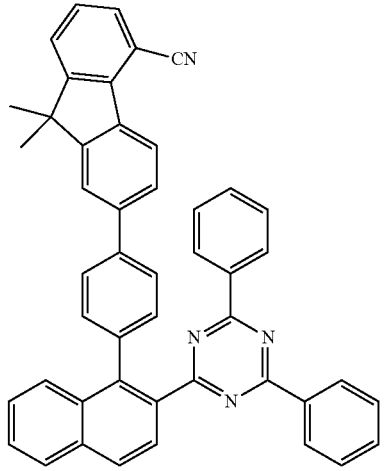
Compound 3-25
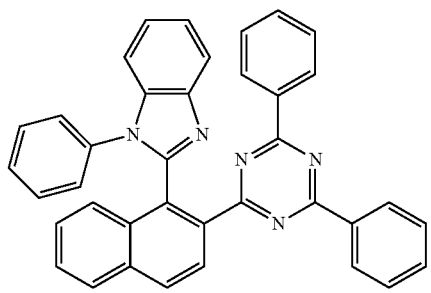
Compound 3-26
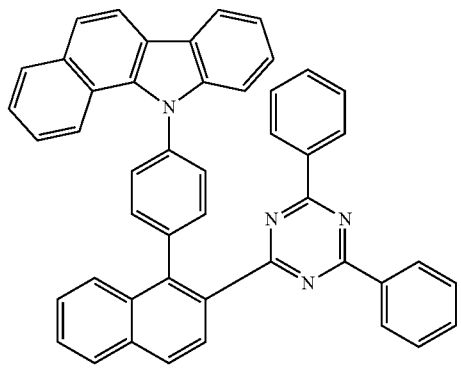

Compound 3-27
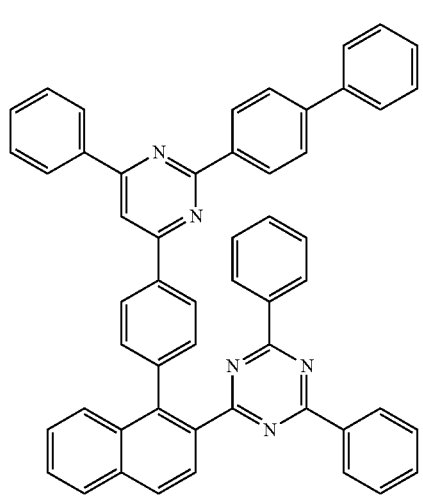
Compound 3-28
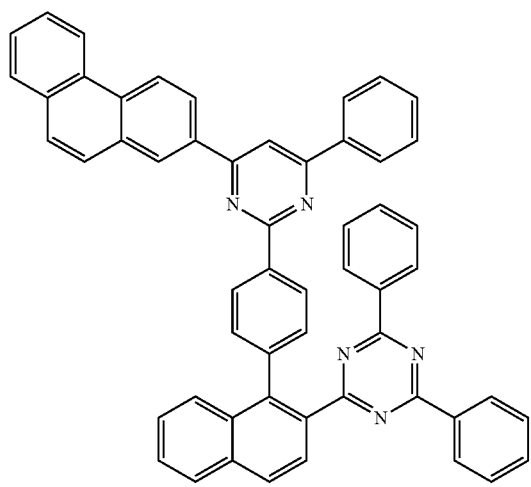
Compound 3-29
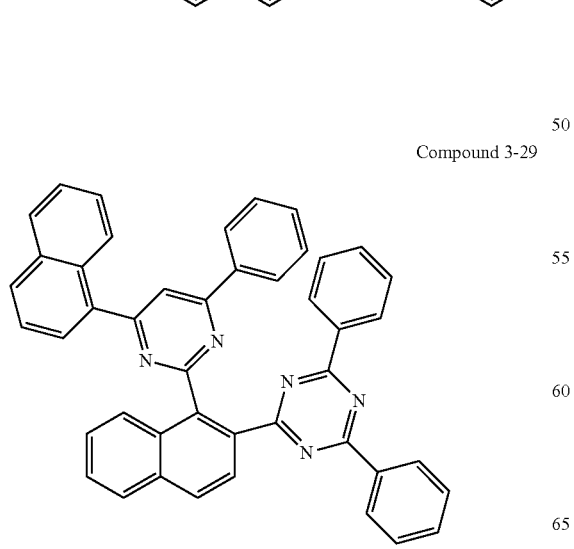
Compound 3-30
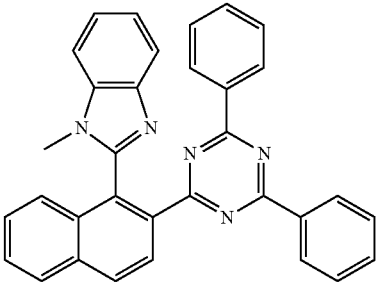
Compound 3-31
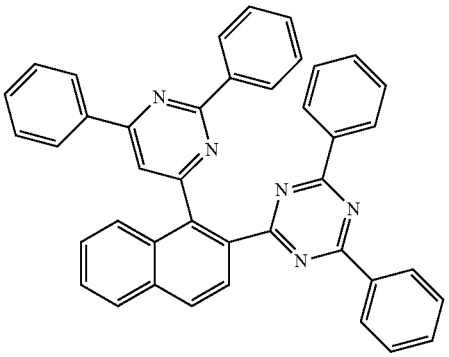
Compound 3-32
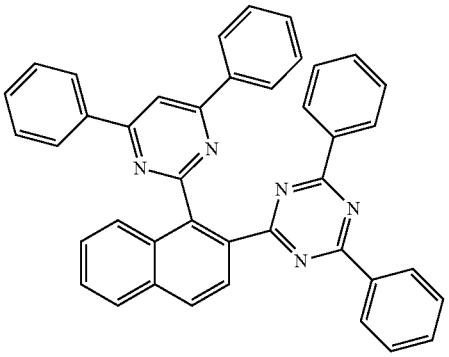
Compound 3-33
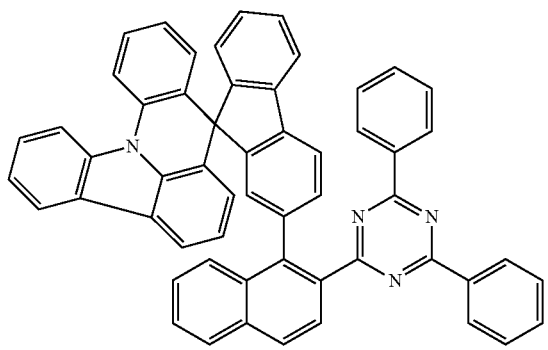

Compound 3-34
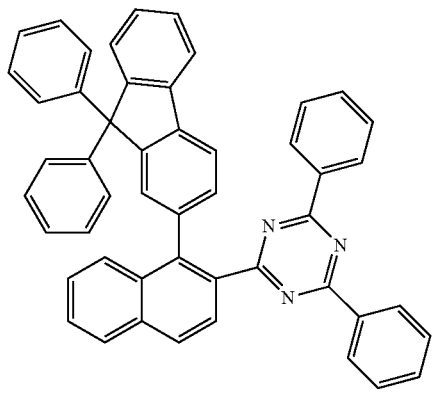
Compound 3-35
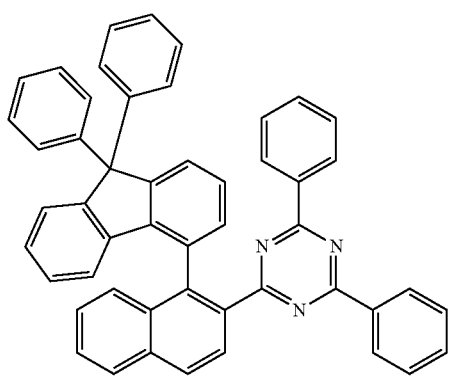
Compound 3-36
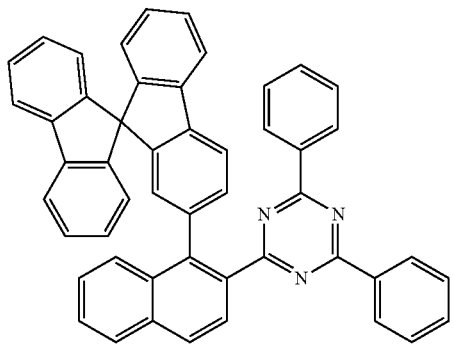
Compound 3-37
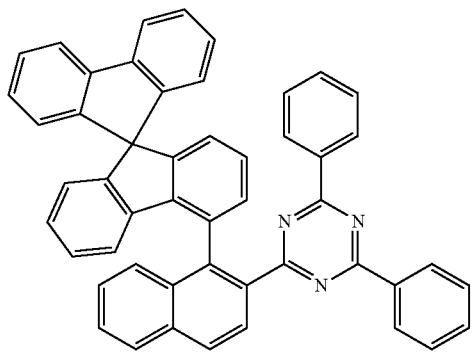
Compound 3-38
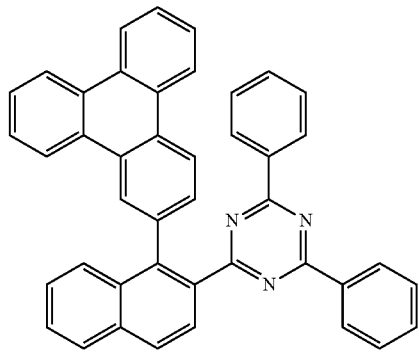
Compound 3-39
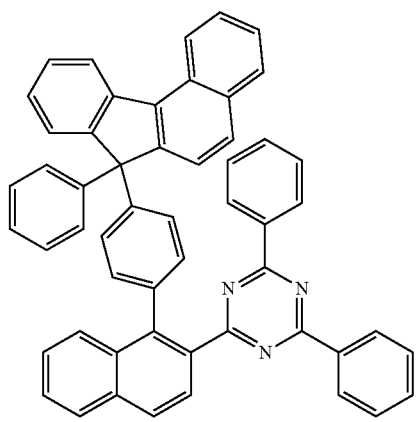
Compound 3-40
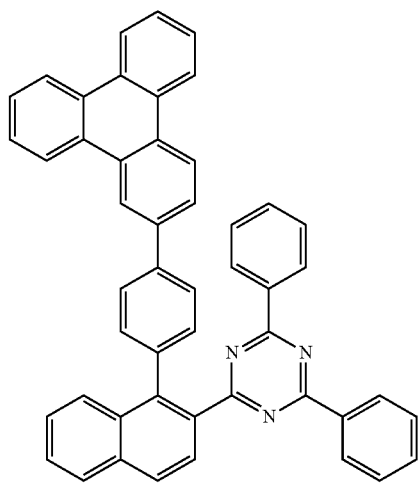

Compound 3-41
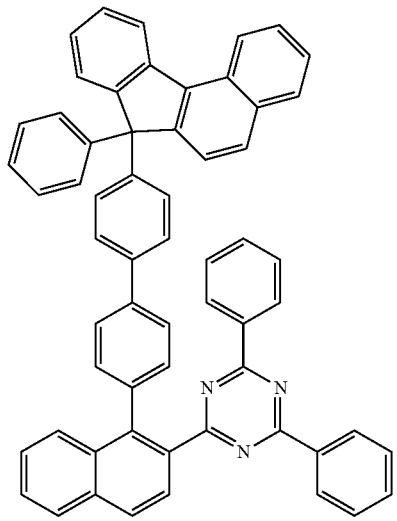
Compound 3-42
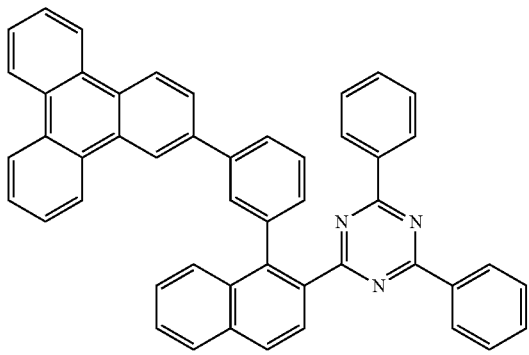
Compound 3-43
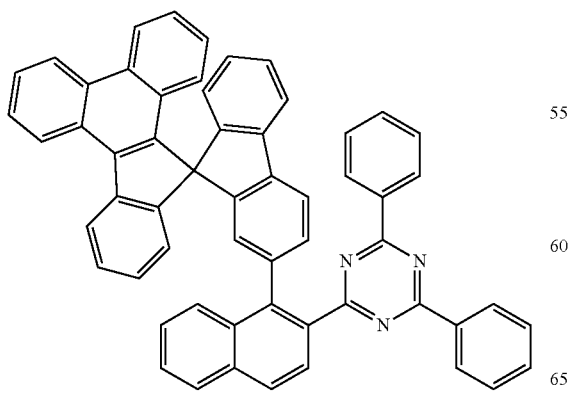
Compound 3-44
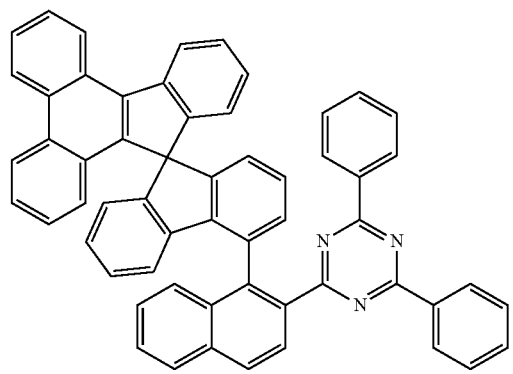
Compound 3-45
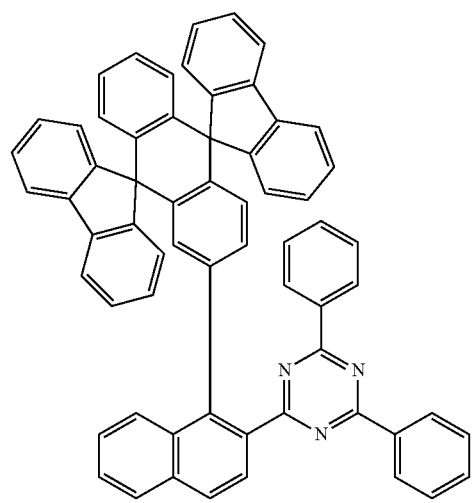
Compound 3-46
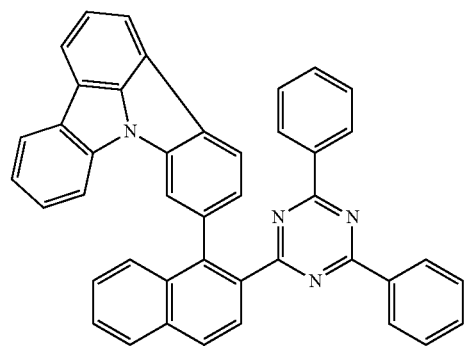

Compound 3-47
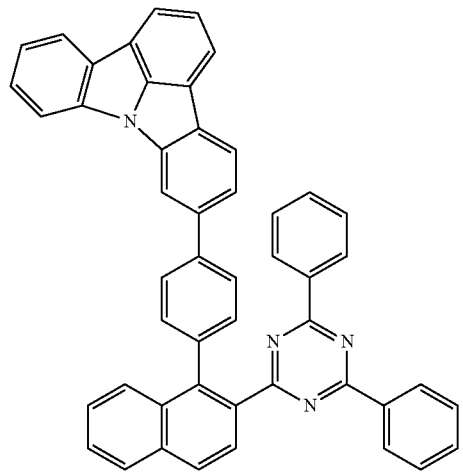
Compound 3-48
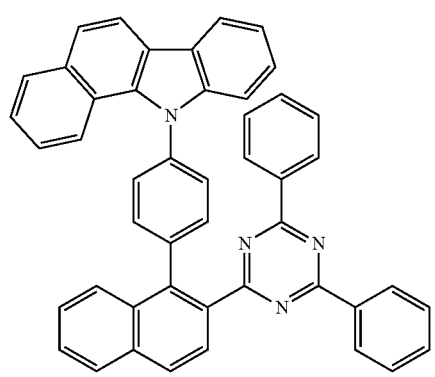
Compound 3-49
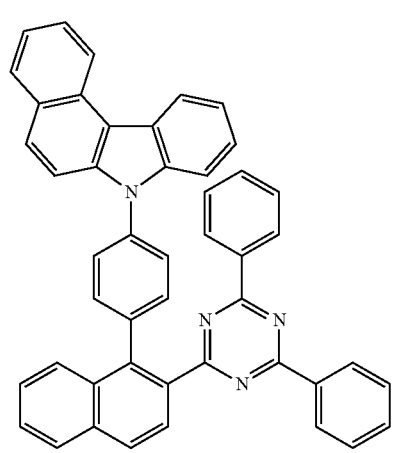
Compound 3-50
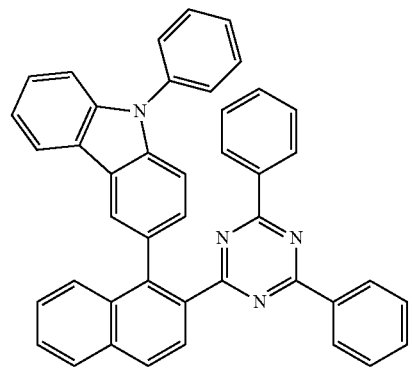
Compound 4-1
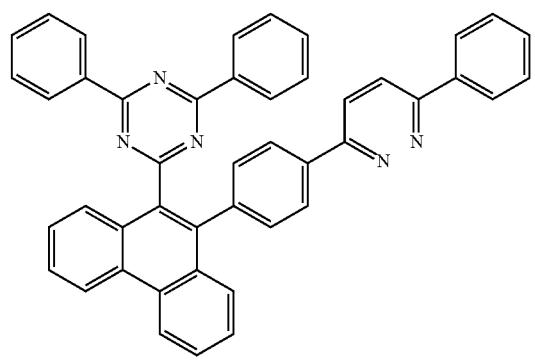
Compound 4-2
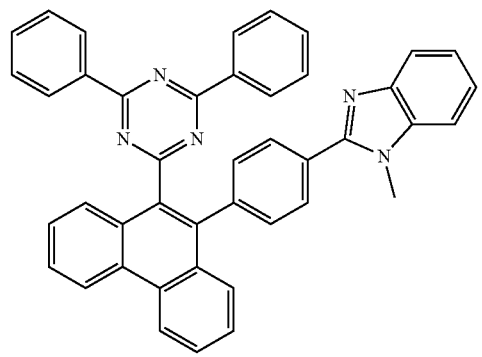
Compound 4-3

Compound 4-4
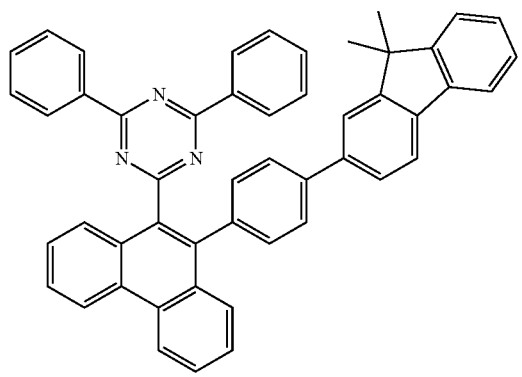
Compound 4-5
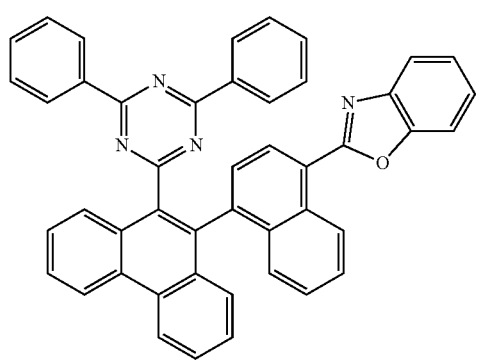
Compound 4-6
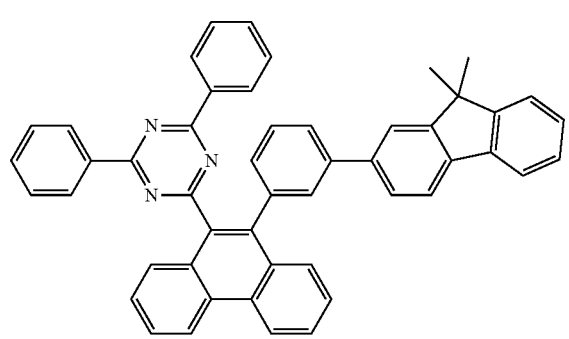
Compound 4-7
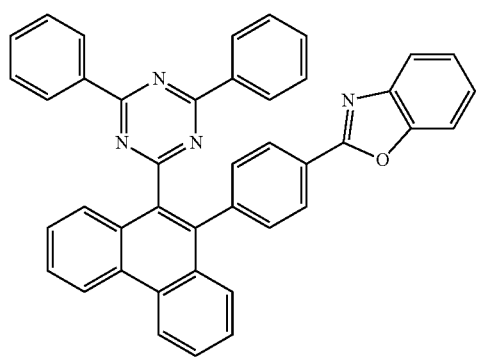
Compound 4-8
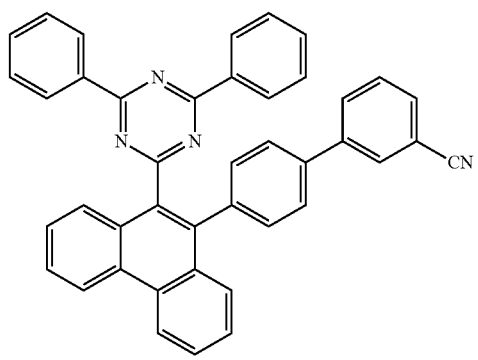
Compound 4-9
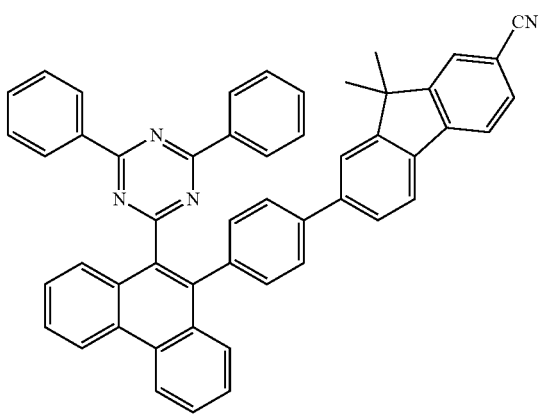
Compound 4-10
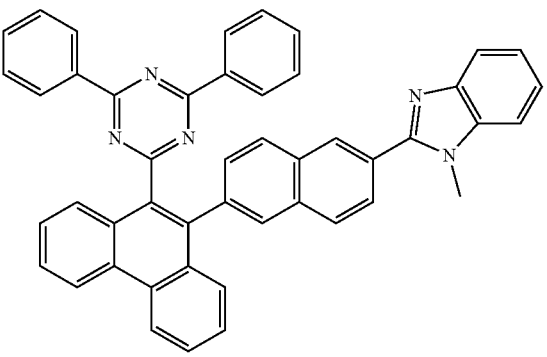
Compound 4-11
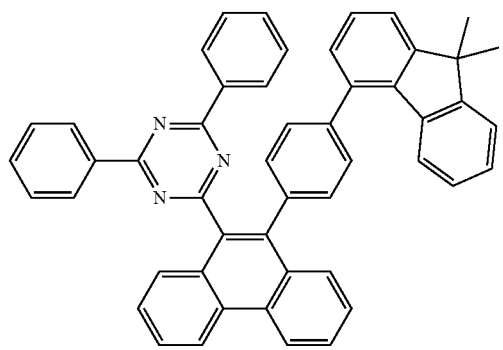

Compound 4-12
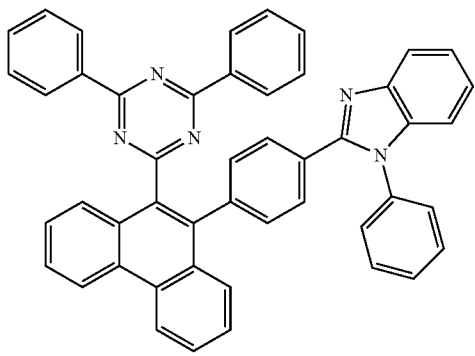
Compound 4-13
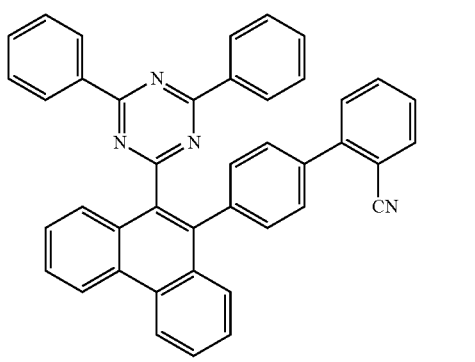
Compound 4-14
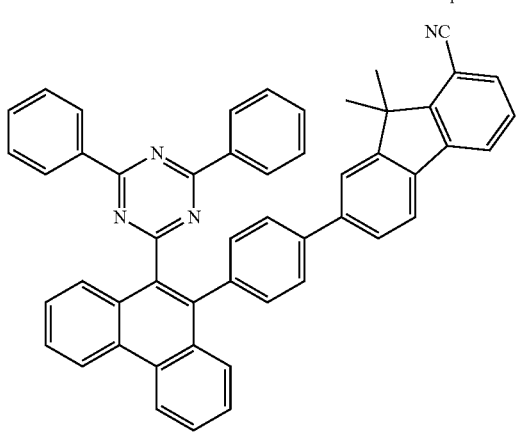
Compound 4-15
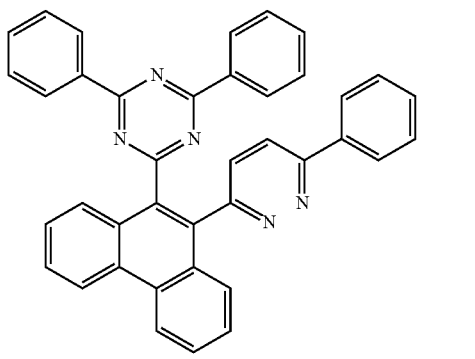
Compound 4-16
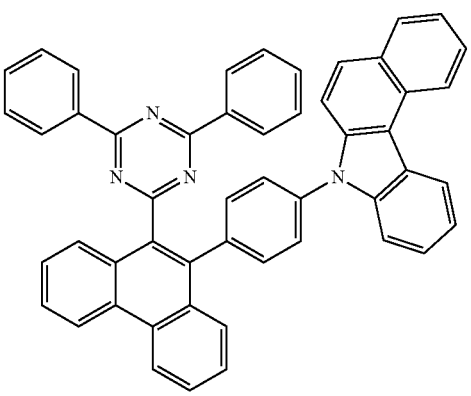
Compound 4-17
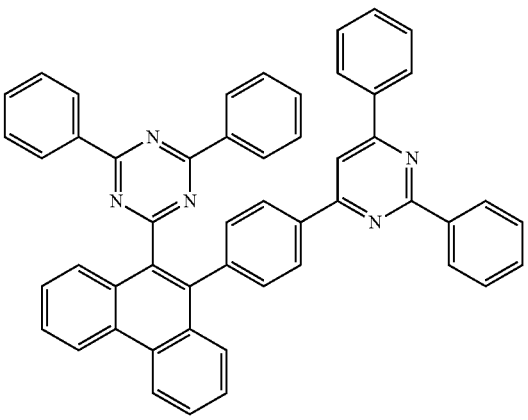
Compound 4-18
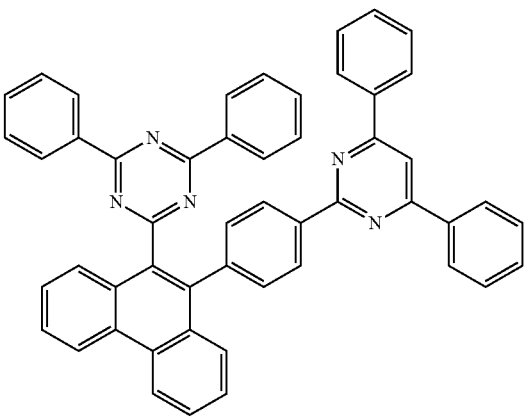

Compound 4-19
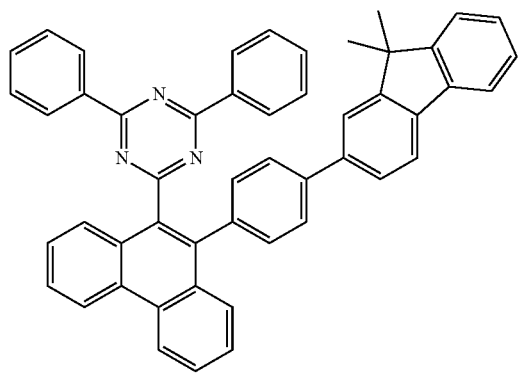
Compound 4-20
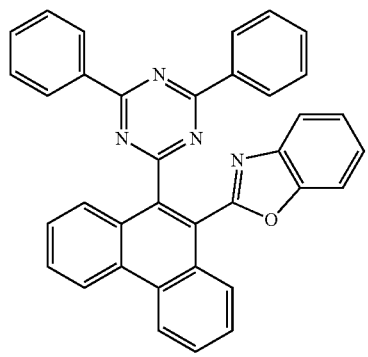
Compound 4-21
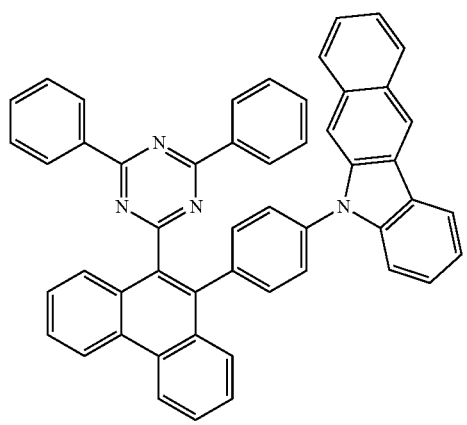
Compound 4-22
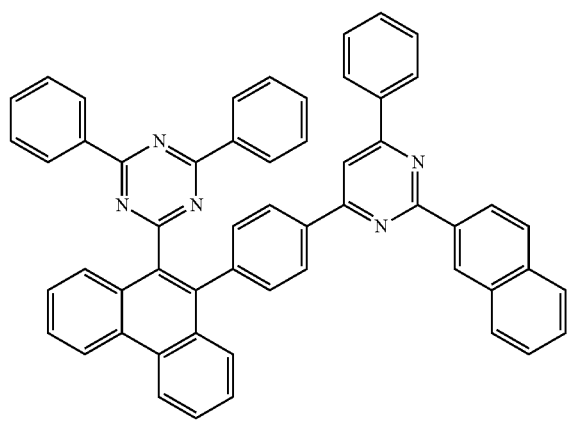
Compound 4-23
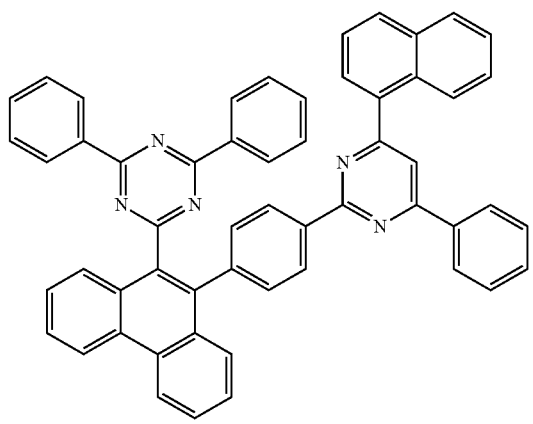
Compound 4-24
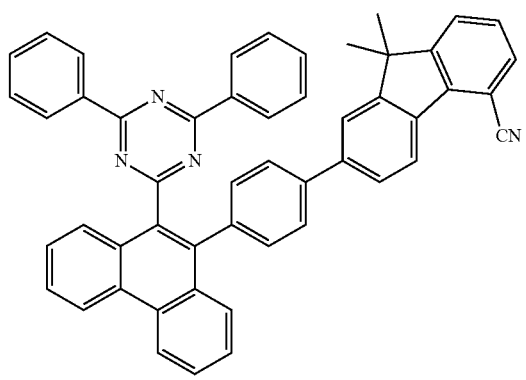
Compound 4-25
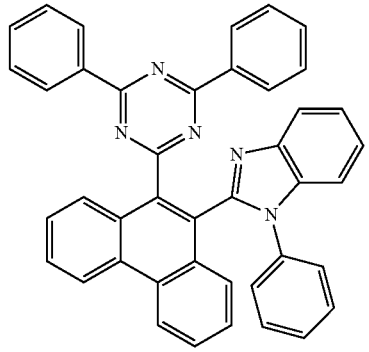
Compound 4-26
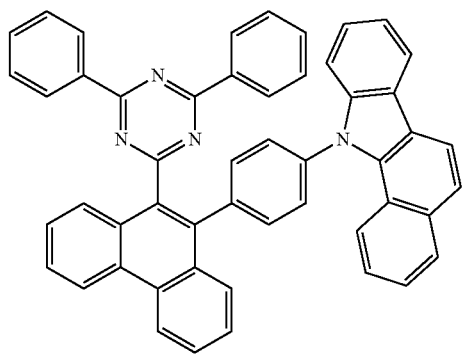

Compound 4-27
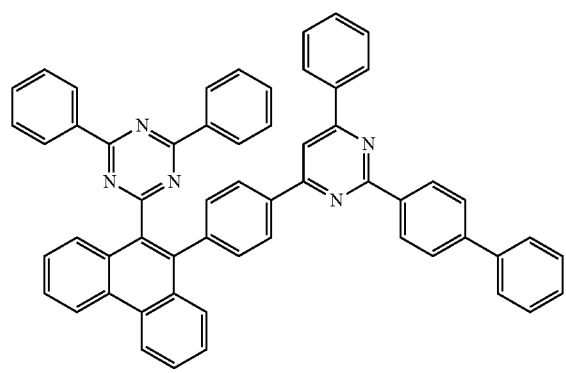
Compound 4-30
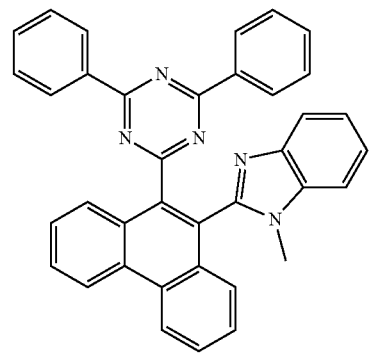
Compound 4-31
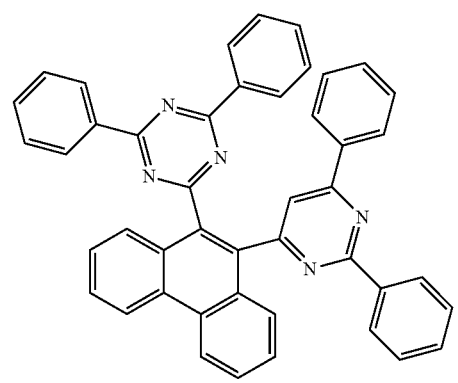
Compound 4-28
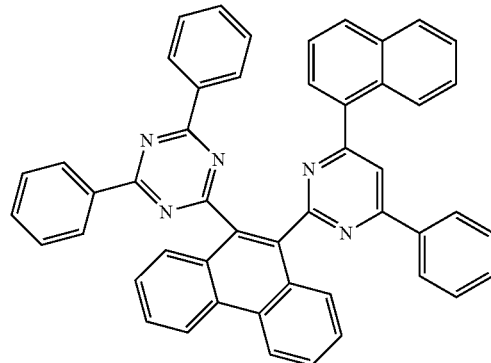
Compound 4-32
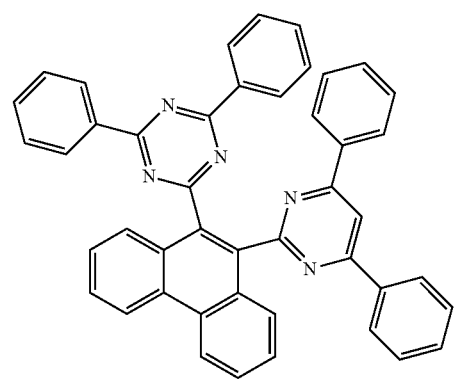
Compound 4-29
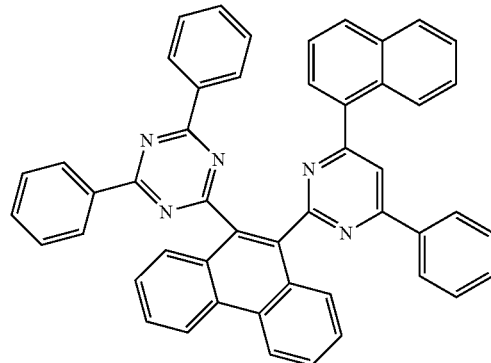
Compound 4-33
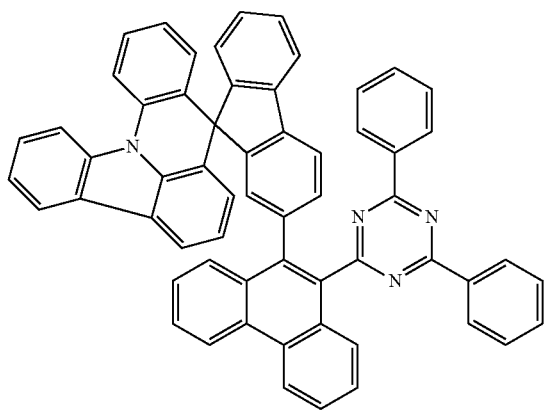

Compound 4-34
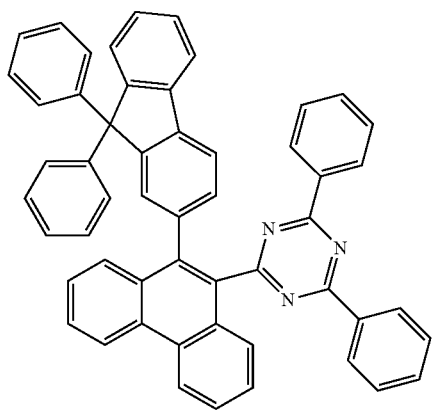
Compound 4-35
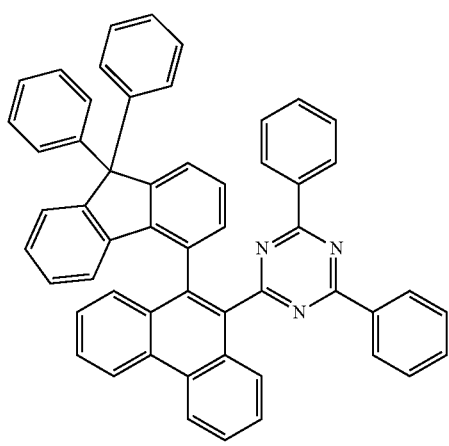
Compound 4-36
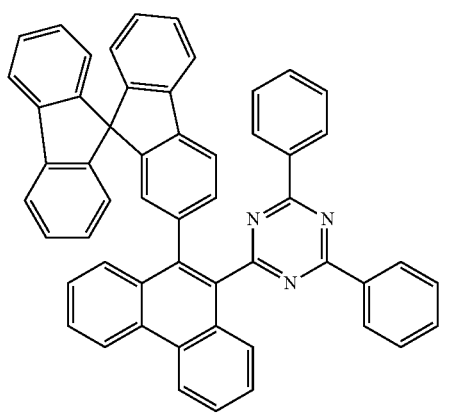
Compound 4-37
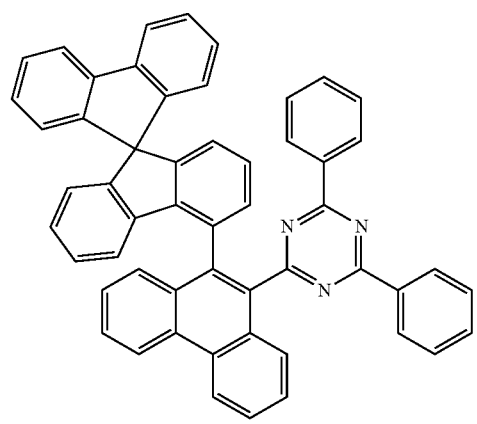
Compound 4-38
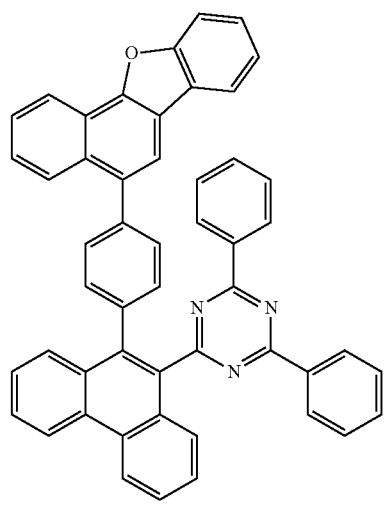
Compound 4-39
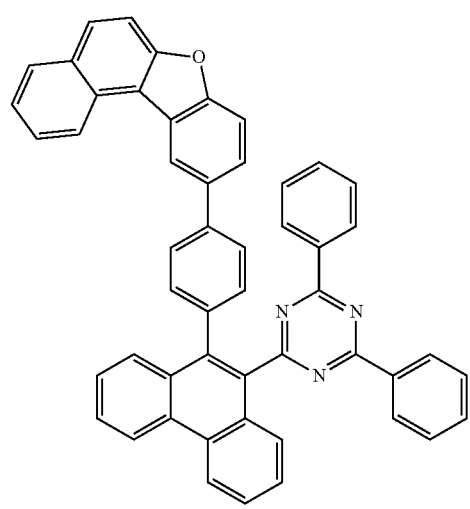

Compound 4-40
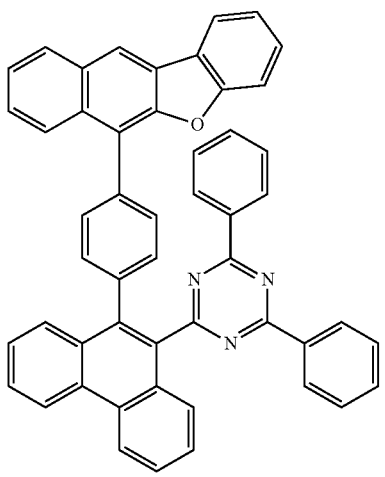
Compound 4-41
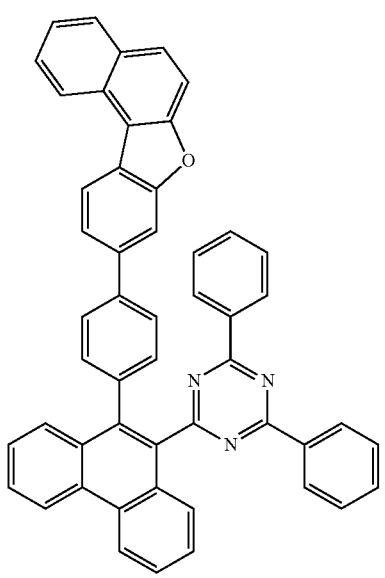
Compound 4-42
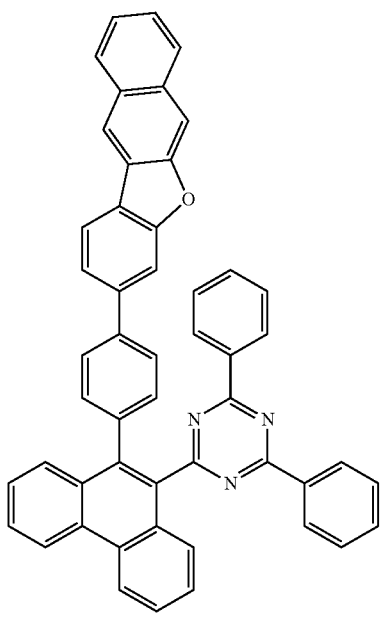
Compound 4-43
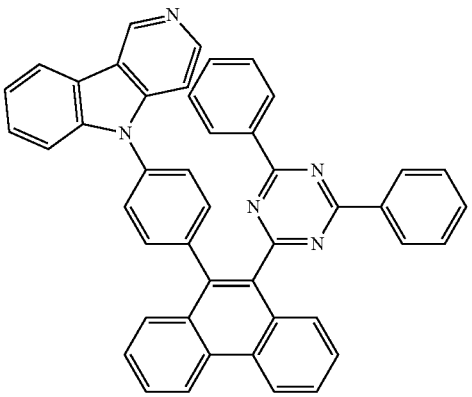
Compound 4-44
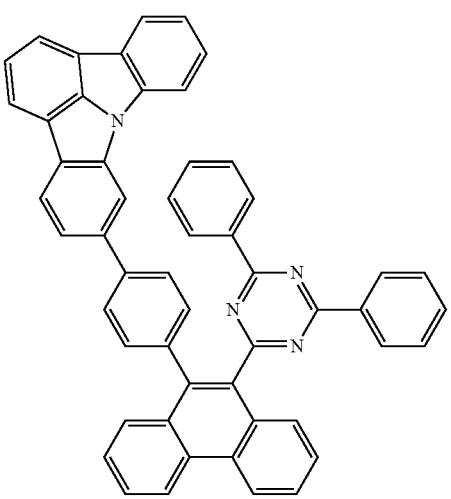
Compound 4-45
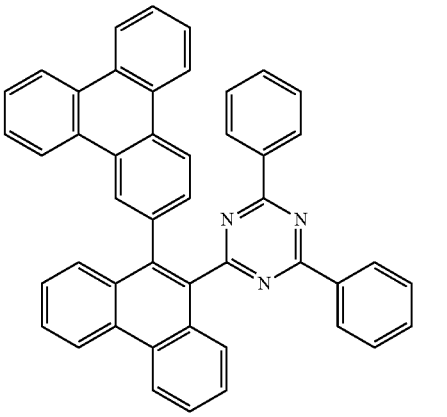

Compound 4-46
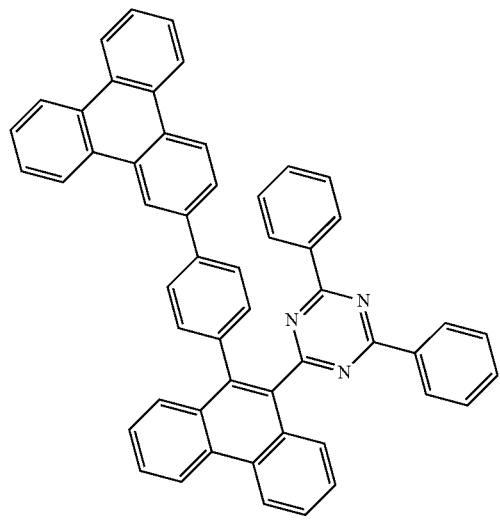
Compound 4-49
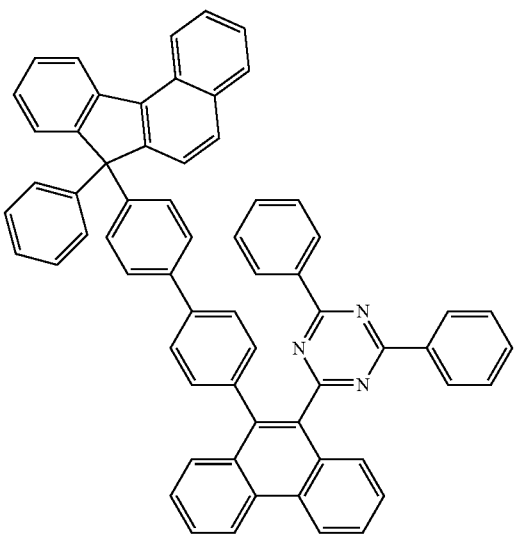
Compound 4-47
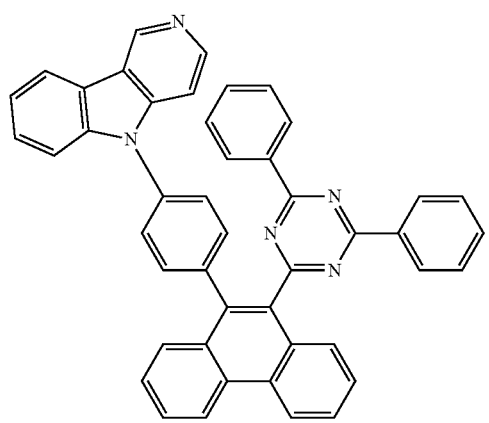
Compound 4-50
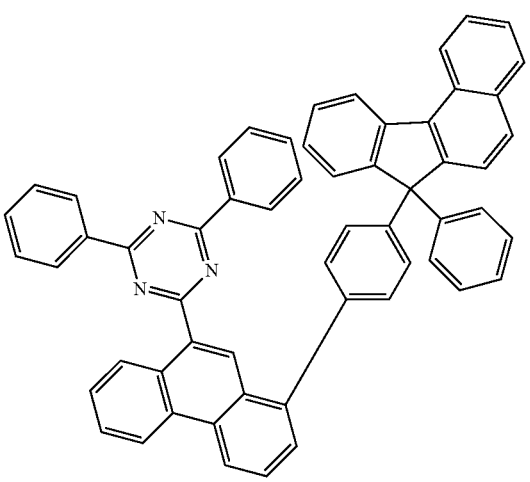
Compound 4-48
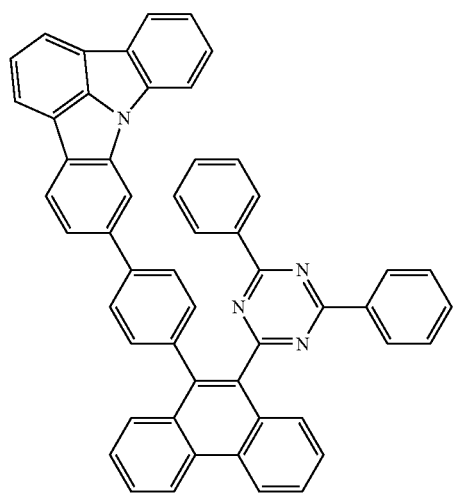
Compound 4-51
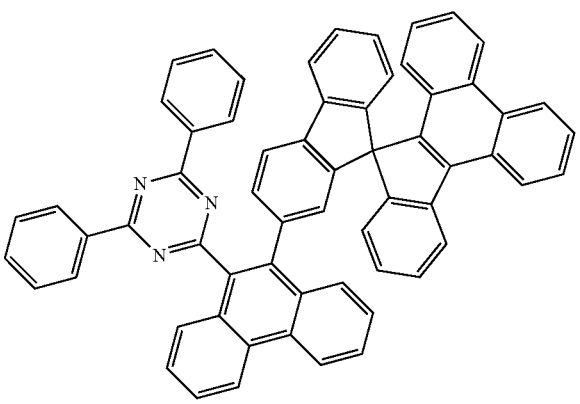

Compound 4-52
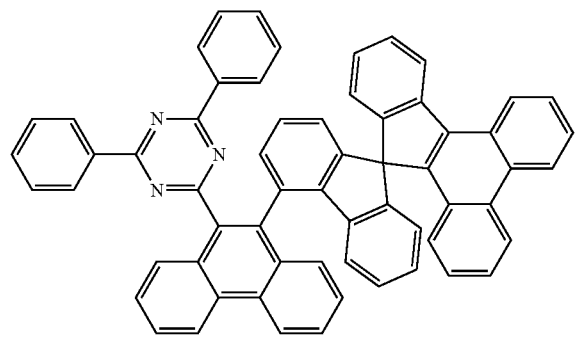
Compound 4-53
Compound 4-54
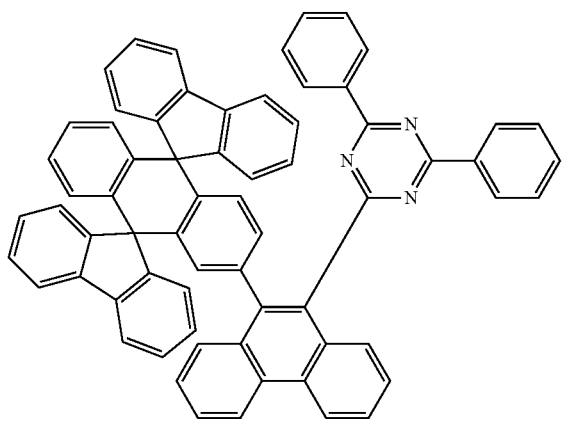
Compound 4-55
Compound 5-1
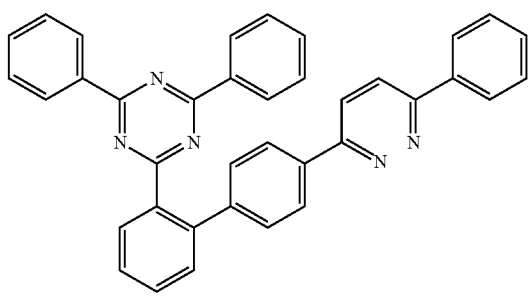
Compound 5-2
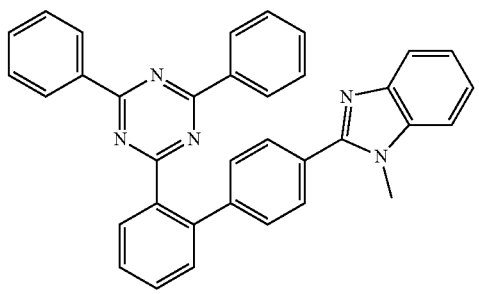
Compound 5-3
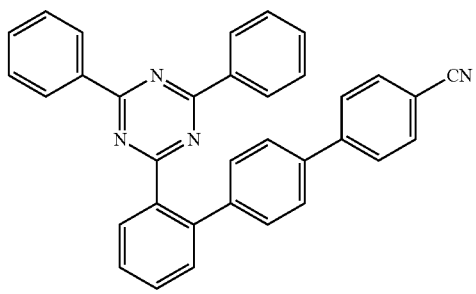
Compound 5-4
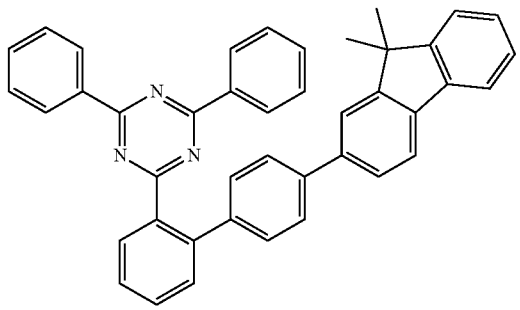
Compound 5-5
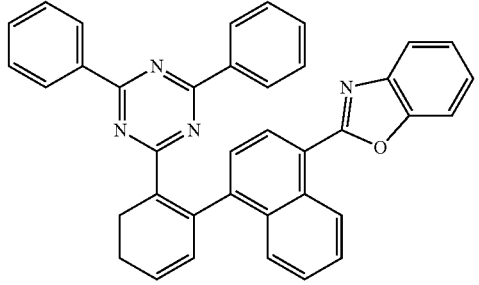

Compound 5-6
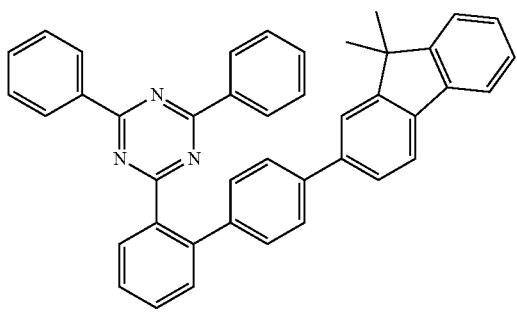
Compound 5-7
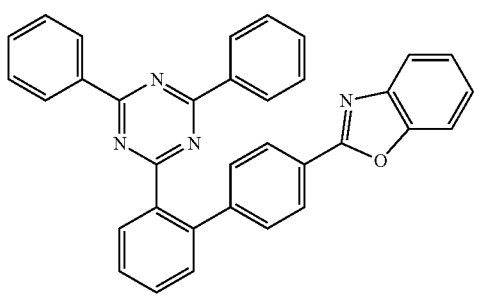
Compound 5-8
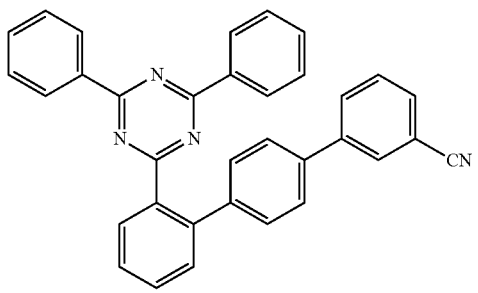
Compound 5-9
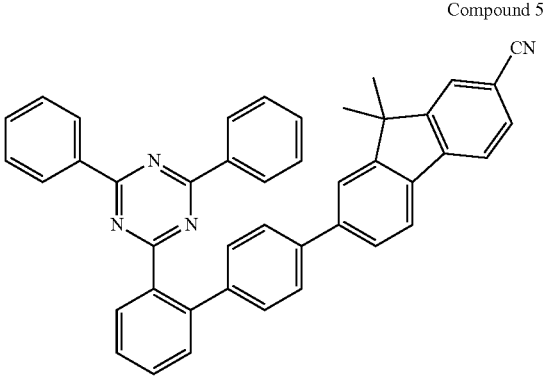
Compound 5-10
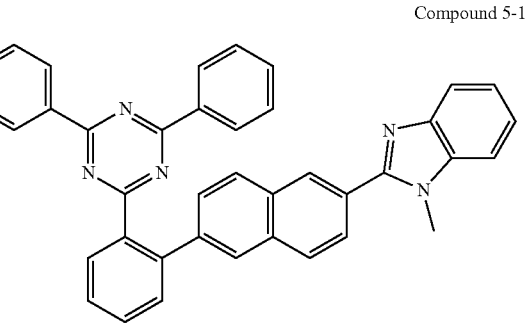
Compound 5-11
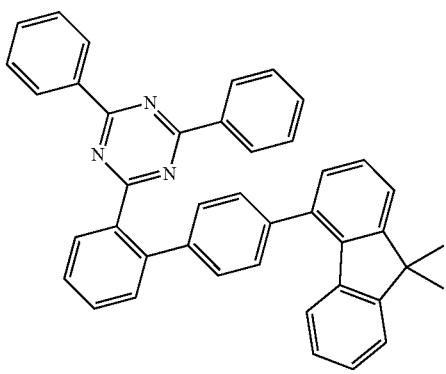
Compound 5-12
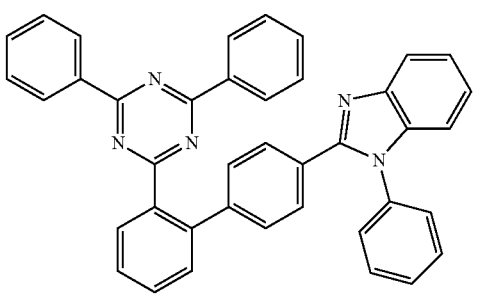
Compound 5-13
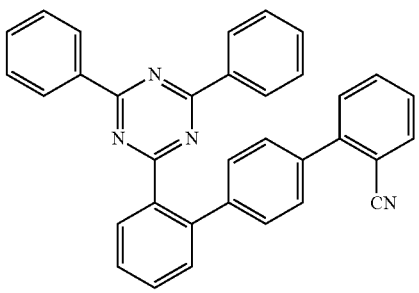
Compound 5-14
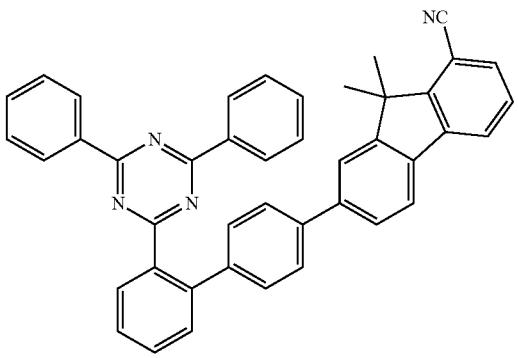

Compound 5-15
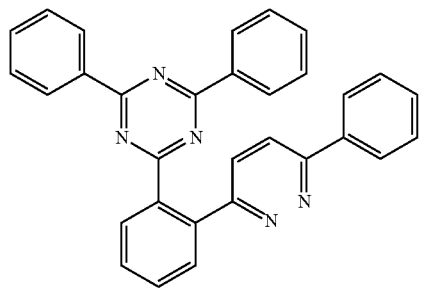
Compound 5-16
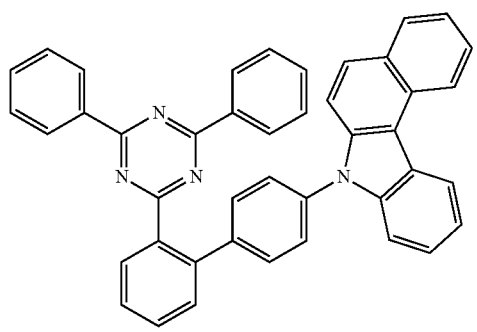
Compound 5-17
Compound 5-18
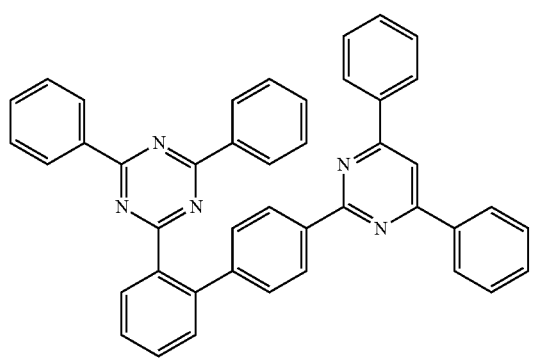
Compound 5-19
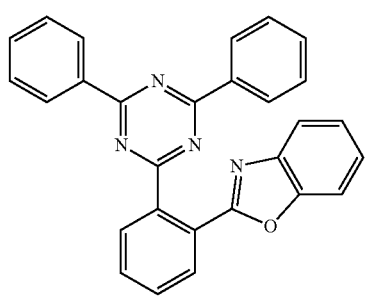
Compound 5-20
Compound 5-21
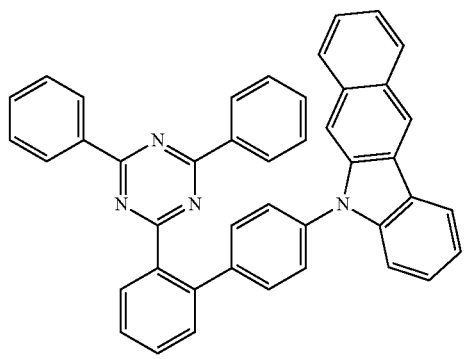
Compound 5-22
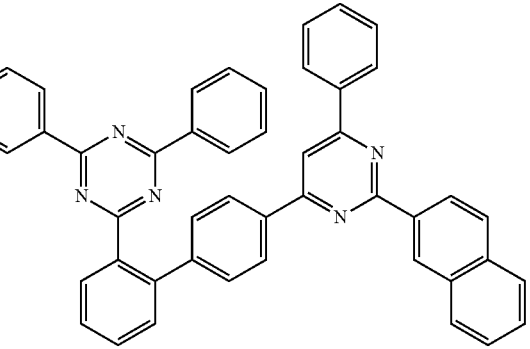

Compound 5-23
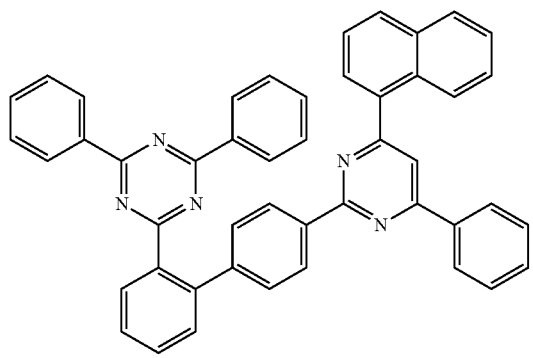
Compound 5-28
Compound 5-24
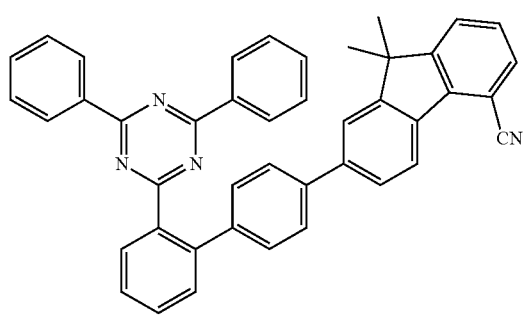
Compound 5-29
Compound 5-25
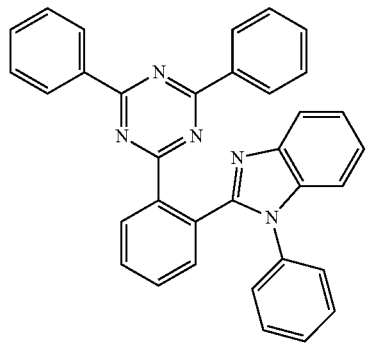
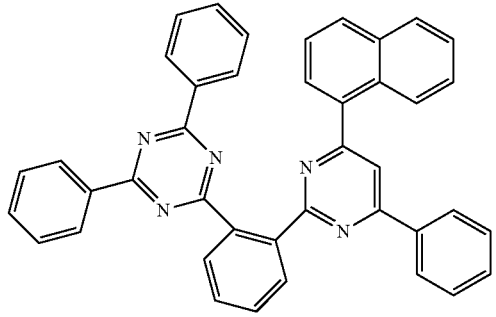
Compound 5-30
Compound 5-27
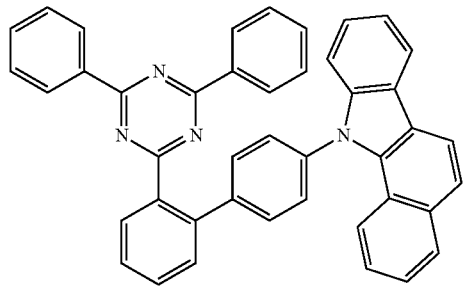
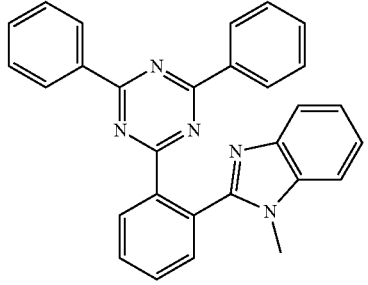
Compound 5-31

Compound 5-32
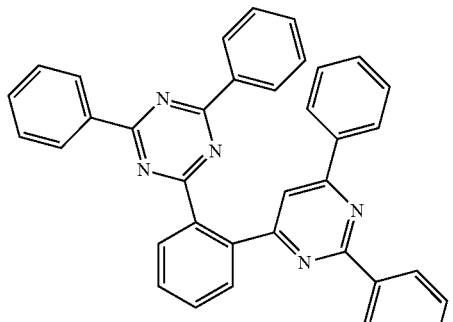
Compound 5-33
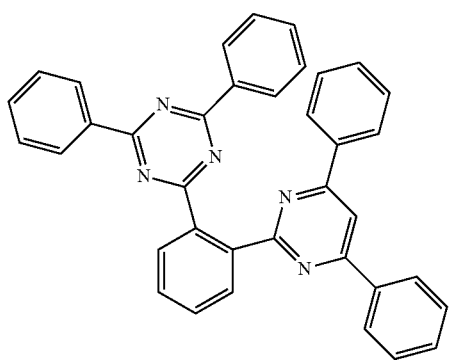
Compound 5-34
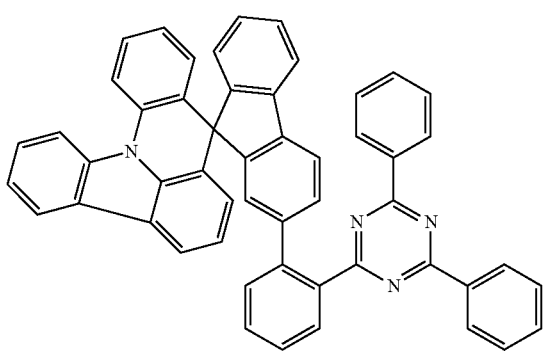
Compound 5-35
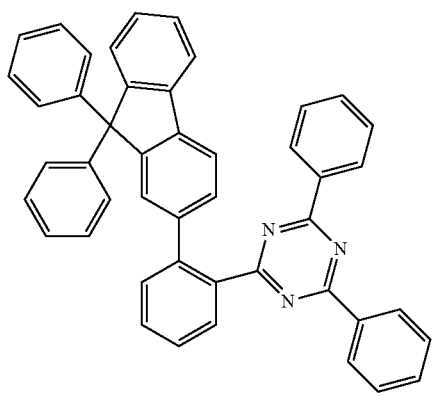
Compound 5-36
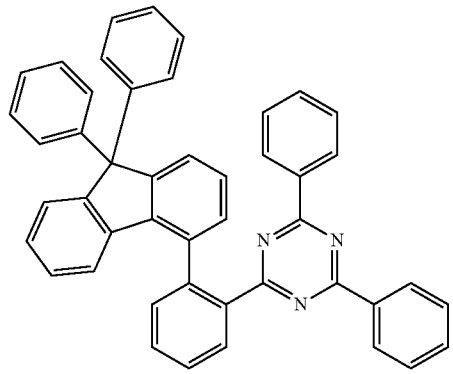
Compound 5-37
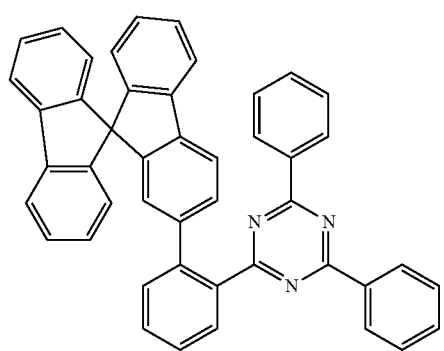
Compound 5-38
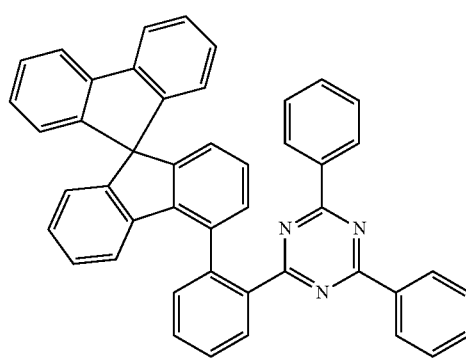
Compound 5-39
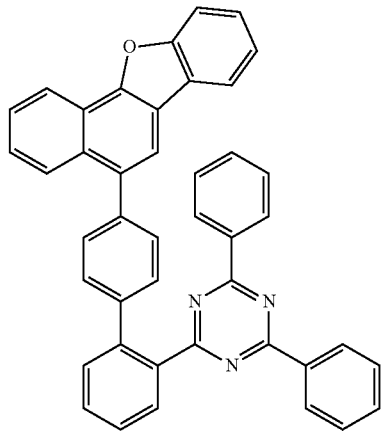

Compound 5-40
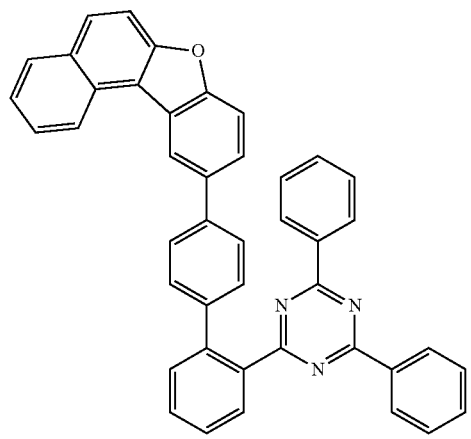
Compound 5-43
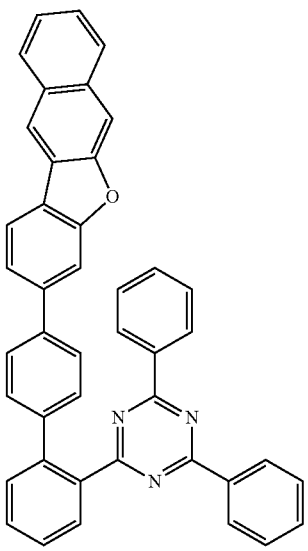
Compound 5-41
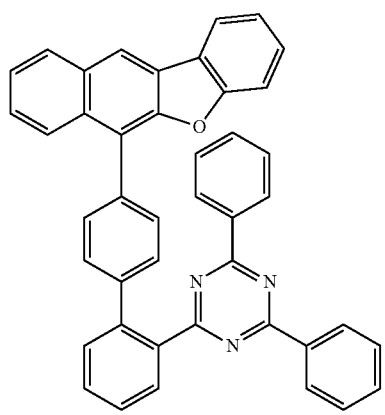
Compound 5-44
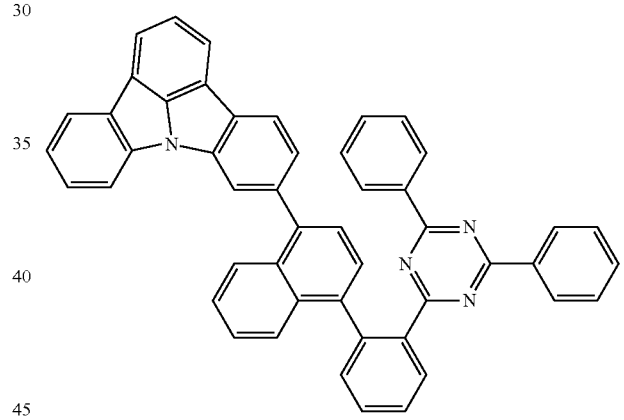
Compound 5-42
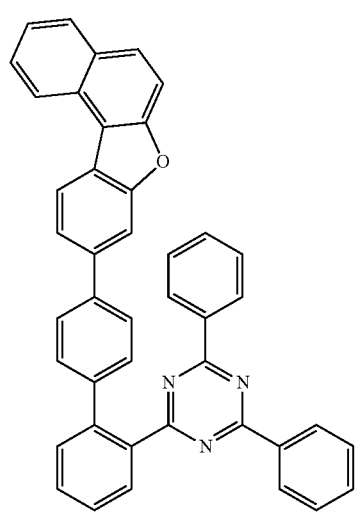
Compound 5-45
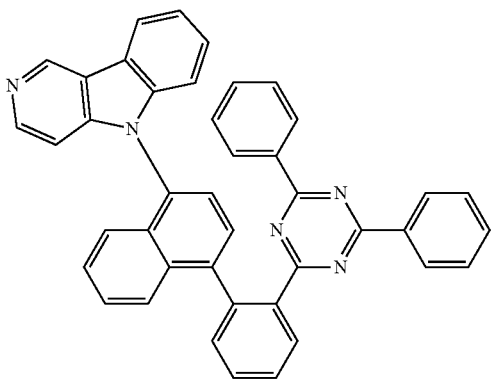

-continued

Compound 5-46

Compound 5-47

Compound 5-48

Compound 5-49

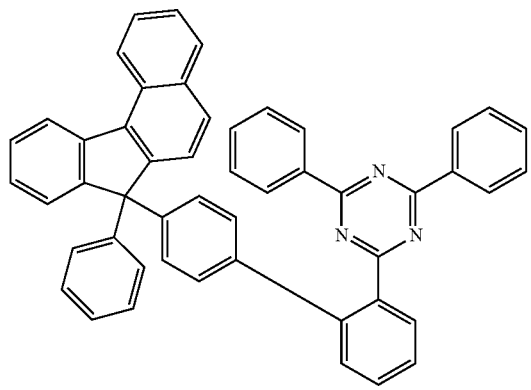
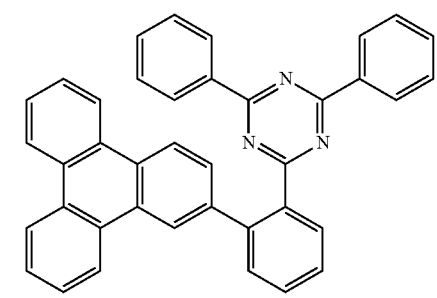

-continued

Compound 5-50

Compound 5-51

Compound 5-52

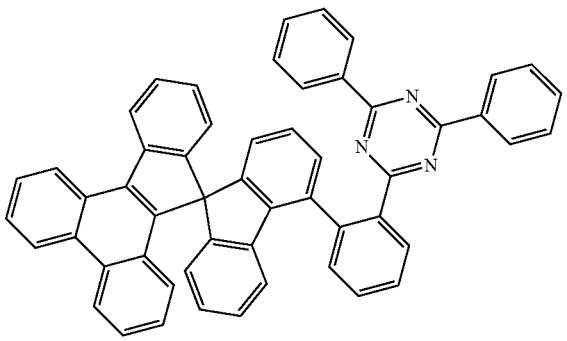
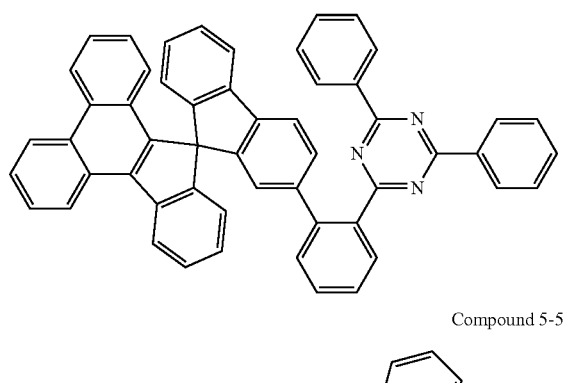
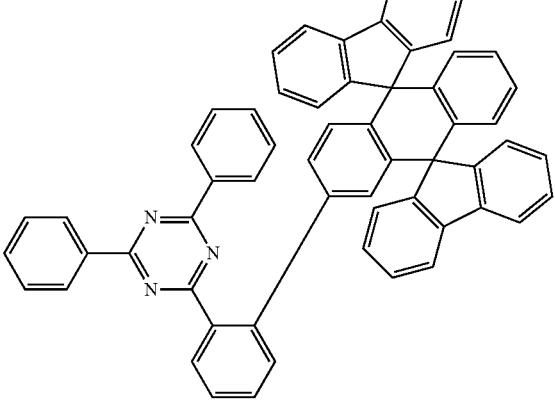

9. The organic light emitting device of claim 1, wherein $Ar_4$ and $Ar_5$ are the same as or different from each other, and are each independently a substituted or unsubstituted $C_6$ to $C_{20}$ aryl group.

10. The organic light emitting device of claim 1, wherein $L_3$ is a direct bond; or a substituted or unsubstituted $C_6$ to $C_{20}$ arylene group.

11. The organic light emitting device of claim 1, wherein $Ar_6$ is a substituted or unsubstituted spirofluoreneindoloacridine group; a substituted or unsubstituted indolocarbazole group; a substituted or unsubstituted benzocarbazole group; a substituted or unsubstituted carbazole group; a substituted or unsubstituted spirobifluorenyl group; or a substituted or unsubstituted fluorenyl group.

12. The organic light emitting device of claim 1, wherein the compound represented by Chemical Formula 11 is any one selected from the following structural formulae:

Compound 6-1
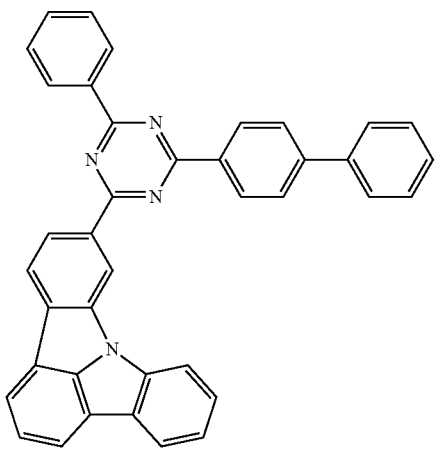
Compound 6-2
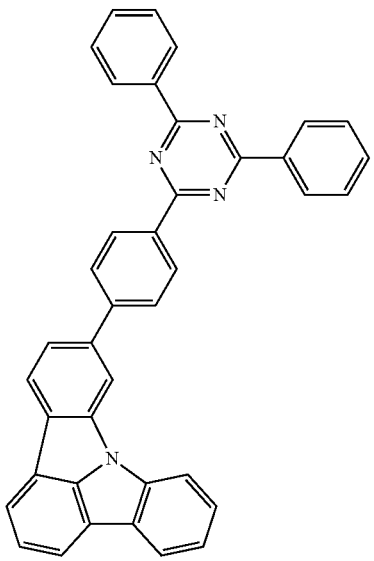
Compound 6-3
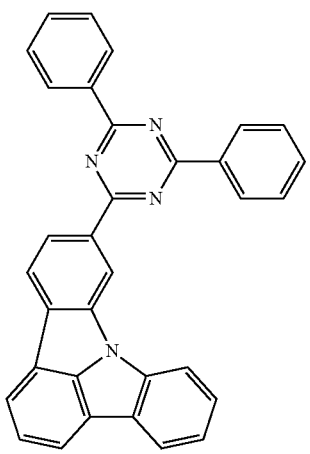
Compound 6-4
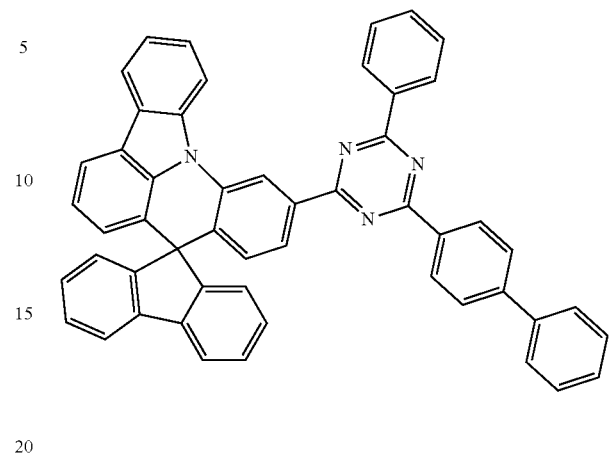
Compound 6-5
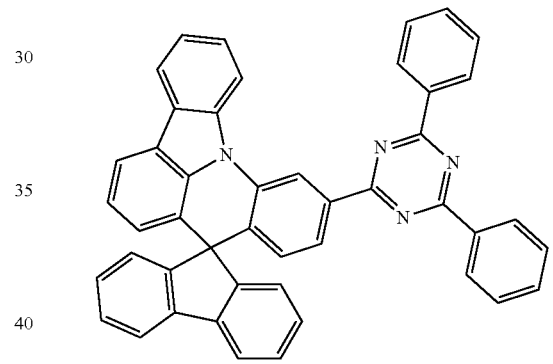
Compound 6-6
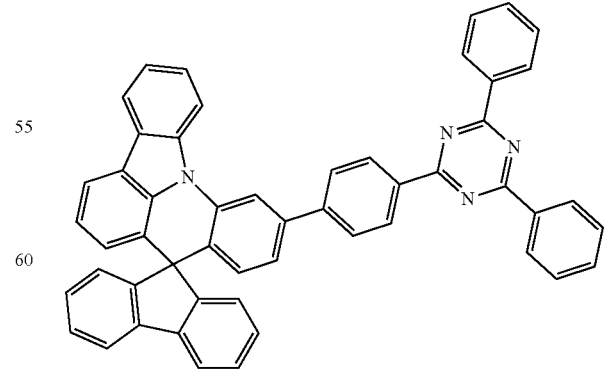

Compound 6-7
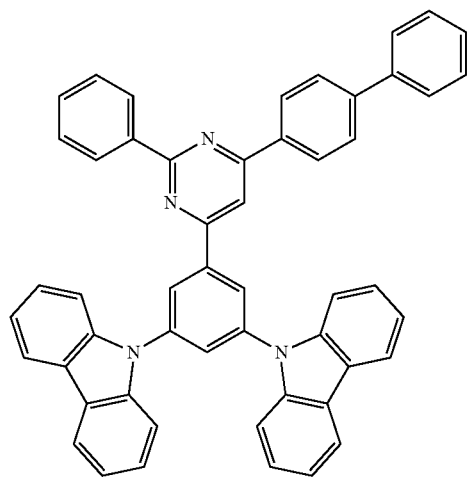
Compound 6-8
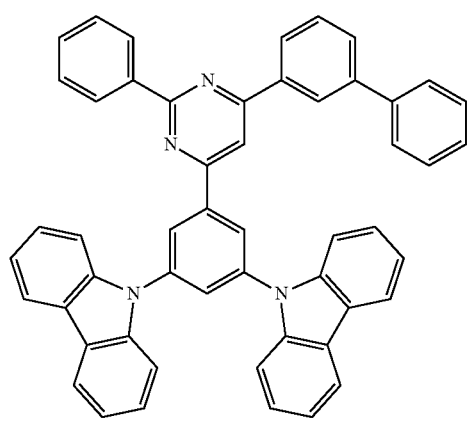
Compound 6-9
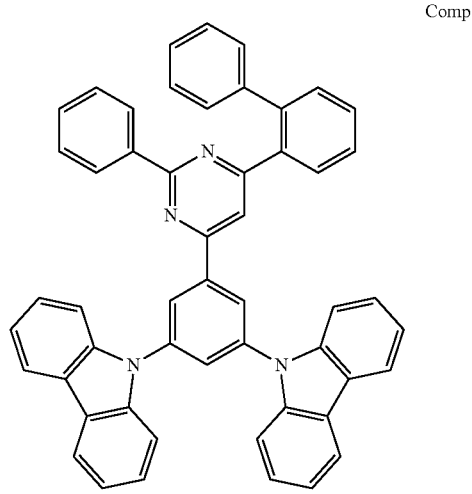
Compound 6-10
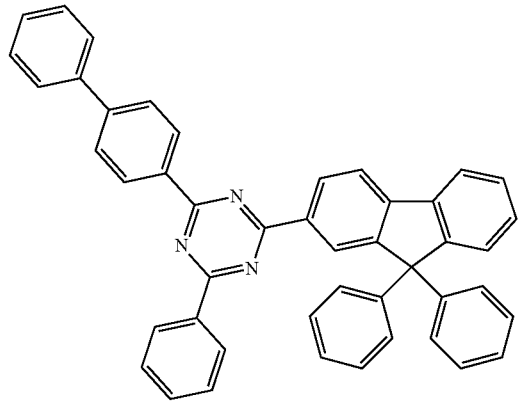
Compound 6-11
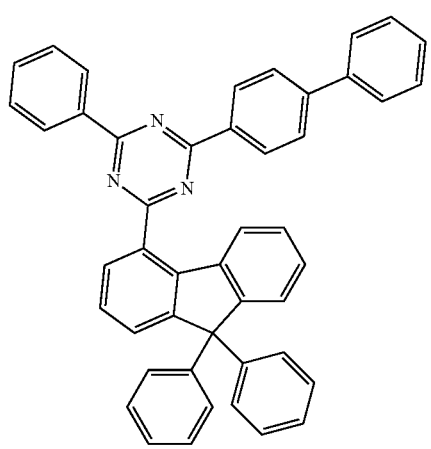
Compound 6-12
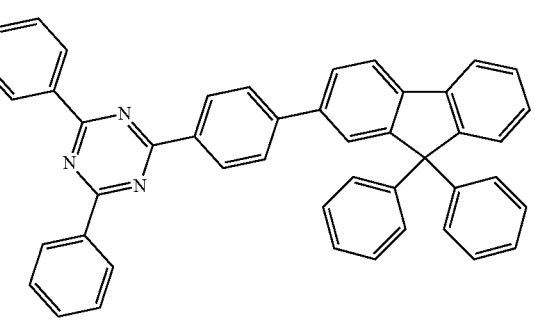
Compound 6-13
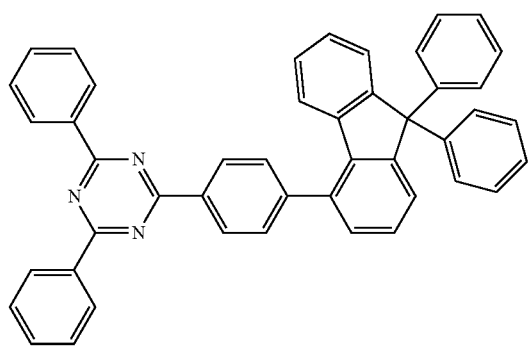

Compound 6-14
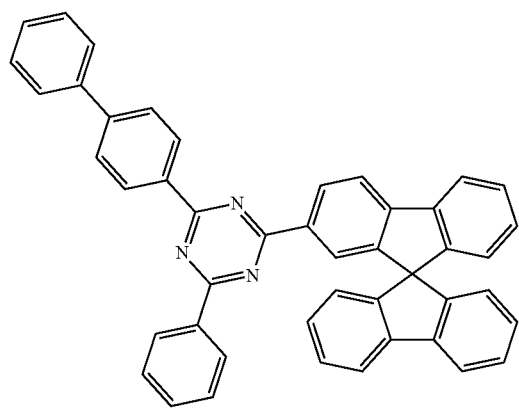
Compound 6-15
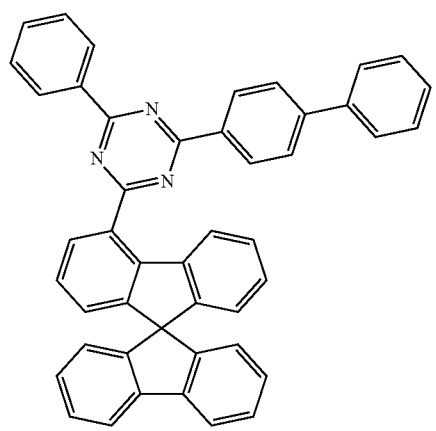
Compound 6-16
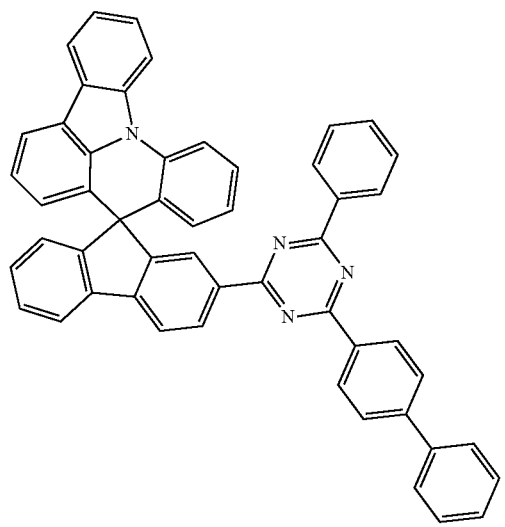
Compound 6-17
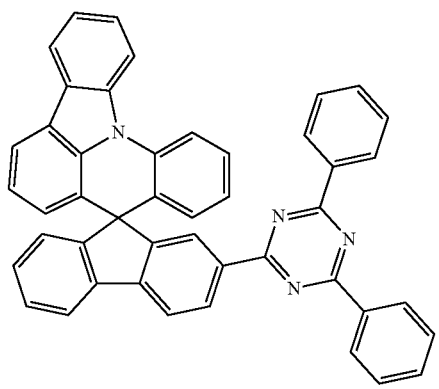
Compound 6-18
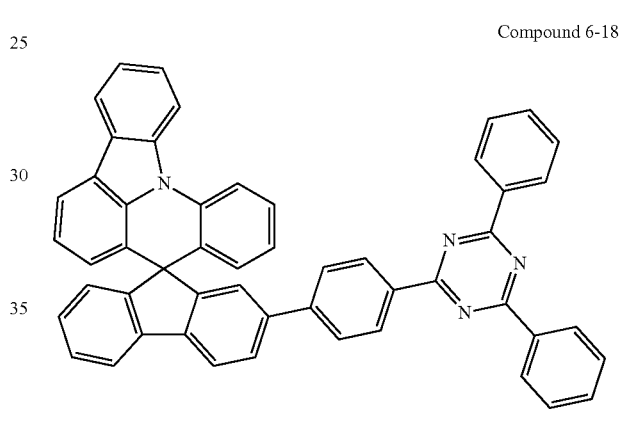
Compound 6-19
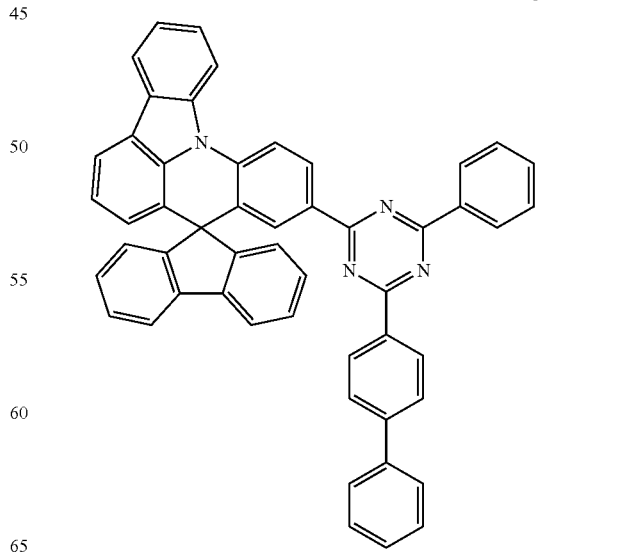

-continued
Compound 6-20
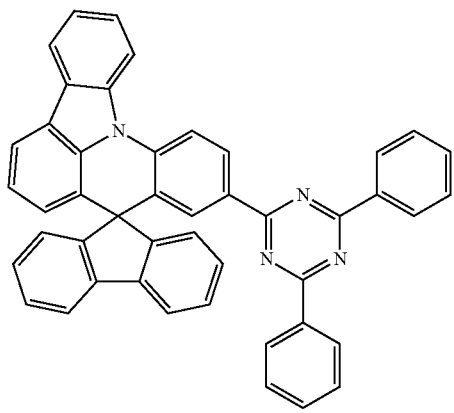
Compound 6-21
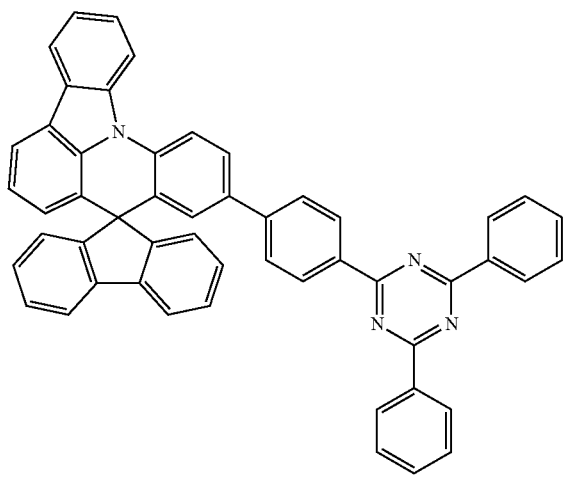
Compound 6-22
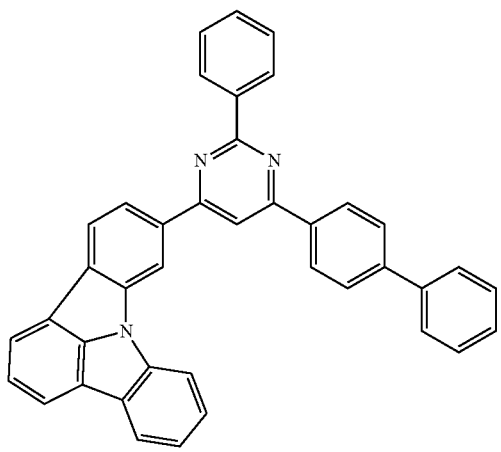
-continued
Compound 6-23
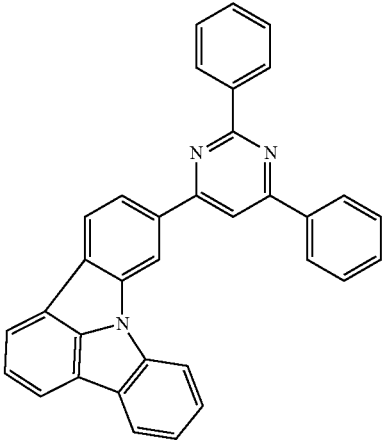
Compound 6-24
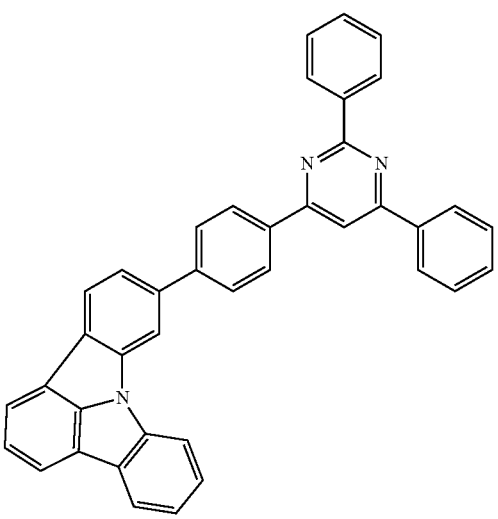
Compound 6-25
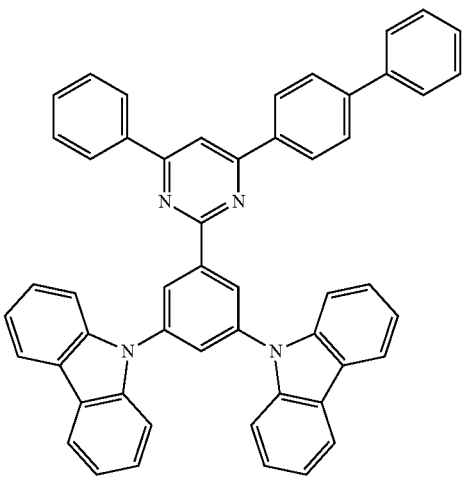

Compound 6-26
Compound 6-29
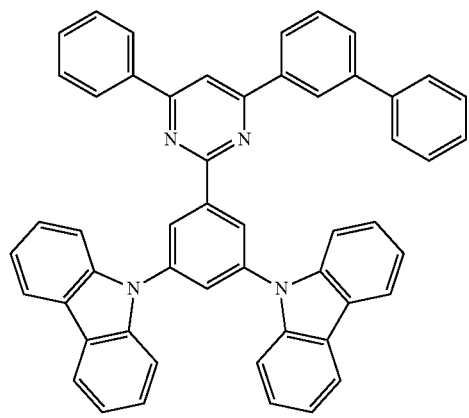
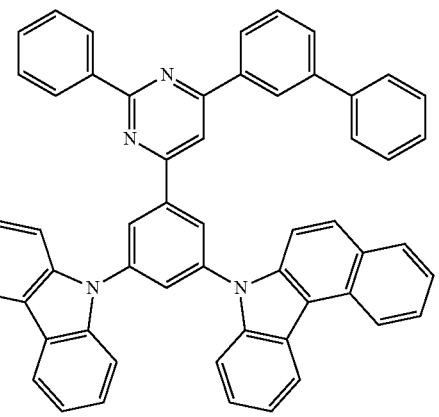
Compound 6-27
Compound 6-30
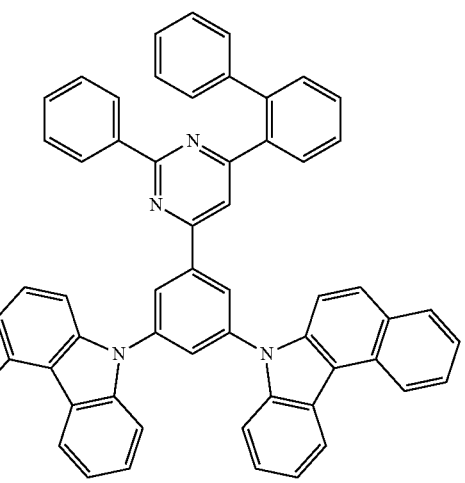
Compound 6-28
Compound 6-30
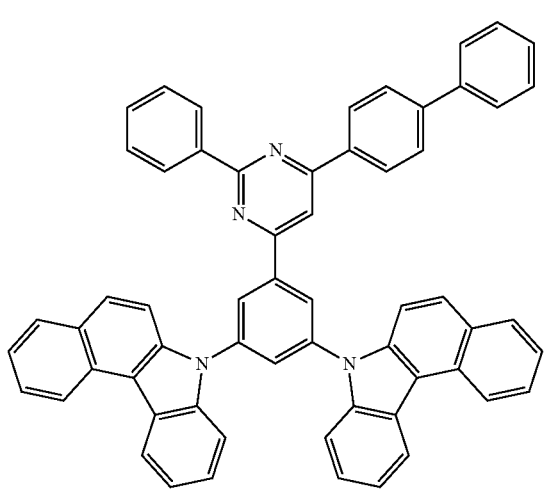

Compound 6-31
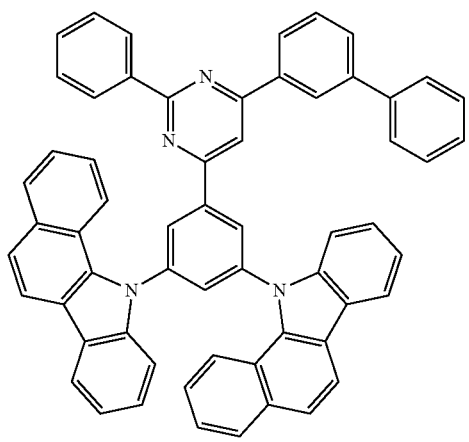
Compound 6-32
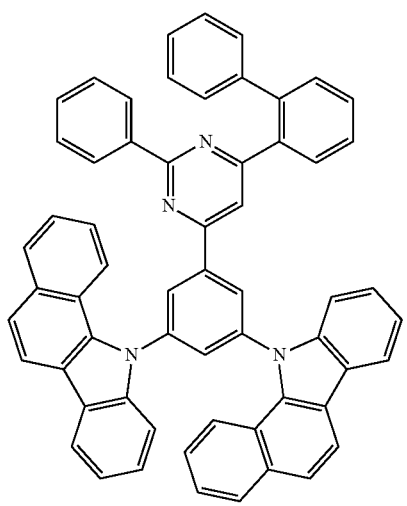
Compound 6-33
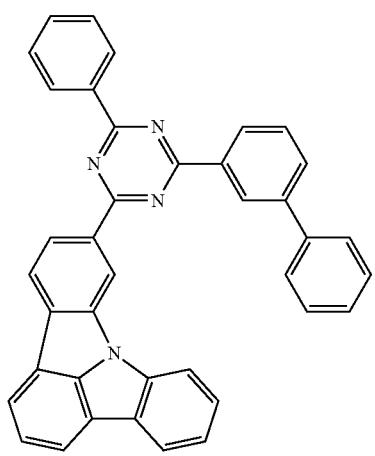
Compound 6-34
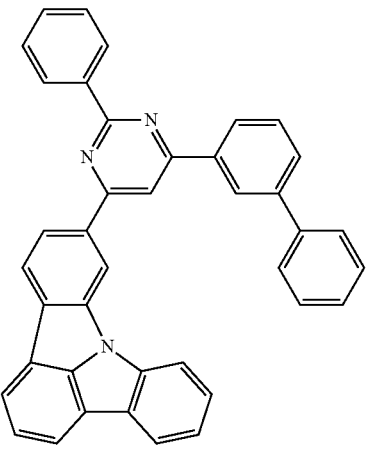
Compound 6-35
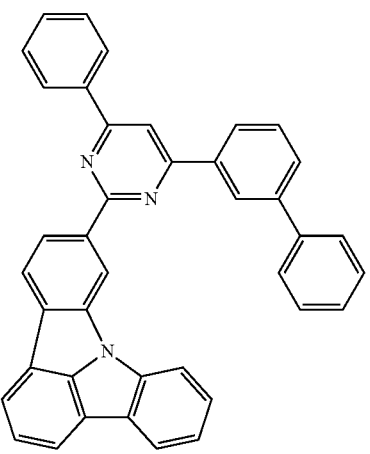
Compound 6-36
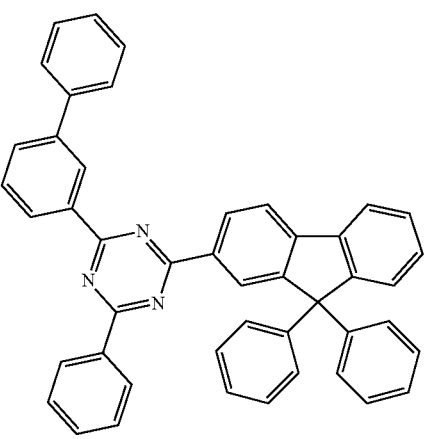

Compound 6-37

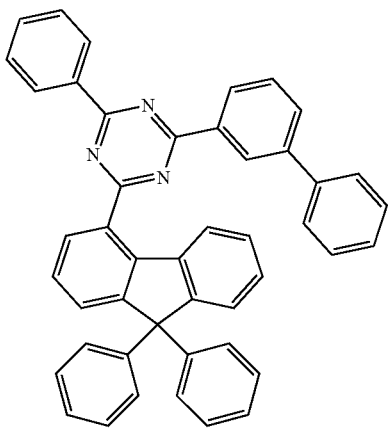

Compound 6-38

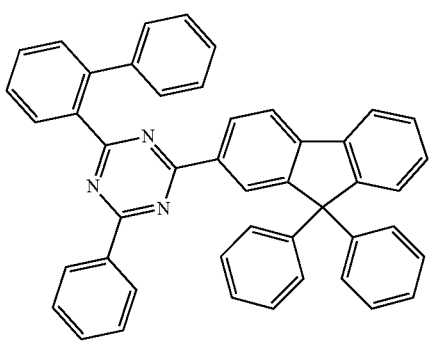

Compound 6-39

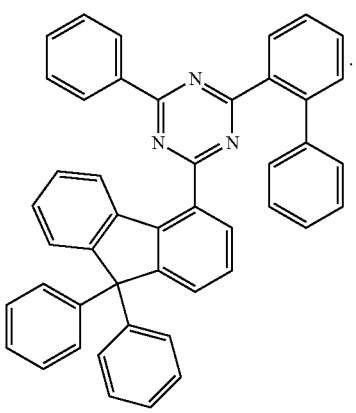

13. The organic light emitting device of claim 1, wherein the electron adjusting layer is provided between a light emitting layer and the electron transport layer.

14. The organic light emitting device of claim 1, further comprising:
one or two or more layers selected from a group consisting of a hole injection layer, a hole transport layer, a light emitting layer, an electron injection layer, an electron blocking layer, and a hole blocking layer.

15. The organic light emitting device of claim 1, wherein the organic material layer comprises a light emitting layer, and
the light emitting layer comprises a compound of the following Chemical Formula A-1:

[Chemical Formula A-1]

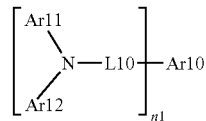

in Chemical Formula A-1, n1 is an integer of 1 or more,

Ar10 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L10 is a direct bond; a substituted or unsubstituted arylene group; or a substituted or unsubstituted heteroarylene group, Ar11 and Ar12 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heterocyclic group, or optionally combine with each other to form a substituted or unsubstituted ring, and when n1 is 2 or more, two or more structures in the parenthesis are the same as or different from each other.

16. The organic light emitting device of claim 1, wherein the organic material layer comprises a light emitting layer, and the light emitting layer comprises a compound represented by the following Chemical Formula A-2:

[Chemical Formula A-2]

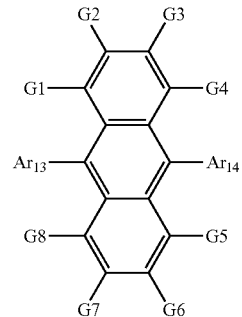

in Chemical Formula A-2,

Ar13 and Ar14 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

17. The organic light emitting device of claim 15, wherein the light emitting layer further comprises a compound represented by the following Chemical Formula A-2:

[Chemical Formula A-2]

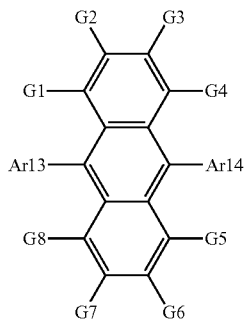

in Chemical Formula A-2,

Ar13 and Ar14 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

* * * * *